(12) United States Patent
Lerchl et al.

(10) Patent No.: US 8,088,974 B2
(45) Date of Patent: Jan. 3, 2012

(54) PRODUCTION OF POLYUNSATURATED FATTY ACIDS, NOVEL BIOSYNTHESIS GENES, AND NOVEL PLANT EXPRESSION CONSTRUCTS

(75) Inventors: Jens Lerchl, Svalöv (SE); Andreas Renz, Limburgerhof (DE); Ernst Heinz, Hamburg (DE); Frederic Domergue, Hamburg (DE); Ulrich Zähringer, Ahrensburg (DE)

(73) Assignee: BASF Plant Science GmbH (DE)

( * ) Notice: Subject to any disclaimer, the term of this patent is extended or adjusted under 35 U.S.C. 154(b) by 109 days.

(21) Appl. No.: 12/565,799

(22) Filed: Sep. 24, 2009

(65) Prior Publication Data

US 2010/0021976 A1  Jan. 28, 2010

Related U.S. Application Data

(62) Division of application No. 10/250,553, filed as application No. PCT/EP02/00462 on Jan. 18, 2002, now Pat. No. 7,615,679.

(30) Foreign Application Priority Data

Jan. 19, 2001 (DE) .................................. 101 02 337

(51) Int. Cl.
  C12N 15/82  (2006.01)
  A01H 5/00   (2006.01)
  C07H 21/04  (2006.01)
(52) U.S. Cl. ..... 800/281; 800/298; 435/419; 435/252.3; 536/23.2
(58) Field of Classification Search .................. None
  See application file for complete search history.

(56) References Cited

U.S. PATENT DOCUMENTS

| | | | |
|---|---|---|---|
| 5,614,393 | A | 3/1997 | Thomas et al. |
| 6,043,411 | A | 3/2000 | Nishizawa et al. |
| 2004/0049805 | A1 | 3/2004 | Lerchl et al. |

FOREIGN PATENT DOCUMENTS

| | | |
|---|---|---|
| EP | 0550162 A1 | 7/1993 |
| EP | 0794250 A1 | 9/1997 |
| WO | WO-91/13972 A1 | 9/1991 |
| WO | WO-93/06712 A1 | 4/1993 |
| WO | WO-93/11245 A1 | 6/1993 |
| WO | WO-94/11516 A1 | 5/1994 |
| WO | WO-94/18337 A1 | 8/1994 |
| WO | WO-95/18222 A1 | 6/1995 |
| WO | WO-96/13591 A2 | 5/1996 |
| WO | WO-96/21022 A1 | 7/1996 |
| WO | WO-97/21340 A1 | 6/1997 |
| WO | WO-97/30582 A1 | 8/1997 |
| WO | WO-98/46765 A1 | 10/1998 |
| WO | WO-99/27111 A1 | 6/1999 |

OTHER PUBLICATIONS

Broun et al, Science 282: 1315-1317, Nov. 13, 1998.*

Van de Loo et al, PNAS, USA 92: 6743-6747, Jul. 1995.*
Doerks et al, TIG 14(6): 248-250, Jun. 1998.*
Brenner, S.E. TIG 15(4): 132-133, Apr. 1999.*
Bork et al, TIG 12(10): 425-427, Oct. 1996.*
Stukey, J. E., et al., "The OLE1 Gene of *Saccharomyces cerevisiae* Encodes the Δ9 Fatty Acid Desaturase and Can be Functionally Replaced by the Rat Stearoyl-CoA Desaturase Gene", The Journal of Biological Chemistry, vol. 265, No. 33, 1990, pp. 20144-20149.
Wade, H., et al., "Enhancement of chilling tolerance of a cyanobacterium by genetic manipulation of fatty acid desaturation," Nature, vol. 347, 1990, pp. 200-203.
Huang, Y.-S., et al., "Cloning of Δ12- and Δ6-Desaturases from *Mortierella alpina* and Recombinant Production of γ-Linolenic Acid in *Saccharomyces cerevisiae*", Lipids, vol. 34, No. 7, 1999, pp. 649-659.
McKeon et al., "Stearoyl-Acyl Carrier Protein Desaturase from Safflower Seeds", in Methods in Enzymology, vol. 71, Lipids, Part C, Academic Press, NY, 1981, pp. 275-281.
Wang, X.-M., et al., "Synthesis and regulation of linolenic acid in higher plants", Physiol. Biochem., vol. 26, No. 6, 1988, pp. 777-792.
Napier, J.A., et al., "Identification of a *Caenorhabditis elegans* Δ6-fatty-acid-desaturase by heterologous expression in *Saccharomyces cerevisiae*", Biochem J., vol. 330, 1998, pp. 611-614.
Obukowicz, M. G., et al., "Identification and Characterization of a Novel Δ6/Δ5 Fatty Acid Desaturase Inhibitor As a Potential Anti-Inflammatory Agent", Biochemical Pharmacology, 1998, vol. 55, pp. 1045-1058.
Moreno, V. J., et al., "Biosynthesis of Unsaturated Fatty Acids in the Diatom *Phaeodactylum tricornutum*", Lipids, vol. 14, No. 1, 1979, pp. 15-19.
Abbadi, A., et al., "Transgenic oilseeds as sustainable source of nutritionally relevant C20 and C22 polyunsaturated fatty acids?", Eur. J. Lipid Sci. Technol., vol. 103, 2001, pp. 106-113.
Domergue, F., et al., "Cloning and functional characterization of *Phaeodactylum tricornutum* front-end desaturases involved in eicosapentaenoic acid biosynthesis", Eur. J. Biochem., vol. 269, 2002, pp. 4105-4113.

(Continued)

*Primary Examiner* — Elizabeth McElwain
(74) *Attorney, Agent, or Firm* — Connolly Bove Lodge & Hutz LLP

(57) ABSTRACT

The present invention relates to a method for the production of unsaturated fatty acids with at least two double bonds. The invention furthermore relates to the use of nucleic acid sequences SEQ ID NO: 1, SEQ ID NO: 3, SEQ ID NO: 5 and SEQ ID NO: 11 encoding polypeptides having desaturase activity in the method and for generating a transgenic organism, preferably a transgenic plant or a transgenic microorganism, with an increased content of fatty acids, oils or lipids with unsaturated $C_{18}$-, $C_{20}$-, or $C_{22}$-fatty acids, and to their homologs or derivatives, to gene constructs encompassing these genes, and to their use alone or in combination with biosynthesis genes of polyunsaturated fatty acids. The invention also relates to multiexpression cassettes for seed-specific expression, and to vectors or organisms which encompass a desaturase gene alone or in combination with further desaturases and/or elongase genes or homologs using said expression cassettes.

20 Claims, 5 Drawing Sheets

OTHER PUBLICATIONS

Broun et al., Science, vol. 282, (1998), pp. 1315-1317.
Van De Loo et al., PNAS, USA, vol. 92, (1995), pp. 6743-6747.
Doerks, et al., TIG, vol. 14, No. 6, (1998), pp. 248-250.
Smith, et al., Nature Biotechnology, vol. 15, (1997), pp. 1222-1223.
Brenner, S.E., TIG, vol. 15, No. 4, (1999), pp. 132-133.
Bork et al., TIG, vol. 12, No. 10, (1996), pp. 425-427.
Deluca, V., AgBiotech News and Information, vol. 5, No. 6, (1993), pp. 225N-229N.

* cited by examiner

Figure 1: Polypeptide alignment of the coding region of Pp_des 6 (top row) with the EST sequence of PT001078032R (bottom row)

```
398 WKPLVWMAVTELMSCMLLCFVFVLSHNGMEVYNSSKEFVSAQI-------------VSTR 444
    W+    + +  +  + L +F LSHN    + S+     +A +            V T
430 WRVFGNTMLMGVAESLALAVLFSLSHN-----FESADRDPTAPLKKTGEPVDWFKTQVETS 263
445 DIKGNIFNDWFTGGLNRQIEHHLFPTMPRHNLNKIAPRVEVFCKKEGLVY 494
         G   +   FTGGLN Q+EHHLFP M          IAP+V   C KHG+ Y
262 CTYGGFLSGCFTGGLNFQVEHHLFERMSSAWYXYIAPKVREICAKHGVHY 113
```

Figure 2: Polypeptide alignment of coding regions of Ma_des12 (top sequence) with PT001070010R

```
105 GVWVLAHECGHQSFSTSKTLNN 126
    G WVLAHECGH +FS +++L +
533 GFWVLAHECGHGAFSKNRSLQD 598
```

Figure 2a: Polypeptide alignment of coding regions of Ma_des12 (top sequence) with PT001072031R

```
117 SFSTSKTLNNTVGWILHSMLLVPYHSWRISHSKHH 151
    ++S S+T N+ VG+I+H   LLVPY +W+ +H+KHH
465 AYSDSQTFNDVVGFIVHQALLVPYFAWQYTHAKHH 569
```

Figure 3: Polypeptide alignment of coding regions of a PCR product of the primer pair F6a and R4a2 encoding a Phaeodactylum desaturase fragment (top row) with the Streptomyces coelicolor sequence T36617 (bottom row)

```
1   WWKNKHNGHHAVPNLHCSSAVAQDGDPDIDTMPLLAWSVQQAQSYRELQADGKDSGLVKF 60
    WW++KH  HHA PN        +D DPDI   LL WS  QA++            +GL +
114 WWQDKHTRHHANPN-------TEDLDPDIGP-DLLVWSPDQARAA---------TGLPRL 156
61  MIRNQSYFYFPILLLARLSWLNESFKCAFGLGAASENAALELKAKGLQYPLLEKAGILLH 120
    + R Q++ +FP+L L        E F   G A N  L+ +A       L+ A +L H
157 LGRWQAFLFFPLLTL-------EGFNLHVASGRAMANRRLKRRA-------LDGALLLAH 202
121 YAWMLTVSSGFGRXXXXXXXXXXXXXXXXXCGFLLAIVFGLGHNGMATYNADARPDFWKLQ 180
      A  LT   F                    G  L   F  H GM    AD RPDF + Q
203 CAVYLTAL--FWVLPPGMAIAFLAVHQCLFGVYLGSAFAPNHKGMPILTADDRPDFLRRQ 260
181 VTTTRNVTGGHGFPQAFVDWFCGGLQYQVDHHLFPS 216
    V T+RNV GG      F D   GGL +Q++HHLFPS
261 VLTSRNVNGG-----LFTDLALGGLNHQIEHHLFPS 291
```

Figure 4: Polypeptide alignment of coding regions of Pp_des6 (top row) in comparison with Pt_des6 (bottom row)

```
 51 KRLTSKKRVSESAAVQCISAEVQRNSSTQGTAEALAESVVKPTRRRSSQW 100
                                         - |   |.|-
  1 ................................MGKGGDARASKG 12
                    .             .             .
101 KKSTHPLS..EVAVHNKPSDCWIVVKNKVYDVSNFADEHPGGSVISTYFG 148
     .   :|  ||  |   |  | ||: ||||||||.  ||||-|| |: |
 13 STAARKISWQEVKTHASPEDAWIIHSNKVYDVSNW.HEHPGGAVIFTHAG 61
              -                -           -         -
149 RDGTDVFSSFHAASTWKILQDFYIGDV..ERVEPTPELL...KDFREMRA 193
    | ||:|..|||  .  ::. |||:. |      |: :   | :|::|.
 62 DDMTDIFAAFHAPGSQSIMKKFYIGELLPETTGKEPQQIAFEKGYRDLRS 111
                 .             .             .
194 LFLREQLFKSSKLYYVMKLLTNVAIFAASIAIICWSKTISAVLASACMMA 243
      :  :|||-| :||  |  |.|.|.||.||. |:: :|      |||| |:
112 KLIMMGMFKSNKWFYVYKCLSNMAIWAAACALVFYSDRFWVHLASAVMLG 161
                 .             .             .
244 LCFQQCGWL.SHDFLHNQVFETRWLNEVVGYVIGNAVLGFSTGWWKEKHNL 293
    ||| |||-||||||.||| |  :. |  || . |:|  ||| |||
162 TFFQQSGWLAHDFLHHQVFTKRKHGDLGGLFWGNLMQGYSVQWWKNKHNG 211
                 .             .             .
294 HHAAPN.ECDQTY.QPIDEDIDTLPLIAWS.......KDILATVENKTFL 334
    ||| ||   |    |  | ||||:||:|||        ::: |  ..  .
212 HHAVPNLECSSAVAQDGDPDIDTMPLLAWSVQQAQSYRELQADGKDSGLV 261
                 .             .             .
335 R.ILQYQHLFFMGLLFFARGSWLFWSWR.......YTSTAVLSPVDR... 373
    : .:. | |: :|  ||  ||| |.:            . | |    :
262 KFMIRNQSYFYFPILLLARLSWLNESFKCAFGLGAASENAALELKAKGLQ 311
                 .             .             .
374 ..LLEKGTVLFHYFWFVGTAC.YLLPGWKPLVWMAVTELMS.CMLLCFVF 419
      ||||  :| ||| | . .  :     .  . .| |  || ||
312 YPLLEKAGILLHYAWMLTVSSGFGRFSFAYTAFYFLTATASCGFLLAIVF 361
                 .             .             .
420 VLSHNGMEVYNSS..KEFVSAQIVSTRDIKG.....NIFNDWFTGGLNRQ 462
    | |||| ||.  :|  |: -||.: |       | ||| ||| |
362 GLGHNGMATYNADARPDFWKLQVTTTRNVTGGHGFPQAFVDWFCCCLQYQ 411
                 .             .             .
463 IEHHLFPTMPRHNLNKIAPRVEVFCKKHGLVYEDVSIATGTCKVLKALKE 512
    ::|||||.:|||||  |   || |||. |- | |  :  :  || -|| |
412 VDHHLFPSLPRHNLAKTHALVESFCKEWGVQYHEADLVDGTMEVLHHLGS 461
                 .
513 VAEAAAEQHATTS.... 525
    ||                 |
462 VAGEFVVDFVRDGPAM. 477
```

Figure 5: Polypeptide alignment of coding regions of Pp_des6 (top row) in comparison with Pt_des5 (bottom row).

```
 51 KRLTSKKRVSESAAVQCISAEVQRNSSTQGTAEALAESVVKPTRRRSSQW 100
                                   :|   |  .|...
  1 ..............................MAPDADKLRQRQTTAV  16

101 KKSTHPLSEVAVHNKPSDC......WIVVKNKVYDVSNFADEHPGGSVIS 144
     | | . :.  :          : : :||. .| :||||   |
 17 AK..HNAATISTQERLCSLSSLKGEEVCIDGIIYDLQSF..DHPGGETIK  62

145 TYFGRDGTDVFSSFHAASTWKILQDF.YIGDVERVEPTPELLKDF.REM. 191
    : | |  :   |    | | |:   :| |     .  :| ||.
 63 MFGGNDVTVQYKMIHPYHTEKHLEKMKRVGKVTDFVCEYKFDTEFEREIK 112

192 RALFLREQLFKS.SKLYYVMKLLTNVAIFAASIAIICWSKT.ISAVLASA 239
    | .|  . |    | :  :   :|||     |  |  | .|| |
113 REVFKIVRRGKDFGTLGWFFRAFCYIAIF..FYLQYHWVTTGTSWLLAVA 160

240 CMMALCFQQCGWLSHDFLHNQVFETRWLNEVVGYVIGNAVLGFSTGWWKE 289
     ..           . ||   |   . |.|:..|  :|   :| |   |.|
161 YGISQAMIGMN.VQHDANHGATSKRPWVNDMLG..LGADFIGGSKWLWQE 207

290 KHNLHHAAPNECDQTYQPIDEDIDTLPLIAWSKDILATVENKTFLRILQY 339
    .|  ||| |  :    | :      |::  ..  |        :|.|    .:
208 QHWTHHAYTNHAEM..DP..DSFGAEPMLLFN.DYPLDHPARTWLH..RF 250

340 QHLFFMGLLFFARGSWLFWSWR.....YTSTAVLS...PVDRLLEKGTVL 381
    |  |:| .|     | | |    .           | |      . |
251 QAFFYMPVL...AGYWLSAVFNPQILDLQQRGALSVGIRLDNAFIHSRRK 297

382 FHYFW...FVC....TACYLLPG....WKPLVWMAVTELMSGMLLGFVFV 420
    :  ||    ::            |   |      |:   . . .  : |  .|
298 YAVFWRAVYIAVNVIAPFYTNSGLEWSWRVFGNIMLMGVAESIALAVLFS 347

421 LSHN..........GMEVYNSSKEFVSAQIVSTRDIKGNIFNDWFTGGLN 460
    ||||                :.        :.    | | |   |  .  |||||
348 LSHNFESADRDPTAPLKKTGEPVDWFKTQ.VETSCTYGGFLSGCFTGGLN 396

461 RQIEHHLFPTMPRHNLNKIAPRVEVFCKKHGLVYEDVS.IATGTCKVLKA 509
    |:||||||  |        |||:|    | |||. |  |       .:
397 FQVEHHLFPRMSSAWYPYIAPKVREICAKHGVHYAYYPWIHQNFLSTVRY 446

510 LKEVAEAAA.EQHATTS....... 525
     :       |  | | .    |
447 MHAAGTGANWRQMARENPLTGRA. 469
```

Figure 6: Polypeptide alignment of coding regions of the Mortierella alpina Δ12-desaturase (Ma_des12), top row, with the homologous Phaeodactylum tricornutum sequence (Pt_des12), bottom row.

```
 40 KEIRECIPAHCFERSGLRGLCHVAIDLTWASLL..FLAATQIDKFE..NP  85
    |::|  ||  |||    : | :..:  |  .:|   . |   :   :  ||
107 KDLRAVIPKDCFEPDTAKSLGYLSVS.TMGTILCSVVGANLLSVLDPSNP 155

86 LIRYLAWPVYWIMQGIVCTGVWVLAHECGHQSFSTSKTLNNTVGWILHSM 135
    | : | |  . | | |.||||||||| .|| .:.| . ||:|:||.
156 L.TWPLWAAYGAVTGTVAMGLWVLAHECGHGAFSKNRSLQDAVGYIIHSI 204

136 LLVPYHSWRISHSKHHKATGHMTKDQVFVPKTRSQVGLPPKENAAAAVQE 185
    :||||  ||.  ||.  ||.  | ||    :   ||    .|    | . |   |
205 MLVPYFSWQRSHAVHHQYTNHMELGETHVPDRADKEG....EKSLALRQF 250

186 EDMSVHLDEEAPIVTLFWMVIQFLFGWPAYLIMNASGQDYGRWTSHFHTY 235
         |    |.              :    :   ||||||:.  |.|       |.||:
251 MLDSFGKDKGMKAYGGLQSFLHLIVCWPAYLLIGATGGPDRGMTNHFYP. 299

236 SPIFEP....RNFF......DIIISDLGVLAALGALIYASMQLSLLTVTK 275
    .|:   |    :  |         :   ||:|: |  .|||| .     |   |
300 NPLSTPTQPKKELFPGNWKEKVYQSDIGIAAVVGALIAWTATSGLAPVMA 349

276 YYIVPYLFVNFWLVLITFLQHTDPKLPHYREGAWNFQRGALCTVDRSFGK 325
    |  |  :  :|  ||||  |.||||| .||:     || :|||  |:|| : |
350 LYGGPLIVINAWLVLYTWLQHTDTDVPHFSSDNHNFVKGALHTIDRPYDK 399

326 .....FLDHMFHGIVHTHVAHHLFSQMPFYHAEEATYHLKKLLGEYYVYD 370
         :|  :  | |    |||||| |  .| | |: ||    :|      |  |.||
400 LDPWGIIDFLHHKICTTHVAHHFDSTIPHYKAQIATDAIKAKFPEVYLYD 449

371 PSPIVVAVWRSFRECRFVEDQGDVVFFK 398
    |.||    |.||  :  |  ||  .||    .|
450 PTPIPQAMWRVAKGCTAVEQRGDAWVWK 477
```

Figure 7: Polypeptide alignment of coding regions of the Mortierella alpina Δ12-desaturase (Ma_des12), top row, with the homologous sequence of Phaeodactylum tricornutum clone PT001072031R (Pt_des12.2), bottom row

```
 22 NSAKPAFERNYQLPEFTIKEIRECIPAHCFERSGLRGLCHVAIDLTWASL  71
    .|  |  . .:||  |  :|:  ||  ||:||     :.  ||  |.
 33 SSYNPLAKDSPELP..TKGQIKAVIPKECFQRSAFWSTFYLMRDLAMAAA  80

72 LFLAATQIDKFENP......LIRYLAWPVYWIMQCIVCTGVWVLAHECGH 115
    .|:   : |        |   | | ||     | : ||  ||.|||||
 81 FCYGTSQVLSTDLPQDATLILPWALGWGVYAFWMGTILTGPWVVAHECGH 130

116 QSFSTSKTLNNTVGWILHSMLLVPYHSWRISHSKHHKATGHMTKDQVFVP 165
    .:|  |.|  |. ||.|.|  ||||  .|.  .|.|||:  | |:    ||
131 GAYSDSQTFNDVVGFIVHQALLVPYFAWQYTHAKHHRRTNHLVDGESHVP 180

166 KTRSQVGLPP..KENAAAAVQEEDMSVHLDEEAPIVTLFWMVIQFLFGWP 213
    |    ||  |  . |.  |    | |      :  |    |       |||
181 STAKDNGLGPHNERNSFYAAWHEAMG....DGAFAVFQVWS..HLFVGWP 224

214 AYLI.MNASGQ..DYGRW.......TSHFHTYSPIFEPRNFFDIIISDLG 253
    ||  :  ..|.    ||       ||  ||.|   :     |  :|
225 LYLAGLASTGKLAHEGWWLEERNAIADHFRPSSPMFPAKIRAKIALSSAT 274

254 VLAALGALIYASMQLSLLTVTKYYIVPYLFVNFWLVLITFLQHTDPKLPH 303
    ||  |  |:|    |.   | |   :|  || |||  |||| |-|||||| :||
275 ELAVLAGLLYVGTQVGHLPVLLWYWGPYTFVNAWLVLYTWLQHTDPSIPH 324

304 YREGAWNFQRGALCTVDRSFGKFLDHMFHGIVHTHVAHHLFSQMPFYHAE 353
    |  ||  |  .  :|||  |:||  :|  ||   [   |  ||| ||||  :||.|.|
325 YGEGEWTWVKGALSTIDRDYGIF.DFFHHTIGSTHVVHHLFHEMPWYNAG 373

354 EATYHLKKLLGE..YYVYDPSPIVVAVWRSFRECRFVEDQGDVVFFK    398
    ||  -|.  |      |  |||.|   |.||    |  |  :||     |  :||
374 IATQKVKEFLEPQGLYNYDPTPWYKAMWRIARTCHYVESNEGVQYFK    420
```

PRODUCTION OF POLYUNSATURATED FATTY ACIDS, NOVEL BIOSYNTHESIS GENES, AND NOVEL PLANT EXPRESSION CONSTRUCTS

RELATED APPLICATIONS

This application is a divisional application of U.S. application Ser. No. 10/250,553 filed Jul. 2, 2003, which is a national stage application (under 35 U.S.C. 371) of PCT/EP2002/00462 filed Jan. 18, 2002, which claims benefit of Germany application 10102337.2 filed Jan. 19, 2001. The entire content of each above-mentioned application is hereby incorporated by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_List_12810_00928. The size of the text file is 468 KB, and the text file was created on Sep. 23, 2009.

FIELD OF THE INVENTION

The present invention relates to a method for the production of unsaturated fatty acids with at least two double bonds and/or a method for the production of triglycerides with an increased content of polyunsaturated fatty acids with at least two double bonds. The invention furthermore relates to the advantageous use of the nucleic acid sequences SEQ ID NO: 1, SEQ ID NO: 3, SEQ ID NO: 5 or 11 in the method and for generating a transgenic organism, preferably a transgenic plant or a transgenic microorganism, with an increased content of fatty acids, oils or lipids with unsaturated $C_{18}$-, $C_{20}$-, or $C_{22}$-fatty acids.

The invention furthermore relates to novel desaturases with the [lacuna] in the sequences SEQ ID NO: 1, SEQ ID NO: 3, SEQ ID NO: 5 and SEQ ID NO: 11 or its homologs, derivatives and analogs, and to gene constructs encompassing these genes or their homologs, derivatives or analogs, and to their use alone or in combination with biosynthesis genes of polyunsaturated fatty acids as shown advantageously in SEQ ID NO: 7 and SEQ ID NO: 9.

In addition, the invention relates to isolated nucleic acid sequences; expression cassettes comprising the nucleic acid sequences, vectors and transgenic organisms comprising at least one nucleic acid sequence or one expression cassette. In addition, the invention relates to unsaturated fatty acids with at least two double bonds and to triglycerides with an increased content of unsaturated fatty acids with at least two double bonds, and to their use.

Moreover, the invention relates to multiexpression cassettes for seed-specific expression, and to vectors or organisms which encompass a desaturase gene alone or in combination with further desaturases with the sequence SEQ ID NO:7 and/or elongase genes with the sequence SEQ ID NO: 9 or its homologs, derivatives or analogs using said expression cassettes.

BACKGROUND OF THE INVENTION

A series of products and by-products of naturally occurring metabolic processes in microorganisms, animal cells and plant cells has utility for a wide array of industries, including the feed, food, cosmetics and pharmaceutical industries. These molecules, which are collectively termed "fine chemicals", also include, for example, lipids and fatty acids, one representative class of which are the polyunsaturated fatty acids. Fatty acids and triglycerides have a multiplicity of uses in the food industry, in animal nutrition, in cosmetics and in the pharmacological sector. Depending on whether they take the form of free saturated or unsaturated fatty acids or else triglycerides with an increased content of saturated or unsaturated fatty acids, they are suitable for a variety of uses; thus, for example, polyunsaturated fatty acids (PUFAs) are added to baby formula for increasing the nutritional value. Moreover, PUFAs have a positive effect on the cholesterol level in the blood of humans and are therefore useful for protection against heart disease. Thus, they are used in a variety of dietetic foods or in medicaments.

Microorganisms which are particularly useful for the production of PUFAs are microorganisms such as Thraustochytria or Schizochytria strains, algae such as *Phaeodactylum tricornutum* or *Crypthecodinium* species, ciliates such as *Stylonychia* or *Colpidium*, fungi such as *Mortierella*, *Entomophthora* or *Mucor*. Through strain selection, a number of mutant strains of the respective microorganisms have been developed which produce an array of desirable compounds including PUFAs. However, the selection of strains in which the production of a particular molecule is improved is a time-consuming and difficult process.

Alternatively, fine chemicals can conveniently be produced via producing, on a large scale, plants which have been developed in such a way that they produce the abovementioned PUFAs. Particularly well suited plants for this purpose are oil crop plants which comprise large amounts of lipid compounds, such as oilseed rape, canola, linseed, soybean, sunflower, borage and evening primrose. However, other useful plants comprising oils or lipids and fatty acids are also well suited as mentioned in the detailed description of this invention. By means of conventional breeding, an array of mutant plants has been developed which produce a spectrum of desirable lipids and fatty acids, cofactors and enzymes. However, the selection of novel plant cultivars in which the production of a particular molecule is improved is a time-consuming and difficult process or indeed impossible if the compound does not occur naturally in the respective plant, as is the case of polyunsaturated $C_{18}$-, $C_{20}$-fatty acids and $C_{22}$-fatty acids and those with longer carbon chains.

Owing to the positive properties of unsaturated fatty acids, there has been no lack of attempts in the past to make available genes which are involved in the synthesis of fatty acids or triglycerides for the production, in various organisms, of oils with a modified content of unsaturated fatty acids. Thus, WO 91/13972 and its US equivalent describe a Δ9-desaturase. A Δ15-desaturase is claimed in WO 93/11245 and a Δ12-desaturase is claimed in WO 94/11516. Δ6-desaturases are described in WO 93/06712, U.S. Pat. No. 5,614,393, WO 96/21022 and WO 99/27111. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. A Δ6-palmitoyl ACP desaturase is described and claimed in WO 96/13591. However, the biochemical characterization of the various desaturases is incomplete as yet since the enzymes, being membrane-bound proteins, can only be isolated and characterized with great difficulty (McKeon et al., Methods in Enzymol. 71, 1981: 12141-12147, Wang et al., Plant Physiol. Biochem., 26, 1988: 777-792).

In yeasts, both a shift in the fatty acid spectrum toward unsaturated fatty acids and an increase in productivity have been found (see Huang et al., Lipids 34, 1999: 649-659, Napier et al., Biochem. J., Vol. 330, 1998: 611-614). However, the expression of the various desaturases in transgenic plants did not show the desired success. While a shift in the fatty acid spectrum toward unsaturated fatty acids was demonstrated, it emerged that the synthesis performance of the transgenic plants dropped drastically, i.e. only smaller amounts of oils were isolated compared with the original plants.

Neither yeasts nor plants naturally produce polyunsaturated $C_{20}$- and/or $C_{22}$-fatty acids with at least two double bonds in the fatty acid molecule, such as arachidonic acid (ARA) and/or eicosapentaenoic acid (EPA) and/or docosahexaenoic acid (DHA).

This is why there still exists a great demand for novel genes which encode enzymes which are involved in the biosynthesis of unsaturated fatty acids and which make possible their production on an industrial scale. None of the prior-art biotechnological methods for the production of polyunsaturated fatty acids yields the abovementioned fatty acids in economically useful quantities.

It is an object of the present invention to provide further enzymes for the synthesis of polyunsaturated fatty acids and to use these enzymes, with or without other enzymes, in a method for the production of polyunsaturated fatty acids.

BRIEF DESCRIPTION OF THE DRAWINGS

FIG. 1 shows the polypeptide alignment of the coding region of Pp_des 6 (top row; SEQ ID NO: 8) with the EST sequence of PT001078032R (bottom row; SEQ ID NO: 2).

FIG. 2 shows the polypeptide alignment of coding regions of Ma_des12 (top sequence; Accession Number AF110509) with PT001070010R (SEQ ID NO: 6).

FIG. 2a shows the polypeptide alignment of coding regions of Ma_des12 (top sequence; Accession Number AF110509) with PT001072031R (SEQ ID NO: 12).

FIG. 3 shows the polypeptide alignment of coding regions of a PCR product of the primer pair F6a and R4a2 encoding a *Phaeodactylum* desaturase fragment (top row; SEQ ID NO: 19) with the *Streptomyces coelicolor* sequence T36617 (bottom row).

FIG. 4 shows the polypeptide alignment of coding regions of Pp_des6 (top row; SEQ ID NO: 8) in comparison with Pt_des6 (bottom row; SEQ ID NO: 4).

FIG. 5 shows the polypeptide alignment of coding regions of Pp_des6 (top row; SEQ ID NO: 8) in comparison with Pt_des5 (bottom row; SEQ ID NO: 2).

FIG. 6 shows the polypeptide alignment of coding regions of the *Mortierella alpina* D 12-desaturase, Ma_des12 (top row; Accession Number AF110509) with the homologous *Phaeodactylum tricornutum* sequence, Pt_des12 (bottom row; SEQ ID NO: 6).

FIG. 7 shows the polypeptide alignment of coding regions of the *Mortierella alpina* D 12-desaturase, Ma_des12, (top row; Accession Number AF110509) with the homologous sequence of *Phaeodactylum tricornutum* clone PT001072031R, Pt_des12.2 (bottom row; SEQ ID NO: 12).

DETAILED DESCRIPTION OF THE INVENTION

We have found that this object is achieved by the novel method for the production of fatty acid esters with an increased content of polyunsaturated fatty acids with at least two double bonds, which comprises introducing, into a fatty-acid-ester-producing organism, at least one nucleic acid sequence selected from the group consisting of a) a nucleic acid sequence with the sequence shown in SEQ ID NO: 1, SEQ ID NO: 3, SEQ ID NO: 5 or SEQ ID NO: 11, b) nucleic acid sequences which, owing to the degeneracy of the genetic code, are obtained by backtranslating the amino acid sequences shown in SEQ ID NO: 2, SEQ ID NO: 4, SEQ ID NO: 6 or SEQ ID NO: 12, c) derivatives of the nucleic acid sequence shown in SEQ ID NO: 1, SEQ ID NO: 3, SEQ ID NO: 5 or SEQ ID NO: 11, which encode polypeptides with the amino acid sequences shown in SEQ ID NO: 2, SEQ ID NO: 4, SEQ ID NO: 6 or SEQ ID NO: 12 and have at least 50% homology at the amino acid level, without essentially reducing the enzymatic action of the polypeptides, growing the organism, and isolating the fatty acid esters present in the organism.

The nucleic acid sequences used in the method according to the invention are isolated nucleic acid sequences which encode polypeptides with Δ5-, Δ6- or Δ12-desaturase activity.

It is advantageous to produce fatty acid esters with polyunsaturated $C_{18}$-, $C_{20}$- and/or $C_{22}$-fatty acid molecules with at least two double bonds in the fatty acid ester by the method according to the invention. These fatty acid molecules preferably comprise three, four or five double bonds and advantageously lead to the synthesis of arachidonic acid (ARA), eicosapentaenoic acid (EPA) or docosahexaenoic acid (DHA).

The fatty acid esters with polyunsaturated $C_{18}$-, $C_{20}$- and/or $C_{22}$-fatty acid molecules can be isolated from the organisms used for the production of the fatty acid esters in the form of an oil or lipid for example in the form of compounds such as sphingolipids, phosphoglycerides, lipids, glycolipids, phospholipids, monoacyl glycerides, diacyl glycerides, triacyl glycerides or other fatty acid esters comprising the polyunsaturated fatty acids with at least two double bonds.

Suitable organisms for the production by the method according to the invention are, in principle, all prokaryotic or eukaryotic organisms such as prokaryotic or eukaryotic microorganisms such as Gram-positive or Gram-negative bacteria, fungi, yeasts, algae, ciliates, animal or plant cells, animals or plants such as mosses, dicotyledonous or monocotyledonous plants. It is advantageous to use, in the method according to the invention, organisms which belong to the oil-producing organisms, that is to say which are used for the production of oils, such as microorganisms such as *Crypthecodinium, Thraustochytrium, Phaeodactylum* and *Mortierella, Entomophthora, Mucor,* and other algae or fungi, and animals or plants, in particular plants, preferably oil crop plants which contain large amounts of lipid compounds, such as soybean, peanut, oilseed rape, canola, sunflower, safflower, evening primrose, linseed, borage, trees (oil palm, coconut) or crops such as maize, wheat, rye, oats, triticale, rice, barley, cotton, cassava, pepper, *Tagetes*, solanaceous plants such as potato, tobacco, aubergine and tomato, *Vicia* species, pea, alfalfa or bush plants (coffee, cacao, tea), *Salix* species, and also perennial grasses and fodder crops. Plants according to the invention which are especially preferred are oil crop plants such as soybean, peanut, oilseed rape, canola, linseed, evening primrose, sunflower, safflower or trees (oil palm, coconut).

The method according to the invention comprises either breeding a suitable transgenic organism or transgenic microorganism or breeding transgenic plant cells, tissues, organs or intact plants comprising the nucleotide sequences according to the invention of SEQ ID NO: 1, 3, 5 or 11, if appropriate in connection with the sequences shown in SEQ ID NO: 7 and/or SEQ ID NO: 9 alone or in combination with sequences of expression constructs from SEQ ID NO: 13-17 or their homologs, derivatives or analogs or a gene construct which encompasses SEQ ID NO: 1, 3, 5 or 11, if appropriate in connection with SEQ ID NO: 7 and/or 9 or their homologs, derivatives or analogs, or a vector comprising this sequence or the gene construct which brings about the expression of nucleic acid molecules according to the invention, so that a fine chemical is produced. In a preferred embodiment, the process furthermore comprises the step of obtaining a cell comprising such nucleic acid sequences according to the invention, wherein a cell is transformed with a desaturase nucleic acid sequence, a gene construct or a vector which bring about the expression of a desaturase nucleic acid according to the invention, alone or in combination. In a further preferred embodiment, this method furthermore comprises the step of obtaining the fine chemical from the culture. In an especially preferred embodiment, the cell belongs to the order of the ciliates, to microorganisms such as fungi, or to the plant kingdom, in particular to oil crop plants; especially preferred are microorganisms or oil crop plants, for example peanut, oilseed rape, canola, linseed, soybean, safflower (thistle), sunflowers or borage.

Transgenic/recombinant is to be understood as meaning, for the purposes of the invention, that the nucleic acids according to the invention are not at their natural location in the genome of an organism; it is possible here for the nucleic acids to be expressed homologously or heterologously. However, transgenic/recombinant also means that the nucleic acids according to the invention are at their natural location in the genome of an organism, but that the sequence has been modified over the natural sequence and/or that the regulatory sequences of the natural sequences have been modified. Transgenic/recombinant preferably describes the expression of the nucleic acids according to the invention at an unnatural location in the genome, that is to say a homologous or, preferably, heterologous expression of the nucleic acids exists. Preferred transgenic organisms are the abovementioned transgenic plants, preferably oil crop plants.

The polyunsaturated fatty acids contained in the fatty acid esters produced by the method according to the invention can be liberated, for example, via treatment with alkali such as aqueous KOH or NaOH, advantageously in the presence of an alcohol such as methanol or ethanol, and can be isolated via, for example, phase separation and subsequent acidification, with, for example, $H_2SO_4$.

A further subject matter of the invention are oils, lipids and/or fatty acids containing at least two double bonds in the fatty acid molecules, preferably three, four, five or six double bonds, which have been produced by the above-described method according to the invention. A further subject matter of the invention are also compositions comprising the abovementioned oils, lipids and/or fatty acids, and the use of the oils, lipids and/or fatty acids or of the compositions in feed, foodstuffs, cosmetics or pharmaceuticals.

A further aspect of the invention relates to methods of modulating the production of a molecule by a microorganism. These methods encompass the contacting of the cell with a substance which modulates the desaturase activity according to the invention alone or in combination or the desaturase nucleic acid expression, so that a cell-associated activity is modified in relation to the same activity in the absence of the substance. In a preferred embodiment, one or two metabolic pathway(s) of the cell for lipids and fatty acids, cofactors and enzymes is/are modulated, or the transport of compounds through these membranes is modulated, so that the yield or the production rate of a desired fine chemical by this microorganism is improved. The substance which modulates the desaturase activity can be a substance which stimulates the desaturase activity or desaturase nucleic acid expression or which can be used as intermediate in fatty acid biosynthesis. Examples of substances which stimulate the desaturase activity or desaturase nucleic acid expression are, inter alia, small molecules, active desaturases and desaturase-encoding nucleic acids which have been introduced into the cell. Examples of substances which inhibit the desaturase activity or desaturase expression are, inter alia, small molecules and antisense desaturase nucleic acid molecules.

A further aspect of the invention relates to methods of modulating the yields of a desired compound from a cell, comprising introducing, into a cell, a wild-type or mutant desaturase gene which is either maintained on a separate plasmid or integrated into the genome of the host cell. Upon integration into the genome, integration can be random or can be effected by recombination in such a way that the native gene is replaced by the copy introduced, thereby modulating the production of the desired compound by the cell, or by using a gene in trans, so that the gene is linked operably to a functional expression unit comprising at least one sequence which ensures the expression of a gene and at least one sequence which ensures the polyadenylation of a functionally transcribed gene.

In a preferred embodiment, the yields are modified. In a further preferred embodiment, the desired chemical is augmented, it being possible to reduce undesired interfering compounds. In an especially preferred embodiment, the desired fine chemical is a lipid or a fatty acid, a cofactor or an enzyme. In an especially preferred embodiment, this chemical is a polyunsaturated fatty acid. More preferably, it is selected from among arachidonic acid (ARA), eicosapentaenoic acid (EPA) or docosahexaenoic acid (DHA).

The present invention provides novel nucleic acid molecules which are suitable for identifying and isolating desaturases of PUFA biosynthesis and which can be used for the modification of oils, fatty acids, lipids, lipid-derived compounds and, most preferably, for the production of polyunsaturated fatty acids.

The invention furthermore provides multiexpression cassettes and constructs for the multiparallel seed-specific expression of gene combinations in plants.

Microorganisms such as *Crypthecodinium, Thraustochytrium, Phaeodactylum* and *Mortierella, Entomophthora* and *Mucor*, and other algae and fungi and plants, in particular oil crop plants, are preferred organisms for the method according to the invention.

Cloning vectors and techniques for the genetic manipulation of the abovementioned microorganisms and ciliates, algae or related organisms such as *Phaeodactylum tricornutum*, are described in WO 98/01572 or in Falciatore et al., 1999, Marine Biotechnology 1(3):239-251, and Dunahay et al., 1995, Genetic transformation of diatoms, J. Phycol. 31:1004-1012 and the references cited therein. Thereby, the abovementioned nucleic acid molecules can be used in the method according to the invention by modifying the organisms by means of genetic engineering so that they become better or more efficient producers of one or more fine chemicals. This improved production or production efficiency of a fine chemical can be brought about by a direct effect of the manipulation of a gene according to the invention or by an indirect effect of this manipulation. Fine chemicals for the purposes of the invention are understood as being fatty acid esters containing polyunsaturated fatty acids with at least two double bonds, such as sphingolipids, phosphoglycerides, lipids, glycolipids, phospholipids, monoacyl glycerides, diacyl glycerides, triacyl glycerides or other fatty acid esters containing the polyunsaturated fatty acids with at least two double bonds. They are furthermore understood as being compounds such as vitamins, for example vitamin E, vitamin C, vitamin B2, vitamin B6, pantolactone, carotenoids such as astaxanthin, β-carotene, zeaxanthin and others.

Mosses and algae are the only plant systems known which produce substantial amounts of polyunsaturated fatty acids such as arachidonic acid (ARA) and/or eicosapentaenoic acid (EPA) and/or docosahexaenoic acid (DHA). Mosses contain PUFAs in membrane lipids, while algae, organisms related to algae and some fungi also accumulate substantial amounts of PUFAs in the triacylglycerol fraction. Nucleic acid molecules which are isolated from such strains which also accumulate PUFAs in the triacylglycerol fraction are therefore particularly advantageously suitable for modifying the lipid and PUFA production system in a host, in particular in microorganisms, such as in the microorganisms mentioned above, and plants such as oil crop plants, for example oilseed rape, canola, linseed, soybean, sunflowers, borage. They can therefore be used advantageously in the method according to the invention.

The nucleic acids according to the invention are therefore particularly advantageously suitable for isolating nucleic acids from triacylglycerol-accumulating microorganisms and for identifying such DNA sequences and the enzymes encoded by them in other species which are suitable for modifying the biosynthesis of PUFA-precursor molecules in the organisms in question.

Microorganisms such as *Crypthecodinium cohnii, Thraustochytrium* and *Phaeodactylum* species are microorganisms which are capable of accumulating PUFAs such as ARA, EPA or DHA in triacylglycerols. Thraustochytria are phylogenetically also closely related to strains of Schizochytria. The ability to identify desaturases with reference to the nucleic acids according to the invention, for example predicting the substrate specificity of enzymes, can therefore be of enormous significance. Furthermore, these nucleic acid molecules can act as reference sequences for mapping related genomes or for deriving PCR primers.

The nucleic acid molecules according to the invention encode proteins termed desaturases. These desaturases can exert, for example, a function involved in the metabolism (for example in the biosynthesis or the degradation) of compounds required for the synthesis of lipids or fatty acids, such as PUFAs, or can participate in the transmembrane transport of one or more lipid/fatty acid compounds, either into the cell or out of the cell.

The nucleic acid sequences according to the invention encode desaturases which are suitable for the production of long-chain polyunsaturated fatty acids, preferably having more than sixteen, eighteen or twenty carbon atoms in the carbon skeleton of the fatty acid and/or at least two double bonds in the carbon chain, a nucleic acid according to the invention encoding an enzyme capable of introducing double bonds at the Δ5 position, in another case at the Δ6 position and in a further case at the Δ12 position. Large amounts of PUFAs may be obtained in the triacylglycerol fraction with the aid of these nucleic acids. Furthermore, further desaturases have been isolated which, alone or together with a Δ4 desaturase, can be utilized for a method for the production of polyunsaturated fatty acids. In the application, the singular, i.e. a desaturase gene or protein, is also understood as meaning the plural, i.e. the desaturase genes or proteins.

The production of a trienoic acid with $C_{18}$-carbon chain with the aid of desaturases has already been demonstrated. However, in these methods known from the literature, the production of γ-linolenic acid was claimed. As yet, however, nobody has been able to demonstrate the production of very long-chain polyunsaturated fatty acids (with $C_{20}$ carbon chain and longer and of trienoic acids and higher unsaturated types) by modified organisms alone.

To produce the long-chain PUFAs according to the invention, the polyunsaturated $C_{18}$-fatty acids must first be elongated by at least two carbon atoms by the enzymatic activity of an elongase. Following an elongation cycle, this enzyme activity leads to $C_{20}$-fatty acids, and after two, three and four elongation cycles, to $C_{22}$-, $C_{24}$- or $C_{26}$-fatty acids. The nucleic acid sequences disclosed in the present invention which encode various desaturases can, in concert with elongases, lead to very long-chain polyunsaturated fatty acids. The activity of the desaturases according to the invention preferably leads to $C_{18}$-, $C_{20}$- and/or $C_{22}$-fatty acids with at least two double bonds in the fatty acid molecule, preferably with three, four, five or six double bonds, especially preferably to $C_{18}$- and/or $C_{20}$-fatty acids with at least two double bonds in the fatty acid molecule, preferably with three, four or five double bonds in the molecule. The elongation of the fatty acid can be effected by combining the desaturases according to the invention with an elongase activity, it being possible to use the elongase encoded by SEQ ID NO: 9 in an advantageous fashion. After the elongation by the enzyme(s) according to the invention has taken place, further desaturation steps such as, for example, a desaturation at the Δ5 position, may take place. The combination with other elongases such as those which lead to an elongation from $C_{18}$- to $C_{20}$-chains or from $C_{20}$- to $C_{22-24}$-chains as disclosed in WO 00/12720 may also be used and/or a desaturase with activity for the Δ4 position can advantageously be employed in order to obtain the highly desaturated fatty acids. The products of the desaturase activities and the possible further desaturation therefore lead to preferred PUFAs with a higher degree of desaturation, such as dihomo-γ-linolenic acid, docosadienoic acid, arachidonic acid, ω6-eicosatrienedihomo-γ-linolenic acid, eicosapentaenoic acid, ω3-eicosatrienoic acid, ω3-eicosatetraenoic acid, docosapentaenoic acid or docosahexaenoic acid. Substrates of the enzyme activity according to the invention are, for example, taxoleic acid; 6,9-octadecadienoic acid, linoleic acid, pinolenic acid, α- or γ-linolenic acid or stearidonic acid and arachidonic acid, eicosatetraenoic acid, docosapentaenoic acid, eicosapentaenoic acid. Preferred substrates are linoleic acid, γ-linolenic acid and/or α-linolenic acid and arachidonic acid, eicosatetraenoic acid, docosapentaenoic acid, eicosapentaenoic acid. Especially preferred products of the process according to the invention are arachidonic acid, docosapentaenoic acid, eicosapentaenoic acid. The $C_{18}$-fatty acids with at least two double bonds in the fatty acid can be elongated by the enzymatic activity according to the invention in the form of the free fatty acid or in the form of the esters, such as phospholipids, glycolipids, sphingolipids, phosphoglycerides, monoacyl glycerides, diacyl glycerides or triacyl glycerides.

Of particular importance for human nutrition is the conjugated linoleic acid "CLA". CLA is understood as meaning in particular fatty acids such as $C18:2^{9\ cis,\ 11 trans}$ or the isomer $C18:2^{10 trans,\ 12\ cis}$, which, once taken up, can be desaturated or elongated in the body owing to human enzyme systems and can contribute to health-promoting effects. The desaturases according to the invention (Δ12-desaturase) also allow those conjugated fatty acids with at least two double bonds in the molecule to be desaturated and thus allow such health promoting fatty acids to be made available for human nutrition. Further examples of conjugated fatty acids are α-parinaric acid, punicic acid, eleostearic acid and calendulic acid.

Using cloning vectors in plants and in the transformation of plants like those which are published and cited in: Plant Molecular Biology and Biotechnology (CRC Press, Boca Raton, Fla.), Chapter 6/7, pp. 71-119 (1993); F. F. White, Vectors for Gene Transfer in Higher Plants; in: Transgenic Plants, Vol. 1, Engineering and Utilization, Eds.: Kung and R. Wu, Academic Press, 1993, 15-38; B. Jenes et al., Techniques for Gene Transfer, in: Transgenic Plants, Vol. 1, Engineering and Utilization, Eds.: Kung and R. Wu, Academic Press (1993), 128-143; Potrykus, Annu. Rev. Plant Physiol. Plant Molec. Biol. 42 (1991), 205-225)), the nucleic acids according to the invention can be used for the recombinant modification of a broad spectrum of plants so that this plant becomes a better or more efficient producer of one or more lipid-derived products, such as PUFAs. This improved production or production efficiency of a lipid-derived product, such as PUFAs, can be brought about by a direct action of the manipulation or an indirection action of this manipulation.

A series of mechanisms exist by means of which the modification of a desaturase protein according to the invention can have a direct effect on the yield, production and/or production efficiency of a fine chemical from an oil crop plant or a microorganism, owing to a modified protein. The number or activity of the desaturase protein or desaturase gene and of gene combinations of desaturases and elongases can be increased, so that larger amounts of these compounds are produced de novo since the organisms lacked this activity and ability to biosynthesize them prior to introduction of the gene in question. This also applies analogously to the combination with further desaturases or elongases or further enzymes of the lipid metabolism. The use of various divergent sequences, i.e. sequences which differ at the DNA sequence level, may also be advantageous, or else the use of promoters for gene expression which makes possible a different temporal gene expression, for example as a function of the degree of maturity of the seed or oil-storing tissue.

The introduction of a desaturase gene according to the invention, or several saturase genes, into an organism, alone or in combination with other genes in a cell can not only increase the biosynthesis flux toward the end product, but also increase, or generate de novo, the corresponding triacylglycerol composition. Likewise, the number or activity of other genes which participate in the import of nutrients required for the biosynthesis of one or more fine chemicals (for example fatty acids, polar and neutral lipids) can be increased, so that the concentration of the precursors, cofactors or intermediates within the cells or within the storage compartment is increased, thus further increasing the ability of the cells to produce PUFAs as described hereinbelow. Fatty acids and lipids themselves are desirable as fine chemicals; by optimizing the activity or increasing the number of one or more desaturases which participate in the biosynthesis of these compounds, or by destroying the activity of one or more desaturases which participate in the breakdown of these compounds, it can be possible to increase the yield, production and/or production efficiency of fatty acid and lipid molecules from plants or microorganisms.

The mutagenesis of the desaturase gene(s) according to the invention may furthermore lead to a desaturase protein with modified activities which have a direct or indirect effect on the production of one or more desired fine chemicals. For example, the number or activity of the desaturase gene(s) according to the invention may be increased so that the normal metabolic wastes or by-products of the cell (possibly increased in quantity due to the overproduction of the desired fine chemical) are exported efficiently before they can damage other molecules or processes within the cell (which would decrease the viability of the cell) or to interfere with the fine chemical biosynthetic pathways (which would decrease the yield, production or production efficiency of the desired fine chemical). Furthermore, the relatively large intracellular quantities of the desired fine chemical may themselves be toxic to the cell or interfere with enzyme feedback mechanisms, such as allosteric regulation; for example, by increasing the activity or number of other downstream enzymes or detoxification enzymes of the PUFA pathway, it might increase the allocation of the PUFA to the triacylglycerol fraction; the viability of seed cells might be increased, in turn leading to better development of cultured cells or to seeds which produce the desired fine chemical. The desaturase according to the invention may also be manipulated in such a way that the relative amounts of the various lipid and fatty acid molecules are produced. This may have a profound effect on the lipid composition of the membrane of the cell and generates novel oils in addition to the occurrence of newly-synthesized PUFAs. Since each type of lipid has different physical properties, a change in the lipid composition of a membrane may significantly alter membrane fluidity. Changes in membrane fluidity can have an effect on the transport of molecules across the membrane and on the integrity of the cell, both of which have a profound effect on the production of fine chemicals. In plants, these changes may additionally impact on other traits, such as tolerance to abiotic and biotic stress situations.

Biotic and abiotic stress tolerance is a general trait which it is desired to transmit to a broad spectrum of plants such as maize, wheat, rye, oats, triticale, rice, barley, soybeans, peanut, cotton, linseed, flax, oilseed rape and canola, cassava, pepper, sunflower and *Tagetes*, solanaceous plants such as potato, tobacco, egg-plant and tomato, *Vicia* species, pea, alfalfa, bush plants (coffee, cacao, tea), *Salix* species, trees (oil palm, coconut) and perennial grasses and fodder crops. Being a further embodiment of the invention, these crops are also preferred target plants for genetic engineering. Especially preferred plants according to the invention are oil crop plants such as soybean, peanut, oilseed rape, canola, sunflower, linseed, safflower, trees (oil palm, coconut) or crops such as maize, wheat, rye, oats, triticale, rice, barley, alfalfa, or bush plants (coffee, cacao, tea).

Accordingly, an aspect of the invention relates to isolated nucleic acid molecules (for example cDNAs) encompassing nucleotide sequences which encode one desaturase or several desaturases or biologically active parts thereof, or nucleic acid fragments which are suitable as primers or hybridization probes for detecting or amplifying desaturase-encoding nucleic acids (for example DNA or mRNA). In especially preferred embodiments, the nucleic acid molecule encompasses one of the nucleotide sequences shown in sequence ID NO:1 or 3 and 5 or the coding region or a complement of one of these nucleotide sequences. In other especially preferred embodiments, the isolated nucleic acid molecule according to the invention encompasses a nucleotide sequence which hybridizes with a nucleotide sequence as shown in the sequence SEQ ID NO: 1, 3, 5 or 11 or a portion thereof or which has at least 50% homology, preferably at least approximately 60% homology, more preferably at least approximately 70%, 80% or 90% homology and very especially preferably at least approximately 95%, 96%, 97%, 98%, 99% or more homology therewith. In other preferred embodiments, the isolated nucleic acid molecule encodes one of the amino acid sequences shown in sequence SEQ ID NO: 2, 4, 6 or 12. The preferred desaturase gene according to the invention preferably also has at least one of the desaturase activities described herein.

In a further embodiment, the isolated nucleic acid molecule encodes a protein or a portion thereof, the protein or the portion thereof comprising an amino acid sequence which has sufficient homology with an amino acid sequence of the sequence SEQ ID NO: 2, 4, 6 or 12 that the protein or the portion thereof retains a desaturase activity. Preferably, the protein or the portion thereof encoded by the nucleic acid molecule retains the ability of participating in the metabolism of compounds required for the synthesis of cell membranes of plants or in the transport of molecules across these membranes. In one embodiment, the protein encoded by the nucleic acid molecule has at least approximately 50% homology, preferably at least approximately 60% homology, more preferably at least approximately 70%, 80% or 90% and very especially preferably at least approximately 95%, 96%, 97%, 98%, 99% or more homology with an amino acid sequence of the sequence SEQ ID NO: 2, 4, 6 or 12. In a further preferred embodiment, the protein is a full-length protein which is essentially in parts homologous to a complete amino acid sequence of SEQ ID NO: 2, 4, 6 or 12 (which is derived from the open reading frame shown in SEQ ID NO: 1, 3, 5 or 11).

In other embodiments, the isolated desaturase encompasses an amino acid sequence which has at least approximately 50% homology with one of the amino acid sequences of SEQ ID NO: 2, 4, 6 or 12 and which can participate in the metabolism of compounds required for the synthesis of fatty acids in a microorganism or plant cell or in the transport of molecules across these membranes, desaturated $C_{18}$- or $C_{20-22}$-carbon chains being understood with double bonds in at least two positions.

In another preferred embodiment, the isolated nucleic acid molecule originates from *Phaeodactylum tricornutum* UTEX646 and encodes a protein (for example a desaturase fusion protein) containing a biologically active domain which has at least approximately 50% or more homology with an amino acid sequence of the sequence SEQ ID NO: 2, 4, 6 or 12 and retains the ability of participating in the metabolism of compounds required in the synthesis of cell membranes of plants or in the transport of molecules across these membranes or has at least one of the desaturation activities resulting in PUFAs such as GLA, ALA, dihomo-γ-linolenic acid, ARA, EPA or DHA or their precursor molecules, and also encompasses heterologous nucleic acid sequences which encode a heterologous polypeptide or regulatory proteins.

As an alternative, the isolated desaturase can comprise an amino acid sequence which is encoded by a nucleotide sequence which hybridizes with a nucleotide sequence of SEQ ID NO: 1, 3, 5 or 11, for example under stringent conditions, or which has at least approximately 50% homology, preferably at least approximately 60% homology, more preferably at least approximately 70%, 80% or 90% homology and even more preferably at least approximately 95%, 96%, 97%, 98%, 99% or more homology therewith. It is also preferred for the preferred desaturase forms likewise to have one of the desaturase activities described herein.

In another embodiment, the isolated nucleic acid molecule is at least 15, 25, 50, 100, 250 or more nucleotides in length and hybridizes under stringent conditions with a nucleic acid molecule comprising a nucleotide sequence of SEQ ID NO: 1, 3, 5 or 17. Preferably, the isolated nucleic acid molecule corresponds to a naturally occurring nucleic acid molecule. More preferably, the isolated nucleic acid molecule encodes naturally occurring *Phaeodactylum* desaturase or a biologically active portion thereof.

A further embodiment of the invention are expression cassettes which make possible the expression of the nucleic acids according to the invention with the sequences SEQ ID NO: 1, 3, 5 or 11 in the various organisms such as microorganisms, for example bacteria, fungi, yeasts, ciliates, algae or animal or plant cells, or in animals or plants.

The expression cassette (=nucleic acid construct or fragment) according to the invention is to be understood as meaning the sequences mentioned in SEQ ID NO: 1, SEQ ID NO: 3, SEQ ID NO: 5 or SEQ ID NO: 11 which are the result of the genetic code and/or the functional or nonfunctional derivatives thereof which had been linked functionally to one or more regulatory signals for advantageously increasing gene expression and which govern the expression of the coding sequence in the host cell. These regulatory sequences are intended to make possible the targeted expression of the genes and of protein expression. Depending on the host organism, this may mean, for example, that the gene is first induced and only then expressed and/or overexpressed, or that it is expressed and/or overexpressed immediately. For example, these regulatory sequences are sequences to which inductors or repressors bind, thus regulating the expression of the nucleic acid. In addition to these novel regulatory sequences, or instead of these sequences, the natural regulation of these sequences before the actual structural genes may still be present and, if appropriate, may have been genetically modified so that the natural regulation has been eliminated and gene expression increased. However, the gene construct may also have a simpler construction, that is to say no additional regulatory sequences were inserted before the nucleic acid sequence or its derivatives, and the natural promoter together with its regulation has not been removed. Instead, the natural regulatory sequence was mutated in such a way that regulation no longer takes place and/or gene expression is increased. These modified promoters can be inserted before the natural gene in the form of part-sequences (=promoter with parts of the nucleic acid sequences according to the invention) or else alone, in order to increase the activity. Moreover, the gene construct can additionally advantageously also comprise one or more of what are known as enhancer sequences linked functionally to the promoter, and these make possible an increased expression of the nucleic acid sequence. Additional advantageous sequences, such as further regulatory elements or terminators, may also be inserted at the 3' end of the DNA sequences. The Δ5 desaturase/Δ6 desaturase and/or Δ12 desaturase genes may be present in the expression cassette (=gene construct) in one or more copies.

As described above, the regulatory sequences or factors can preferably have a positive effect on the gene expression of the introduced gene, thus increasing it. Thus, an enhancement of the regulatory elements can advantageously take place at transcription level, by using strong transcription signals such as promoters and/or enhancers. In addition, however, enhanced translation is also possible, for example by improving the stability of the mRNA.

A further aspect of the invention relates to vectors, for example recombinant expression vectors, comprising at least one nucleic acid molecule according to the invention, and to host cells into which these vectors have been introduced, in particular microorganisms, plant cells, plant tissues, plant organs or intact plants. In one embodiment, such a host cell can store fine chemical compounds, in particular PUFAs; to isolate the desired compound, the cells are harvested. The compound (oils, lipids, triacyl glycerides, fatty acids) or the desaturase can then be isolated from the medium or from the host cell which, in the case of plants, are cells comprising or storing the fine chemicals, most preferably cells of storage tissues such as seed coats, tubers, epidermis cells and seed cells, endosperm or embryo tissue.

Yet another aspect of the invention relates to a genetically modified transgenic plant, preferably an oil crop plant as mentioned above, especially preferably an oilseed rape or linseed plant into which a desaturase gene has been introduced. In one embodiment, the genome of oilseed rape or linseed has been modified by introducing, as transgene, a nucleic acid molecule according to the invention which encodes a wild-type or mutated desaturase sequence. In another embodiment, an endogenous desaturase gene in the genome of the donor organism *Phaeodactylum* has been destroyed functionally by mutagenesis and detection by means of DNA sequences or has been repressed by means of antisense technology. In a preferred embodiment, oilseed rape or linseed is also used for the production of a desired compound such as lipids and fatty acids, with PUFas being especially preferred.

In yet another preferred embodiment, the moss *Physcomitrella patens* can be used for demonstrating the function of a desaturase gene using homologous recombination on the basis of the nucleic acids described in the present invention.

Yet another aspect of the invention relates to an isolated desaturase gene or a part, for example a biologically active part, thereof. In a preferred embodiment, the isolated desaturase or a part thereof can participate in the metabolism of compounds required for the synthesis of cell membranes in a microorganism or a plant cell or in the transport of molecules via its membranes. In a further preferred embodiment, the isolated desaturase or the part thereof has sufficient homology with an amino acid sequence of SEQ ID NO: 2, 4, 6 or 12 to retain the ability to participate in the metabolism of compounds required for the synthesis of cell membranes in microorganisms or plant cells or in the transport of molecules via these membranes.

The invention also provides an isolated preparation of a desaturase in the form of a crude extract or as a pure protein.

The desaturase polypeptide or a biological active part thereof can advantageously be linked functionally to a further polypeptide which has an enzymatic activity other than the desaturases, for example an elongase, acyltransferase or other activity, to form a fusion protein. This fusion protein advantageously has an activity which differs from that of the desaturase alone. In other preferred embodiments, this fusion protein participates in the metabolism of compounds which are required for the synthesis of lipids and fatty acids, cofactors and enzymes in microorganisms or plants, or in the transport of molecules via these membranes. Especially preferably, the introduction of this fusion protein into a host cell modulates the production of a desired compound within a cell and by the cell. In a preferred embodiment, these fusion proteins also contain Δ4-, Δ5- or Δ6-, Δ8-, Δ15-, Δ17- or Δ19-desaturase activities, alone or in combination. Preferred embodiments are, in particular, those gene combinations which are selected from among SEQ ID NO: 7 or 9, or parts thereof, derivatives or their homologs. Particularly preferred are those combinations which contain the complete protein activity as in SEQ ID NO: 1, 3, 5 or 11 and, inserted into multiexpression cassettes defined by SEQ ID NO: 13, 14, 15, 16 and 17, are suitable for the transformation of plants and expression in plants.

DETAILED DESCRIPTION OF THE INVENTION

The invention relates to (an) isolated nucleic acid sequence(s) encoding a polypeptide with desaturase activity selected from the group consisting of
a) a nucleic acid sequence with the sequence shown in SEQ ID NO: 1, SEQ ID NO: 3, SEQ ID NO: 5 or SEQ ID NO: 11,
b) nucleic acid sequences which, owing to the degeneracy of the genetic code, are obtained by backtranslating the amino acid sequences shown in SEQ ID NO: 2, SEQ ID NO: 4, SEQ ID NO: 6 or SEQ ID NO: 12,
c) derivatives of the nucleic acid sequence shown in SEQ ID NO: 1, SEQ ID NO: 3, SEQ ID NO: 5 or SEQ ID NO: 11, which encode polypeptides with the amino acid sequences shown in SEQ ID NO: 2, SEQ ID NO: 4, SEQ ID NO: 6 or SEQ ID NO: 12 and have at least 50% homology at the amino acid level, without essentially reducing the enzymatic action of the polypeptides.

The invention furthermore relates to (an) amino acid sequence(s) which is/are encoded by the abovementioned nucleic acid sequence(s) (for the purposes of the invention, the singular is intended to comprise the plural and vice versa). Specifically, the invention relates to amino acid sequences encoded by the sequence shown in SEQ ID NO: 1, SEQ ID NO: 3, SEQ ID NO: 5 or SEQ ID NO: 11.

The present invention provides nucleic acids and protein molecules with desaturase activity which participate in the metabolism of lipids and fatty acids, PUFA cofactors and enzymes in the moss *Physcomitrella patens* or in the transport of lipophilic compounds via membranes. The compounds according to the invention can be used for modulating the production of fine chemicals from organisms, for example microorganisms, such as ciliates, fungi, yeasts, bacteria, algae and/or plants such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and *Tagetes*, Solanaceae plants such as potato, tobacco, eggplant and tomato, *Vicia* species, pea, cassava, alfalfa, bush plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) or they can have an indirect effect which nevertheless leads to an increased yield, production and/or production efficiency of the desired compound or to a decrease in undesired compounds (for example when the modulation of the metabolism of lipids and fatty acids, cofactors and enzymes leads to changes in yield, production and/or production efficiency or the composition of the desired compound within the cells, which, in turn, may have an effect on the production of one or more fine chemicals). Aspects of the invention are illustrated in greater detail hereinbelow.

I. Fine Chemicals and PUFAs

The term "fine chemical" is known in the art and encompasses molecules which have been produced by an organism and which are used in a variety of industries such as, by way of example but not by way of limitation, the pharmaceuticals industry, agro industry, food industry and cosmetics industry. These compounds encompass lipids, fatty acids, cofactors and enzymes and the like (as described, for example, in Kuninaka, A. (1996) Nucleotides and related compounds, pp. 561-612, in Biotechnology Vol. 6, Rehm et al., Ed., VCH Weinheim and references cited therein), lipids, saturated and unsaturated fatty acids (for example arachidonic acid), vitamins and cofactors (as described in Ullmann's Encyclopedia of Industrial Chemistry, Vol. A27, Vitamins, pp. 443-613 (1996) VCH Weinheim and references cited therein; and Ong, A. S., Niki, E., & Packer, L. (1995) Nutrition, Lipids, Health and Disease Proceedings of the UNESCO/Confederation of Scientific and Technological Associations in Malaysia and the Society for Free Radical Research—Asia, held Sep. 1-3, 1994, in Penang, Malaysia, AOCS Press (1995)), enzymes and all other chemicals described by Gutcho (1983) in Chemicals by Fermentation, Noyes Data Corporation, ISBN: 0818805086, and references cited therein. The metabolism and the uses of certain fine chemicals are illustrated in greater detail hereinbelow.

The combination of various precursor molecules and biosynthetic enzymes leads to the production of various fatty acid molecules, which has a decisive effect on membrane composition. It can be assumed that PUFAs are not only just incorporated into triacylglycerol, but also into membrane lipids.

Membrane synthesis is a well characterized process in which a number of components, including lipids as part of the bilayer membrane, are involved. The production of novel fatty acids such as PUFAs can therefore generate novel properties of membrane functions within a cell or an organism.

Cell membranes serve a multiplicity of functions in a cell. First and foremost, a membrane delimits the contents of a cell from the environment, thus imparting integrity to the cell. Membranes can also act as barriers against the influx of dangerous or undesired compounds or else against the efflux of desired compounds.

For more detailed descriptions and involvements of membranes and the mechanisms involved, see Bamberg, E., et al. (1993) Charge transport of ion pumps on lipid bilayer membranes, Q. Rev. Biophys. 26:1-25; Gennis, R. B. (1989) Pores, Channels and Transporters, in: Biomembranes, Molecular Structure and Function, Springer: Heidelberg, pp. 270-322; and Nikaido, H., and Saier, H. (1992) Transport proteins in bacteria: common themes in their design, Science 258:936-942, and the citations contained in each of these references.

Lipid synthesis can be divided into two parts: the synthesis of fatty acids and their binding to sn-glycerol-3-phosphate, and the addition or modification of a polar head group. Customary lipids used in membranes encompass phospholipids, glycolipids, sphingolipids and phosphoglycerides. Fatty acid synthesis starts with the conversion of acetyl-CoA either into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydration reactions to give a saturated fatty acid molecule with the desired chain length. The production of the unsaturated fatty acids from these molecules is catalyzed by specific desaturases, either aerobically by means of molecular oxygen or anaerobically (as regards fatty acid synthesis in microorganisms, see F. C. Neidhardt et al. (1996) *E. coli* and *Salmonella*. ASM Press: Washington, D.C., pp. 612-636 and references contained therein; Lengeler et al. (Ed.) (1999) Biology of Procaryotes. Thieme: Stuttgart, New York, and the references contained therein, and Magnuson, K., et al. (1993) Microbiological Reviews 57:522-542 and the references contained therein).

Examples of precursors for PUFA biosynthesis are oleic acid, linoleic acid and linolenic acid. These $C_{18}$ carbon fatty acids must be elongated to $C_{20}$ and $C_{22}$ to give fatty acids of the eicosa and docosa chain type. Various desaturases such as enzymes which have Δ12-desaturase, Δ15-desaturase, Δ6-desaturase, Δ5- and Δ4-desaturase activity, can lead to arachidonic acid, eicosapentaenoic acid and docosahexaenoic acid and various other long-chain PUFAs which can be extracted and used for various purposes in food and feed, cosmetic or pharmaceutical applications.

To produce long-chain PUFAs, the polyunsaturated $C_{18}$- or $C_{20}$-fatty acids must be polydesaturated as mentioned above. The nucleic acid sequences according to the invention encode first functionally active desaturases from *Phaeodactylum tricornutum*, a microorganism comprising PUFAs in the triacylglycerol fraction. Double bonds can be introduced into the Δ5, Δ6 or Δ12 position with the desaturases according to the invention. The activities of the desaturases according to the invention preferably lead to $C_{18}$-+$C_{20}$-fatty acids with at least two, three, four or five double bonds in the fatty acid molecule, preferably to $C_{20}$-fatty acids with, advantageously, three, four or five double bonds in the fatty acid molecule. Desaturation can be effected before or after elongation of the fatty acid in question. The products of the desaturase activities and of the possible further desaturation and elongation therefore lead to preferred PUFAs with a higher degree of desaturation, including a further elongation of $C_{20}$- to $C_{22}$-fatty acids, to fatty acids such as linoleic acid, docosadienoic acid, dihomo-γ-linolenic acid, arachidonic acid, ω6-eicosatrienedihomo-γ-linolenic acid, eicosapentaenoic acid, ω3-eicosatrienoic acid, ω3-eicosatetraenoic acid, docosapentaenoic acid or docosahexaenoic acid. Preferred substrates of this enzyme activity according to the invention are taxoleic acid, 6,9-octadecadienoic acid, oleic acid, linoleic acid, γ-linolenic acid, pinolenic acid, α-linolenic acid, arachidonic acid, eicosapentaenoic acid or stearidonic acid. Preferred substrates are linoleic acid, γ-linolenic acid and/or α-linolenic acid, dihomo-γ-linolenic acid or arachidonic acid, eicosatetraenoic acid or eicosapentaenoic acid. The $C_{18}$- or $C_{20}$-fatty acids with at least two double bonds in the fatty acid can be elongated by the enzyme activity according to the invention in the form of the free acid or in the form of the esters, such as phospholipids, glycolipids, sphingolipids, phosphoglycerides, monoacyl glycerides, diacyl glycerides, triacyl glycerides or other esters.

Furthermore, fatty acids must subsequently be transported to various locations of modification and incorporated into the triacylglycerol storage lipid. Another important step in lipid synthesis is the transfer of fatty acids to the polar head groups, for example by glycerol fatty acid acyl transferase (see Frentzen, 1998, Lipid, 100(4-5):161-166).

For publications on plant fatty acid biosynthesis, desaturation, lipid metabolism and the membrane transport of fatty compounds, beta-oxidation, fatty acid modification and cofactors, triacylglycerol storage and assembly including the references cited therein, see the following articles: Kinney, 1997, Genetic Engeneering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

Vitamins, cofactors and nutraceuticals, such as PUFAs, encompass a group of molecules which higher animals can no longer synthesize and therefore have to take up, or which higher animals can no longer synthesize themselves to a sufficient degree and must therefore take up additionally, even though they are readily synthesized by other organisms such as bacteria. The biosynthesis of these molecules in organisms which are capable of producing them, such as in bacteria, has been largely characterized (Ullmann's Encyclopedia of Industrial Chemistry, "Vitamins", Vol. A27, pp. 443-613, VCH Weinheim, 1996; Michal, G. (1999) Biochemical Pathways: An Atlas of Biochemistry and Molecular Biology, John Wiley & Sons; Ong, A. S., Niki, E., & Packer, L. (1995) "Nutrition, Lipids, Health and Disease" Proceedings of the UNESCO/Confederation of Scientific and Technological Associations in Malaysia and the Society for Free Radical Research Asia, held Sep. 1-3, 1994, in Penang, Malaysia, AOCS Press, Champaign, Ill. X, 374 pp.).

The abovementioned molecules are either biologically active molecules themselves or precursors of biologically active substances which act either as electron carriers or as intermediates in a multiplicity of metabolic pathways. Besides their nutritional value, these compounds also have a significant industrial value as colorants, antioxidants and catalysts or other processing auxiliaries. (For a review over structure, activity and industrial applications of these compounds, see, for example, Ullmann's Encyclopedia of Industrial Chemistry, "Vitamins", Vol. A27, pp. 443-613, VCH Weinheim, 1996). Polyunsaturated fatty acids have a variety of functions and health-promoting effects, for example in the case of coronary heart disease, inflammatory mechanisms, children's nutrition and the like. For publications and references including the references cited therein, see: Simopoulos, 1999, Am. J. Clin. Nutr. 70 (3rd Suppl.):560-569, Takahata et al., Biosc. Biotechnol. Biochem. 1998, 62(11):2079-2085, Willich and Winther, 1995, Deutsche Medizinische Wochenschrift 120(7):229 et seq.

II. Elements and Processes of the Invention

The present invention is based, inter alia, on the discovery of novel molecules termed herein desaturase nucleic acid and desaturase protein molecules, which exert an effect on the production of cell membranes and lipids in *Phaeodactylum tricornutum* and, for example, have an effect on the movement of molecules via these membranes. In one embodiment, the desaturase molecules participate in the metabolism of compounds required for the synthesis of cell membranes in organisms, such as microorganisms and plants, or indirectly affect the transport of molecules via these membranes. In a preferred embodiment, the activity of the desaturase molecules according to the invention for regulating the production of membrane components and membrane transport has an effect on the production of the desired fine chemical by this organism. In an especially preferred embodiment, the activity of the desaturase molecules according to the invention is modulated so that the yield, production and/or production efficiency of the metabolic pathways of microorganisms or plants which regulate the desaturases according to the invention are modulated and the transport efficiency of compounds through the membranes is modified, which either directly or indirectly modulates the yield, production and/or production efficiency of a desired fine chemical by microorganisms and plants.

The term "desaturase" or "desaturase polypeptide" encompasses proteins which participate in the desaturation of fatty acids. Examples of desaturases are disclosed in SEQ ID NO: 1, 3, 5, 11 or their homologues, derivatives or analogs. The terms desaturase or desaturase nucleic acid sequence(s) encompass nucleic acid sequences which encode a desaturase and part of which can be a coding region and also corresponding 5'- and 3'-untranslated sequence regions. Examples of desaturase genes are those shown in SEQ ID NO: 1, 3, 5 or 11. The terms production and productivity are known in the art and encompass the concentration of the fermentation product (for example of the desired fine chemical) which is formed within a specific period and in a specific fermentation volume (for example kg product per hour per liter). The term production efficiency encompasses the time required for achieving a particular production quantity (for example the time required by the cell to establish its particular throughput rate of a fine chemical). The term yield or product/carbon yield is known in the art and encompasses the efficiency with which the carbon source is converted into the product (i.e. the fine chemical). This is usually expressed as, for example, kg product per kg carbon source. Increasing the yield of production of the compound increases the amount of the molecules obtained or of the suitable molecules of this compound obtained in a specific quantity of culture over a defined period. The terms biosynthesis or biosynthetic pathway are known in the art and encompass the synthesis of a compound, preferably of an organic compound, by a cell from intermediates, for example in a multi-step process which is subject to strong regulation. The terms catabolism or catabolic pathway are known in the art and encompass the cleavage of a compound, preferably of an organic compound, by a cell into catabolytes (in general terms, smaller or less complex molecules), for example in a multi-step process which is subject to strong regulation. The term metabolism is known in the art and encompasses the totality of the biochemical reactions which take place in an organism. The metabolism of a certain compound (for example the metabolism of a fatty acid) thus encompasses the totality of the biosynthetic, modification and catabolic pathways of this compound in the cell which are relevant to this compound.

In another embodiment, the nucleic acid sequences according to the invention which encode desaturase molecules can modulate the production of a desired molecule, such as a fine chemical, in a microorganism or in plants. There exist a series of mechanisms by which the modification of a sequence according to the invention can directly affect the yield, production and/or production efficiency of a fine chemical from a microorganism strain or plant strain comprising this modified protein. The number or activity of desaturases participating in the transport of molecules of fine chemicals within, or out of, the cell can be increased, so that greater amounts of these compounds are transported via membranes, from which they can be obtained and converted into each other with greater ease. Furthermore, fatty acids, triacylglycerols and/or lipids are desirable fine chemicals themselves; optimizing the activity or increasing the number of one or more desaturases according to the invention which participate in the biosynthesis of these compounds, or by interfering with the activity of one or more desaturases which participate in the catabolism of these compounds, makes increasing the yield, production and/or production efficiency of fatty acid molecules and lipid molecules from organisms such as microorganisms or plants, possible.

The mutagenesis of the nucleic acid sequences according to the invention can give rise to desaturases with modified activities which indirectly affect the production of one or more desired fine chemicals from microorganisms or plants. For example, desaturases according to the invention which participate in the export of waste products can exhibit a greater number or higher activity, so that the normal metabolic waste products of the cell (whose quantity might be increased owing to the overproduction of the desired fine chemical) are exported efficiently before they can damage the molecules in the cell (which would reduce cell viability) or interfere with the biosynthetic pathways of the fine chemicals (which would reduce the yield, production or production efficiency of a desired fine chemical). The relatively large intracellular amounts of the desired fine chemical themselves can furthermore be toxic to the cell, so that increasing the activity or number of transporters capable of exporting these compounds from the cell results in an increased viability of the cell in culture, which, in turn, leads to a higher number of cells in the culture which produce the desired fine chemical. The desaturases according to the invention can also be manipulated in such a way that the corresponding amounts of different lipid molecules and fatty acid molecules are produced. This can have a substantial effect on the lipid concentration of the cell membrane. Since each lipid type has different physical properties, a modification of the lipid composition of a membrane can significantly modify membrane fluidity. Modifications of the membrane fluidity can affect the transport of molecules via the membrane and cell integrity, each of which has a substantial effect on the production of fine chemicals from microorganisms and plants in large-scale fermentation culture. Plant membranes impart specific properties such as tolerance to high and low temperatures, salt, drought and tolerance with respect to pathogens such as bacteria and fungi. The modulation of the membrane components may therefore have a critical effect on the ability of the plants to survive under the abovementioned stress parameters. This can take place via changes in signal cascades or directly via the modified membrane composition (see, for example, Chapman, 1998, Trends in Plant Science, 3(11):419-426) and signal cascades (see Wang 1999, Plant Physiology, 120:645-651) or affect the tolerance of low temperatures, as disclosed in WO 95/18222.

The isolated nucleic acid sequences according to the invention are present, for example, in the genome of a *Phaeodactylum tricornutum* UTEX646 strain which is available via the algae collection of the University of Texas, Austin.

The nucleotide sequence of the *Phaeodactylum tricornutum* cDNA and the derived amino acid sequences of the desaturases are shown in SEQ ID NO: 1 to 6 and 11 and 12. Computer analyses were carried out which classify and/or identify these nucleotide sequences as sequences which encode proteins participating in the metabolism of cell membrane components or which participate in the transport of compounds via cell membranes, or of PUFA biosynthesis. ESTs with the database input NO: PT001070010R and PT001078032R by the inventors constitute the sequences according to the invention in SEQ ID NO: 1 and 3. The sequence of the fragment of EST PT0010700100R was determined and is as shown in SEQ ID NO: 5. In a similar manner, the sequence of clone PT001078032R is shown in SEQ ID NO: 1. Gene names were assigned to the clones. The abbreviations denote: Pp=*Physcomitrella patens*, Pt=*Phaeodactylum tricornutum*. PT001070010R of SEQ ID NO: 5 encodes a novel gene which is homologous to Δ12-desaturase and PT001078032R encodes a novel Δ5-desaturase. Pt_des6 can be isolated in accordance with Example 5a by means of polymerase chain reaction with the aid of degenerate oligonucleotides. A fragment obtained in this way can be isolated for screening a *Phaeodactylum tricornutum* cDNA library, and the coding region of a *Phaeodactylum tricornutum* Δ6-desaturase can be obtained. A gene isolated in this way is termed Pt_des6 in Table 1 and is shown in SEQ ID NO: 3. The corresponding amino acid sequences are obtained by translating the genetic code of sequence ID NO: 1, 3 and 5 and are defined as SEQ ID NO: 2, 4 and 6 (see also Table 1). A further nucleic acid sequence which encodes a Δ12-desaturase can also be found in Table 1. It has the clone number PT001072031R.

TABLE 1

| Gene name | Clone name | Nucleic acid SEQ ID NO: | Polypeptide SEQ ID NO: |
|---|---|---|---|
| Δ5-desaturase | Pt_des5 | PT001078032R | 1 | 2 |
| Δ6-desaturase | Pt_des6 | Pt_des6 | 3 | 4 |
| Δ12-desaturase | Pt_des12 | PT001070010R | 5 | 6 |
| Δ6-desaturase | Pp_des6 | Pp_des6 | 7 | 8 |
| Δ6-elongase | Pp_PSE1 | PP001019019F | 9 | 10 |
| Δ12-desaturase | Pt des12.2 | PT001072013R | 11 | 12 |

The present invention also relates to proteins with an amino acid sequence which is essentially homologous with an amino acid sequence of SEQ ID NO:2, 4, 6 or 12. As used in the present context, a protein with an amino acid sequence which is essentially homologous with a selected amino acid sequence has at least approximately 50% homology with the selected amino acid sequence, for example the complete amino acid sequence selected. A protein with an amino acid sequence which is essentially homologous with a selected amino acid sequence can also have at least approximately 50 to 60% homology, preferably at least approximately 60 to 70% homology and more preferably at least approximately 70 to 80%, 80 to 90% or 90 to 95% homology and most preferably at least approximately 96%, 97%, 98%, 99% or more homology with a selected amino acid sequence.

The desaturase according to the invention or the biologically active part or the fragment thereof can participate in the metabolism of lipids required for the synthesis of membranes or storage lipids in microorganisms and can, in combination with further genes, in particular those with elongase activity, contribute to activities required for the elongation of $C_{18}$- or $C_{20-22}$-PUFAs so that $C_{18}$-, $C_{20}$-, $C_{22}$- or $C_{24}$-PUFAs and related PUFAs are obtained. In this context, desaturases according to the invention can be cloned in combination with elongases and other desaturases in expression cassettes according to the invention and employed for the transformation of plants with the aid of *Agrobacterium*.

Various aspects of the invention are described in greater detail in the subsections which follow.

A. Isolated Nucleic Acid Molecules

One embodiment of the invention are isolated nucleic acids derived from PUFA-producing microorganisms and encoding polypeptides which desaturate $C_{18}$- or $C_{20-22}$-fatty acids with at least one, two, three or four double bonds in the fatty acid.

A further embodiment according to the invention are isolated nucleic acids encompassing nucleotide sequences encoding polypeptides which desaturate $C_{18}$- or $C_{20}$-fatty acids with at least one, two, three or four double bonds in the fatty acid and which are selected from the group consisting of a) a nucleic acid sequence with the sequence shown in SEQ ID NO: 1, SEQ ID NO: 3, SEQ ID NO: 5 or SEQ ID NO: 11, b) nucleic acid sequences which, owing to the degeneracy of the genetic code, are obtained by backtranslating the amino acid sequences shown in SEQ ID NO: 2, SEQ ID NO: 4, SEQ ID NO: 6 or SEQ ID NO: 12, c) derivatives of the nucleic acid sequence shown in SEQ ID NO: 1, SEQ ID NO: 3, SEQ ID NO: 5 or SEQ ID NO: 11, which encode polypeptides with the amino acid sequences shown in SEQ ID NO: 2, SEQ ID NO: 4, SEQ ID NO: 6 or SEQ ID NO: 12 and have at least 50% homology at the amino acid level, without essentially reducing the enzymatic action of the polypeptides.

The abovementioned nucleic acid according to the invention is derived from organisms such as ciliates, fungi, algae or dinoflagellates which are capable of synthesizing PUFAs, preferably from *Phaeodactylum tricornutum* or closely related organisms.

One aspect of the invention relates to isolated nucleic acid molecules which encode desaturase polypeptide or biologically active parts thereof, and to nucleic acid fragments which suffice for use as hybridization probes or primers for identifying or amplifying a desaturase-encoding nucleic acid (for example desaturase DNA). The term "nucleic acid molecule" as used in the present context is intended to encompass DNA molecules (for example cDNA or genomic DNA) and RNA molecules (for example mRNA) and DNA or RNA analogs which are generated by means of nucleotide analogs. This term additionally encompasses the untranslated sequence on the 3' and the 5' ends of the coding gene region: at least 500, preferably 200, especially preferably 100, nucleotides of the sequence upstream of the 5' end of the coding region and at least 100, preferably 50, especially preferably 20, nucleotides of the sequence downstream of the 3' end of the coding gene region. The nucleic acid molecule can be single- or double-stranded, but is preferably double-stranded DNA. An "isolated" nucleic acid molecule is separated from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences located at the 5' and 3' ends of the nucleic acid). In various embodiments, the isolated desaturase nucleic acid molecule can comprise, for example, less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived (for example a *Physcomitrella patens* cell). An "isolated" nucleic acid molecule, such as a cDNA molecule, can moreover be essentially free from other cellular material or culture medium if it is generated by recombinant techniques, or free from chemical precursors or other chemicals if it is synthesized chemically.

A nucleic acid molecule according to the invention, for example a nucleic acid molecule with a nucleotide sequence of SEQ ID NO: 11 or a part thereof, can be isolated using standard techniques of molecular biology and the sequence information provided herein. Also, for example a homologous sequence or homologous, conserved sequence regions can be identified at DNA or amino acid level with the aid of alignment algorithms. For example, a *Phaeodactylum tricornutum* cDNA can be isolated from a *Phaeodactylum tricornutum* library by using the complete SEQ ID NO:1, 3, 5 or 11 or a part thereof as hybridization probe and standard hybridization techniques (as described, for example, in Sambrook et al., Molecular Cloning: A Laboratory Manual. 2nd Ed., Cold Spring Harbor Laboratory, Cold Spring Harbor Laboratory Press, Cold Spring Harbor, N.Y., 1989). Moreover, a nucleic acid molecule encompassing a complete sequence of SEQ ID NO: 1, 3, 5 or 11 or a part thereof can be isolated by polymerase chain reaction, where oligonucleotide primers which are generated on the basis of this sequence or parts thereof, in particular regions around motifs of Example 5a or modifications of the same in individual defined amino acids are used (for example, a nucleic acid molecule encompassing the complete sequence of SEQ ID NO: 1, 3, 5 or 11 or a part thereof can be isolated by polymerase chain reaction using oligonucleotide primers which have been generated on the basis of this same sequence of SEQ ID NO: 1, 3, 5 or 11). For example, mRNA can be isolated from cells (for example by the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for amplification by means of polymerase chain reaction can be generated on the basis of one of the sequences shown in SEQ ID NO: 1, 3, 5 or 11 and in FIG. 5 or with the aid of the amino acid sequences shown in SEQ ID NO: 2, 4, 6 or 12. A nucleic acid according to the invention can be amplified using cDNA or, alternatively, genomic DNA as template and suitable oligonucleotide primers, in accordance with standard PCR amplification techniques. The nucleic acid amplified in this way can be cloned into a suitable vector and characterized by means of DNA sequence analysis. Oligonucleotides which correspond to a desaturase nucleotide sequence can be generated by standard synthesis methods, for example using an automatic DNA synthesizer.

The cDNA shown in SEQ ID NO: 1, 3, 5 or 11 encompasses sequences which encode desaturases (i.e. the "coding region"), and 5'-untranslated sequences and 3'-untranslated sequences. Alternatively, the nucleic acid molecule can only encompass the coding region of one of the sequences in SEQ ID NO: 1, 3, 5 or 11 or can comprise complete genomic fragments which have been isolated from genomic DNA.

In a further preferred embodiment, an isolated nucleic acid molecule according to the invention encompasses a nucleic acid molecule which is a complement of one of the nucleotide sequences shown in SEQ ID NO: 1, 3, 5 or 11 or a part thereof. A nucleic acid molecule which is complementary to one of the nucleotide sequences shown in SEQ ID NO: 1, 3, 5 or 11 is sufficiently complementary if it is capable of hybridizing with one of the sequences stated in SEQ ID NO: 1, 3, 5 or 11, giving rise to a stable duplex.

Homologs of the novel desaturase nucleic acid sequences with the sequence SEQ ID NO: 1, 3, 5 or 11 means, for example, allelic variants with at least approximately 50 to 60% homology, preferably at least approximately 60 to 70% homology, more preferably at least approximately 70 to 80%, 80 to 90% or 90 to 95% homology and even more preferably at least approximately 95%, 96%, 97%, 98%, 99% or more homology with one of the nucleotide sequences shown in SEQ ID NO: 1, 3, 5 or 11 or their homologs, derivatives, analogs or parts thereof. In a further preferred embodiment, an isolated nucleic acid molecule according to the invention encompasses a nucleotide sequences which hybridizes with one of the nucleotide sequences shown in SEQ ID NO: 1, 3, 5 or 11 or a part thereof, for example under stringent conditions. Allelic variants encompass, in particular, functional variants which can be obtained by the deletion, insertion or substitution of nucleotides from/into the sequence shown in SEQ ID NO: 1, 3, 5 or 11, it being intended, however, for the enzyme activity of the resulting proteins which are synthesized to be advantageously retained for the insertion of one or more genes. Proteins which retain the enzymatic activity of desaturase, that is to say whose activity is essentially not reduced, means proteins with at least 10%, preferably 20%, especially preferably 30%, very particularly preferably 40%, of the original enzyme activity compared with the protein encoded by SEQ ID NO: 2, 4, 6 or 12.

Homologs of SEQ ID NO: 1, 3, 5 or 11 also means, for example, bacterial, fungal and plant homologs, truncated sequences, single-stranded DNA or RNA of the coding and noncoding DNA sequence.

Homologs of SEQ ID NO: 1, 3, 5 or 11 also means derivatives such as, for example, promoter variants. The promoters upstream of the nucleotide sequences stated can be modified by one or more nucleotide substitutions, by insertion(s) and/or deletion(s), without, however, interfering with the functionality or activity of the promoters. It is furthermore possible for the activity of the promoters to be increased by modifying their sequence or for them to be replaced completely by more active promoters, even from heterologous organisms.

Moreover, the nucleic acid molecule according to the invention may only encompass part of the coding region of one of the sequences in SEQ ID NO: 1, 3, 5 or 11, for example a fragment which can be used as probe or primer, or a fragment which encodes a biologically active segment of a desaturase. The nucleotide sequences determined from cloning the *Phaeodactylum tricornutum* desaturase gene allow the generation of probes and primers which are designed for identifying and/or cloning desaturase homologs in other cell types and organisms and desaturase homologs from other microalgae or related species. The probe/primer usually encompasses an essentially purified oligonucleotide. The oligonucleotide usually encompasses a nucleotide sequence region which hybridizes under stringent conditions to at least approximately 12, preferably approximately 16, more preferably approximately 25, 40, 50 or 75 successive nucleotides of a sense strand of one of the sequences stated in SEQ ID NO: 1, 3, 5 or 11, of an antisense strand of one of the sequences stated in SEQ ID NO: 1, 3, 5 or 11 or its homologs, derivatives or analogs or naturally occurring mutants thereof. Primers based on a nucleotide sequence of SEQ ID NO: 1, 3, 5 or 11 can be used in PCR reactions for cloning desaturase homologs. Probes based on the desaturase nucleotide sequences can be used for detecting transcripts or genomic sequences which encode the same or homologous proteins. In preferred embodiments, the probe additionally encompasses a labeling group bound thereto, for example a radioisotope, a fluorescent compound, an enzyme or an enzyme cofactor. These probes can be used as part of a test kit for genomic markers for identifying cells which misexpress a desaturase, for example by measuring an amount of a desaturase-encoding nucleic acid in a cell sample, for example measuring the desaturase mRNA level, or for determining whether a genomic desaturase gene is mutated or deleted.

In one embodiment, the nucleic acid molecule according to the invention encodes a protein or part thereof which encompasses an amino acid sequence with sufficient homology with an amino acid sequence of SEQ ID NO: 2, 4, 6 or 12 for the protein or part thereof to retain the ability to participate in the metabolism of compounds required for the synthesis of the cell membranes in microorganisms or plants or in the transport of molecules via these membranes. As used in the present context, the term "sufficient homology" refers to proteins or parts thereof whose amino acid sequences have a minimum number of amino acid residues which are identical with or equivalent to an amino acid sequence of SEQ ID NO:2 (for example an amino acid residue with a similar side chain, such as an amino acid residue in one of the sequences of SEQ ID NO:2) so that the protein or the part thereof can participate in the metabolism of compounds required for the synthesis of cell membranes in microorganisms or plants or in the transport of molecules via these membranes. As described herein, protein components of these metabolic pathways for membrane components or membrane transport systems can play a role in the production and secretion of one or more fine chemicals. Examples of these activities are also described herein. Thus, the "function of a desaturase" contributes either directly or indirectly to the yield, production and/or production efficiency of one or more fine chemicals. Examples of desaturase substrate specificity of the catalytic activity are stated in Tables 5 and 6.

In a further embodiment, derivatives of the nucleic acid molecule according to the invention encode proteins with at least approximately 50 to 60% homology, preferably at least approximately 60 to 70% homology and more preferably at least approximately 70 to 80%, 80 to 90%, 90 to 95% homology, and most preferably at least approximately 96%, 97%, 98%, 99% or more homology with a complete amino acid sequence of SEQ ID NO:2. The homology of the amino acid sequence can be determined over the entire sequence region using the program PileUp (J. Mol. Evolution, 25, 351-360, 1987, Higgins et al., CABIOS, 5, 1989:151-153) or BESTFIT or GAP (Henikoff, S. and Henikoff, J. G. (1992). Amino acid substitution matrices from protein blocks. Proc. Natl. Acad. Sci. USA 89: 10915-10919).

Parts of proteins encoded by the desaturase nucleic acid molecules according to the invention are preferably biologically active parts of one of the desaturases. As used herein, the term "biologically active part of a desaturase" is intended to encompass a segment, for example a domain/motif, of a desaturase which can participate in the metabolism of compounds required for the synthesis of cell membranes in microorganisms or plants or in the transport of molecules via these membranes or which has an activity stated in Tables 5 and 6. An assay of the enzymatic activity can be carried out in order to determine whether a desaturase or a biologically active part thereof can participate in the metabolism of compounds required for the synthesis of cell membranes in microorganisms or plants or in the transport of molecules via these membranes. These assay methods as described in detail in Example 8 of the examples section are known to the skilled worker.

Additional nucleic acid fragments which encode biologically active segments of a desaturase can be generated by isolating part of one of the sequences in SEQ ID NO: 1, 3, 5 or 11, expressing the encoded segment of the desaturase or of the peptide (for example by recombinant expression in vitro) and determining the activity of the encoded part of the desaturase or of the peptide.

Moreover, the invention encompasses nucleic acid molecules which differ from one of the nucleotide sequences shown in SEQ ID NO: 1, 3, 5 or 11 (and parts thereof) owing to the degeneracy of the genetic code and which thus encode the same desaturase as the one encoded by the nucleotide sequences shown in SEQ ID NO: 1, 3, 5 or 11. In another embodiment, an isolated nucleic acid molecule according to the invention has a nucleotide sequence which encodes a protein with an amino acid sequence shown in SEQ ID NO: 2, 4, 6 or 12. In a further embodiment, the nucleic acid molecule according to the invention encodes a full-length desaturase protein which is essentially homologous to an amino acid sequence of SEQ ID NO: 2, 4, 6 or 12 (which is encoded by an open reading frame shown in SEQ ID NO: 1, 3, 5 or 11) and which can be identified and isolated by customary methods.

In addition to the desaturase nucleotide sequence shown in SEQ ID NO: 1, 3, 5 or 11, the skilled worker recognizes that DNA sequence polymorphisms may exist which lead to changes in the amino acid sequences of the desaturases within a population (for example the *Phaeodactylum tricornutum* population). These genetic polymorphisms in the desaturase gene can exist between individuals within a population owing to natural variation. As used in the present context, the terms "gene" and "recombinant gene" refer to nucleic acid molecules with an open reading frame which encodes a desaturase, preferably a *Phaeodactylum tricornutum* desaturase.

These natural variants usually cause a variance of 1 to 5% in the nucleotide sequence of the desaturase gene. All of these nucleotide variations and resulting amino acid polymorphisms in desaturase which are the result of natural variation and do not alter the functional activity of desaturases are intended to come within the scope of the invention.

Nucleic acid molecules which correspond to the natural variants and non-*Phaeodactylum-tricornutum*-homologs, -derivatives and -analogs of the *Phaeodactylum tricornutum* cDNA can be isolated in accordance with standard hybridization techniques under stringent hybridization conditions owing to their homology with the *Phaeodactylum tricornutum* desaturase nucleic acid disclosed herein using the *Phaeodactylum tricornutum* cDNA or part thereof as hybridization probe. In another embodiment, an isolated nucleic acid molecule according to the invention has a minimum length of 15 nucleotides and hybridizes under stringent conditions to the nucleic acid molecule which encompasses a nucleotide sequence of SEQ ID NO:1, 3, 5 or 11.

In other embodiments, the nucleic acid has a minimum length of 25, 50, 100, 250 or more nucleotides. The term "hybridizes under stringent conditions" as used in the present context is intended to describe hybridization and wash conditions under which nucleotide sequences which have at least 60% homology to each other usually remain hybridized to each other. The conditions are preferably such that sequences which have at least approximately 65% homology, more preferably approximately 70% homology and even more preferably at least approximately 75% or more homology to each other usually remain hybridized to each other. These stringent conditions are known to the skilled worker and can be found in Current Protocols in Molecular Biology, John Wiley & Sons, N.Y. (1989), 6.3.1-6.3.6. A preferred, nonlimiting example of stringent hybridization conditions are hybridizations in 6× sodium chloride/sodium citrate (=SSC) at approximately 45° C., followed by one or more wash steps in 0.2×SSC, 0.1% SDS at 50 to 65° C. It is known to the skilled worker that these hybridization conditions differ depending on the type of nucleic acid and, for example, when organic solvents are present, with regard to the temperature and the concentration of the buffer. The temperature differs, for example, under "standard hybridization conditions" depending on the type of the nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably for example 0.1×SSC and 30° C. to 55° C., preferably between 45° C. and 55° C. The abovementioned hybridization temperatures are determined for example for a nucleic acid approximately 100 bp (=base pairs) in length and a G+C content of 50% in the absence of formamide. The skilled worker knows how the hybridization conditions required can be determined with reference to textbooks, such as the one mentioned above, or from the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press.

Preferably, an isolated nucleic acid molecule according to the invention which hybridizes under stringent conditions to a sequence of SEQ ID NO:1, 3, 5 or 11 corresponds to a naturally occurring nucleic acid molecule. As used in the present context, a "naturally occurring" nucleic acid molecule refers to an RNA or DNA molecule with a nucleotide sequence which occurs in nature (for example which encodes a natural protein). In one embodiment, the nucleic acid encodes a naturally occurring *Phaeodactylum tricornutum* desaturase.

In addition to naturally occurring variants of the desaturase sequence which may exist in the population, the skilled worker furthermore recognizes that changes by means of mutation may also be introduced into a nucleotide sequence of SEQ ID NO: 1, 3, 5 or 11, which leads to changes in the amino acid sequence of the encoded desaturase without adversely affecting the functionality of the desaturase protein. For example, nucleotide substitutions which lead to amino acid substitutions on "nonessential" amino acid residues can be generated in a sequence of SEQ ID NO: 2, 4, 6 or 12. A "nonessential" amino acid residue is a residue which can be altered in a wild-type sequence of one of the desaturases (SEQ ID NO: 2, 4, 6 or 12) without altering, that is to say essentially reducing, the activity of the desaturase, while an "essential" amino acid residue is required for the desaturase activity. Other amino acid residues (for example those which are not conserved, or only semi-conserved, in the domain with desaturase activity), however, may not be essential for the activity and can therefore be modified without modifying the desaturase activity.

Accordingly, a further aspect of the invention relates to nucleic acid molecules which encode desaturases comprising modified amino acid residues which are not essential for the desaturase activity. These desaturases differ from a sequence in SEQ ID NO: 2, 4, 6 or 12 with regard to the amino acid sequence while still retaining at least one of the desaturase activities described herein. In one embodiment, the isolated nucleic acid molecule encompasses a nucleotide sequence encoding a protein, the protein encompassing an amino acid sequence with at least approximately 50% homology with an amino acid sequence of SEQ ID NO: 2, 4, 6 or 12 and being able to participate in the metabolism of compounds required for the synthesis of the cell membranes in *Phaeodactylum tricornutum* or in the transport of molecules via these membranes. The protein encoded by the nucleic acid molecule preferably has at least approximately 50 to 60% homology with one of the sequences in SEQ ID NO:2, 4, 6 or 12, more preferably at least approximately 60 to 70% homology with one of the sequences in SEQ ID NO:2, 4, 6 or 12, even more preferably at least approximately 70 to 80%, 80 to 90%, 90 to 95% homology with one of the sequences in SEQ ID NO: 2, 4, 6 or 12 and most preferably at least 96%, 97%, 98% or 99% homology with one of the sequences in SEQ ID NO: 2, 4, 6 or 12.

To determine the percentage homology of two amino acid sequences (for example one of the sequences of SEQ ID NO: 2, 4, 6 or 12 and a mutated form thereof) or of two nucleic acids, the sequences are written one underneath the other to allow optimum comparison (for example, gaps may be introduced into the sequence of a protein or of a nucleic acid in order to generate an optimal alignment with the other protein or the other nucleic acid). Then, the amino acid residues or nucleotides at the corresponding amino acid positions or nucleotide positions are compared. If a position in a sequence (for example one of the sequences of SEQ ID NO: 2, 4, 6 or 12) is occupied by the same amino acid residue or the same nucleotide as the corresponding position in the other sequence (for example a mutated form of the sequence selected from SEQ ID NO: 2, 4, 6 or 12), then the molecules are homologous at this position (i.e. amino acid or nucleic acid "homology" as used in the present context corresponds to amino acid or nucleic acid "identity"). The percentage homology between the two sequences is a function of the number of identical positions which the sequences share (i.e. % homology=number of identical positions/total number of positions×100). The terms homology and identity are thus to be considered as being synonymous.

An isolated nucleic acid molecule which encodes a desaturase which is homologous with a protein sequence of SEQ ID NO: 2, 4, 6 or 12 can be generated by introducing one or more nucleotide substitutions, additions or deletions into a nucleotide sequence of SEQ ID NO: 1, 3, 5 or 11 so that one or more amino acid substitutions, additions or deletions are introduced into the encoded protein. Mutations can be introduced into one of the sequences of SEQ ID NO: 1, 3, 5 or 11 by standard techniques, such as site-directed mutagenesis and PCR-mediated mutagenesis. Preferably, conservative amino acid substitutions are generated at one or more of the predicted nonessential amino acid residues. In a "conservative amino acid substitution", the amino acid residue is exchanged for an amino acid residue with a similar side chain. Families of amino acid residues with similar side chains have been defined in the specialist field. These families encompass amino acids with basic side chains (for example lysine, arginine, hystidine), acidic side chains (for example aspartic acid, glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in a desaturase is thus preferably exchanged for another amino acid residue from the same side-chain family. As an alternative, in another embodiment, the mutations can be introduced randomly over all or part of the desaturase-encoding sequence, for example by saturation mutagenesis, and the resulting mutants can be screened for the desaturase activity in order to identify mutants which retain desaturase activity. Following the mutagenesis of one of the sequences of SEQ ID NO: 1, 3, 5 or 11, the encoded protein can be expressed recombinantly, and the activity of the protein can be determined, for example using the assays described herein (see examples section).

In addition to the nucleic acid molecules which encode the above-described desaturases, a further aspect of the invention relates to isolated nucleic acid molecules which are "antisense" to the nucleic acid sequences according to the invention. An "antisense" nucleic acid encompasses a nucleotide sequence which is complementary to a "sense" nucleic acid which encodes a protein, for example complementary to the coding strand of a double-stranded cDNA molecule or complementary to an mRNA sequence. Accordingly, an antisense nucleic acid can bind to a sense nucleic acid by hydrogen bonds. The antisense nucleic acid can be complementary to a complete desaturase-encoding strand or only to part thereof. In one embodiment, an antisense nucleotide acid molecule is "antisense" to a "coding region" of the coding strand of a nucleotide sequence encoding a desaturase. The term "coding region" refers to the region of the nucleotide sequence which encompasses codons which are translated into amino acid residues (for example the entire coding region which starts and ends with the stop codon, i.e. the last codon before the stop codon). In a further embodiment, the antisense nucleic acid molecule is "antisense" to a "noncoding region" of the coding strand of a nucleotide sequence encoding desaturase. The term "noncoding region" refers to 5' and 3' sequences which flank the coding region and are not translated into amino acids (i.e. which are also termed 5'- and 3'-untranslated regions).

Given the desaturase-encoding sequences disclosed herein of the coding strand (for example the sequences shown in SEQ ID NO: 1, 3, 5 or 11), antisense nucleic acids according to the invention can be designed in accordance with the rules of Watson-Crick base pairing. The antisense nucleic acid molecule can be complementary to all of the coding region of desaturase mRNA, but is more preferably an oligonucleotide which is "antisense" to only part of the coding or noncoding region of the desaturase mRNA. The antisense oligonucleotide can be complementary, for example, to the region around the translation start of desaturase mRNA. An antisense oligonucleotide can have a length of, for example, approximately 5, 10, 15, 20, 25, 30, 35, 40, 45 or 50 and more nucleotides. An antisense nucleic acid according to the invention can be constructed by processes known in the art using chemical synthesis and enzymatic ligation reactions. An antisense nucleic acid (for example an antisense oligonucleotide) can, for example, be synthesized chemically, making use of naturally occurring nucleotides or variously modified nucleotides which are such that they increase the biological stability of the molecules or increase the physical stability of the duplex formed between the antisense and the sense nucleic acid; for example, phosphorothioate derivatives and acridine-substituted nucleotides may be used. Examples of modified nucleotides which may be used for generating the antisense nucleic acid are, inter alia, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentyladenine, uracil-5-oxyacetic acid (v), wybutoxosin, pseudouracil, queosine, 2-thiocytosine, 5-methyl-2-thiouracil, 2-thiouracil, 4-thiouracil, 5-methyluracil, methyl uracil-5-oxyacetate, uracil-5-oxyacetic acid (v), 5-methyl-2-thiouracil, 3-(3-amino-3-N-2-carboxypropyl) uracil, (acp3)w and 2,6-diaminopurine. The antisense nucleic acid can, alternatively, be generated biologically using an expression vector into which a nucleic acid has been subcloned in antisense orientation (i.e. RNA which is transcribed by the nucleic acid introduced is in antisense orientation relative to a target nucleic acid of interest, which is described in greater detail in the subsection which follows).

The antisense nucleic acid molecules according to the invention are usually administered to a cell or generated in situ so that they hybridize with, or bind to, the cellular mRNA and/or the genomic DNA encoding a desaturase, thus inhibiting expression of the protein, for example by inhibiting transcription and/or translation. Hybridization can be effected by conventional nucleotide complementarity with the formation of a stable duplex or, for example in the case of an antisense nucleic acid molecule which binds DNA duplices, by specific interactions in the major groove of the double helix. The antisense molecule can be modified in such a manner that it specifically binds to a receptor or to an antigen expressed at the selected cell surface, for example by binding the antisense nucleic acid molecule to a peptide or an antibody, each of which binds to a cell surface receptor or an antigen. The cells can also be provided with the antisense nucleic acid molecule using the vectors described herein. Vector constructs in which the antisense nucleic acid molecule is under the control of a strong prokaryotic, viral or eukaryotic promoter, including a plant promoter, are preferred for achieving sufficient intracellular concentrations of the antisense molecules.

In a further embodiment, the antisense nucleic acid molecule according to the invention is an α-anomeric nucleic acid molecule. An α-anomeric nucleic acid molecule forms specific double-stranded hybrids with complementary RNA, the strands running parallel to each other, in contrast to ordinary β units (Gaultier et al. (1987) Nucleic Acids Res. 15:6625-6641). Moreover, the antisense nucleic acid molecule can encompass a 2'-o-methylribonucleotide (Inoue et al. (1987) Nucleic Acids Res. 15:6131-6148) or a chimeric RNA-DNA analog (Inoue et al. (1987) FEBS Lett. 215:327-330).

In a further embodiment, an antisense nucleic acid according to the invention is a ribozyme. Ribozymes are catalytic RNA molecules with ribonuclease activity which can cleave a single-stranded nucleic acid, such as an mRNA, to which they have a complementary region. Thus, ribozymes (for example hammerhead ribozymes (described in Haselhoff and Gerlach (1988) Nature 334:585-591)) can be used for the catalytic cleavage of desaturase-mRNA transcripts, in order thereby to inhibit the translation of desaturase mRNA. A ribozyme with specificity for a desaturase-encoding nucleic acid can be designed on the basis of the nucleotide sequence of one of the desaturase-cDNAs disclosed in SEQ ID NO: 1, 3, 5 or 11 (i.e. or on the basis of a heterologous sequence to be isolated in accordance with the methods taught in the present invention). For example, a derivative of a Tetrahymena-L-19-IVS RNA can be constructed in which the nucleotide sequence of the active site is complementary to the nucleotide sequence to be cleaved in a desaturase-encoding mRNA. See, for example, Cech et al., U.S. Pat. No. 4,987,071 and Cech et al., U.S. Pat. No. 5,116,742. As an alternative, desaturase mRNA can be used for selecting a catalytic RNA with a specific ribonuclease activity from among a pool of RNA molecules. See, for example, Bartel, D., and Szostak, J. W. (1993) Science 261:1411-1418.

As an alternative, desaturase gene expression can be inhibited by directing nucleotide sequences which are complementary to the regulatory region of a desaturase nucleotide sequence (for example a desaturase promoter and/or enhancer) in such a way that triple helix structures are formed which inhibit the transcription of a desaturase gene in target cells. See, in general, Helene, C. (1991) Anticancer Drug Res. 6(6) 569-84; Helene, C., et al. (1992) Ann. N.Y. Acad. Sci. 660:27-36; and Maher. L. J. (1992) Bioassays 14(12):807-815.

B. Gene Construct (=Nucleic Acid Construct, Nucleic Acid Fragment or Expression Cassette)

The expression cassette according to the invention is to be understood as meaning the sequences mentioned in SEQ ID NO: 1, SEQ ID NO: 3, SEQ ID NO: 5 or SEQ ID NO: 11 which are the result of the genetic code, and/or their functional or nonfunctional derivatives, which were advantageously linked functionally to one or more regulatory signals for increasing gene expression and which advantageously control the expression of the coding sequence in the host cell. These regulatory sequences are intended to make possible the targeted expression of the genes and the protein expression. Depending on the host organism, this may mean, for example, that the gene is expressed and/or overexpressed only after induction or else that it is expressed and/or overexpressed immediately. For example, these regulatory sequences take the form of sequences to which inductors or repressors bind, thus regulating the expression of the nucleic acid. In addition to these novel regulatory sequences, or instead of these sequences, the natural regulation of these sequences may still be present before the actual structural genes and, if appropriate, may have been modified genetically, so that natural regulation was eliminated and the expression of the genes increased. However, the gene construct may also have a simpler structure, that is to say no additional regulatory signals have been inserted before the nucleic acid sequence or its derivatives, and the natural promoter together with its regulation has not been removed. Instead, the natural regulatory sequence has been mutated in such a way that regulation no longer takes place and/or gene expression is increased. These modified promoters may also be arranged by themselves in the form of part-sequences (=promoter with parts of the nucleic acid sequences according to the invention) before the natural gene in order to increase the activity. Moreover, the gene construct may advantageously also comprise one or more of what are known as enhancer sequences linked functionally to the promoter, and these make possible an increased expression of the nucleic acid. It is also possible to insert additional advantageous sequences on the 3' end of the DNA sequences, such as further regulatory elements or terminators. The Δ5-desaturase/Δ6-desaturase and/or Δ12-desaturase genes may be present in one or more copies in the expression cassette (=gene construct).

In this context, the regulatory sequences or factors can preferably have a positive effect on, and thus increase, the expression of the genes introduced, as has been described above. An enhancement of the regulatory elements can advantageously take place at the transcriptional level by using strong transcription signals such as promoters and/or enhancers. In addition, however, translation may also be enhanced, for example by increasing the stability of the mRNA.

A further embodiment of the invention are one or more gene constructs comprising one or more sequences which are defined by SEQ ID NO: 1, 3, 5, 7, 9 or 11 and which encode polypeptides in accordance with SEQ ID NO: 2, 4, 6, 8, 10 or 12. SEQ ID NO: 1, 3, 5, 7 and 11 are derived from desaturases, while SEQ ID NO: 9 encodes an elongase. Desaturases encode enzymes which introduce a double bond at the Δ5, Δ6 or Δ12 position, the substrate having one, two, three or four double bonds. The sequence shown in SEQ ID NO: 9 encodes an enzyme activity which elongates a fatty acid by at least two carbon atoms, and the homologs, derivatives or analogs which are linked functionally to one or more regulatory signals, advantageously for increasing gene expression. Examples of these regulatory sequences are sequences to which inductors or repressors bind, thus regulating the expression of the nucleic acid. In addition to these novel regulatory sequences, the natural regulation of these sequences may still be present before the actual structural genes and, if appropriate, can have been genetically modified so that the natural regulation has been eliminated and the expression of the genes has been increased.

However, the gene construct may also have a simpler structure, that is to say no additional regulatory signals have been inserted before the sequence SEQ ID NO: 1, 3, 5 or 11 or their homologs and the natural promoter with its regulation has not been deleted. Instead, the natural regulatory sequence has been mutated in such a way that regulation no longer takes place and gene expression is enhanced. The gene construct may furthermore advantageously encompass one or more of what are known as enhancer sequences which are linked functionally to the promoter and which make possible increased expression of the nucleic acid sequence. It is also possible additionally to insert advantageous sequences at the 3' end of the DNA sequences, for example further regulatory elements or terminators. The desaturase genes and the elongase gene may be present in one or more copies in the gene construct. They may be present in one gene construct or more than one gene construct. This gene construct or the gene constructs can be expressed together in the host organism. In this context, the gene construct or the gene constructs can be inserted into one or more vectors and be present in the cell in free form or else inserted into the genome. It is advantageous for the insertion of further genes into organisms if further genes are present in the gene construct.

Advantageous regulatory sequences for the novel process exist, for example, in promoters such as the cos, tac, trp, tet, trp-tet, lpp, lac, lpp-lac, lacI$^{q-}$, T7, T5, T3, gal, trc, ara, SP6, λ-P$_R$ or λ-P$_L$ promoter and are advantageously used in Gram-negative bacteria. Further advantageous regulatory sequences exist, for example, in the Gram-positive promoters amy and SPO2, in the yeast or fungal promoters ADC1, MFα, AC, P-60, CYC1, GAPDH, TEF, rp28, ADH or in the plant promoters CaMV 35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzylsulfonamide-inducible), Plant J. 2, 1992:397-404 (Gatz et al., tetracyclin-inducible), EP-A-0 335 528 (abscisic-acid-inducible) or WO 93/21334 (ethanol- or cyclohexenol-inducible). Further suitable plant promoters are the promoter of cytosolic FBPase or the potato ST-LSI promoter (Stockhaus et al., EMBO J. 8, 1989, 2445), the *Glycine max* phosphoribosylpyrophosphate amidotransferase promoter (Genbank Accession No. U87999) or the node-specific promoter described in EP-A-0 249 676. Especially advantageous promoters are those which allow expression in tissues which are involved in fatty acid biosynthesis. Very especially advantageous are seed-specific promoters such as the USP promoter in accordance with the embodiment, and also other promoters such as the LEB4 (Baeumlein et al., Plant J., 1992, 2 (2):233-239), DC3 (Thomas, Plant Cell 1996, 263:359-368), the phaseolin or the napin promoter. Further especially advantageous promoters are seed-specific promoters which can be used for monocots or dicots which are described in U.S. Pat. No. 5,608,152 (oilseed rape napin promoter), WO 98/45461 (*Arabidopsis* oleosin promoter), U.S. Pat. No. 5,504,200 (*Phaseolus vulgaris* phaseolin promoter), WO 91/13980 (Brassica Bce4 promoter), by Baeumlein et al., Plant J., 1992, 2 (2):233-239 (LeB4 promoter from a legume), these promoters being suitable for dicots. The following promoters are suitable, for example, for monocots: the barley 1pt-2 or 1pt-1 promoter (WO 95/15389 and WO 95/23230), the barley Hordein promoter, and other suitable promoters described in WO 99/16890.

In principle, it is possible to use all natural promoters with their regulatory sequences, such as those mentioned above, for the novel process. It is also possible and advantageous additionally to use synthetic promoters.

As described above, the gene construct can also encompass further genes which are to be introduced into the organisms. It is possible and advantageous to introduce into the host organisms, and to express therein, regulatory genes such as genes for inductors, repressors or enzymes which, owing to the enzymatic activity, engage in the regulation of one or more genes of a biosynthetic pathway. These genes can be of heterologous or homologous origin. Moreover, the nucleic acid construct or gene construct may advantageously comprise further biosynthesis genes of the fatty acid or lipid metabolism or else these genes may be present on a further, or several further, nucleic acid constructs. A biosynthesis gene of the fatty acid or lipid metabolism which is advantageously selected is a gene from the group consisting of acyl-CoA dehydrogenase(s), acyl-ACP[=acyl carrier protein] desaturase(s), acyl-ACP thioesterase(s), fatty acid acyltransferase(s), fatty acid synthase(s), fatty acid hydroxylase(s), acetyl-coenzyme A carboxylase(s), acyl-coenzyme, A-oxidase(s), fatty acid desaturase(s), fatty acid acetylenases, lipoxygenases, triacylglycerol lipases, allenoxide synthases, hydroperoxide lyases or fatty acid elongase(s) or their combinations.

For expressing the other genes which are present, gene constructs advantageously encompass further 3'- and/or 5'-terminal regulatory sequences for enhancing expression, and these are selected for optimal expression as a function of the host organism chosen and the gene(s). These regulatory sequences, as mentioned above, are intended to make possible the specific expression of the genes and protein expression. Depending on the host organism, this may mean, for example, that the gene is expressed or overexpressed only after induction, or that it is expressed and/or overexpressed immediately.

Moreover, the regulatory sequences or regulatory factors can preferably have an advantageous effect on the expression of the genes which have been introduced, thus enhancing them. In this manner, it is possible that the regulatory elements are advantageously enhanced at the transcriptional level, using strong transcription signals such as promoters and/or enhancers. However, it is furthermore also possible to enhance translation, for example by improving mRNA stability.

C. Recombinant Expression Vectors and Host Cells

A further aspect of the invention relates to vectors, preferably expression vectors, comprising a nucleic acid encoding a desaturase alone (or a part thereof) or a nucleic acid construct described under item B in which the nucleic acid according to the invention is present alone or in combination with further biosynthesis genes of the fatty acid or lipid metabolism, such as desaturases or elongases. As used in the present context, the term "vector" refers to a nucleic acid molecule which can transport another nucleic acid to which it is bound. One type of vector is a "plasmid", which represents a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with a bacterial origin of replication, and episomal mammalian vectors). Other vectors (for example nonepisomal mammalian vectors) are integrated into the genome of a host cell upon introduction into the host cell and are thus replicated together with the host genome. In addition, certain vectors can govern the expression of genes to which they are linked functionally. These vectors are referred to as "expression vectors" herein. Usually, expression vectors which are suitable for recombinant DNA techniques can take the form of plasmids. In the present description, "plasmid" and "vector" may be used interchangeably since the plasmid is the most frequently used form of vector. However, the invention is intended to encompass these other forms of expression vectors, such as viral vectors (for example replication-deficient retroviruses, adenoviruses and adeno-related viruses) which exert similar functions. Furthermore, the term vector is also intended to encompass other vectors known to the skilled worker, such as phages, viruses such as SV40, CMV, baculovirus, adenovirus, transposons, IS elements, phasmids, phagemids, cosmids, linear or circular DNA.

The recombinant expression vectors according to the invention encompass a nucleic acid according to the invention or a gene construct according to the invention in a form which is suitable for expressing the nucleic acid in a host cell, which means that the recombinant expression vectors encompass one or more regulatory sequences, selected on the basis of the host cells to be used for expression, which is/are linked functionally to the nucleic acid sequence to be expressed. In a recombinant expression vector "linked functionally" means that the nucleotide sequence of interest is bound to the regulatory sequence(s) in such a way that expression of the nucleotide sequence is possible and that they are bound to each other so that both sequences fulfil the predicted function which has been ascribed to the sequence (for example in an in-vitro transcription/translation system or in a host cell, when the vector is introduced into the host cell). The term "regulatory sequence" is intended to encompass promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnolgy, CRC Press, Boca Raton, Fla., Ed.: Glick and Thompson, Chapter 7, 89-108, including the references therein. Regulatory sequences encompass those which control the constitutive expression of a nucleotide sequence in many types of host cell and those which control the direct expression of the nucleotide sequence only in certain host cells under certain conditions. The skilled worker knows that the design of the expression vector may depend on factors such as the choice of the host cell to be transformed, the extent to which the desired protein is expressed, and the like. The expression vectors according to the invention can be introduced into host cells in order to produce proteins or peptides, including fusion proteins or fusion peptides, which are encoded by the nucleic acids as described herein (for example desaturases, mutant forms of desaturases, fusion proteins and the like).

The recombinant expression vectors according to the invention can be designed for expressing desaturases and elongases in prokaryotic and eukaryotic cells. For example, desaturase genes can be expressed in bacterial cells, such as C. glutamicum, insect cells (using baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi", in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates of the following types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella and Stylonychia, in particular the species Stylonychia lemnae, using vectors and following a transformation method as described in WO 98/01572, and cells of multicelled plants (see Schmidt, R. and Willmitzer, L. (1988) "High efficiency Agrobacterium tumefaciens-mediated transformation of Arabidopsis thaliana leaf and cotyledon explants" Plant Cell Rep.: 583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)) or mammalian cells. Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7 promoter regulatory sequences and T7 polymerase.

In prokaryotes, proteins are usually expressed with vectors containing constitutive or inducible promoters which control the expression of fusion proteins or nonfusion proteins. Fusion vectors add a series of amino acids to a protein encoded therein, usually on the amino terminus of the recombinant protein, but also on the C terminus or fused within suitable regions in the proteins. These fusion vectors usually have three tasks: 1) to enhance the expression of recombinant protein; 2) to increase the solubility of the recombinant protein and 3) to support the purification of the recombinant protein by acting as ligand in affinity purification. In the case of fusion expression vectors, a proteolytic cleavage site is frequently introduced at the site where the fusion moiety and the recombinant protein are linked, so that the recombinant protein can be separated from the fusion unit after purification of the fusion protein. These enzymes and their corresponding recognition sequences encompass factor Xa, thrombin and enterokinase.

Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E-binding protein or protein A is fused to the recombinant target protein. In one embodiment, the desaturase-encoding sequence is cloned into a pGEX expression vector to generate a vector encoding a fusion protein which encompasses, from the N terminus to the C terminus, GST-thrombin cleavage site-X-protein. The fusion protein can be purified by affinity chromatography using glutathione-agarose resin. Recombinant desaturase which is not fused to GST can be obtained by cleaving the fusion protein with thrombin.

Examples of suitable inducible non-fusion E. coli expression vectors are, inter alia, pTrc (Amann et al. (1988) Gene 69:301-315) and pET 11d (Studier et al., Gene Expression Technology Methods in Enzymology 185, Academic Press, San Diego, Calif. (1990) 60-89). Target gene expression of the pTrc vector is based on the transcription by host RNA polymerase from a hybrid trp-lac fusion promoter. Target gene expression from the pET 11d vector is based on transcription from a T7-gn10-lac fusion promoter which is mediated by a coexpressed viral RNA polymerase (T7 gn1). This viral polymerase is provided by the host strains BL21 (DE3) or HMS174 (DE3) by a resident λ prophage which harbors a T7 gn1 gene under the transcriptional control of the lacUV 5 promoter.

Other vectors which are suitable for use in prokaryotic organisms are known to the skilled worker; these vectors are, for example, in E. coli pLG338, pACYC184, the pBR series such as pBR322, the pUC series such as pUC18 or pUC19, the M113 mp series, pKC30, pRcp4, pIIS1, pHS2, pPLc236, pMBL24, pLG200, pUR290, pIN-III[113]-B1, λgt11 or pBdCI, in Streptomyces pIJ101, pIJ364, pIJ702 or pIJ361, in Bacillus pUB110, pC194 or pBD214, in Corynebacterium pSA77 or pAJ667. A strategy of maximizing the expression of recombinant protein is to express the protein in a host bacterium whose ability to cleave the recombinant protein proteolytically is disrupted (Gottesman, S., Gene Expression Technology: Methods in Enzymology 185, Academic Press, San Diego, Calif. (1990) 119-128). A further strategy is to modify the nucleic acid sequence of the nucleic acid to be inserted into an expression vector, so that the individual codons for each amino acid are those which are preferentially used in a bacterium selected for expression, such as *C. glutamicum*, et al. (Wada et al. (1992) Nucleic Acids Res. 20:2111-2118). Modification of these nucleic acid sequences according to the invention is carried out by standard techniques of DNA synthesis.

In a further embodiment, the desaturase expression vector is a yeast expression vector. Examples of vectors for expression in the yeast *S. cerevisiae* include pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and methods for the construction of vectors which are suitable for use in other fungi, such as the filamentous fungi, include those which are described in detail in: van den Hondel, C. A. M. J. J., & Punt, P. J. (1991) "Gene transfer systems and vector development for filamentous fungi", in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, the desaturases according to the invention can be expressed in insect cells using baculovirus expression vectors. Baculovirus vectors which are available for expressing proteins in cultured insect cells (for example Sf9 cells) include the pAc series (Smith et al. (1983) Mol. Cell. Biol. 3:2156-2165) and the pVL series (Lucklow and Summers (1989) Virology 170:31-39).

The abovementioned vectors are just a short review of possible suitable vectors. Further plasmids are known to the skilled worker and are described, for example, in: Cloning Vectors (Ed. Pouwels, P. H., et al., Elsevier, Amsterdam-New York-Oxford, 1985, ISBN 0 444 904018).

In yet a further embodiment, a nucleic acid according to the invention is expressed in mammalian cells using a mammalian expression vector. Mammals for the purposes of the invention are to be understood as all non-human mammals. Examples of mammalian expression vectors include pCDM8 (Seed, B. (1987) Nature 329:840) and pMT2PC (Kaufman et al. (1987) EMBO J. 6:187-195). When used in mammalian cells, the control functions of the expression vector are frequently provided by viral regulatory elements. Promoters which are usually used are derived, for example, from polyoma, adenovirus2, cytomegalovirus and Simian Virus 40. Other suitable expression systems for prokaryotic and eukaryotic cells can be found in Chapters 16 and 17 of Sambrook, J., Fritsch, E. F., and Maniatis, T., Molecular Cloning: A Laboratory Manual, 2nd Edition, Cold Spring Harbor Laboratory, Cold Spring Harbor Laboratory Press, Cold Spring Harbor, N.Y., 1989.

In another embodiment, the recombinant mammalian expression vector can control the expression of the nucleic acid preferably in a specific cell type (for example, tissue-specific regulatory elements are used for expressing the nucleic acid). Tissue-specific regulatory elements are known in the art. Nonlimiting examples of suitable tissue-specific promoters are, inter alia, the albumen promoter (liver-specific; Pinkert et al. (1987) Genes Dev. 1:268-277), lymphoid-specific promoters (Calame and Eaton (1988) Adv. Immunol. 43:235-275), in particular promoters of T-cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (for example neurofilament promoter; Byrne and Ruddle (1989) PNAS 86:5473-5477), pancreas-specific promoters (Edlund et al., (1985) Science 230:912-916) and mamma-specific promoters (for example milk serum promoter; U.S. Pat. No. 4,873,316 and European Patent Application document No. 264,166). Also included are development-regulated promoters, for example the mouse hox promoters (Kessel and Gruss (1990) Science 249:374-379) and the fetoprotein promoter (Campes and Tilghman (1989) Genes Dev. 3:537-546).

In a further embodiment, the desaturases according to the invention can be expressed in single-celled plant cells (such as algae), see Falciatore et al., 1999, Marine Biotechnology 1 (3):239-251 and references cited therein, and plant cells from higher plants (for example spermatophytes such as crops). Examples of plant expression vectors include those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, pp. 15-38.

A plant expression cassette preferably comprises regulatory sequences which can control gene expression in plant cells and which are linked functionally so that each sequence can fulfil its function, such as transcriptional termination, for example polyadenylation signals. Preferred polyadenylation signals are those derived from *Agrobacterium tumefaciens* T-DNA, such as gene 3 of the Ti plasmid pTiACH5, which is known as octopine synthase (Gielen et al., EMBO J. 3 (1984) 835 et seq.) or functional equivalents thereof, but all other terminators which are functionally active in plants are also suitable.

Since plant gene expression is very frequently not limited to the transcription level, a plant expression cassette preferably comprises other functionally linked sequences, such as translation enhancers, for example the overdrive sequence, which contains the 5'-untranslated tobacco mosaic virus leader sequence, which increases the protein/RNA ratio (Gallie et al., 1987, Nucl. Acids Research 15:8693-8711).

Plant gene expression must be linked functionally to a suitable promoter which effects gene expression in a cell- or tissue-specific manner with the correct timing. Preferred promoters are those which lead to constitutive expression (Benfey et al., EMBO J. 8 (1989) 2195-2202), such as those which are derived from plant viruses such as 35S CAMV (Franck et al., Cell 21 (1980) 285-294), 19S CaMV (see also U.S. Pat. No. 5,352,605 and WO 84/02913) or plant promoters such as the Rubisco small subunit promoter described in U.S. Pat. No. 4,962,028.

Other sequences which are preferred for use for functional linkage in plant gene expression cassettes are targeting sequences which are required for targeting the gene product into its corresponding cell compartment (for a review, see Kermode, Crit. Rev. Plant Sci. 15, 4 (1996) 285-423 and references cited therein), for example into the vacuole, the nucleus, all types of plastids such as amyloplasts, chloroplasts, chromoplasts, the extracellular space, the mitochondria, the endoplasmic reticulum, elaioplasts, peroxisomes and other compartments of plant cells.

Plant gene expression can also be facilitated via a chemically inducible promoter (for a review, see Gatz 1997, Annu. Rev. Plant Physiol. Plant Mol. Biol., 48:89-108). Chemically inducible promoters are particularly suitable when it is desired for gene expression to take place in a specific manner with regard to timing. Examples of such promoters are a salicylic acid-inducible promoter (WO 95/19443), a tetracyclin-inducible promoter (Gatz et al. (1992) Plant J. 2, 397-404) and an ethanol-inducible promoter.

Other suitable promoters are promoters which respond to biotic or abiotic stress conditions, for example the pathogen-induced PRP1 gene promoter (Ward et al., Plant. Mol. Biol. 22 (1993) 361-366), the heat-inducible tomato hsp80 promoter (U.S. Pat. No. 5,187,267), the low temperature-inducible potato alpha-amylase promoter (WO 96/12814) or the wound-inducible pinII promoter (EP-A-0 375 091).

Promoters which are particularly preferred are those which lead to gene expression in tissues and organs in which lipid and oil biosynthesis take place, in seed cells such as endosperm cells and cells of the developing embryo. Promoters which are suitable are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumin B4 promoter (LeB4; Baeumlein et al., 1992, Plant Journal, 2 (2):233-9), and promoters which lead to the seed-specific expression in monocots such as maize, barley, wheat, rye, rice and the like. Notable promoters which are suitable are the barley 1pt2 or 1pt1 gene promoter (WO 95/15389 and WO 95/23230) or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene).

The multiparallel expression of desaturases according to the invention, alone or in combination with other desaturases or elongases, may be desired in particular. The introduction of such expression cassettes can be effected by a simultaneous transformation of a plurality of individual expression constructs or by combining a plurality of expression cassettes on one construct. Also, a plurality of vectors can be transformed with in each case a plurality of expression cassettes, and transferred to the host cell.

Promoters which are also particularly suitable are those which lead to plastid-specific expression, since plastids are the compartment in which the precursors and some end products of lipid biosynthesis are synthesized. Suitable promoters such as the viral RNA polymerase promoter are described in WO 95/16783 and WO 97/06250, and the *Arabidopsis* clpP promoter, described in WO 99/46394.

The invention furthermore provides a recombinant expression vector encompassing a DNA molecule according to the invention which is cloned into the expression vector in antisense orientation, i.e. the DNA molecule is linked functionally to a regulatory sequence in such a way that it allows the expression (by transcribing the DNA molecule) of an RNA molecule which is "antisense" to the desaturase mRNA. Regulatory sequences may be selected which are linked functionally to a nucleic acid cloned in antisense orientation and which control the continuous expression of the antisense RNA molecule in a multiplicity of cell types, for example, viral promoters and/or enhancers or regulatory sequences may be selected which control the constitutive, tissue-specific or cell-type-specific expression of antisense RNA. The antisense expression vector may be present in the form of a recombinant plasmid, phagemid or attenuated virus in which the antisense nucleic acids are produced under the control of a highly effective regulatory region whose activity can be determined by the cell type into which the vector has been introduced. For an explanation of the regulation of gene expression by means of antisense genes, see Weintraub, H., et al., Antisense-RNA as a molecular tool for genetic analysis, Reviews—Trends in Genetics, Vol. 1 (1) 1986.

A further aspect of the invention relates to host cells into which a recombinant expression vector according to the invention has been introduced. The terms "host cell" and "recombinant host cell" are used interchangeably in the present context. Naturally, these terms do not only refer to the particular target cell, but also to the progeny or potential progeny of this cell. Since specific modifications may occur in subsequent generations owing to mutation or environmental effects, this progeny is not necessarily identical with the parental cell, but remains within the scope of the term as used in the present context.

The terms recombinant or transgene, for example recombinant expression vector or recombinant host or host cells is to be understood as meaning, for the purpose of the invention, that the nucleic acids according to the invention and/or their natural regulatory sequences at the 5' and 3' positions of the nucleic acids are not in their natural environment, that is to say either the location of the sequences in the original organism was altered or the nucleic acid sequences and/or the regulatory sequences were mutated in it or the nucleic acid sequences according to the invention were transferred into an organism other than the original organism or their regulatory sequences. Combinations of these modifications are also possible. Natural environment is to be understood as meaning the location of a nucleic acid sequence in an organism as it occurs in nature.

A host cell may be a prokaryotic or eukaryotic cell. For example a desaturase can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms such as *C. glutamicum*. Other suitable host cells are known to the skilled worker.

Vector DNA can be introduced into prokaryotic or eukaryotic cells by conventional transformation or transfection techniques. The terms "transformation" and "transfection", conjugation and transduction as used in the present context are intended to encompass a multiplicity of methods known in the art for introducing foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual, 2nd Ed., Cold Spring Harbor Laboratory, Cold Spring Harbor Laboratory Press, Cold Spring Harbor, N.Y., 1989) and other laboratory text books, such as Methods in Molecular Biology, 1995, Vol. 44, *Agrobacterium* protocols, Ed.: Gartland and Davey, Humana Press, Totowa, N.J.

It is known about the stable transfection of mammalian cells that only a small number of the cells integrate the foreign DNA into their genome, depending on the expression vector used and the transfection technique used. To identify and select these integrants, a gene which encodes a selectable marker (for example resistance to antibiotics) is usually introduced into the host cells together with the gene of interest. Preferred selectable markers encompass those which impart resistance to drugs such as G418, hygromycin and methotrexate, or, in plants, those which impart resistance to a herbicide such as glyphosate or glufosinate. Further suitable markers are, for example, markers which encode genes which are involved in the biosynthetic pathways of, for example, sugars or amino acids, such as β-galactosidase, ura3 or ilv2. Markers which encode genes such as luciferase, gfp or other fluorescence genes are also suitable. These markers can be used in mutants in which these genes are not functional since they have been deleted for example by means of conventional methods. Furthermore, markers which encode a nucleic acid which encodes a selectable marker can be introduced into a host cell on the same vector as the one which encodes a desaturase, or can be introduced on a separate vector. Cells which have been transfected stably with the nucleic acid introduced can be identified for example by drug selection (for example, cells which have the selectable marker integrated survive, whereas the other cells die).

To generate a microorganism with homologous recombination, a vector is generated which contains at least one segment of a desaturase gene into which a deletion, addition or substitution has been introduced in order to modify the desaturase gene hereby, for example to functionally disrupt it. This desaturase gene is preferably a *Phaeodactylum tricornutum* desaturase gene, but a homolog or analog from other organisms, even from mammalian, fungal or insect cells, can also be used. In a preferred embodiment, the vector is designed in such a way that the endogenous desaturase gene is functionally disrupted (i.e. no longer encodes a functional protein, also termed knock-out vector) upon homologous recombination. As an alternative, the vector can be designed in such a way that the endogenous desaturase gene is mutated or modified otherwise upon homologous recombination while still encoding a functional protein (for example, the upstream regulatory region can be modified in such a way that this leads to a modification of the expression of the endogenous desaturase). To generate a point mutation via homologous recombination, DNA-RNA hybrids, which are also known as chimeraplasty, and which are known from Cole-Strauss et al., 1999, Nucleic Acids Research 27(5):1323-1330 and Kmiec, Gene therapy, 1999, American Scientist, 87(3): 240-247 can also be used.

In the vector for homologous recombination, the modified segment of the desaturase gene is flanked at its 5' and 3' end by additional nucleic acid of the desaturase gene, so that homologous recombination is possible between the exogenous desaturase gene which is present on the vector and an endogenous desaturase gene in a microorganism or plant. The additional flanking desaturase nucleic acid is sufficiently long for successful homologous recombination with the endogenous gene. Usually, several hundred base pairs up to kilobases of flanking DNA (both on the 5' and on the 3' end) are present in the vector (for a description of vectors for homologous recombination, see, for example, Thomas, K. R., and Capecchi, M. R. (1987) Cell 51:503 or for the recombination in *Physcomitrella patens* on cDNA basis, see Strepp et al., 1998, Proc. Natl. Acad. Sci. USA 95 (8):4368-4373). The vector is introduced into a microorganism or plant cell (for example by means of polyethylene glycol-mediated DNA), and cells in which the desaturase gene introduced has undergone homologous recombination with the endogenous desaturase gene are selected using techniques known in the art.

In another embodiment, recombinant organisms such as microorganisms can be generated which contain selected systems which allow regulated expression of the gene introduced. The inclusion of a desaturase gene in a vector, where it is placed under the control of the lac operon, allows, for example, expression of the desaturase gene only in the presence of IPTG. These regulatory systems are known in the art.

A host cell according to the invention, such as a prokaryotic or eukaryotic host cell, growing either in culture or in a field, can be used for producing (i.e. expressing) a desaturase. In plants, an alternative method can additionally be used by directly transferring DNA into developing flowers via electroporation or *Agrobacterium*-mediated gene transfer. Accordingly, the invention furthermore provides methods of producing desaturases using the host cells according to the invention. In one embodiment, the method encompasses growing the host cell according to the invention (into which a recombinant expression vector encoding a desaturase has been introduced or into whose genome a gene encoding a wild-type or modified desaturase has been introduced) in a suitable medium until the desaturase has been produced. In a further embodiment, the method encompasses isolating the desaturases from the medium or the host cell.

Host cells which are suitable in principle for taking up the nucleic acid according to the invention, the gene product according to the invention or the vector according to the invention are all prokaryotic or eukaryotic organisms. The host organisms which are used advantageously are organisms such as bacteria, fungi, yeasts, animal cells or plant cells. Further advantageous organisms are animals or, preferably, plants or parts thereof. Fungi, yeasts or plants are preferably used, especially preferably fungi or plants, very especially preferably plants such as oil crop plants which contain large amounts of lipid compounds, such as oilseed rape, evening primrose, canola, peanut, linseed, soybean, safflower, sunflower, borage, or plants such as maize, wheat, rye, oats, triticale, rice, barley, cotton, cassava, pepper, *tagetes*, Solanaceae plants such as potato, tobacco, egg-plant and tomato, *Vicia* species, pea, alfalfa, bush plants (coffee, cacao, tea), *Salix* species, trees (oil palm, coconut) and perennial grasses and fodder crops. Especially preferred plants according to the invention are oil crop plants such as soybean, peanut, oilseed rape, canola, linseed, evening primrose, sunflower, safflower, trees (oil palm, coconut).

D. Isolated Desaturase

A further aspect of the invention relates to isolated desaturases and biologically active parts thereof. An "isolated" or "purified" protein or a biologically active part thereof is essentially free of cellular material when it is produced by recombinant DNA techniques, or free from chemical precursors or other chemicals when it is synthesized chemically. The term "essentially free of cellular material" encompasses desaturase preparations in which the protein is separated from cellular components of the cells in which it is produced naturally or recombinantly. In one embodiment, the term "essentially free of cellular material" encompasses desaturase preparations with less than approximately 30% (based on the dry weight) of non-desaturase (also referred to herein as "contaminating protein"), more preferably less than approximately 20% of non-desaturase, even more preferably less than approximately 10% of non-desaturase and most preferably less than approximately 5% of non-desaturase. If the desaturase or a biologically active part thereof has been produced recombinantly, it is also essentially free of culture medium, i.e. the culture medium amounts to less than approximately 20%, more preferably less than approximately 10% and most preferably less than approximately 5% of the volume of the protein preparation. The term "essentially free from chemical precursors or other chemicals" encompasses desaturase preparations in which the protein is separate from chemical precursors or other chemicals which are involved in the synthesis of the protein. In one embodiment, the term "essentially free of chemical precursors or other chemicals" encompasses desaturase preparations with less than approximately 30% (based on the dry weight) of chemical precursors or non-desaturase chemicals, more preferably less than approximately 20% of chemical precursors or non-desaturase chemicals, even more preferably less than approximately 10% of chemical precursors or non-desaturase chemicals and most preferably less than approximately 5% of chemical precursors or non-desaturase chemicals. In preferred embodiments, isolated proteins or biologically active parts thereof exhibit no contaminating proteins from the same organisms from which the desaturase originates. These proteins are usually produced by recombinant expression, for example, *Phaeodactylum tricornutum* desaturase in plants such as *Physcomitrella patens* or abovementioned microorganisms, for example bacteria such as *E. coli, Bacillus subtilis, C. glutamicum*, fungi such as *Mortierella*, yeasts such as *Saccharomyces*, or ciliates such as *Colpidium* or algae such as *Phaeodactylum*.

An isolated desaturase according to the invention or a part thereof can also participate in the metabolism of compounds required for the synthesis of cell membranes in *Phaeodactylum tricornutum* or in the transport of molecules via these membranes. In preferred embodiments, the protein or the part thereof encompasses an amino acid sequence which has sufficient homology with an amino acid sequence of SEQ ID NO: 2, 4, 6 or 12 for the protein or part thereof to retain the ability to participate in the metabolism of compounds required for the synthesis of cell membranes in *Phaeodactylum tricornutum* or in the transport of molecules via these membranes. The part of the protein is preferably a biologically active part as described herein. In a further preferred embodiment, a desaturase according to the invention has one of the amino acid sequences shown in SEQ ID NO: 2, 4, 6 or 12. In a further preferred embodiment, the desaturase has an amino acid sequence which is encoded by a nucleotide sequence which hybridizes with a nucleotide sequence of SEQ ID NO: 1, 3, 5 or 11, for example under stringent conditions. In yet another preferred embodiment, the desaturase has an amino acid sequence which is encoded by a nucleotide sequence which has at least approximately 50 to 60%, preferably at least approximately 60 to 70%, more preferably at least approximately 70 to 80%, 80 to 90%, 90 to 95%, and even more preferably at least approximately 96%, 97%, 98%, 99% or more homology with one of the amino acid sequences of SEQ ID NO: 2, 4, 6 or 18. The desaturase preferred according to the invention preferably also has at least one of the desaturase activities described herein. For example, a desaturase preferred according to the invention encompasses an amino acid sequence encoded by a nucleotide sequence which hybridizes with a nucleotide sequence of SEQ ID NO: 1, 3, 5 or 11, for example under stringent conditions, and which can participate in the metabolism of compounds required for the synthesis of cell membranes in *Phaeodactylum tricornutum* or in the transport of molecules via these membranes and is capable of introducing a double bond into a fatty acid with one, two, three or four double bonds and a chain length of $C_{18}$, $C_{20}$ or $C_{22}$.

In other embodiments, the desaturase is essentially homologous with an amino acid sequence of SEQ ID NO: 2, 4 or 6 and retains the functional activity of the protein of one of the sequences of SEQ ID NO: 2, 4 or 6, the amino acid sequence differing, however, owing to natural variation or mutagenesis as described in detail in the above subsection I.

In a further embodiment, the desaturase is, accordingly, a protein encompassing an amino acid sequence which has at least approximately 50 to 60% homology, preferably approximately 60 to 70% homology and more preferably at least approximately 70 to 80%, 80 to 90%, 90 to 95% homology and most preferably at least approximately 96%, 97%, 98%, 99% or more homology with a complete amino acid sequence of SEQ ID NO: 2, 4 or 6 and has at least one of the desaturase activities described herein. In another embodiment, the invention relates to a complete *Phaeodactylum tricornutum* protein which is essentially homologous with a complete amino acid sequence of SEQ ID NO: 2, 4 or 6.

Biologically active parts of a desaturase encompass peptides encompassing amino acid sequences derived from the amino acid sequence of a desaturase, for example an amino acid sequence shown in SEQ ID NO: 2, 4 or 6 or the amino acid sequence of a protein which is homologous with a desaturase, which peptides have fewer amino acids than the full-length desaturase or the full-length protein which is homologous with a desaturase and have at least one activity of a desaturase. Biologically active parts (peptides, for example peptides with a length of, for example, 5, 10, 15, 20, 30, 35, 36, 37, 38, 39, 40, 50, 100 or more amino acids) usually encompass a domain or a motif with at least one activity of a desaturase. Moreover, other biologically active parts in which other regions of the protein are deleted can be generated by recombinant techniques and examined for one or more of the activities described herein. The biologically active parts of the desaturase preferably encompass one or more selected domains/motifs or parts thereof with biological activity.

Desaturases are preferably produced by recombinant DNA techniques. For example, a nucleic acid molecule encoding the protein is cloned into an expression vector (as described above), the expression vector is introduced into a host cell (as described above), and the desaturase is expressed in the host cell. The desaturase can then be isolated from the cells by a suitable purification scheme using standard techniques of protein purification. As an alternative to the recombinant expression, a desaturase, a desaturase polypeptide or a desaturase peptide can be synthesized chemically by means of standard techniques of peptide synthesis. Moreover, native desaturase can be isolated from cells (for example endotheliol cells), for example using an anti-desaturase antibody which can be raised by standard techniques, using a desaturase according to the invention or a fragment thereof.

The invention also provides chimeric desaturase proteins or desaturase fusion proteins. As used in the present context, a "chimeric desaturase protein" or "desaturase fusion protein" encompasses a desaturase polypeptide which is bound functionally to a non-desaturase polypeptide. A "desaturase polypeptide" refers to a polypeptide with an amino acid sequence which corresponds to a desaturase, whereas a "non-desaturase polypeptide" refers to a polypeptide with an amino acid sequence which corresponds to a protein which is essentially not homologous with the desaturase, for example a protein which differs from the desaturase and which originates from the same or another organism. Within the fusion protein, the term "linked functionally" is understood as meaning that the desaturase polypeptide and the non-desaturase polypeptide are fused to each other in such a way that both sequences fulfil the predicted function which has been ascribed to the sequence used. The non-desaturase polypeptide can be fused to the N terminus or the C terminus of the desaturase polypeptide. In one embodiment, the fusion protein is, for example, an EST-desaturase fusion protein in which the desaturase sequences are fused to the C terminus of the GST sequences. These fusion proteins can facilitate the purification of the recombinant desaturases. In a further embodiment, the fusion protein is a desaturase which has a heterologous signal sequence (N terminus). In specific host cells (for example mammalian host cells), the expression and/or secretion of a desaturase can be increased by using a heterologous signal sequence.

A chimeric desaturase protein or desaturase fusion protein according to the invention is produced by standard recombinant DNA techniques. For example, DNA fragments which encode different polypeptide sequences are ligated to each other in-frame using conventional techniques, for example by employing blunt ends or overhanging ends for ligation, restriction enzyme cleavage for providing suitable ends, filling up cohesive ends, as required, treatment with alkaline phosphatase to avoid undesired linkages, and enzymation ligation. In a further embodiment, the fusion gene can be synthesized by conventional techniques including DNA synthesizers. As an alternative, PCR amplification of gene fragments can be carried out using anchor primers which generate complementary overhangs between successive gene fragments which can subsequently be hybridized with each other and reamplified to give rise to a chimeric gene sequence (see, for example, Current Protocols in Molecular Biology, Ed. Ausubel et al., John Wiley & Sons: 1992). Moreover, a large number of expression vectors which already encode a fusion unit (for example a GST polypeptide) are commercially available. A desaturase-encoding nucleic acid can be cloned into such an expression vector so that the fusion unit is linked in-frame to the desaturase protein.

Desaturase homologs can be generated by mutagenesis, for example by specific point mutation or by truncating the desaturase. The term "homologs" as used in the present context refers to a variant form of the desaturase which acts as agonist or antagonist with the desaturase activity. A desaturase agonist can essentially retain the same activity as the desaturase, or some of the biological activities of the desaturase. A desaturase antagonist can inhibit one or more activities of the naturally occurring desaturase form, for example by competitive binding to an upstream or downstream element of the metabolic cascade for cell membrane components which encompass the desaturase, or by binding to a desaturase which mediates the transport of compounds via cell membranes, thus inhibiting translocation.

In an alternative embodiment, desaturase homologs can be identified by screening combinatory libraries of desaturase mutants, for example truncated mutants, with regard to desaturase agonist or antagonist activity. In one embodiment, a variegated library of desaturase variants is generated at nucleic acid level by combinatory mutagenesis and encoded by a variegated genetic library. A variegated library of desaturase variants can be generated for example by enzymatic ligation of a mixture of synthetic oligonucleotides into gene sequences so that a degenerate set of potential desaturase sequences can be expressed as individual polypeptides or, alternatively, as a set of larger fusion proteins (for example for phage display) which comprise this set of desaturase sequences. There is a multiplicity of methods which can be used for generating libraries of potential desaturase homologs from a degenerate oligonucleotide sequence. The chemical synthesis of a degenerate gene sequence can be carried out in a DNA synthesizer, and the synthetic gene can then be ligated into a suitable expression vector. The use of the degenerate set of genes allows all sequences which encode the desired set of potential desaturase sequences to be provided in a mixture. Methods for the synthesis of degenerate oligonucleotides are known in the art (see, for example, Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In addition, libraries of desaturase fragments can be used for generating a variegated population of desaturase fragments for screening and for the subsequent selection of homologs of a desaturase. In one embodiment, a library of fragments of the coding sequence can be generated by treating a double-strand PCR fragment of a coding desaturase sequence with a nuclease under conditions under which double-strand breaks only occur approximately once per molecule, denaturing the double-stranded DNA, renaturing the DNA with the formation of double-stranded DNA which can encompass sense/antisense pairs of various products with double-strand breaks, removal of single-stranded sections from newly formed duplices by treatment with S1 nuclease, and ligating the resulting fragment library into an expression vector. Using this method, an expression library can be derived which encodes N-terminal, C-terminal and internal desaturase fragments of various sizes.

A number of techniques for screening gene products in combinatory libraries which have been generated by point mutation or truncation and for screening cDNA libraries for gene products with a selected property are known in the art. These techniques can be adapted to rapid screening of the gene libraries which have been generated by combinatory mutagenesis of desaturase homologs. The most frequently used techniques for screening large gene libraries which can be subjected to high-throughput analysis usually encompass cloning the gene library into replicable expression vectors, transforming suitable cells with the resulting vector library, and expressing the combinatory genes under conditions under which detecting the desired activity facilitates the isolation of the vector encoding the gene whose product has been detected. Recursive ensemble mutagenesis (REM), a novel technique which increases the frequency of functional mutants in the libraries, can be used in combination with the screening assays for identifying desaturase homologs (Arkin and Yourvan (1992) Proc. Natl. Acad. Sci. USA 89:7811-7815; Delgrave et al. (1993) Protein Engineering 6 (3):327-331).

A further known technique for modifying catalytic properties of enzymes or the genes encoding them is gene shuffling (see, for example, Stemmer, PNAS 1994, 91: 10747-10751, WO 97/20078 or WO 98/13487), which is a combination of gene fragments where this new combination can additionally be varied by erroneous polymerase chain reactions thus creating a high sequence diversity to be assayed. However, the prerequisite for using such an approach is a suitable screening system for testing the resulting gene diversity for functionality.

A screening method which identifies a PUFA-dependent enzyme activity or activities, is a prerequisite in particular for screening desaturase activities. As regards desaturase activities with a specificity for PUFAs, the toxicity of arachidonic acid in the presence of a toxic metabolyte (here: salicylic acid or salicylic acid derivatives) can be exploited in *Mucor* species which can be transformed with desired gene constructs by known transformation methods (Eroshin et al., Mikrobiologiya, Vol. 65, No. 1 1996, pages 31-36), to carry out a growth-based primary screening. Resulting clones can then be analyzed for their lipid constituents by means of gas chromatography and mass spectroscopy in order to identify the nature and quantity of starting materials and products.

In a further embodiment, cell-based assays can be made use of for analyzing a variegated desaturase library using further processes known in the art.

E. Uses and Processes/Methods According to the Invention

The nucleic acid molecules, proteins, protein homologs, fusion proteins, primers, vectors and host cells described herein can be used in one or more of the processes/methods which follow: identification of *Phaeodactylum* and related organisms, genome mapping of organisms which are related to *Phaeodactylum tricornutum*, identification and localization of *Phaeodactylum tricornutum* sequences of interest, evolutionary studies, determination of desaturase protein regions required for the function, modulation of a desaturase activity, modulation of the metabolism of one or more cell membrane components, modulation of the transmembrane transport of one or more compounds, and modulation of the cellular production of a desired compound such as a fine chemical. The desaturase nucleic acid molecules according to the invention have a multiplicity of uses. Firstly, they can be used for identifying an organism as *Phaeodactylum tricornutum* or a close relative thereof. They can also be used for identifying the presence of *Phaeodactylum tricornutum* or of a relative thereof in a mixed population of microorganisms. The invention provides the nucleic acid sequences of a series of *Phaeodactylum tricornutum* genes; the presence or absence of this organism can be determined by screening the extracted genomic DNA of a culture of a uniform or mixed population of microorganisms under stringent conditions with a probe covering a region of a *Phaeodactylum tricornutum* gene or parts thereof, which gene is unique to this organism. *Phaeodactylum tricornutum* itself is used for the commercial production of polyunsaturated acids and is additionally suitable for the production of PUFAs, also in other organisms, in particular when it is intended for the resulting PUFAs also to be incorporated into the triacylglycerol fraction.

Furthermore, the nucleic acid and protein molecules according to the invention can act as markers for specific regions of the genome. This is suitable not only for mapping the genome, but also for functional *Phaeodactylum tricornutum* proteins. To identify the genome region to which a certain DNA-binding protein of *Phaeodactylum tricornutum* binds, it might be possible, for example, to fragment the *Phaeodactylum tricornutum* genome, and the fragments could be incubated with the DNA-binding protein. Those which bind the protein can additionally be screened with the nucleic acid molecules according to the invention, preferably with readily detectable markers; the binding of such a nucleic acid molecule to the genome fragment makes possible the localization of the fragment on the genome map of *Phaeodactylum tricornutum* and, if this is carried out repeatedly with different enzymes, facilitates a rapid determination of the nucleic acid sequence to which the protein binds. Moreover, the nucleic acid molecules according to the invention can have sufficient homology with the sequences of related species for these nucleic acid molecules to be able to act as markers for the construction of a genomic map in related fungi or algae.

The desaturase nucleic acid molecules according to the invention are also suitable for evolutionary studies and studies of the protein structure. The metabolic and transport processes in which the molecules according to the invention are involved are utilized by many prokaryotic and eukaryotic cells; the evolutionary degree of relatedness of the organisms can be determined by comparing the sequences of the nucleic acid molecules according to the invention with those which encode similar enzymes from other organisms. Accordingly, such a comparison allows the determination of which sequence regions are conserved and which are not conserved, and this may be helpful when determining regions of the protein which are essential for enzyme function. This type of determination is valuable for protein engineering studies and may provide a clue of how much mutagenesis the protein can tolerate without losing its function.

Manipulation of the desaturase nucleic acid molecules according to the invention can lead to the production of desaturases with functional differences to the wild-type desaturases. The efficiency or activity of these proteins can be improved, they can be present in the cell in larger numbers than usual, or their efficiency or activity can be reduced. An improved efficiency or activity means, for example, that the enzyme has a higher selectivity and/or activity, preferably an activity which is at least 10% higher, especially preferably an activity which is at least 20% higher, very especially preferably an activity which is at least 30% higher than that of the original enzyme.

There exists a series of mechanisms by which modification of a desaturase according to the invention can directly affect the yield, production and/or production efficiency of a fine chemical comprising such a modified protein. Obtaining fine chemical compounds from cultures of ciliates, algae or fungi on a large scale is significantly improved when the cell secretes the desired compounds, since these compounds can be isolated readily from the culture medium (in contrast to extraction from the biomass of the cultured cells). Otherwise, purification can be improved when the cell stores compounds in-vivo in a specialized compartment with a sort of concentration mechanism. In plants which express desaturases, an increased transport may lead to better distribution within the plant tissue and the plant organs. Increasing the number or the activity of transporter molecules which export fine chemicals from the cell may allow the quantity of the fine chemicals produced, which is present in the extracellular medium, to be increased, thus facilitating harvesting and purification or, in the case of plants, more efficient distribution. In contrast, increased amounts of cofactors, precursor molecules and intermediates for the suitable biosynthetic pathways are required for efficient overproduction of one or more fine chemicals. Increasing the number and/or the activity of transporter proteins involved in the import of nutrients such as carbon sources (i.e. sugars), nitrogen sources (i.e. amino acids, ammonium salts), phosphate and sulfur can improve the production of a fine chemical owing to the elimination of all limitations of the nutrients available in the biosynthetic process. Fatty acids such as PUFAs and lipids comprising PUFAs are desirable fine chemicals themselves; optimizing the activity or increasing the number of one or more desaturases according to the invention involved in the biosynthesis of these compounds, or disrupting the activity of one or more desaturases involved in the catabolism of these compounds, can thus increase the yield, production and/or production efficiency of fatty acids and lipid molecules in ciliates, algae, plants, fungi, yeasts or other microorganisms.

The manipulation of one or more desaturase genes according to the invention can likewise lead to desaturases with modified activities which indirectly affect the production of one or more desired fine chemicals from algae, plants, ciliates or fungi. The normal biochemical metabolic processes leaked, for example, to the production of a multiplicity of waste products (for example hydrogen peroxide and other reactive oxygen species) which can actively disrupt these metabolic processes (for example, peroxynitrite is known to nitrate tyrosine side chains, thus inactivating some enzymes with tyrosin in the active center (Groves, J. T. (1999) Curr. Opin. Chem. Biol. 3 (2); 226-235)). While these waste products are normally excreted, the cells used for fermentative production on a large scale are optimized for the overproduction of one or more fine chemicals and can therefore produce more waste products than is customary for a wild-type cell. Optimizing the activity of one or more desaturases according to the invention involved in the export of waste molecules allows the improvement of the viability of the cell and the maintenance of an efficient metabolic activity. Also, the presence of high intracellular amounts of the desired fine chemical can in fact be toxic to the cell, so that the viability of the cell can be improved by increasing the ability of the cell to secrete these compounds.

Furthermore, the desaturases according to the invention can be manipulated in such a way that the relative amounts of various lipids and fatty acid molecules are modified. This can have a decisive effect on the lipid composition of the cell membrane. Since each lipid type has different physical properties, a modification of the lipid composition of the membrane can significantly modify membrane fluidity. Changes in membrane fluidity can affect the transport of molecules via the membrane which, as explained above, can modify the export of waste products or of the fine chemical produced or the import of nutrients which are required. These changes in membrane fluidity can also have a decisive effect on cell integrity; cells with comparatively weaker membranes are more susceptible to abiotic and biotic stress conditions which can damage or kill the cell. Manipulation of desaturases involved in the production of fatty acids and lipids for membrane synthesis so that the resulting membrane has a membrane composition which is more susceptible to the environmental conditions prevailing in the cultures used for the production of fine chemicals should allow more cells to survive and multiply. Larger numbers of producing cells should manifest themselves in greater yields, higher production or higher production efficiency of the fine chemical from the culture.

The abovementioned mutagenesis strategies for desaturases intended to lead to elevated yields of a fine chemical are not to be construed as limiting; variations of these strategies are readily obvious to the skilled worker. Using these mechanisms, and with the aid of the mechanisms disclosed herein, the nucleic acid and protein molecules according to the invention can be used for generating algae, ciliates, plants, animals, fungi or other microorganisms such as *C. glutamicum*, which express mutated desaturase nucleic acid and protein molecules so that the yield, production and/or production efficiency of a desired compound is improved. This desired compound can be any natural product of algae, ciliates, plants, animals, fungi or bacteria which encompasses the end products of biosynthetic pathways and intermediates of naturally occurring metabolic pathways, and also molecules which do not naturally occur in the metabolism of these cells, but which are produced by the cells according to the invention.

A further embodiment according to the invention is a process for the production of PUFAs, which comprises culturing an organism which contains a nucleic acid according to the invention, a gene construct according to the invention or a vector according to the invention which encode a polypeptide which elongates $C_{18}$-, $C_{20}$- or $C_{22}$-fatty acids with at least two double bonds in the fatty acid molecule by at least two carbon atoms under conditions under which PUFAs are produced in the organism. PUFAs produced by this process can be isolated by harvesting the organisms either from the culture in which they grow or from the field, and disrupting and/or extracting the harvested material with an organic solvent. The oil, which contains lipids, phospholipids, sphingolipids, glycolipids, triacylglycerols and/or free fatty acids with a higher PUFA content can be isolated from this solvent. The free fatty acids with a higher PUFA content can be isolated by basic or acid hydrolysis of the lipids, phospholipids, sphingolipids, glycolipids and triacylglycerols. A higher PUFA content means at least 5%, preferably 10%, especially preferably 20%, very especially preferably 40% more PUFAs than the original organism which does not have additional nucleic acid encoding the desaturase according to the invention.

The PUFAs produced by this process are preferably $C_{18}$- or $C_{20-22}$-fatty acid molecules with at least two double bonds in the fatty acid molecule, preferably three, four, in combination with a further elongase and a Δ4-desaturase five or six double bonds. These $C_{18}$- or $C_{20-22}$-fatty acid molecules can be isolated from the organism in the form of an oil, lipid or a free fatty acid. Examples of suitable organisms are those mentioned above. Preferred organisms are transgenic plants.

An embodiment according to the invention are oils, lipids or fatty acids or fractions thereof which have been prepared by the above-described process, especially preferably an oil, a lipid or a fatty acid composition comprising PUFAs and originating from transgenic plants.

A further embodiment according to the invention is the use of the oil, lipid or fatty acid composition in feeds, foods, cosmetics or pharmaceuticals.

The invention further relates to a method of identifying an antagonist or agonist of desaturases, comprising
a) contacting the cells which express the polypeptide of the present invention with a candidate substance;
b) testing the desaturate activity;
c) comparing the desaturase activity with a standard activity in the absence of the candidate material, where an increase in the desaturase activity beyond the standard indicates that the candidate material is an agonist and a reduction in the desaturase activity indicates that the candidate material is an antagonist.

The candidate substance mentioned can be a substance which has been synthesized chemically or produced by microbes and can occur, for example, in cell extracts of, for example, plants, animals or microorganisms. Moreover, the substance mentioned, while being known in the prior art, may not be known as yet as increasing or reversing the activity of the desaturases. The reaction mixture can be a cell-free extract or encompass a cell or cell culture. Suitable methods are known to the skilled worker and are described in general terms for example in Alberts, Molecular Biology the cell, 3rd Edition (1994), for example Chapter 17. The substances mentioned can be added for example to the reaction mixture or the culture medium or else injected into the cells or sprayed onto a plant.

When a sample comprising an active substance by the method according to the invention has been identified, it is either possible directly to isolate the substance from the original sample or else the sample can be divided into various groups, for example when they consist of a multiplicity of various components, in order to reduce the number of the various substances per sample and then to repeat the method according to the invention with such a "subset" of the original sample. Depending on the complexity of the sample, the above-described steps can be repeated repeatedly, preferably until the sample identified in accordance with the method according to the invention only still contains a small number of substances, or only one substance. Preferably, the substance identified in accordance with the method according to the invention, or derivatives of the substance, are formulated further so that it is suitable for use in plant breeding or in plant cell or tissue culture.

The substances which have been assayed and identified in accordance with the method according to the invention can be: expression libraries, for example cDNA expression libraries, peptides, proteins, nucleic acids, antibodies, small organic substances, hormones, PNAs or the like (Milner, Nature Medicin 1 (1995), 879-880; Hupp, Cell. 83 (1995), 237-245; Gibbs, Cell. 79 (1994), 193-198 and references cited therein). These substances can also be functional derivatives or analogs of the known inhibitors or activators. Methods of preparing chemical derivatives or analogs are known to the skilled worker. The derivatives and analogs mentioned can be assayed in accordance with prior-art methods. Moreover; computer-aided design or peptidomimetics can be used for producing suitable derivatives and analogs. The cell or the tissue which can be used for the method according to the invention is preferably a host cell according to the invention, a plant cell according to the invention or a plant tissue as described in the abovementioned embodiments.

Accordingly, the present invention also relates to a substance which has been identified in accordance with the above methods according to the invention. The substance is, for example, a homolog of the desaturases according to the invention. Homologs of the desaturases can be generated by mutagenesis, for example by point mutation or deletion of the desaturases. The term "homolog" as used in the present context denotes a variant form of the desaturases which acts as agonist or antagonist for the activity of the desaturases. An agonist can have essentially the same or part of the biological activity of the desaturases. An antagonist of the desaturases can inhibit one or more activities of the naturally occurring forms of the desaturases, for example can undergo competitive banding to a downstream or upstream member of the fatty acid synthesis metabolic pathways, which include the desaturases, or can bind to desaturases and thus reduce or inhibit the activity.

Moreover, the present invention also relates to an antibody or a fragment thereof as are described herein, which antibody or fragment inhibits the activity of the desaturases according to the invention.

In one aspect, the present invention relates to an antibody which specifically recognizes, or binds to, the above-described agonist or antagonist according to the invention.

A further aspect relates to a composition comprising the antibody, the stop identified by the method according to the invention or the antisense molecule.

In a further embodiment, the present invention relates to a kit comprising the nucleic acid according to the invention, the gene construct according to the invention, the amino acid sequence according to the invention, the antisense nucleic acid molecule according to the invention, the antibody and/or composition according to the invention, an antagonist or agonist prepared by the method according to the invention, and/or oils, lipids and/or fatty acids according to the invention or a fraction thereof. Equally, the kit can comprise the host cells, organisms, plants according to the invention or parts thereof, harvestable parts of the plants according to the invention or propagation material or else the antagonist or agonist according to the invention. The components of the kit of the present invention can be packaged in suitable containers, for example with or in buffers or other solutions. One or more of the abovementioned components may be packaged in one and the same container. In addition, or as an alternative, one or more of the abovementioned components can be adsorbed onto a solid surface, for example nitrocellulose filters, glass sheets, chips, nylon membranes or microtiter plates. The kit can be used for any of the methods and embodiments described herein, for example for the production of host cells, transgenic plants, for the detection of homologous sequences, for the identification of antagonists or agonists and the like. Furthermore, the kit can comprise instructions for the use of the kit for one of the abovementioned applications.

The present invention is illustrated in greater detail by the examples which follow, and which must not be construed as limiting. The content of any references, patent applications, patents and published patent applications cited in the present patent application is herewith incorporated by reference.

EXAMPLES SECTION

Example 1

General Methods a) General Cloning Methods:

Cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, the culture of bacteria and the sequence analysis of recombinant DNA were carried out as described in Sambrook et al. (1989) (Cold Spring Harbor Laboratory Press: ISBN 0-87969-309-6) or Kaiser, Michaelis and Mitchell (1994) "Methods in Yeast Genetics" (Cold Spring Harbor Laboratory Press: ISBN 0-87969-451-3). The transformation and culture of algae such as *Chlorella* or *Phaeodactylum* are carried out as described by El-Sheekh (1999), Biologia Plantarum 42:209-216; Apt et al. (1996) Molecular and General Genetics 252 (5):872-9.

b) Chemicals

Unless otherwise specified in the text, the chemicals used were obtained in analytical quality from Fluka (Neu-Ulm), Merck (Darmstadt), Roth (Karlsruhe), Serva (Heidelberg) and Sigma (Deisenhofen). Solutions were supplied using pure pyrogen-free water, referred to in the following text as $H_2O$, on a Milli-Q water system water purification unit (Millipore, Eschborn). Restriction endonucleases, DNA-modifying enzymes and molecular biology kits were obtained from AGS (Heidelberg), Amersham (Braunschweig), Biometra (Göttingen), Boehringer (Mannheim), Genomed (Bad Oeynhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, the Netherlands). Unless otherwise specified, they were used following the manufacturer's instructions.

c) Cell Material

The isolated nucleic acid sequences according to the invention are present in the genome of a *Phaeodactylum tricornutum* UTEX646 strain, which is available from the algae collection of the University of Texas, Austin.

*Phaeodactylum tricornutum* was cultured at 25° C. at a light/dark photo period of 14:10 hours at 22° C. and 35 microEinstein (corresponds to micromol of photons per square meter and second) in glass tubes into which air was passed in from the bottom.

The culture medium used for *Phaeodactylum tricornutum* was the f/2 culture medium supplemented with 10% organic medium of Guillard, R. R. L. (1975; Culture of phytoplankton for feeding marine invertebrates. In: Smith, W. L. and Chanley, M. H. (Eds.) Culture of marine Invertebrate animals, NY Plenum Press, pp. 29-60):

It Comprises 995.5 ml of (artificial) sea water 1 ml of $NaNO_3$ (75 g/l), 1 ml of $NaH_2PO_4$ (5 g/l), 1 ml of trace element solution, 1 ml of Tris/Cl pH 8.0, 0.5 ml of f/2 vitamin solution Trace element solution: $Na_2EDTA$ (4.36 g/l), $FeCl_3$ (3.15 g/l), Primary trace elements: $CuSO_4$ (10 g/l), $ZnSO_4$ (22 g/l), $CoCl_2$ (10 g/l), $MnCl_2$ (18 g/l), $NaMoO_4$ (6.3 g/l)

f/2 vitamin solution: biotin: 10 mg/l, thiamine 200 mg/l, vitamin B12 0.1 mg/l
org medium: sodium acetate (1 g/l), glucose (6 g/l), sodium succinate (3 g/l), Bacto-tryptone (4 g/l), yeast extract (2 g/l)

Example 2

Isolation of Total DNA from *Phaeodactylum tricornutum* UTEX646 for Hybridization Experiments The details of the isolation of total DNA refer to the work-up of plant material with a fresh weight of one gram.

CTAB buffer: 2% (w/v) N-acetyl-N,N,N-trimethylammonium bromide (CTAB); 100 mM Tris-HCl, pH 8.0; 1.4 M NaCl; 20 mM EDTA.

N-Laurylsarcosine buffer: 10% (w/v) of N-laurylsarcosine; 100 mM Tris-HCl, pH 8.0; 20 mM EDTA.

*Phaeodactylum tricornutum* cell material was triturated in a mortar under liquid nitrogen to give a fine powder which was transferred into 2 ml Eppendorf vessels. The frozen plant material was then covered with a layer of 1 ml of break buffer (1 ml of CTAB buffer, 100 ml of N-laurylsarcosine buffer, 20 ml of β-mercaptoethanol and 10 ml of proteinase K solution, 10 mg/ml) and incubated at 60° C. for one hour with continuous shaking. The homogenate obtained was distributed into two Eppendorf vessels (2 ml) and extracted twice by shaking with an equal volume of chloroform/isoamyl alcohol (24:1). For phase separation, centrifugation was carried out at 8 000×g and RT (=room temperature=~23° C.) for 15 minutes in each case. The DNA was then precipitated for 30 minutes at −70° C. using ice-cold isopropanol. The precipitated DNA was sedimented for 30 minutes at 10 000 g at 4° C. and resuspended in 180 ml of TE buffer (Sambrook et al., 1989, Cold Spring Harbor Laboratory Press: ISBN 0-87969-309-6). For further purification, the DNA was treated with NaCl (final concentration 1.2 M) and reprecipitated for 30 minutes at −70° C. using twice the volume of absolute ethanol. After a wash step with 70% strength ethanol, the DNA was dried and subsequently taken up in 50 ml of $H_2O$+RNase (final concentration 50 mg/ml). The DNA was dissolved overnight at 4° C., and the RNase cleavage was subsequently carried out for 1 hour at 37° C. The DNA was stored at 4° C.

Example 3

Isolation of Total RNA and Poly(A)$^+$RNA from Plants and *Phaeodactylum tricornutum*

Total RNA was isolated from plants such as linseed and oilseed rape and the like by a method described by Logemann et al. (1987, Anal. Biochem. 163, 21). The total RNA from moss can be obtained from protonema tissue using the GTC method (Reski et al., 1994, Mol. Gen. Genet., 244:352-359).

RNA Isolation of *Phaeodactylum tricornutum*:

Frozen samples of algae (−70° C.) were triturated in an ice-cold mortar under liquid nitrogen to give a fine powder. 2 volumes of homogenization medium (12.024 g of sorbitol, 40.0 ml of 1M Tris-HCl, pH 9 (0.2 M); 12.0 ml of 5 M NaCl (0.3 M), 8.0 ml of 250 mM EDTA, 761.0 mg of EGTA, 40.0 ml of 10% SDS were made up to 200 ml with $H_2O$ and the pH was brought to 8.5) and 4 volumes of phenol with 0.2% mercaptoethanol were added to the frozen cell powder at 40 to 50° C. while mixing thoroughly. Then, 2 volumes of chloroform were added and the mixture was stirred vigorously for 15 minutes. The mixture was centrifuged for 10 minutes at 10 000 g and the aqueous phase was extracted with phenol/chloroform (2 volumes) and subsequently extracted with chloroform.

The resulting volume of the aqueous phase was treated with 1/20 volume of 4 M sodium acetate (pH 6) and 1 volume of isopropanol (ice cold), and the nucleic acids were precipitated overnight at −20° C. The mixture was then centrifuged for 30 minutes at 000 g and the supernatant pipetted off. This was followed by a wash step with 70% strength EtOH and another centrifugation. The sediment was taken up in Tris-borate buffer (80 mM Tris-borate buffer, 10 mM EDTA, pH 7.0). The supernatant was then treated with 1/3 volume of 8 M LiCl, mixed and incubated for 30 minutes at 4° C. After recentrifugation, the sediment was washed with 70% strength ethanol, centrifuged and the sediment was dissolved in RNase-free water.

Poly(A)$^+$ RNA was isolated using Dyna Beads® (Dynal, Oslo, Norway) following the instructions in the manufacturer's protocol.

After the RNA or poly(A)$^+$ RNA concentration had been determined, the RNA was precipitated by adding 1/10 volume of 3 M sodium acetate, pH 4.6, and 2 volumes of ethanol and stored at −70° C.

For the analysis, 20 μg portions of RNA were separated in a formaldehyde-containing 1.5% strength agarose gel and transferred to nylon membranes (Hybond, Amersham). Specific transcripts were detected as described by Amasino ((1986) Anal. Biochem. 152, 304)).

Example 4

Construction of the cDNA Library

To construct the cDNA library from *Phaeodactylum tricornutum*, the first-strand synthesis was carried out using murine leukaemia virus reverse transcriptase (Roche, Mannheim, Germany) and oligo-d(T) primers, while the second-strand synthesis was carried out by incubation with DNA polymerase I, Klenow enzyme and RNase H cleavage at 12° C. (2 hours), 16° C. (1 hour) and 22° C. (1 hour). The reaction was quenched by incubation at 65° C. (10 minutes) and subsequently transferred to ice. Double-stranded DNA molecules were made blunt-ended with T4 DNA polymerase (Roche, Mannheim) at 37° C. (30 minutes). The nucleotides were removed by extraction with phenol/chloroform and Sephadex G50 spin columns. EcoRI/XhoI adapters (Pharmacia, Freiburg, Germany) were ligated to the cDNA ends by means of T4 DNA ligase (Roche, 12° C., overnight), recut with XhoI and phosphorylated by incubation with polynucleotide kinase (Roche, 37° C., 30 min). This mixture was subjected to separation on a low-melting agarose gel. DNA molecules with over 300 base pairs were eluted from the gel, extracted with phenol, concentrated on Elutip D columns (Schleicher and Schüll, Dassel, Germany) and ligated to vector arms and packaged into lambda-ZAP-Express phages using the Gigapack Gold kit (Stratagene, Amsterdam, the Netherlands), using the manufacturer's material and following their instructions.

Example 5

DNA Sequencing and Computer Analysis cDNA libraries as described in Example 4 were used for DNA sequencing by standard methods, in particular the chain termination method using the ABI PRISM Big Dye Terminator Cycle Sequencing Ready Reaction Kit (Perkin-Elmer, Weiterstadt, Germany). Sequencing of random clones which had been singled out was carried out following preparative plasmid preparation from cDNA libraries via in-vivo mass excision and retransformation of DH10B on agar plates (details on materials and protocol: Stratagene, Amsterdam, the Netherlands). Plasmid DNA was prepared from *E. coli* cultures grown overnight in Luria broth supplemented with ampicillin (see Sambrook et al. (1989) (Cold Spring Harbor Laboratory Press: ISBN 0-87969-309-6)) using a Qiagen DNA preparation robot (Qiagen, Hilden) following the manufacturer's protocols. Sequencing primers with the following nucleotide sequences were used:

```
5'-CAGGAAACAGCTATGACC-3'      (SEQ ID NO: 32)
5'-CTAAAGGGAACAAAAGCTG-3'     (SEQ ID NO: 33)
5'-TGTAAAACGACGGCCAGT-3'      (SEQ ID NO: 34)
```

The sequences were processed and annotated using the EST-MAX standard software package, which is commercially available from Bio-Max (Munich, Germany). Exploiting comparative algorithms, and using the search sequence shown in SEQ ID NO: 8, homologous genes were searched for using the BLAST program (Altschul et al. (1997) "Gapped BLAST and PSI-BLAST: a new generation of protein database search programs", Nucleic Acids Res. 25:3389-3402). Two sequences from *Phaeodactylum tricornutum* with homologies with the *Physcomitrella patens* search sequence were characterized in greater detail.

Example 5a

Isolation of *Phaeodactylum tricornutum* Desaturases Via Polymerase Chain Reaction with the Aid of Degenerate Oligonucleotides Published desaturases allow motifs to be identified which are typical of Δ5- and Δ6-desaturases. Oligonucleotide sequences with possible variations are shown in the following text. Underneath the oligonucleotide sequence, the amino acid from which the base combination can be derived is shown in the one-letter code. For example, A/G means that either an A or a G is randomly incorporated at this position in the oligonucleotide when the unit is synthesized, since the base triplet derived from the corresponding amino acid can either be AAA or AAG. The DNA sequence may also contain an inosine (i) if the determination of a base at this position permits three or four different bases owing to the genetic code. The following sequences and primers can be used:

```
5'-forward primer:
F1a:    TGG TGG AA A/G TGG   AAi CA T/C AA                  (SEQ ID NO: 35)

F1b:    TGG TGG AA A/G TGG   ACi CA T/C AA                  (SEQ ID NO: 36)

F1a:    W   W   K      W     N/T H  K/N                     (SEQ ID NO: 37)

F1b:    W   W   K      W     K   H  K/N                     (SEQ ID NO: 38)

F2a:       Gi TGG AA A/G GAi  A/C Ai CA T/C   AA             (SEQ ID NO: 39)

F2b:       Gi TGG AA A/G TTG  A/C Ai CA T/C   AA             (SEQ ID NO: 40)

F2a:       G/W W   K      E/D  K/Q/N H       K/N             (SEQ ID NO: 41)

F2b:       G/W W   K      W    K/Q/N H       K/N             (SEQ ID NO: 42)

F3a:    T A/T i    TTG  AAi  A/C A A/G  C/A G/A i   CA       (SEQ ID NO: 43)

F3b:    T A/T i    TTG  AAi  A/C A A/G  CAi         CA       (SEQ ID NO: 44)

F3a:    W         W    K/N   H/N        R/Q         H        (SEQ ID NO: 45)

F3b:    Y         W    K/N   H/N        R/Q         H        (SEQ ID NO: 46)

F4a:       GTi TGG A A/T G/A    GA A/G      CA A/G CA        (SEQ ID NO: 47)

F4b:       GTi TGG A A/T G/A    A/T A T/C   CA A/G CA        (SEQ ID NO: 48)

F4a:       V   W   K/M         E             Q    H          (SEQ ID NO: 49)

F4b:       V   W   K/M         N/Y           Q    H          (SEQ ID NO: 50)

F5a1:      CA T/C  TA T/C  TGG AA A/G AA T/C  CA G  C        (SEQ ID NO: 51)

F5a1:      CA T/C  TA T/C  TGG AA A/G AA T/C  CA A  C        (SEQ ID NO: 52)

F5a1:      H       Y       W   K      N       Q   H/Q        (SEQ ID NO: 53)

F6a:    TTG TTG AAi   A/C A A/G AA i       CA T/C  AA        (SEQ ID NO: 54)

F6a:    W   W   K/N   H/N       K/N        H      K/N        (SEQ ID NO: 55)

3'-reverse primer
R1b:        GG  A/G AA   iAG G/A TG G/A TG   T/C TC          (SEQ ID NO: 56)

R1b:        GG  A/G AA   iAA G/A TG G/A TG   T/C TC          (SEQ ID NO: 57)

R1a:         P   F    L       H      H       E               (SEQ ID NO: 58)
```

```
R1b:        P       F       F       H       H           E               (SEQ ID NO: 59)

R2a1:  AA      iAG     A/G TG   A/G TG    iA C/T    iA/G    T/C TG      (SEQ ID NO: 60)

R2a2:  AA T/C AA   A/G TG   A/G TG    iA C/T    iA/G    T/C TG          (SEQ ID NO: 61)

R2a1:  F       L       H       H       V/I         V/A        Q         (SEQ ID NO: 62)

R3a1:  AT      iTG     iGG     A/G AA   iAA      A/G TG    A/G TG       (SEQ ID NO: 63)

R3a2:  AT      A/G TT  iGG     A/G AA   iAA      A/G TG    A/G TG       (SEQ ID NO: 64)

R3a3:  AT      iTG     iGG     A/G AA   iAG      A/G TG    A/G TG       (SEQ ID NO: 65)

R3a4:  AT      A/G TT  iGG     A/G AA   iAG      A/G TG    A/G TG       (SEQ ID NO: 66)

R3a1:  I/M     H/Q     P       F        F         H         H           (SEQ ID NO: 67)

R3a2:  I/M     N       P       F        L         H         H           (SEQ ID NO: 68)

R4a1:          CT      iGG     A/G AA   iA A/G   A/G TG    A/G TG       (SEQ ID NO: 69)

R4a2:          GA      iGG     A/G AA   iA A/G   A/G TG    A/G TG       (SEQ ID NO: 70)

R4a3:          GT      iGG     A/G AA   iA A/G   A/G TG    A/G TG       (SEQ ID NO: 71)

R4a1:  =     T/R/S     P       F        F/L       H         H_          (SEQ ID NO: 72)

R5a1:  AA iAA      A/G TG   A/G TG T/C TC    T/A/G AT   T/C TG          (SEQ ID NO: 73)

R5a2:  AA iAG      A/G TG   A/G TG T/C TC    T/A/G AT   T/C TG          (SEQ ID NO: 74)

R5a1:  F   F           H       H       E        I                Q      (SEQ ID NO: 75)

R5a2:  F   L           H       H       E        I                Q      (SEQ ID NO: 76)

R6a1:  T       iGG iA A/G     iAA     A/G TG    A/G TG    iAC           (SEQ ID NO: 77)

R6a1:  T       iGG iA A/G     iAG     A/G TG    A/G TG    iAC           (SEQ ID NO: 78)

R6a1:  T/N     P       L       F/L     H         H         V            (SEQ ID NO: 79)
```

Owing to various possibilities of variations, a large number of derived oligonucleotides are possible, but surprisingly it has been found that oligonucleotides shown can be particularly suitable for isolating desaturases.

The primers can be employed for polymerase chain reactions in all combinations. Individual combinations allowed desaturase fragments to be isolated when the following conditions were taken into consideration: for PCR reactions, in each case 10 nMol of primer and 10 ng of a plasmid library obtained by in-vivo excision were employed. It was possible to isolate the plasmid library from the phage library following the protocols of the manufacturer (Stratagene). The PCR reaction was carried out in a thermocycler (Biometra) using Pfu DNA polymerase (Stratagene) and the following temperature program: 3 minutes at 96° C. followed by 35 cycles with 30 seconds at 96° C., 30 seconds at 55° C. and 1 minute at 72° C. After the first step at 55° C., the annealing temperature was lowered stepwise by in each case 3° C., and, after the fifth cycle, an annealing temperature of 40° C. was retained. Finally, a 10-minute-cycle at 72° C. was carried out, and the reaction was stopped by cooling to 4° C.

The primer combinations F6a and R4a2 are shown underlined in the text, and it was possible to exploit them successfully for isolating a desaturase fragment. It was possible to verify the resulting fragment by sequencing; it showed homologies with *Streptomyces coelicolor* desaturase with the Genbank Accession No. T36617. The homology was obtained with the aid of the BLASTP program. The alignment is shown in FIG. 4. Identities of 34% and a homology of 43% with sequence T36617 were revealed. The DNA fragment was employed in accordance with the invention as shown in Example 7 in a hybridization experiment for isolating a full-length gene under standard conditions.

The coding region of a DNA sequence isolated in this way was obtained by translating the genetic code into a polypeptide sequence. SEQ ID NO: 3 shows a sequence 1434 base pairs in length which was isolated by the method described. The sequence has a start codon in positions 1 to 3 and a stop codon in positions 1432-1434 and it was possible to translate it into a polypeptide 477 amino acids in length. In the alignment with the gene sequence described in WO 98/46763, it was found that a nonidentical, but homologous, *Phaeodactylum tricornutum* fragment encoding 87 amino acids had previously been described. However, WO 98/46763 discloses neither a complete, functionally active desaturase nor position or substrate specificity. This is also made clear by the fact that homologies with both the Δ5- and Δ6-desaturase from *Mortierella alpina* are reported without indicating a specific function. The sequence according to the invention, in contrast, encodes a functionally active Δ6-acyl lipid desaturase.

Example 6

Identification of DNA Sequences Encoding *Phaeodactylum tricornutum* Desaturases The full-length sequence of the Δ6-acyl lipid desaturase Pp_des6 AJ222980 (NCBI Genbank Accession No.) from the moss *Physcomitrella patens* (see also Table 1) and the Δ12-acyl lipid desaturase sequence (Table 1, see Ma_des12) from Mortierella alpina AF110509 (AF110509 NCBI Genbank Accession No.) were employed for sequence alignment with the aid of the TBLASTN search algorithm.

The EST sequences PT0010070010R, PT001072031R and PT001078032R were first considered as target gene among further candidate genes owing to weak homologies with the search sequences from Physcomitrella and Mortierella. FIGS. 1, 2 and 2a show the result of the two EST sequences found. The sequences found are part of the nucleic acids according to the invention of SEQ ID NO: 1 (gene name: Pt_des5, inventors' own database No. PT001078032R), SEQ ID NO: 5. (gene name: Pt_des12, inventors' own database No. PT0010070010R) and SEQ ID NO: 11 (gene name: Pt_des12.2, inventor's own database No. PT001072031R). Letters indicate identical amino acids, while the plus symbol indicates a chemically similar amino acid. The identities and homologies of all sequences found in accordance with the invention can be seen from the summary in Table 2.

Desaturases can have cytochrome b5 domains which also occur in other genes which do not code for desaturases. Thus, cytochrome b5 domains show high homologies, even though the gene functions are different. Within weakly conserved regions, desaturases can only be identified as putative candidate genes and must be tested for the enzyme activity and position specificity of the enzymatic function. For example, various hydroxylases, acetylenases and epoxygenases, like desaturases, also show histidine box motifs, so that a specific function must be proven experimentally and only the additional verification of the double bond makes possible a guaranteed enzyme activity and position specificity of a desaturase. Surprisingly, it has been found that Δ6- and Δ5-desaturases according to the invention have particularly suitable substrate specificities and are particularly suitable for being exploited, in combination with a Physcomitrella Δ6-elongase, for producing polyunsaturated fatty acids such as arachidonic acid, eicosapentaenoic acid and docosahexanoic acid.

Sequencing of the full cDNA fragment from clone PT001078032R revealed a sequence 1652 base pairs in length. The sequence encodes a polypeptide of 469 amino acids shown in SEQ ID NO: 2. It was obtained by translating the genetic code of SEQ ID NO: 1 with a start codon in base pair position 115-117 and with a stop codon in base pair position 1522-1524. The clone comprises a complete desaturase polypeptide, as can be seen from the sequence alignment in FIG. 13 lines denote identical amino acids, while colons and dots represent chemically exchangeable, i.e. chemically equivalent, amino acids. The alignment was carried out using Henikoff & Henikoff's BLOSUM62 substitution matrix ((1992) Amino acid substitution matrices from protein blocks. Proc. Natl. Acad. Sci. USA 89: 10915-10919). Parameters used: Gap Weight: 8; Average Match: 2.912, Length Weight: 2, Average Mismatch: -2.003.

FIG. 6 and FIG. 7 show the alignment of the MA_des12 peptide sequence with the sequences found.

Sequencing of the complete cDNA fragment from clone PT0010070010R revealed a sequence 1651 base pairs in length and shown in SEQ ID NO: 5 with a start codon in position 67-69 and a stop codon in position 1552-1554. The polypeptide sequence according to the invention is shown in SEQ ID NO: 6.

Sequencing the complete cDNA fragment identified from clone PT0010072031R revealed a sequence 1526 base pairs in length and shown in SEQ ID NO: 11 with a start codon in position 92-94 and a stop codon in position 1400-1402. The polypeptide sequence according to the invention is shown in SEQ ID NO: 12.

Table 2 shows the identities and homologies of desaturases according to the invention with each other and with the Physcomitrella patens and Mortierella alpina desaturase. The data were obtained with the aid of the Bestfit program under given parameters as defined hereinbelow as a subprogram of the following software: Wisconsin Package Version 10.0 (Genetics Computer Group (GCG), Madison, Wis., USA). Henikoff, S. and Henikoff, J. G. (1992). Amino acid substitution matrices from protein blocks. Proc. Natl. Acad. Sci. USA 89: 10915-10919.

Furthermore, FIG. 5 shows the alignment of the Physcomitrella patens Δ6-acyl lipid desaturase with the polypeptide sequence of clone Pt_des6.

TABLE 2

| Homology/identity in % | Search sequence Pp_des6 | Search sequence Ma_des12 |
|---|---|---|
| Pt_des5 | 34.92/26.37 | n.d. |
| Pt_des6 | 50.69/41.06 | n.d. |
| Pt_des12 | n.d. | 48.58/38.92 |
| Pt_des12.2 | n.d. | 48.37/41.60 | n.d. = not determined

With the aid of the algorithm TBLASTN 2.0.10: Altschul et al. 1997, "Gapped BLAST and PSI-BLAST: a new generation of protein database search programs", Nucleic Acids Res. 25; 3389-3402, sequences with the highest sequence homology or identity were identified via a local database alignment. The results are shown in Table 2A hereinbelow.

TABLE 2A

Homologs with the highest sequence homologies or identities with polypeptide sequences according to the invention of SEQ ID NO. 2, 4, 6 or 12

| Homology/ identity (%) | Search sequence PT001070010R | Search sequence PT001072031R | Search sequence PT001078032R | Search sequence PT_des6 |
|---|---|---|---|---|
| L26296: Fad2 A. thaliana | 50%/37% | n.d. | n.d. | n.d. |
| U86072 Petroselinum crispum Fad2 | n.d. | 51/40 | n.d. | n.d. |
| AL358652 L. major putative desaturase | n.d. | n.d. | 45/30 | n.d. |
| AB020032 M. alpina Δ6 desaturase | n.d. | n.d. | n.d. | 53/38 |

Example 7

Identification of Genes by Means of Hybridization

Gene sequences can be used for identifying homologous or heterologous genes from cDNA or genomic libraries.

Homologous genes (i.e. full-length cDNA clones which are homologous, or homologs) can be isolated via nucleic acid hybridization using, for example, cDNA libraries: the method can be used in particular for isolating functionally active full-length genes of those shown in SEQ ID NO: 3. Depending on the frequency of the gene of interest, 100 000 up to 1 000 000 recombinant bacteriophages are plated out and transferred to a nylon membrane. After denaturation with alkali, the DNA was immobilized on the membrane, for example by UV crosslinking. Hybridization is performed under high-stringency conditions. The hybridization and the wash steps are carried out in aqueous solution at an ionic strength of 1 M NaCl and a temperature of 68° C. Hybridization probes were generated for example by labeling with radioactive ($^{32}$P-) nick transcription (High Prime, Roche, Mannheim, Germany). The signals are detected by autoradiography.

Partially homologous or heterologous genes which are related but not identical can be identified analogously to the process described above using low-stringency hybridization and wash conditions. For the aqueous hybridization, the ionic strength was usually kept at 1 M NaCl, and the temperature was lowered gradually from 68 to 42° C.

The isolation of gene sequences which only exhibit homologies with an individual domain of, for example, 10 to 20 amino acids can be carried out using synthetic, radiolabeled oligonucleotide probes. Radiolabeled oligonucleotides are generated by phosphorylating the 5' end of two complementary oligonucleotides with T4 polynucleotide kinase. The complementary oligonucleotides are hybridized and ligated to each other to give rise to concatemers. The double-stranded concatemers are radiolabeled for example by nick transcription. Hybridization is usually carried out under low-stringency conditions using high oligonucleotide concentrations. Oligonucleotide Hybridization Solution:
6×SSC
0.01 M sodium phosphate
1 mM EDTA (pH 8)
0.5% SDS
100 µg/ml denatured salmon sperm DNA
0.1% dry low-fat milk During the hybridization, the temperature is lowered stepwise to 5 to 10° C. below the calculated oligonucleotide Tm or down to room temperature (unless otherwise specified, RT=~23° C. in all experiments), followed by wash steps and autoradiography. Washing is carried out at extremely low stringency, for example three wash steps using 4×SSC. Further details are as described by Sambrook, J., et al. (1989), "Molecular Cloning: A Laboratory Manual", Cold Spring Harbor Laboratory Press, or Ausubel, F. M., et al. (1994) "Current Protocols in Molecular Biology", John Wiley & Sons.

Example 8

Identification of Target Genes by Screening Expression Libraries with Antibodies To generate recombinant protein, for example E. coli, cDNA sequences were used (for example Qiagen QIAexpress pQE system). The recombinant proteins were then affinity-purified, usually via Ni-NTA affinity chromatography (Qiagen). The recombinant proteins were then used for raising specific antibodies, for example using standard techniques for immunizing rabbits. The antibodies were then affinity-purified using an Ni-NTA column which is desaturated with recombinant antigen, as described by Gu et al., (1994) BioTechniques 17:257-262. The antibody can then be used for screening expression cDNA libraries by immunological screening (Sambrook, J., et al. (1989), "Molecular Cloning: A Laboratory Manual", Cold Spring Harbor Laboratory Press, or Ausubel, F. M., et al. (1994) "Current Protocols in Molecular Biology", John Wiley & Sons).

Example 9

Transformation of Agrobacterium

Agrobacterium-mediated plant transformation can be effected for example using the Agrobacterium tumefaciens strain GV3101-(pMP90-) (Koncz and Schell, Mol. Gen. Genet. 204 (1986) 383-396) or LBA4404-(Clontech) or C58C1 pGV2260 (Deblaere et al 1984, Nucl. Acids Res. 13, 4777-4788). The transformation can be carried out by standard transformation techniques (Deblaere et al., 1984, IBID.).

Example 10

Plant Transformation

Agrobacterium-mediated plant transformation can be effected using standard transformation and regeneration techniques (Gelvin, Stanton B., Schilperoort, Robert A., Plant Molecular Biology Manual, 2nd Ed., Dordrecht: Kluwer Academic Publ., 1995, in Sect., Ringbuc Zentrale Signatur: BT11-P ISBN 0-7923-2731-4; Glick, Bernard R., Thompson, John E., Methods in Plant Molecular Biology and Biotechnology, Boca Raton: CRC Press, 1993, 360 pp., ISBN 0-8493-5164-2).

For example, oilseed rape can be transformed by means of cotyledon or hypocotyl transformation (Moloney et al., Plant Cell 8 (1989) 238-242; De Block et al., Plant Physiol. 91 (1989) 694-701). The use of antibiotics for the selection of agrobacteria and plants depends on the binary vector and the agrobacterial strain used for the transformation. The selection of oilseed rape is normally carried out using kanamycin as selectable plant marker.

Agrobacterium-mediated gene transfer in linseed (Linum usitatissimum) can be carried out for example using a technique described by Mlynarova et al. (1994) Plant Cell Report 13:282-285.

The transformation of soybean can be carried out for example using a technique described in EP-A-0 0424 047 (Pioneer Hi-Bred International) or in EP-A-0 0397 687, U.S. Pat. No. 5,376,543, U.S. Pat. No. 5,169,770 (University Toledo).

Plant transformation using particle bombardment, polyethylene glycol-mediated DNA uptake or via the silicon carbonate fiber technique is described, for example, by Freeling and Walbot "The maize handbook" (1993) ISBN 3-540-97826-7, Springer Verlag New York).

Example 11

Plasmids for Plant Transformation

Binary vectors such as pBinAR (Höfgen and Willmitzer, Plant Science 66 (1990) 221-230) or pGPTV (Becker et al 1992, Plant Mol. Biol. 20:1195-1197) or derivatives of these can be used for transforming plants. The binary vectors can be constructed by ligating the cDNA in sense or antisense orientation into T-DNA. 5' of the cDNA, a plant promoter activates cDNA transcription. A polyadenylation sequence is located 3' of the cDNA. The binary vectors can contain different marker genes. In particular, the nptII marker gene encoding kanamycin resistance mediated by neomycin phosphotransferase can be exchanged for the herbicide-resistant form of an acetolactate synthase gene (abbreviation: AHAS or ALS). The ALS gene is described in Ott et al., J. Mol. Biol. 1996, 263:359-360. The v-ATPase-c1 promoter can be cloned into plasmid pBin19 or pGPTV and exploited for marker gene expression by cloning it before the ALS coding region. The promoter stated corresponds to a 1153 base pair fragment from *Beta vulgaris* (Plant Mol. Biol., 1999, 39:463-475). Both sulfonylureas and imidazolinones such as imazethapyr or sulfonylureas can be used as antimetabolites for selection.

Tissue-specific expression can be achieved by using a tissue-specific promoter. For example, seed-specific expression can be achieved by cloning the DC3 or the LeB4 or the USP promoter or the phaseolin promoter 5' of the cDNA. Any other seed-specific promoter element can also be used, such as, for example, the napin or arcelin promoter (Goossens et al. 1999, Plant Phys. 120 (4):1095-1103 and Gerhardt et al. 2000, Biochimica et Biophysica Acta 1490 (1-2):87-98). The CaMV 35S promoter or a v-ATPase C1 promoter can be used for constitutive expression in intact plants.

In particular, genes encoding desaturases and elongases can be cloned into a binary vector one after the other by constructing several expression cassettes in order to imitate the metabolic pathway in plants.

Within an expression cassette, the protein to be expressed can be targeted into a cellular compartment using a signal peptide, for example for plastids, mitochondria or the endoplasmic reticulum (Kermode, Crit. Rev. Plant Sci. 15, 4 (1996) 285-423). The signal peptide is cloned 5' in-frame with the cDNA in order to achieve subcellular localization of the fusion protein.

Examples of multiexpression cassettes are given hereinbelow.

I.) Promoter-Terminator Cassettes

Expression cassettes are composed of at least two functional units, such as a promoter and a terminator. Further desired gene sequences such as targeting sequences, terminator. In order to construct expression cassettes, promoters and terminators (USP promoter: Baeumlein et al., Mol. Gen. Genet., 1991, 225 (3):459-67); OCS terminator: Gielen et al. EMBO J. 3 (1984) 835 et seq.) are isolated with the aid of polymerase chain reaction and tailor-made as desired with flanking sequences based on synthetic oligonucleotides.

Examples of the oligonucleotides which can be used are the following:

```
USP1 front:  CCGGAATTCGGCGCGCCGAGCTCCTCGAGCAAATTTACACATTGCCA     (SEQ ID NO: 80)
USP2 front:  CCGGAATTCGGCGCGCCGAGCTCCTCGAGCAAATTTACACATTGCCA     (SEQ ID NO: 80)
USP3 front:  CCGGAATTCGGCGCGCCGAGCTCCTCGAGCAAATTTACACATTGCCA     (SEQ ID NO: 80)
USP1 back:   AAAACTGCAGGCGGCCGCCCACCGCGGTGGGCTGGCTATGAAGAAATT    (SEQ ID NO: 81)
USP2 back:   CGCGGATCCGCTGGCTATGAAGAAATT                         (SEQ ID NO: 82)
USP3 back:   TCCCCCGGGATCGATGCCGGCAGATCTGCTGGCTATGAAGAAATT       (SEQ ID NO: 83)
OCS1 front:  AAAACTGCAGTCTAGAAGGCCTCCTGCTTTAATGAGATAT            (SEQ ID NO: 84)
OCS2 front:  CGCGGATCCGATATCGGGCCCGCTAGCGTTAACCCTGCTTTAATGAGATAT (SEQ ID NO: 85)
OCS3 front:  TCCCCCGGGCCATGGCCTGCTTTAATGAGATAT                   (SEQ ID NO: 86)
OCS1 back:   CCCAAGCTTGGCGCGCCGAGCTCGAATTCGTCGACGGACAATCAGTAAATTGA (SEQ ID NO: 87)
OCS2 back:   CCCAAGCTTGGCGCGCCGAGCTCGAATTCGTCGACGGACAATCAGTAAATTGA (SEQ ID NO: 87)
OCS3 back:   CCCAAGCTTGGCGCGCCGAGCTCGTCGACGGACAATCAGTAAATTGA       (SEQ ID NO: 88)
```

The methods are known to the skilled worker in the art and are generally known from the literature.

In a first step, a promoter and a terminator are amplified via PCR. Then, the terminator is cloned into a recipient plasmid and, in a second step, the promoter is inserted before the terminator. This gives an expression cassette on a carrier plasmid. Plasmids pUT1, pUT2 and pUT3 are generated on the basis of plasmid pUC19.

The constructs are defined in accordance with the invention in SEQ ID NO: 13, 14 and 15. Based on pUC19, they comprise the USP promoter and the OCS terminator. Based on these plasmids, construct pUT12 is generated by cutting pUT1 with SalI/ScaI and cutting pUT2 with XhoI/ScaI. The fragments in the expression cassette are ligated and transformed into *E. coli* XLI blue MRF. After singling out ampicillin-resistant colonies, DNA is prepared, and those clones which comprise two expression cassettes are identified by restriction analysis. The XhoI/SalI ligation of compatible ends has eliminated the two cleavage sites XhoI and SalI between the expression cassettes. This gives rise to plasmid pUT12, which is defined in SEQ ID NO: 16. pUT12 is subsequently cut again with SalI/ScaI and pUT3 with XhoI/ScaI. The fragments comprising the expression cassettes are ligated and transformed into *E. coli* XLI blue MRF. After singling out ampicillin-resistant columns, DNA is prepared, and those clones which comprise three expression cassettes are identified by restriction analysis. In this manner, a set of multiexpression cassettes is created which can be exploited for inserting the desired DNA and is described in Table 3 and can additionally incorporate further expression cassettes.

They comprise the following elements:

TABLE 3

| pUC19 derivate | Cleavage sites for the USP promoter | Multiple cloning cleavage sites | Cleavage sites behind the OCS terminator |
|---|---|---|---|
| pUT1 | EcoRI/AscI/SacI/XhoI | BstXI/NotI/PstI/XbaI/StuI | SalI/EcoRI/SacI/AscI/HindIII |
| pUT2 | EcoRI/AscI/SacI/XhoI | BamHI/EcoRV/ApaI/NheI/HpaI | SalI/EcoRI/SacI/AscI/HindIII |
| pUT3 | EcoRI/AscI/SacI/XhoI | BglII/NaeI/ClaI/SmaI/NcoI | SalI/SacI/AscI/HindIII |
| pUT12 Double expression cassette | EcoRI/AscI/SacI/XhoI | BstXI/NotI/PstI/XbaI/StuI and BamHI/EcoRV/ApaI/NheI/HpaI | SalI/EcoRI/SacI/AscI/HindIII |
| pUT123 Triple expression cassette | EcoRI/AscI/SacI/XhoI | 1. BstXI/NotI/PstI/XbaI/StuI and 2. BamHI/EcoRV/ApaI/NheI/HpaI and 3. BglII/NaeI/ClaI/SmaI/NcoI | SalI/SacI/AscI/HindIII |

Furthermore, further multiexpression cassettes can be generated and employed for the seed-specific gene expression, as described and as specified in greater detail in Table 4, with the aid of the
i) USP promoter or with the aid of the
ii) approx. 700 base pair 3' fragment of the LeB4 promoter or with the aid of the
iii) DC3 promoter.

The DC3 promoter is described in Thomas, Plant Cell 1996, 263:359-368 and consists merely of the region −117 to +27, which is why it therefore constitutes one of the smallest known seed-specific promoters. The expression cassettes can comprise several copies of the same promoter or else be constructed via three different promoters.

question (pBUT1 is shown in SEQUENCE ID NO: 20, pBUT2 is shown in SEQUENCE ID NO: 21, pBUT3 is shown in SEQUENCE ID NO: 22, pBUT 12 is shown in SEQUENCE ID NO: 22 and pBUT123 is shown in SEQUENCE ID NO: 24) are available in accordance with the invention in kit form. As an alternative, gene sequences can be inserted into the pUC19-based expression cassettes and inserted into pGPTV+AscI in the form of an AscI fragment.

In pUT12, the Δ6-elongase Pp_PSE1 is first inserted into the first cassette via BstXI and XbaI. Then, the moss Δ6-desaturase (Pp_des6) is inserted into the second cassette via BamHI/NaeI. This gives rise to the construct pUT-ED. The AscI fragment from plasmid pUT-ED is inserted into the AscI-cut vector pGPTV+AscI, and the orientation of the inserted fragment is determined by restriction or sequencing.

TABLE 4

Multiple expression cassettes

| Plasmid name of the pUC19 derivative | Cleavage sites before the respective promoter | Multiple cloning cleavage sites | Cleavage sites behind the OCS terminator |
|---|---|---|---|
| pUT1 (pUC19 with USP-OCS1) | EcoRI/AscI/SacI/XhoI | (1)BstXI/NotI/PstI/XbaI/StuI | SalI/EcoRI/SacI/AscI/HindIII |
| pDCT (pUC19 with DC3-OCS) | EcoRI/AscI/SacI/XhoI | (2)BamHI/EcoRV/ApaI/NheI/HpaI | SalI/EcoRI/SacI/AscI/HindIII |
| pLeBT (pUC19-with LeB4(700)-OCS) | EcoRI/AscT/SacI/XhoI | (3)BglII/NaeI/ClaI/SmaI/NcoI | SalI/SacI/AscI/HindIII |
| pUD12 (pUC 19 with USP-OCS1 and with DC3-OCS) | EcoRI/AscI/SacI/XhoI | (1)BstXI/NotI/PstI/XbaI/StuI and (2)BamHI/EcoRV/ApaI/NheI/HpaI | SalI/EcoRI/SacI/AscI/HindIII |
| pUDL123 Triple expression cassette (pUC19 with USP/DC3 and LeB4-700) | EcoRI/AscI/SacI/XhoI | (1)BstXI/NotI/PsfI/XbaI/StuI and (2)BamHI/(EcoRV*)/ApaI/NheI/HpaI and (3)BglII/NaeI/ClaI/SmaI/NcoI | SalI/SacI/AscI/HindIII |

*EcoRV cleavage site in the 700 base-pair fragment of the LeB4 promoter (LeB4-700).

Further promoters for multi-gene constructs can be generated analogously, in particular using the
a) 2.7 kb fragment of the LeB4 promoter or with the aid of the
b) phaseolin promoter or with the aid of the
c) constitutive v-ATPase c1 promoter.

It may be particularly desirable to use further especially suitable promoters for constructing seed-specific multi-expression cassettes such as, for example, the napin promoter or the arcelin-5 promoter.

ii) Generation Of Expression Construct in pUC19 Derivatives Or pGPTV Derivatives Receiving Promoter and Terminator and Comprised in Combination With Desired Gene Sequences for PUFA Gene Expression in Plant Expression Cassettes.

Using AscI, multi-expression cassettes can be inserted directly from pUC19 derivatives of Table 3 into the vector pGPTV+AscI (see iii.)) via the AscI cleavage site and are available for inserting target genes. The gene constructs in question This gives rise to plasmid pB-DHGLA, whose complete sequence is shown in SEQUENCE ID NO. 25. The coding region of the *Physcomitrella* Δ6-elongase is shown in SEQUENCE ID NO. 26, that of the *Physcomitrella* Δ6-desaturase in SEQUENCE ID NO; 27.

In pUT123, the Δ6-elongase Pp_PSE1 is first inserted into the first cassette via BstXI and XbaI. Then, the moss Δ6-desaturase (Pp_des6) is inverted into the second cassette via BamHI/NaeI, and, finally, the *Phaeodactylum* Δ5-desaturase (Pt_des5) is inserted into the third cassette via BglII. The triple construct is given the name pARA1. Taking into consideration sequence-specific restriction cleavage sites, further expression cassettes termed pARA2, pARA3 and pARA4 can be generated, as shown in Table 5.

The AscI fragment from plasmid pARA1 is inserted into the AscI-cut vector pGPTV+AscI and the orientation of the inserted fragment is determined by means of restriction or sequencing. The complete sequence of the resulting plasmid pBARA1 is shown in SEQUENCE ID NO. 28. The coding region of the *Physcomitrella* Δ6-elongase is shown in SEQUENCE ID NO. 29, that of the *Physcomitrella* Δ6-desaturase in SEQUENCE ID NO: 30 and that of the *Phaeodactylum tricornutum* Δ5-desaturase in SEQUENCE ID NO: 31.

TABLE 5

Combinations of desaturases and elongases

| Gene Plasmid | Δ6-desaturase | Δ5-desaturase | Δ6-elongase |
|---|---|---|---|
| 1 PUT_ED | Pp_des6 | — | Pp_PSE1 |
| 2 pARA1 | Pt_des6 | Pt_des5 | Pp_PSE1 |
| 3 pARA2 | Pt_des6 | Ce_des5 | Pp_PSE1 |
| 4 pARA3 | Pt_des6 | Ce_des5 | Pp_PSE1 |
| 5 pARA4 | Ce_des6 | Ce_des5 | Ce_PSE1 |
| 6 PBDHGLA | Pt_des6 | — | Pp_PSE1 |
| 7 PBARAI | Pt_des6 | Pt_des5 | Pp_PSE1 |

Plasmids 1 to 5 are pUC derivatives, plasmids 6 to 7 are binary plant transformation vectors
Pp=*Physcomitrella patens*, Pt=*Phaeodactylum tricornutum*
Pp_PSE1 corresponds to the sequence of SEQ ID NO: 9.
PSE=PUFA-specific Δ6-elongase
Ce_des5=*Caenorhabditis elegans* Δ5-desaturase (Genbank Acc. No. AF078796)
Ce_des6=*Caenorhabditis elegans* Δ6-desaturase (Genbank Acc. No. AF031477, bases 11-1342)
Ce_PSE1=*Caenorhabditis elegans* Δ6-elongase (Genbank Acc. No. AF244356, bases 1-867)
Further desaturases or elongase gene sequences can also be inserted into expression cassettes of the above-described type, such as, for example, Genbank Acc. No. AF231981, NM_013402, AF206662, AF268031, AF226273, AF110510 or AF110509.

iii) Transfer of Expression Cassettes Into Vectors for the Transformation of *Agrobacterium tumefaciens* and for the Transformation of Plants Chimeric gene constructs based on those described in pUC19 can be inserted into the binary vector pGPTV by means of AscI. For this purpose, the multiple cloning sequence is extended by an AscI cleavage site. For this purpose, the polylinker is newly synthesized as two double-stranded oligonucleotides, an additional AscI DNA sequence being inserted. The oligonucleotide is inserted into the vector pGPTV by means of EcoRI and HindIII. This gives rise to plasmid pGPTV+AscI. The cloning techniques required are known to the skilled worker and can simply be found as described in Example 1.

Example 12

In-Vivo Mutagenesis

The in-vivo mutagenesis of microorganisms can be performed by passaging the plasmid DNA (or any other vector DNA) via *E. coli* or other microorganisms (for example *Bacillus* spp. or yeasts such as *Saccharomyces cerevisiae*) in which the ability of maintaining the integrity of the genetic information is disrupted. Conventional mutator strains have mutations in the genes for the DNA repair system (for example mutHLS, mutD, mutT and the like; as reference, see Rupp, W. D. (1996) DNA repair mechanisms, in: *Escherichia coli* and *Salmonella*, pp. 2277-2294, ASM: Washington). These strains are known to the skilled worker. The use of these strains is illustrated for example in Greener, A., and Callahan, M. (1994) Strategies 7:32-34. The transfer of mutated DNA molecules into plants is preferably effected after the microorganisms have been selected and tested. Transgenic plants are generated in accordance with various examples in the examples section of the present document.

Example 13

Studying the Expression of a Recombinant Gene Product in a Transformed Organism

The activity of a recombinant gene product in the transformed host organism can be measured at the transcription and/or translation level.

A suitable method for determining the amount of transcription of the gene (which indicates the amount of RNA available for translation of the gene product) is to carry out a Northern blot as specified hereinbelow (for reference, see Ausubel et al. (1988) Current Protocols in Molecular Biology, Wiley: New York, or the abovementioned examples section) in which a primer which is designed such that it binds to the gene of interest is labeled with a detectable label (usually radioactivity or chemiluminescent) so that, when the total RNA of a culture of the organism is extracted, separated on a gel, transferred to a stable matrix and incubated with this probe, binding and the extent of binding of the probe indicate the presence and also the quantity of the mRNA for this gene. This information indicates the degree of transcription of the transformed gene. The total cell RNA can be prepared from cells, tissues or organs by a plurality of methods, all of which are known in the art, such as, for example, the method of Bormann, E. R., et al. (1992) Mol. Microbiol. 6:317-326.

Northern Hybridization

For the RNA hybridization, 20 g of total RNA or 1 μg of poly(A)$^+$ RNA were separated by gel electrophoresis in 1.25% strength agarose gel using formaldehyde as described by Amasino (1986, Anal. Biochem. 152, 304), transferred to positively charged nylon membranes (Hybond N+, Amersham, Braunschweig) by capillary attraction using 10×SSC, immobilized by means of UV light and prehybridized for 3 hours at 68° C. using hybridization buffer (10% dextran sulfate w/v, 1 M NaCl, 1% SDS, 100 mg herring sperm DNA). The DNA probe had been labeled with the Highprime DNA labeling kit (Roche, Mannheim, Germany) during the prehybridization stage using alpha-$^{32}$P-dCTP (Amersham, Braunschweig, Germany). The hybridization was carried out after adding the labeled DNA probe in the same buffer at 68° C. overnight. The wash steps were carried out twice for 15 minutes using 2×SSC and twice for 30 minutes using 1×SSC, 1% SDS, at 68° C. The sealed filters were exposed at −70° C. for a period of 1 to 14 days.

Standard techniques such as a Western blot (see, for example, Ausubel et al. (1988) Current Protocols in Molecular Biology, Wiley: New York) can be employed for studying the presence or the relative quantity of protein translated from this mRNA. In this method, the total cell proteins are extracted, separated by means of gel electrophoresis, transferred to a matrix such as nitrocellulose, and incubated with a probe such as an antibody which specifically binds to the desired protein. This probe is usually provided with a chemiluminescent or colorimetric label which can be detected readily. The presence and the quantity of the label observed indicates the presence and quantity of the desired mutated protein which is present in the cell.

Example 14

Analysis of the Effect of the Recombinant Proteins on the Production of the Desired Product The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cell components for the increased production of the desired product (i.e. of lipids or a fatty acid). These analytical techniques are known to the skilled worker and encompass spectroscopy, thin-layer chromatography, various staining methods, enzymatic and microbiological methods, and analytical chromatography such as high-performance liquid chromatography (see, for example, Ullman, Encyclopedia of Industrial Chemistry, Vol. A2, pp. 89-90 and pp. 443-613, VCH Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", pp. 469-714, VCH Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, pp. 1-27, VCH Weinheim; and Dechow, F. J. (1989) Separation and purification techniques in biotechnology, Noyes Publications).

In addition to the abovementioned methods, plant lipids are extracted from plant materials as described by Cahoon et al. (1999) Proc. Natl. Acad. Sci. USA 96 (22):12935-12940, and Browse et al. (1986) Analytic Biochemistry 152:141-145. Qualitative and quantitative lipid or fatty acid analysis is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for producing the desired compound, such as intermediates and byproducts, in order to determine the overall production efficiency of the compound. The analytical methods encompass measurements of the nutrient quantities in the medium (for example sugars, hydrocarbons, nitrogen sources, phosphate and other ions), measurements of biomass concentration and growth, analysis of the production of customary metabolites of biosynthetic pathways, and measurements of gases which are generated during fermentation. Standard methods for these measurements are described in Applied Microbial Physiology; A Practical Approach, P. M. Rhodes and P. F. Stanbury, Ed., IRL Press, S. 103-129; 131-163 and 165-192 (ISBN: 0199635773) and references cited therein.

One example is the analysis of fatty acids (abbreviations: FAME, fatty acid methyl ester; GC-MS, gas-liquid chromatography/mass spectrometry; TAG, triacylglycerol; TLC, thin-layer chromatography).

The unambiguous detection of the presence of fatty acid products can be obtained by analyzing recombinant organisms by analytical standard methods: GC, GC-MS or TLC, as they are described on several occasions by Christie and the references therein (1997, in: Advances on Lipid Methodology, Fourth Edition: Christie, Oily Press, Dundee, 119-169; 1998, gas chromatography/mass spectrometry methods, Lipide 33:343-353).

The material to be analyzed can be disrupted by ultrasonication, grinding in a glass mill, liquid nitrogen and grinding or by other applicable methods. After disruption, the material must be centrifuged. The sediment is resuspended in distilled water, heated for 10 minutes at 100° C., ice-cooled and recentrifuged, followed by extraction in 0.5 M sulfuric acid in methanol with 2% dimethoxypropane for 1 hour at 90° C., which leads to hydrolyzed oil and lipid compounds which give transmethylated lipids. These fatty acid methyl esters are extracted in petroleum ether and finally subjected to GC analysis using a capillary column (Chrompack, WCOT Fused Silica, CP-Wax-52 CB, 25 µm, 0.32 mm) at a temperature gradient between 170° C. and 240° C. for 20 minutes and 5 minutes at 240° C. The identity of the resulting fatty acid methyl esters must be defined using standards which are commercially available (i.e. Sigma).

In the case of fatty acids for which no standards are available, the identity must be demonstrated via derivatization followed by GC/MS analysis. For example, the localization of fatty acids with triple bonds must be demonstrated via GC/MS following derivatization with 4,4-dimethoxyoxazolin derivatives (Christie, 1998, see above).

Expression Constructs in Heterologous Microbial System Strains, Wash Conditions and Plasmids The *Escherichia coli* strain XL1 Blue MRF' kan (Stratagene) was used for subcloning novel *Physcomitrella patens* desaturase pPDesaturase1. For functionally expressing this gene, we used the *Saccharomyces cerevisiae* strain INVSc 1 (Invitrogen Co.). *E. coli* was grown in Luria-Bertini broth (LB, Duchefa, Haarlem, the Netherlands) at 37° C. If necessary, ampicillin (100 mg/liter) was added, and 1.5% of agar (w/v) was added for solid LB media. *S. cerevisiae* was grown at 30° C. either in YPG medium or in complete minimal dropout uracil medium (CMdum; see in: Ausubel, F. M., Brent, R., Kingston, R. E., Moore, D. D., Seidman, J. G., Smith, J. A., Struhl, K., Albright, L. B., Coen, D. M., and Varki, A. (1995) Current Protocols in Molecular Biology, John Wiley & Sons, New York) together with 2% (w/v) of either raffinose or glucose. For solid media, 2% (w/v) of Bacto™-agar (Difco) were added. The plasmids used for cloning an expression are pUC18 (Pharmacia) and pYES2 (Invitrogen Co.).

Example 16

Cloning and Expression of PUFA-Specific *Phaeodactylum tricornutum* Desaturases For the expression in yeast, the *Phaeodactylum tricornutum* cDNA clones from SEQ ID NO: 1, 3, 5 or 11 or the sequences from SEQ ID NO: 7 or 9 or other desired sequences were first modified in such a way that only the coding regions are amplified by means of polymerase chain reaction with the aid of two oligonucleotides. Care was taken that a consensus sequence for the start codon was retained for efficient translation. To this end, either the base sequence ATA or AAA was selected and inserted into the sequence before the ATG (Kozak, M. (1986) Point mutations define a sequence flanking the AUG initiator codon that modulates translation by eukaryotic ribosomes, Cell 44, 283-292). A restriction cleavage site was additionally introduced before this consensus triplet, which restriction cleavage site must be compatible with the cleavage site of the target vector into which the fragment is to be cloned and with the aid of which gene expression is to take place in microorganisms or plants.

The PCR reaction was carried out with plasmid DNA as template in a thermocycler (Biometra) using Pfu DNA (Stratagene) polymerase and the following temperature program: 3 minutes at 96° C., followed by 30 cycles with 30 seconds at 96° C., 30 seconds at 55° C. and 2 minutes at 72° C., 1 cycle with 10 minutes at 72° C. and stop at 4° C. The annealing temperature was varied depending on the oligonucleotides chosen. A synthesis time of approximately one minute can be assumed per kilobase pairs of DNA. Further parameters which have an effect on the PCR, such as, for example, Mg ions, salt, DNA polymerase and the like are known to the skilled worker and can be varied as required.

The correct size of the amplified DNA fragment was controlled by means of agarose TBE gel electrophoresis. The amplified DNA was extracted from the gel using the QIAquick gel extraction kit (QIAGEN) and ligated into the SmaI restriction site of the dephosphorylated vector pUC18 using the Sure Clone Ligations Kit (Pharmacia), giving rise to the pUC derivatives. Following the transformation of E. coli XL1 Blue MRF' kan, a DNA mini preparation (Riggs, M. G., & McLachlan, A. (1986) A simplified screening procedure for large numbers of plasmid mini-preparation. BioTechniques 4, 310-313) was carried out on ampicillin-resistant transformants, and positive clones were identified by means of BamHI restriction analysis. The sequence of the cloned PCR product was confirmed by resequencing using the ABI PRISM Big Dye Terminator Cycle Sequencing Ready Reaction Kit (Perkin-Elmer, Weiterstadt).

```
Δ5 acyl lipid desaturase, Pt_des5
Primer 1
                                    (SEQ ID NO: 89)
GAG CTC ACA TAA TGG CTC CGG ATG CGG ATA AGC Primer 2
                                    (SEQ ID NO: 90)
CTC GAG TTA CGC CCG TCC GGT CAA GGG
```

The PCR fragment (1428 bp) was cloned into pUC18 with the aid of the Sure Clone kit (Pharmacia), the inserted fragment was digested with SacI/XhoI, and the fragment was inserted into pYES2 or pYES6 with the aid of suitable restriction cleavage sites.

```
Δ6 acyl lipid desaturase Pt_des6
Primer 3
                                    (SEQ ID NO: 91)
GGA TCC ACA TAA TGG GCA AAG GAG GGG ACG CTC GGG Primer 4
                                    (SEQ ID NO: 92)
CTC GAG TTA CAT GGC GGG TCC ATC GGG
```

The PCR fragment (1451 bp) was cloned into pUC18 with the aid of the Sure Clone kit (Pharmacia), the inserted fragment was digested with BamHI/XhoI, and the fragment was inserted into pYES2 or pYES6 with the aid of suitable restriction cleavage sites.

```
Δ12 acyl lipid desaturase Pt_des12
Primer 5
                                    (SEQ ID NO: 93)
GGA TCC ACA TAA TGG TTC GCT TTT CAA CAG CC
```

```
Primer 6
                                    (SEQ ID NO: 94)
CTC GAG TTA TTC GCT CGA TAA TTT GC Δ12 acyl lipid desaturase Pt_des12.2
Primer 7
                                    (SEQ ID NO: 95)
GGA TCC ACA TAA TGG GTA AGG GAG GTC AAC G Primer 8
                                    (SEQ ID NO: 96)
CTC GAG TCA TGC GGC TTT GTT TCG C
```

The PCR fragment (1505 bp) was cloned into pUC18 with the aid of the Sure Clone kit (Pharmacia), the inserted fragment was digested with BamHI/XhoI, and the fragment was inserted into pYES2 or pYES6 with the aid of suitable restriction cleavage sites.

The plasmid DNA was cleaved with restriction enzyme(s) to match the introduced cleavage site of the primer sequence, and the fragment obtained was ligated into the compatible restriction sites of the dephosphorylated yeast/E. coli shuttle vector pYES2 or pYES6, giving rise to pYES derivatives. Following the transformation of E. coli, and DNA minipreparation from the transformants, the orientation of the DNA fragment in the vector was verified by suitable restriction cleavage or sequencing. One clone was used for the DNA maxipreparation with the Nucleobond® AX 500 plasmid DNA extraction kit (Macherey-Nagel, Düringen).

Saccharomyces cerevisiae INVSc1 was transformed with the pYES derivatives and pYES blank vector by means of a PEG/lithium acetate protocol (Ausubel et al., 1995). Following selection on CMdum agar plates with 2% glucose, pYES derivative transformants and one pYES2 transformant were selected for further cultivation and functional expression. For pYES6 derivatives, blasticidin was used as antimetabolite. In the case of coexpression based on pYES2 and pYES6, selection was carried out with blasticidin on minimal medium.

Functional Expression of a Desaturase Activity in Yeast

Preculture 20 ml of liquid CMdum dropout uracil medium which, however, contains 2% (w/v) of raffinose were inoculated with the transgenic yeast clones (pYES2) and grown for 3 days at 30° C., 200 rpm, until an optical density at 600 nm ($OD_{600}$) of 1.5 to 2 had been reached. If pYES6 was used as vector, there was additional selection on blasticidin as antimetabolite.

Main Culture

For expression, 20 ml of liquid CMdum dropout uracil medium which, however, contains 2% of raffinose and 1% (v/v) of Tergitol NP-40 were supplemented with fatty acid substrates to a final concentration of 0.003% (w/v). The media were inoculated with the precultures to an $OD_{600}$ of 0.05. Expression was induced for 16 hours at an $OD_{600}$ of 0.2, using 2% (w/v) of galactose, whereupon the cultures were harvested at an $OD_{600}$ of 0.8-1.2.

Fatty Acid Analysis

The total fatty acids were extracted from yeast cultures and analyzed by means of gas chromatography. To this end, cells of 5 ml of culture were harvested by centrifugation (1 000×g, 10 minutes, 4° C.) and washed once with 100 mM $NaHCO_3$, pH 8.0 in order to remove residual medium and fatty acids. To prepare the fatty acid methyl ester(s) (FAMEs or, in the singular, FAME), the cell sediments were treated for 1 hour at 80° C. with 1 M methanolic $H_2SO_4$ and 2% (v/v) dimethoxypropane. The FAMEs were extracted twice with 2 ml of petroleum ether, washed once with 100 mM $NaHCO_3$, pH 8.0, and once with distilled water, and dried with $Na_2SO_4$. The organic solvent was evaporated under a stream of argon, and the FAMEs were dissolved in 50 µl of petroleum ether. The samples were separated on a ZEBRON-ZB Wax capillary column (30 m, 0.32 mm, 0.25 µm; Phenomenex) in a Hewlett Packard 6850 gas chromatograph equipped with flame ionization detector. The oven temperature was programmed from 70° C. (hold for 1 minute) to 200° C. at a rate of 20° C./minute, then to 250° C. (hold for 5 minutes) at a rate of 5° C./minute and finally to 260° C. at a rate of 5° C./minute. Nitrogen was used as the carrier gas (4.5 ml/minute at 70° C.). The fatty acids were identified by comparison with retention times of FAME standards (SIGMA).

Expression Analysis

The ratios of the fatty acid substrates which had been added and taken up were determined, thus recording the quantity and quality of the desaturase reaction in accordance with Table 6, Table 7 and Table 8.

The result of the expression of a *Phaeodactylum tricornutum* Δ6-acyl lipid desaturase in yeast:

The data represent mol % fatty acids of cis-fatty acids.

Further feeding experiments have revealed that C18:1Δ9 was not desaturated in the presence of C18:2Δ9,11 or C18:3Δ9,12,15 or C20:1Δ8 fatty acids, while C18:1 is also desaturated in the presence of C20:1Δ11, C20:2Δ11,14 and C20:3Δ8,11,14. Also, no desaturation took place in the presence of C20:3Δ8,11,14.

When using the protease-deficient yeast strain C13BYS86 (Kunze I. et al., Biochemica et Biophysica Acta (1999) 1410: 287-298) for expressing the *Phaeodactylum tricornutum* Δ5-desaturase on complete medium with blasticidin, it was found that C20:4 Δ8,11,14,17 as substrate of Δ5-desaturase gave a conversion rate of 20% and was thus equally well converted as C20:3Δ8,11,14. As an alternative, the auxotrophism markers leu2, ura3 or his can also be used for gene expression.

In a further coexpression experiment of *Phaeodactylum* Δ5-desaturase and *Physcomitrella* Δ6-elongase, the strain used was UTL7A (Warnecke et al., J. Biol. Chem. (1999) 274 (19): 13048-13059), Δ5-desaturase converting approximately 10% of C20:3 Δ8,11,14 into C20:4 Δ5,8,11,14.

Further feeding experiment with a wide range of other fatty acids alone or in combination (for example linoleic acid, 20:3 Δ5,11,14-fatty acid, α- or γ-linolenic acid, stearidonic acid, arachidonic acid, eicosapentaenoic acid and the like) can be carried out for confirming the substrate specificity and substrate selectivity of these desaturases in greater detail.

TABLE 6

| Fatty acid | pYES2 | pYES2-Ptd6 fed with | | |
|---|---|---|---|---|
| | — | — | +18:2 | +18:3 |
| 16:0 | 13.3 | 18.9 | 28.4 | 16.7 |
| 16:1Δ9 | 45.4 | 44.7 | 12.5 | 16.9 |
| 16:2Δ6, 9 | — | 4.3 | — | — |
| 18:0 | 4.9 | 6.3 | 10.4 | 9.1 |
| 18:1Δ9 | 36.4 | 24.1 | 6.8 | 11.8 |
| 18:2Δ6, 9 | — | 1.8 | — | — |
| 18:2Δ9, 12 | — | — | 33.4 | — |
| 18:3Δ6, 12, 15 | — | — | 4.9 | — |
| 18:3Δ9, 12, 15 | — | — | — | 43.1 |
| 18:4Δ6, 9, 12, 15 | — | — | — | 2.3 |

The data represent mol % of corresponding cis-fatty acids.

Result of the expression of a *Phaeodactylum tricornutum* Δ5-acyl lipid desaturase in yeast:

TABLE 7

| Fatty acid | pYES2 Blank | pYES_PtD5 construct fed with | | | | | | | |
|---|---|---|---|---|---|---|---|---|---|
| | | Control | 18:2 | 18:3 | 20:1 Δ8 | −20:1 Δ11 | 20:2 Δ11,14 | 20:3 Ω3 | 20:3 Ω6 |
| 16:0Δ | 16.9 | 20.4 | 27.7 | 24.4 | 16.2 | 21 | 17.6 | 19.5 | 22.8 |
| 16:1Δ9 | 44.7 | 44.1 | 13.2 | 9.6 | 37.4 | 39.4 | 38.3 | 36.9 | 30.7 |
| 18:0 | 6.1 | 6.9 | 10.54 | 9.8 | 4.7 | 7.9 | 6.3 | 6.8 | 8.2 |
| 18:1Δ9 | 31.72 | 28.1 | 8.77 | 6 | 15 | 26 | 29.5 | 25.6 | 21.1 |
| 18:2Δ5,9 | | 0.17 | 0 | 0 | 0 | 0.09 | 0.21 | 0.09 | 9 |
| 18:2Δ9,12 | — | — | 39.7 | — | — | — | — | — | — |
| 18:3Δ9,12,15 | — | — | — | 49.9 | — | — | — | — | — |
| 20:1Δ8 | — | — | — | — | 25.5 | — | — | — | — |
| 20:1Δ11 | — | — | — | — | — | 5.41 | — | — | — |
| 20:2Δ5,11 | — | — | — | — | — | 0.21 | — | — | — |
| 20:2Δ11,14 | — | — | — | — | — | 6.48 | — | — | — |
| 20:3Δ5,11,14 | — | — | — | — | — | — | 0.76 | — | — |
| 20:3Δ11,14,17 | — | — | — | — | — | — | — | 9.83 | — |
| 20:3Δ8,11,14 | — | — | — | — | — | — | — | — | 13.69 |
| 20:4Δ5,11,14,17 | — | — | — | — | — | — | 1.16 | — | — |
| 20:4Δ5,8,11,14 | — | — | — | — | — | — | — | — | 3.08 |

TABLE 8

Result of coexpressing a *Phaeodactylum tricornutum* Δ5-acyl lipid desaturase and a moss Δ6-elongase in yeast based on the expression vectors pYES2 and pYES6

| | pYES2-Elo | | pYES2-Elo and pYES6-Ptd5 | |
|---|---|---|---|---|
| | +18:3 | +18:4 | +18:3 | +18:4 |
| 16:0 | 15.0 | 14.8 | 15.6 | 15.1 |
| 16:1Δ9 | 27.7 | 29.2 | 27.5 | 29.0 |
| 18:0 | 5.6 | 6.3 | 5.7 | 6.4 |
| 18:1Δ9 | 17.1 | 30.8 | 27.4 | 31.6 |
| 18:3Δ6, 9, 12 | 7.60 | — | 7.8 | — |
| 18:4Δ6, 9, 12, 15 | — | 6.71 | — | 6.4 |
| 20:3Δ8, 11, 14 | 15.92 | — | 13.55 | — |
| 20:4Δ5, 8, 11, 14 | — | — | 1.31 | — |
| 20:4Δ8, 11, 14, 17 | — | 11.4 | — | 10.31 |
| 20:5Δ5, 8, 11, 14, 17 | — | — | — | 0.53 |

The substrate conversions reveal that the Phaeodactylum Δ5-desaturase and the *Physcomitrella patens* Δ6-elongase which were used are suitable with regard to substrate activity and in particular substrate specificity for producing arachidonic acid or eicosapentaenoic acid with the aid of sequences according to the invention.

The fragmentation patterns and mass spectra of DMOX derivatives of standards and the peak fractions of the fatty acids shown in Tables 6, 7 and 8 and identified by GC show, in comparison, identical results, thus confirming the respective position of the double bond beyond simple GC detection.

Example 17

Purification of the Desired Product from Transformed Organisms

The recovery of the desired product from plant material or fungi, algae, ciliates, animal cells or the supernatant of the above-described cultures can be performed by various methods known in the art. If the desired product is not secreted from the cells, the cells can be harvested from the culture by low-speed centrifugation, the cells can be lysed by standard techniques, such as mechanical force or sonication. Organs of plants can be separated mechanically from other tissue or other organs. Following homogenization, the cell debris is removed by centrifugation, and the supernatant fraction comprising the soluble proteins is retained for further purification of the desired compounds. If the product is secreted from desired cells, then the cells are removed from the culture by low-speed centrifugation, and the supernatant fraction is retained for further purification.

The supernatant fraction from each purification method is subjected to chromatography with a suitable resin, the desired molecule either being retained on the chromatography resin while many of the impurities of the sample are not, or the impurities being retained by the resin while the sample is not. These chromatography steps can be repeated if necessary, using the same or different chromatography resins. The skilled worker is familiar with the selection of suitable chromatography resins and their most effective application for a particular molecule to be purified. The purified product can be concentrated by filtration or ultrafiltration, and stored at a temperature at which the stability of the product is maximized.

A wide spectrum of purification methods is known in the art, and the above purification method is not intended to be limiting. These purification methods are described, for example, in Bailey, J. E., & Ollis, D. F., Biochemical Engineering Fundamentals, McGraw-Hill: New York (1986).

The identity and purity of the isolated compounds may be assessed by techniques which are standard in the art. They include high-performance liquid chromatography (HPLC), spectroscopic methods, staining methods, thin-layer chromatography, in particular thin-layer chromatography and flame ionization detection (IATROSCAN, Iatron, Tokyo, Japan), NIRS, enzyme assays or microbiological tests. Such analytical methods are reviewed in: Patek et al. (1994) Appl. Environ. Microbiol. 60:133-140; Malakhova et al. (1996) Biotekhnologiya 11:27-32; and Schmidt et al. (1998) Bioprocess Engineer. 19:67-70. Ulmann's Encyclopedia of Industrial Chemistry (1996) Vol. A27, VCH Weinheim, pp. 89-90, pp. 521-540, pp. 540-547, pp. 559-566, pp. 575-581 and pp. 581-587; Michal, G (1999) Biochemical Pathways An Atlas of Biochemistry and Molecular Biology, John Wiley and Sons; Fallon, A., et al. (1987) Applications of HPLC in Biochemistry in: Laboratory Techniques in Biochemistry and Molecular Biology, Vol. 17.

EQUIVALENTS

The skilled worker recognizes, or will be able to ascertain, a number of equivalents of the specific use forms according to the invention described herein by using no more than routine experiments. These equivalents are intended to be encompassed by the claims.

We claim:

1. A method for the production of fatty acid esters with an increased content of polyunsaturated fatty acids with at least two double bonds, which comprises introducing, into a fatty-acid-ester-producing organism, at least one nucleic acid sequence comprising a sequence selected from the group consisting of
   a) a nucleic acid sequence with the sequence shown in SEQ ID NO: 3,
   b) a nucleic acid sequence encoding the amino acid sequence shown in SEQ ID NO: 4,
   c) a nucleic acid sequence encoding a polypeptide having at least 95% homology with the amino acid sequence shown in SEQ ID NO: 4 and having Δ6-desaturase activity,
   growing the organism, and isolating the fatty acid esters present in the organism, wherein the organism is a microorganism, a yeast, or a plant or plant cell.

2. The method of claim 1, wherein the fatty acid esters produced by the method comprise polyunsaturated $C_{18}$-, $C_{20}$- or $C_{22}$-fatty acid molecules with at least two double bonds in the fatty acid ester.

3. The method of claim 1, wherein the $C_{18}$-, $C_{20}$- or $C_{22}$-fatty acid molecules are isolated from the organism in the form of an oil or lipid.

4. The method of claim 1, wherein a combination of sequences comprising the nucleic acid sequences of SEQ ID NO: 1, SEQ ID NO: 3 and SEQ ID NO: 9 is introduced into the fatty-acid-ester-producing organism.

5. The method of claim 1, wherein the organism is an oil crop plant or plant cell.

6. The method of claim 1, wherein the organism is a transgenic plant.

7. The method of claim 1, wherein the fatty acid esters contain $C_{18}$-, $C_{20}$- or $C_{22}$-fatty acids with three, four or five double bonds in the fatty acid ester.

8. The method of claim 1, wherein the polyunsaturated fatty acids contained in the fatty acid esters are liberated.

9. An isolated nucleic acid sequence encoding a polypeptide with desaturase activity, comprising a sequence selected from the group consisting of:
   a) a nucleic acid sequence with the sequence shown in SEQ ID NO: 3,
   b) a nucleic acid sequence encoding the amino acid sequence shown in SEQ ID NO: 4,
   c) a nucleic acid sequence encoding a polypeptide having at least 95% homology with the amino acid sequence shown in SEQ ID NO: 4 and having Δ6-desaturase activity.

10. A nucleic acid construct comprising the nucleic acid sequence of claim 9, wherein the nucleic acid sequence is linked to one or more regulatory signals.

11. A vector comprising the nucleic acid sequence of claim 9 or a construct comprising the nucleic acid sequence linked to one or more regulatory signals.

12. The isolated nucleic acid sequence of claim 9, wherein the nucleic acid sequence has at least 70% homology to the nucleic acid sequence of SEQ ID NO: 3.

13. An organism comprising the isolated nucleic acid sequence of claim 9, a construct comprising the nucleic acid sequence linked to one or more regulatory signals, or a vector comprising the nucleic acid sequence or the construct, wherein the organism is a microorganism, a yeast, or a plant or plant cell.

14. A transgenic plant or plant cell comprising the isolated nucleic acid sequence of claim 9 or a construct comprising the nucleic acid sequence linked to one or more regulatory signals.

15. The method of claim 1, wherein the at least one nucleic acid sequence comprises a sequence having at least 70% homology to the nucleic acid sequence of SEQ ID NO: 3.

16. The method of claim 1, wherein the at least one nucleic acid sequence comprises a sequence which hybridizes with the nucleic acid sequence of SEQ ID NO: 3 under stringent conditions, wherein the stringent conditions comprise hybridization in 6×SSC at approximately 45° C. followed by one or more wash steps in 0.2×SSC, 0.1% SDS at 50 to 65° C.

17. The method of claim 1, wherein the at least one nucleic acid sequence comprises the nucleic acid sequence of SEQ ID NO: 3 or comprises a nucleic acid sequence which encodes the amino acid sequence of SEQ ID NO: 4.

18. The isolated nucleic acid sequence of claim 9, wherein the nucleic acid sequence comprises the nucleic acid sequence of SEQ ID NO: 3 or comprises a nucleic acid sequence which encodes the amino acid sequence of SEQ ID NO: 4.

19. A transgenic plant cell, plant or part thereof comprising the isolated nucleic acid sequence of claim 18 or a construct comprising said nucleic acid sequence linked to one or more regulatory signals.

20. The isolated nucleic acid sequence of claim 9, wherein the nucleic acid sequence comprises a sequence which hybridizes with the nucleic acid sequence of SEQ ID NO: 3 under stringent conditions, wherein the stringent conditions comprise hybridization in 6×SSC at approximately 45° C. followed by one or more wash steps in 0.2×SSC, 0.1% SDS at 50 to 65° C.

* * * * *

SEQUENCE LISTING

```
<160> NUMBER OF SEQ ID NOS: 96

<210> SEQ ID NO 1
<211> LENGTH: 1652
<212> TYPE: DNA
<213> ORGANISM: Phaeodactylum tricornutum
<220> FEATURE:
<221> NAME/KEY: CDS
<222> LOCATION: (115)..(1524)

<400> SEQUENCE: 1
gacccaacaa acccaacaat cccaacaatc ccatcaacag gaattgggtt tcgttgagtc         60
aataattgct agaatccaaa cagacagaca gagaccaacc gcatctatta caga atg        117
                                                                    Met
                                                                      1 gct ccg gat gcg gat aag ctt cga caa cgc cag acg act gcg gta gcg        165
Ala Pro Asp Ala Asp Lys Leu Arg Gln Arg Gln Thr Thr Ala Val Ala
              5                  10                  15 aag cac aat gct gct acc ata tcg acg cag gaa cgc ctt tgc agt ctg        213
Lys His Asn Ala Ala Thr Ile Ser Thr Gln Glu Arg Leu Cys Ser Leu
         20                  25                  30 tct tcg ctc aaa ggc gaa gaa gtc tgc atc gac gga atc atc tat gac        261
Ser Ser Leu Lys Gly Glu Glu Val Cys Ile Asp Gly Ile Ile Tyr Asp
     35                  40                  45
```

| | | |
|---|---|---|
| ctc caa tca ttc gat cat ccc ggg ggt gaa acg atc aaa atg ttt ggt<br>Leu Gln Ser Phe Asp His Pro Gly Gly Glu Thr Ile Lys Met Phe Gly<br>50                        55                        60                        65 | 309 |
| ggc aac gat gtc act gta cag tac aag atg att cac ccg tac cat acc<br>Gly Asn Asp Val Thr Val Gln Tyr Lys Met Ile His Pro Tyr His Thr<br>                    70                        75                        80 | 357 |
| gag aag cat ttg gaa aag atg aag cgt gtc ggc aag gtg acg gat ttc<br>Glu Lys His Leu Glu Lys Met Lys Arg Val Gly Lys Val Thr Asp Phe<br>                85                        90                        95 | 405 |
| gtc tgc gag tac aag ttc gat acc gaa ttt gaa cgc gaa atc aaa cga<br>Val Cys Glu Tyr Lys Phe Asp Thr Glu Phe Glu Arg Glu Ile Lys Arg<br>          100                   105                   110 | 453 |
| gaa gtc ttc aag att gtg cga cga ggc aag gat ttc ggt act ttg gga<br>Glu Val Phe Lys Ile Val Arg Arg Gly Lys Asp Phe Gly Thr Leu Gly<br>115                      120                   125 | 501 |
| tgg ttc ttc cgt gcg ttt tgc tac att gcc att ttc ttc tac ctg cag<br>Trp Phe Phe Arg Ala Phe Cys Tyr Ile Ala Ile Phe Phe Tyr Leu Gln<br>130                      135                   140                   145 | 549 |
| tac cat tgg gtc acc acg gga acc tct tgg ctg ctg gcc gtg gcc tac<br>Tyr His Trp Val Thr Thr Gly Thr Ser Trp Leu Leu Ala Val Ala Tyr<br>                    150                   155                   160 | 597 |
| gga atc tcc caa gcg atg att ggc atg aat gtc cag cac gat gcc aac<br>Gly Ile Ser Gln Ala Met Ile Gly Met Asn Val Gln His Asp Ala Asn<br>                        165                   170                   175 | 645 |
| cac ggg gcc acc tcc aag cgt ccc tgg gtc aac gac atg cta ggc ctc<br>His Gly Ala Thr Ser Lys Arg Pro Trp Val Asn Asp Met Leu Gly Leu<br>180                      185                   190 | 693 |
| ggt gcg gat ttt att ggt ggt tcc aag tgg ctc tgg cag gaa caa cac<br>Gly Ala Asp Phe Ile Gly Gly Ser Lys Trp Leu Trp Gln Glu Gln His<br>195                      200                   205 | 741 |
| tgg acc cac cac gct tac acc aat cac gcc gag atg gat ccc gat agc<br>Trp Thr His His Ala Tyr Thr Asn His Ala Glu Met Asp Pro Asp Ser<br>210                      215                   220                   225 | 789 |
| ttt ggt gcc gaa cca atg ctc cta ttc aac gac tat ccc ttg gat cat<br>Phe Gly Ala Glu Pro Met Leu Leu Phe Asn Asp Tyr Pro Leu Asp His<br>                    230                   235                   240 | 837 |
| ccc gct cgt acc tgg cta cat cgc ttt caa gca ttc ttt tac atg ccc<br>Pro Ala Arg Thr Trp Leu His Arg Phe Gln Ala Phe Phe Tyr Met Pro<br>                        245                   250                   255 | 885 |
| gtc ttg gct gga tac tgg ttg tcc gct gtc ttc aat cca caa att ctt<br>Val Leu Ala Gly Tyr Trp Leu Ser Ala Val Phe Asn Pro Gln Ile Leu<br>260                      265                   270 | 933 |
| gac ctc cag caa cgc ggc gca ctt tcc gtc ggt atc cgt ctc gac aac<br>Asp Leu Gln Gln Arg Gly Ala Leu Ser Val Gly Ile Arg Leu Asp Asn<br>275                      280                   285 | 981 |
| gct ttc att cac tcg cga cgc aag tat gcg gtt ttc tgg cgg gct gtg<br>Ala Phe Ile His Ser Arg Arg Lys Tyr Ala Val Phe Trp Arg Ala Val<br>290                      295                   300                   305 | 1029 |
| tac att gcg gtg aac gtg att gct ccg ttt tac aca aac tcc ggc ctc<br>Tyr Ile Ala Val Asn Val Ile Ala Pro Phe Tyr Thr Asn Ser Gly Leu<br>                    310                   315                   320 | 1077 |
| gaa tgg tcc tgg cgt gtc ttt gga aac atc atg ctc atg ggt gtg gcg<br>Glu Trp Ser Trp Arg Val Phe Gly Asn Ile Met Leu Met Gly Val Ala<br>                        325                   330                   335 | 1125 |
| gaa tcg ctc gcg ctg gcg gtc ctg ttt tcg ttg tcg cac aat ttc gaa<br>Glu Ser Leu Ala Leu Ala Val Leu Phe Ser Leu Ser His Asn Phe Glu<br>340                      345                   350 | 1173 |
| tcc gcg gat cgc gat ccg acc gcc cca ctg aaa aag acg gga gaa cca<br>Ser Ala Asp Arg Asp Pro Thr Ala Pro Leu Lys Lys Thr Gly Glu Pro<br>355                      360                   365 | 1221 |

```
gtc gac tgg ttc aag aca cag gtc gaa act tcc tgc act tac ggt gga      1269
Val Asp Trp Phe Lys Thr Gln Val Glu Thr Ser Cys Thr Tyr Gly Gly
370                 375                 380                 385 ttc ctt tcc ggt tgc ttc acg gga ggt ctc aac ttt cag gtt gaa cac      1317
Phe Leu Ser Gly Cys Phe Thr Gly Gly Leu Asn Phe Gln Val Glu His
                390                 395                 400 cac ttg ttc cca cgc atg agc agc gct tgg tat ccc tac att gcc ccc      1365
His Leu Phe Pro Arg Met Ser Ser Ala Trp Tyr Pro Tyr Ile Ala Pro
            405                 410                 415 aag gtc cgc gaa att tgc gcc aaa cac ggc gtc cac tac gcc tac tac      1413
Lys Val Arg Glu Ile Cys Ala Lys His Gly Val His Tyr Ala Tyr Tyr
        420                 425                 430 ccg tgg atc cac caa aac ttt ctc tcc acc gtc cgc tac atg cac gcg      1461
Pro Trp Ile His Gln Asn Phe Leu Ser Thr Val Arg Tyr Met His Ala
    435                 440                 445 gcc ggg acc ggt gcc aac tgg cgc cag atg gcc aga gaa aat ccc ttg      1509
Ala Gly Thr Gly Ala Asn Trp Arg Gln Met Ala Arg Glu Asn Pro Leu
450                 455                 460                 465 acc gga cgg gcg taa aagtacacga cacgaccaaa ggtggcgtat ggtgatctct      1564
Thr Gly Arg Ala agaaaacaga catagcctac tggaaatatc gacgtccaaa caataatttt aaagactatt      1624
tttctgcgta aaaaaaaaaa aaaaaaa                                           1652

<210> SEQ ID NO 2
<211> LENGTH: 469
<212> TYPE: PRT
<213> ORGANISM: Phaeodactylum tricornutum

<400> SEQUENCE: 2

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
                20                  25                  30

Leu Ser Ser Leu Lys Gly Glu Glu Val Cys Ile Asp Gly Ile Ile Tyr
            35                  40                  45

Asp Leu Gln Ser Phe Asp His Pro Gly Gly Glu Thr Ile Lys Met Phe
        50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
```

```
                210                 215                 220
Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
                260                 265                 270

Leu Asp Leu Gln Gln Arg Gly Ala Leu Ser Val Gly Ile Arg Leu Asp
                275                 280                 285

Asn Ala Phe Ile His Ser Arg Arg Lys Tyr Ala Val Phe Trp Arg Ala
290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
                340                 345                 350

Glu Ser Ala Asp Arg Asp Pro Thr Ala Pro Leu Lys Lys Thr Gly Glu
                355                 360                 365

Pro Val Asp Trp Phe Lys Thr Gln Val Glu Thr Ser Cys Thr Tyr Gly
                370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
                420                 425                 430

Tyr Pro Trp Ile His Gln Asn Phe Leu Ser Thr Val Arg Tyr Met His
                435                 440                 445

Ala Ala Gly Thr Gly Ala Asn Trp Arg Gln Met Ala Arg Glu Asn Pro
                450                 455                 460

Leu Thr Gly Arg Ala
465

<210> SEQ ID NO 3
<211> LENGTH: 1434
<212> TYPE: DNA
<213> ORGANISM: Phaeodactylum tricornutum
<220> FEATURE:
<221> NAME/KEY: CDS
<222> LOCATION: (1)..(1434)

<400> SEQUENCE: 3 atg ggc aaa gga ggg gac gct cgg gcc tcg aag ggc tca acg gcg gct      48
Met Gly Lys Gly Gly Asp Ala Arg Ala Ser Lys Gly Ser Thr Ala Ala
  1               5                  10                  15 cgc aag atc agt tgg cag gaa gtc aag acc cac gcg tct ccg gag gac      96
Arg Lys Ile Ser Trp Gln Glu Val Lys Thr His Ala Ser Pro Glu Asp
                 20                  25                  30 gcc tgg atc att cac tcc aat aag gtc tac gac gtg tcc aac tgg cac     144
Ala Trp Ile Ile His Ser Asn Lys Val Tyr Asp Val Ser Asn Trp His
             35                  40                  45 gaa cat ccc gga ggc gcc gtc att ttc acg cac gcc ggt gac gac atg     192
Glu His Pro Gly Gly Ala Val Ile Phe Thr His Ala Gly Asp Asp Met
         50                  55                  60 acg gac att ttc gct gcc ttt cac gca ccc gga tcg cag tcg ctc atg     240
Thr Asp Ile Phe Ala Ala Phe His Ala Pro Gly Ser Gln Ser Leu Met
 65                  70                  75                  80
```

-continued

| | | | | | | | | | | | | | | | | |
|---|---|---|---|---|---|---|---|---|---|---|---|---|---|---|---|---|
| aag | aag | ttc | tac | att | ggc | gaa | ttg | ctc | ccg | gaa | acc | acc | ggc | aag | gag | 288 |
| Lys | Lys | Phe | Tyr | Ile | Gly | Glu | Leu | Leu | Pro | Glu | Thr | Thr | Gly | Lys | Glu | |
| | | | | 85 | | | | 90 | | | | | 95 | | | |
| ccg | cag | caa | atc | gcc | ttt | gaa | aag | ggc | tac | cgc | gat | ctg | cgc | tcc | aaa | 336 |
| Pro | Gln | Gln | Ile | Ala | Phe | Glu | Lys | Gly | Tyr | Arg | Asp | Leu | Arg | Ser | Lys | |
| | | | 100 | | | | | 105 | | | | 110 | | | | |
| ctc | atc | atg | atg | ggc | atg | ttc | aag | tcc | aac | aag | tgg | ttc | tac | gtc | tac | 384 |
| Leu | Ile | Met | Met | Gly | Met | Phe | Lys | Ser | Asn | Lys | Trp | Phe | Tyr | Val | Tyr | |
| | 115 | | | | | 120 | | | | | 125 | | | | | |
| aag | tgc | ctc | agc | aac | atg | gcc | att | tgg | gcc | gcc | gcc | tgt | gct | ctc | gtc | 432 |
| Lys | Cys | Leu | Ser | Asn | Met | Ala | Ile | Trp | Ala | Ala | Ala | Cys | Ala | Leu | Val | |
| | 130 | | | | 135 | | | | | 140 | | | | | | |
| ttt | tac | tcg | gac | cgc | ttc | tgg | gta | cac | ctg | gcc | agc | gcc | gtc | atg | ctg | 480 |
| Phe | Tyr | Ser | Asp | Arg | Phe | Trp | Val | His | Leu | Ala | Ser | Ala | Val | Met | Leu | |
| 145 | | | | | 150 | | | | | 155 | | | | | 160 | |
| gga | aca | ttc | ttt | cag | cag | tcg | gga | tgg | ttg | gca | cac | gac | ttt | ctg | cac | 528 |
| Gly | Thr | Phe | Phe | Gln | Gln | Ser | Gly | Trp | Leu | Ala | His | Asp | Phe | Leu | His | |
| | | | | 165 | | | | | 170 | | | | | 175 | | |
| cac | cag | gtc | ttc | acc | aag | cgc | aag | cac | ggg | gat | ctc | gga | gga | ctc | ttt | 576 |
| His | Gln | Val | Phe | Thr | Lys | Arg | Lys | His | Gly | Asp | Leu | Gly | Gly | Leu | Phe | |
| | | | 180 | | | | | 185 | | | | | 190 | | | |
| tgg | ggg | aac | ctc | atg | cag | ggt | tac | tcc | gta | cag | tgg | tgg | aaa | aac | aag | 624 |
| Trp | Gly | Asn | Leu | Met | Gln | Gly | Tyr | Ser | Val | Gln | Trp | Trp | Lys | Asn | Lys | |
| | 195 | | | | | 200 | | | | | 205 | | | | | |
| cac | aac | gga | cac | cac | gcc | gtc | ccc | aac | ctc | cac | tgc | tcc | tcc | gca | gtc | 672 |
| His | Asn | Gly | His | His | Ala | Val | Pro | Asn | Leu | His | Cys | Ser | Ser | Ala | Val | |
| | 210 | | | | 215 | | | | | 220 | | | | | | |
| gcg | caa | gat | ggg | gac | ccg | gac | atc | gat | acc | atg | ccc | ctt | ctc | gcc | tgg | 720 |
| Ala | Gln | Asp | Gly | Asp | Pro | Asp | Ile | Asp | Thr | Met | Pro | Leu | Leu | Ala | Trp | |
| 225 | | | | | 230 | | | | | 235 | | | | | 240 | |
| tcc | gtc | cag | caa | gcc | cag | tct | tac | cgg | gaa | ctc | caa | gcc | gac | gga | aag | 768 |
| Ser | Val | Gln | Gln | Ala | Gln | Ser | Tyr | Arg | Glu | Leu | Gln | Ala | Asp | Gly | Lys | |
| | | | | 245 | | | | | 250 | | | | | 255 | | |
| gat | tcg | ggt | ttg | gtc | aag | ttc | atg | atc | cgt | aac | caa | tcc | tac | ttt | tac | 816 |
| Asp | Ser | Gly | Leu | Val | Lys | Phe | Met | Ile | Arg | Asn | Gln | Ser | Tyr | Phe | Tyr | |
| | | | 260 | | | | | 265 | | | | | 270 | | | |
| ttt | ccc | atc | ttg | ttg | ctc | gcc | cgc | ctg | tcg | tgg | ttg | aac | gag | tcc | ttc | 864 |
| Phe | Pro | Ile | Leu | Leu | Leu | Ala | Arg | Leu | Ser | Trp | Leu | Asn | Glu | Ser | Phe | |
| | | 275 | | | | | 280 | | | | | 285 | | | | |
| aag | tgc | gcc | ttt | ggg | ctt | gga | gct | gcg | tcg | gag | aac | gct | gct | ctc | gaa | 912 |
| Lys | Cys | Ala | Phe | Gly | Leu | Gly | Ala | Ala | Ser | Glu | Asn | Ala | Ala | Leu | Glu | |
| | 290 | | | | | 295 | | | | | 300 | | | | | |
| ctc | aag | gcc | aag | ggt | ctt | cag | tac | ccc | ctt | gaa | aag | gct | ggc | atc | | 960 |
| Leu | Lys | Ala | Lys | Gly | Leu | Gln | Tyr | Pro | Leu | Leu | Glu | Lys | Ala | Gly | Ile | |
| 305 | | | | | 310 | | | | | 315 | | | | | 320 | |
| ctg | ctg | cac | tac | gct | tgg | atg | ctt | aca | gtt | tcg | tcc | ggc | ttt | gga | cgc | 1008 |
| Leu | Leu | His | Tyr | Ala | Trp | Met | Leu | Thr | Val | Ser | Ser | Gly | Phe | Gly | Arg | |
| | | | | 325 | | | | | 330 | | | | | 335 | | |
| ttc | tcg | ttc | gcg | tac | acc | gca | ttt | tac | ttt | cta | acc | gcg | acc | gcg | tcc | 1056 |
| Phe | Ser | Phe | Ala | Tyr | Thr | Ala | Phe | Tyr | Phe | Leu | Thr | Ala | Thr | Ala | Ser | |
| | | | 340 | | | | | 345 | | | | | 350 | | | |
| tgt | gga | ttc | ttg | ctc | gcc | att | gtc | ttt | ggc | ctc | ggc | cac | aac | ggc | atg | 1104 |
| Cys | Gly | Phe | Leu | Leu | Ala | Ile | Val | Phe | Gly | Leu | Gly | His | Asn | Gly | Met | |
| | | 355 | | | | | 360 | | | | | 365 | | | | |
| gcc | acc | tac | aat | gcc | gac | gcc | cgt | ccg | gac | ttc | tgg | aag | ctc | caa | gtc | 1152 |
| Ala | Thr | Tyr | Asn | Ala | Asp | Ala | Arg | Pro | Asp | Phe | Trp | Lys | Leu | Gln | Val | |
| 370 | | | | | 375 | | | | | 380 | | | | | | |
| acc | acg | act | cgc | aac | gtc | acg | ggc | gga | cac | ggt | ttc | ccc | caa | gcc | ttt | 1200 |
| Thr | Thr | Thr | Arg | Asn | Val | Thr | Gly | Gly | His | Gly | Phe | Pro | Gln | Ala | Phe | |
| 385 | | | | | 390 | | | | | 395 | | | | | 400 | |

-continued

```
gtc gac tgg ttc tgt ggt ggc ctc cag tac caa gtc gac cac cac tta    1248
Val Asp Trp Phe Cys Gly Gly Leu Gln Tyr Gln Val Asp His His Leu
            405                 410                 415 ttc ccc agc ctg ccc cga cac aat ctg gcc aag aca cac gca ctg gtc    1296
Phe Pro Ser Leu Pro Arg His Asn Leu Ala Lys Thr His Ala Leu Val
        420                 425                 430 gaa tcg ttc tgc aag gag tgg ggt gtc cag tac cac gaa gcc gac ctt    1344
Glu Ser Phe Cys Lys Glu Trp Gly Val Gln Tyr His Glu Ala Asp Leu
    435                 440                 445 gtg gac ggg acc atg gaa gtc ttg cac cat ttg ggc agc gtg gcc ggc    1392
Val Asp Gly Thr Met Glu Val Leu His His Leu Gly Ser Val Ala Gly
450                 455                 460 gaa ttc gtc gtg gat ttt gta cgc gat gga ccc gcc atg taa            1434
Glu Phe Val Val Asp Phe Val Arg Asp Gly Pro Ala Met
465                 470                 475

<210> SEQ ID NO 4
<211> LENGTH: 477
<212> TYPE: PRT
<213> ORGANISM: Phaeodactylum tricornutum

<400> SEQUENCE: 4

Met Gly Lys Gly Gly Asp Ala Arg Ala Ser Lys Gly Ser Thr Ala Ala
  1               5                  10                  15

Arg Lys Ile Ser Trp Gln Glu Val Lys Thr His Ala Ser Pro Glu Asp
             20                  25                  30

Ala Trp Ile Ile His Ser Asn Lys Val Tyr Asp Val Ser Asn Trp His
         35                  40                  45

Glu His Pro Gly Gly Ala Val Ile Phe Thr His Ala Gly Asp Asp Met
     50                  55                  60

Thr Asp Ile Phe Ala Ala Phe His Ala Pro Gly Ser Gln Ser Leu Met
 65                  70                  75                  80

Lys Lys Phe Tyr Ile Gly Glu Leu Leu Pro Glu Thr Thr Gly Lys Glu
                 85                  90                  95

Pro Gln Gln Ile Ala Phe Glu Lys Gly Tyr Arg Asp Leu Arg Ser Lys
            100                 105                 110

Leu Ile Met Met Gly Met Phe Lys Ser Asn Lys Trp Phe Tyr Val Tyr
        115                 120                 125

Lys Cys Leu Ser Asn Met Ala Ile Trp Ala Ala Cys Ala Leu Val
    130                 135                 140

Phe Tyr Ser Asp Arg Phe Trp Val His Leu Ala Ser Ala Val Met Leu
145                 150                 155                 160

Gly Thr Phe Phe Gln Gln Ser Gly Trp Leu Ala His Asp Phe Leu His
                165                 170                 175

His Gln Val Phe Thr Lys Arg Lys His Gly Asp Leu Gly Gly Leu Phe
            180                 185                 190

Trp Gly Asn Leu Met Gln Gly Tyr Ser Val Gln Trp Trp Lys Asn Lys
        195                 200                 205

His Asn Gly His His Ala Val Pro Asn Leu His Cys Ser Ser Ala Val
    210                 215                 220

Ala Gln Asp Gly Asp Pro Asp Ile Asp Thr Met Pro Leu Leu Ala Trp
225                 230                 235                 240

Ser Val Gln Gln Ala Gln Ser Tyr Arg Glu Leu Gln Ala Asp Gly Lys
                245                 250                 255

Asp Ser Gly Leu Val Lys Phe Met Ile Arg Asn Gln Ser Tyr Phe Tyr
            260                 265                 270
```

```
Phe Pro Ile Leu Leu Leu Ala Arg Leu Ser Trp Leu Asn Glu Ser Phe
        275                 280                 285

Lys Cys Ala Phe Gly Leu Gly Ala Ala Ser Glu Asn Ala Ala Leu Glu
290                 295                 300

Leu Lys Ala Lys Gly Leu Gln Tyr Pro Leu Leu Glu Lys Ala Gly Ile
305                 310                 315                 320

Leu Leu His Tyr Ala Trp Met Leu Thr Val Ser Ser Gly Phe Gly Arg
                325                 330                 335

Phe Ser Phe Ala Tyr Thr Ala Phe Tyr Phe Leu Thr Ala Thr Ala Ser
            340                 345                 350

Cys Gly Phe Leu Leu Ala Ile Val Phe Gly Leu His Asn Gly Met
        355                 360                 365

Ala Thr Tyr Asn Ala Asp Ala Arg Pro Asp Phe Trp Lys Leu Gln Val
370                 375                 380

Thr Thr Thr Arg Asn Val Thr Gly Gly His Gly Phe Pro Gln Ala Phe
385                 390                 395                 400

Val Asp Trp Phe Cys Gly Gly Leu Gln Tyr Gln Val Asp His His Leu
                405                 410                 415

Phe Pro Ser Leu Pro Arg His Asn Leu Ala Lys Thr His Ala Leu Val
            420                 425                 430

Glu Ser Phe Cys Lys Glu Trp Gly Val Gln Tyr His Glu Ala Asp Leu
        435                 440                 445

Val Asp Gly Thr Met Glu Val Leu His His Leu Gly Ser Val Ala Gly
450                 455                 460

Glu Phe Val Val Asp Phe Val Arg Asp Gly Pro Ala Met
465                 470                 475

<210> SEQ ID NO 5
<211> LENGTH: 1651
<212> TYPE: DNA
<213> ORGANISM: Phaeodactylum tricornutum
<220> FEATURE:
<221> NAME/KEY: CDS
<222> LOCATION: (67)..(1554)

<400> SEQUENCE: 5
gaagaaggaa catataaaag taagccatct cctcggcacc atctaaagac ctaatatcta      60 ctcgtc atg gtt cgc ttt tca aca gcc gct cta ctt tct ctg tcg aca       108
       Met Val Arg Phe Ser Thr Ala Ala Leu Leu Ser Leu Ser Thr
        1               5                  10 ttg aca act tca tgt att ggt gcc ttc cag ctg tct tcg cca gca caa       156
Leu Thr Thr Ser Cys Ile Gly Ala Phe Gln Leu Ser Ser Pro Ala Gln
 15                  20                  25                  30 ctt ccg aca agt agg ctt cgt cgg cat acg aac acg gcg ccg ctt tcg       204
Leu Pro Thr Ser Arg Leu Arg Arg His Thr Asn Thr Ala Pro Leu Ser
                 35                  40                  45 gcc gtg gcc gtc gac tcc ggt tct tcc gat ccg gcc ttg gta ggc aac       252
Ala Val Ala Val Asp Ser Gly Ser Ser Asp Pro Ala Leu Val Gly Asn
             50                  55                  60 ctc ccc ctt ccc aac aac aat gat aat gag gac aag aac cgt aga atg       300
Leu Pro Leu Pro Asn Asn Asn Asp Asn Glu Asp Lys Asn Arg Arg Met
 65                  70                  75 cca atg atg gac ttg aaa ggt att gct ctg tct ggt ctc aaa ggg caa       348
Pro Met Met Asp Leu Lys Gly Ile Ala Leu Ser Gly Leu Lys Gly Gln
 80                  85                  90 gct ctt tcc gtc cga gcg gaa gat ttt cct cag gcg aaa gac ttg cgt       396
Ala Leu Ser Val Arg Ala Glu Asp Phe Pro Gln Ala Lys Asp Leu Arg
 95                 100                 105                 110
```

```
gcc gtc att ccg aaa gat tgc ttc gaa ccc gac acg gcc aaa tcg ttg      444
Ala Val Ile Pro Lys Asp Cys Phe Glu Pro Asp Thr Ala Lys Ser Leu
            115                 120                 125 gga tat ctt tcc gtt tca act atg ggg aca att ctc tgc tcc gtc gtc      492
Gly Tyr Leu Ser Val Ser Thr Met Gly Thr Ile Leu Cys Ser Val Val
        130                 135                 140 ggc gcg aac ctc ctt agt gtg ctc gat ccc tcc aat cca tta acc tgg      540
Gly Ala Asn Leu Leu Ser Val Leu Asp Pro Ser Asn Pro Leu Thr Trp
    145                 150                 155 cct ctc tgg gcg gcc tac ggt gcc gtc acg ggg acg gtc gcc atg ggg      588
Pro Leu Trp Ala Ala Tyr Gly Ala Val Thr Gly Thr Val Ala Met Gly
160                 165                 170 ctt tgg gtg ctg gcc cac gaa tgc gga cac ggc gcc ttt tcc aaa aac      636
Leu Trp Val Leu Ala His Glu Cys Gly His Gly Ala Phe Ser Lys Asn
175                 180                 185                 190 cga tcc ctc cag gat gcc gtg ggg tac att atc cat tcc atc atg ctg      684
Arg Ser Leu Gln Asp Ala Val Gly Tyr Ile Ile His Ser Ile Met Leu
                195                 200                 205 gtg cca tac ttt agt tgg cag cga tcg cat gcc gtg cat cac cag tat      732
Val Pro Tyr Phe Ser Trp Gln Arg Ser His Ala Val His His Gln Tyr
            210                 215                 220 acc aat cat atg gaa ctg ggg gaa aca cac gtt cct gat cga gcc gat      780
Thr Asn His Met Glu Leu Gly Glu Thr His Val Pro Asp Arg Ala Asp
        225                 230                 235 aag gag ggc gag aag agc ctg gcg ctc cgc cag ttc atg ttg gat tcc      828
Lys Glu Gly Glu Lys Ser Leu Ala Leu Arg Gln Phe Met Leu Asp Ser
    240                 245                 250 ttt ggt aaa gac aag ggc atg aaa gca tac gga ggc ctc cag tcg ttt      876
Phe Gly Lys Asp Lys Gly Met Lys Ala Tyr Gly Gly Leu Gln Ser Phe
255                 260                 265                 270 ttg cat ctc atc gtg gga tgg cca gcc tac ctc ctg atc ggt gcg acc      924
Leu His Leu Ile Val Gly Trp Pro Ala Tyr Leu Leu Ile Gly Ala Thr
                275                 280                 285 ggt gga ccc gac cgt ggt atg acc aac cat ttt tat ccc aac cct ttg      972
Gly Gly Pro Asp Arg Gly Met Thr Asn His Phe Tyr Pro Asn Pro Leu
            290                 295                 300 tcg acg cca aca cag ccc aag aaa gaa ctt ttc cct ggg aac tgg aaa     1020
Ser Thr Pro Thr Gln Pro Lys Lys Glu Leu Phe Pro Gly Asn Trp Lys
        305                 310                 315 gaa aag gtc tac cag tca gat att gga atc gcc gcc gtt gtc ggc gcc     1068
Glu Lys Val Tyr Gln Ser Asp Ile Gly Ile Ala Ala Val Val Gly Ala
    320                 325                 330 ctc att gct tgg acc gcc act tcg ggt cta gcc ccc gtc atg gcc ttg     1116
Leu Ile Ala Trp Thr Ala Thr Ser Gly Leu Ala Pro Val Met Ala Leu
335                 340                 345                 350 tac ggt ggt ccc ttg atc gtc att aat gcc tgg ctg gta ctg tac acg     1164
Tyr Gly Gly Pro Leu Ile Val Ile Asn Ala Trp Leu Val Leu Tyr Thr
                355                 360                 365 tgg ttg caa cat aca gat acc gat gtt ccg cac ttt tcc tcc gac aac     1212
Trp Leu Gln His Thr Asp Thr Asp Val Pro His Phe Ser Ser Asp Asn
            370                 375                 380 cac aac ttt gtc aag ggc gca ctg cat acg atc gat cgt ccc tac gac     1260
His Asn Phe Val Lys Gly Ala Leu His Thr Ile Asp Arg Pro Tyr Asp
        385                 390                 395 aaa ctt gat ccc tgg gga atc ata gac ttt ctg cac cac aag att gga     1308
Lys Leu Asp Pro Trp Gly Ile Ile Asp Phe Leu His His Lys Ile Gly
    400                 405                 410 aca acg cat gtg gca cac cat ttt gac agt act atc ccc cac tat aag     1356
Thr Thr His Val Ala His His Phe Asp Ser Thr Ile Pro His Tyr Lys
415                 420                 425                 430
```

```
gct cag att gct acc gat gcc atc aaa gcc aag ttt cca gaa gtg tac    1404
Ala Gln Ile Ala Thr Asp Ala Ile Lys Ala Lys Phe Pro Glu Val Tyr
            435                 440                 445 ctc tat gac ccg aca cca att cca caa gcc atg tgg cgc gtc gcc aag    1452
Leu Tyr Asp Pro Thr Pro Ile Pro Gln Ala Met Trp Arg Val Ala Lys
        450                 455                 460 gga tgt act gca gta gag caa cgc ggt gac gcc tgg gtg tgg aaa aac    1500
Gly Cys Thr Ala Val Glu Gln Arg Gly Asp Ala Trp Val Trp Lys Asn
    465                 470                 475 gaa gga ata gaa gat ttg gtg gaa cat cgt caa agc aaa tta tcg agc    1548
Glu Gly Ile Glu Asp Leu Val Glu His Arg Gln Ser Lys Leu Ser Ser
480                 485                 490 gaa taa agcaacatat cgctttatgg aagaacaaac gtccattgtg taaaaccctg     1604
Glu
495 ataatttcaa tattgtgttt tgttttaaaa aaaaaaaaaa aaaaaaa                1651

<210> SEQ ID NO 6
<211> LENGTH: 495
<212> TYPE: PRT
<213> ORGANISM: Phaeodactylum tricornutum

<400> SEQUENCE: 6

Met Val Arg Phe Ser Thr Ala Ala Leu Leu Ser Leu Ser Thr Leu Thr
1               5                   10                  15

Thr Ser Cys Ile Gly Ala Phe Gln Leu Ser Ser Pro Ala Gln Leu Pro
            20                  25                  30

Thr Ser Arg Leu Arg Arg His Thr Asn Thr Ala Pro Leu Ser Ala Val
        35                  40                  45

Ala Val Asp Ser Gly Ser Ser Asp Pro Ala Leu Val Gly Asn Leu Pro
    50                  55                  60

Leu Pro Asn Asn Asn Asp Asn Glu Asp Lys Asn Arg Arg Met Pro Met
65                  70                  75                  80

Met Asp Leu Lys Gly Ile Ala Leu Ser Gly Leu Lys Gly Gln Ala Leu
                85                  90                  95

Ser Val Arg Ala Glu Asp Phe Pro Gln Ala Lys Asp Leu Arg Ala Val
            100                 105                 110

Ile Pro Lys Asp Cys Phe Glu Pro Asp Thr Ala Lys Ser Leu Gly Tyr
        115                 120                 125

Leu Ser Val Ser Thr Met Gly Thr Ile Leu Cys Ser Val Val Gly Ala
    130                 135                 140

Asn Leu Leu Ser Val Leu Asp Pro Ser Asn Pro Leu Thr Trp Pro Leu
145                 150                 155                 160

Trp Ala Ala Tyr Gly Ala Val Thr Gly Thr Val Ala Met Gly Leu Trp
                165                 170                 175

Val Leu Ala His Glu Cys Gly His Gly Ala Phe Ser Lys Asn Arg Ser
            180                 185                 190

Leu Gln Asp Ala Val Gly Tyr Ile Ile His Ser Ile Met Leu Val Pro
        195                 200                 205

Tyr Phe Ser Trp Gln Arg Ser His Ala Val His Gln Tyr Thr Asn
    210                 215                 220

His Met Glu Leu Gly Glu Thr His Val Pro Asp Arg Ala Asp Lys Glu
225                 230                 235                 240

Gly Glu Lys Ser Leu Ala Leu Arg Gln Phe Met Leu Asp Ser Phe Gly
                245                 250                 255

Lys Asp Lys Gly Met Lys Ala Tyr Gly Gly Leu Gln Ser Phe Leu His
            260                 265                 270
```

```
Leu Ile Val Gly Trp Pro Ala Tyr Leu Leu Ile Gly Ala Thr Gly Gly
            275                 280                 285

Pro Asp Arg Gly Met Thr Asn His Phe Tyr Pro Asn Pro Leu Ser Thr
        290                 295                 300

Pro Thr Gln Pro Lys Lys Glu Leu Phe Pro Gly Asn Trp Lys Glu Lys
305                 310                 315                 320

Val Tyr Gln Ser Asp Ile Gly Ile Ala Ala Val Val Gly Ala Leu Ile
                325                 330                 335

Ala Trp Thr Ala Thr Ser Gly Leu Ala Pro Val Met Ala Leu Tyr Gly
            340                 345                 350

Gly Pro Leu Ile Val Ile Asn Ala Trp Leu Val Leu Tyr Thr Trp Leu
        355                 360                 365

Gln His Thr Asp Thr Asp Val Pro His Phe Ser Asp Asn His Asn
370                 375                 380

Phe Val Lys Gly Ala Leu His Thr Ile Asp Arg Pro Tyr Asp Lys Leu
385                 390                 395                 400

Asp Pro Trp Gly Ile Ile Asp Phe Leu His His Lys Ile Gly Thr Thr
                405                 410                 415

His Val Ala His His Phe Asp Ser Thr Ile Pro His Tyr Lys Ala Gln
            420                 425                 430

Ile Ala Thr Asp Ala Ile Lys Ala Lys Phe Pro Glu Val Tyr Leu Tyr
        435                 440                 445

Asp Pro Thr Pro Ile Pro Gln Ala Met Trp Arg Val Ala Lys Gly Cys
450                 455                 460

Thr Ala Val Glu Gln Arg Gly Asp Ala Trp Val Trp Lys Asn Glu Gly
465                 470                 475                 480

Ile Glu Asp Leu Val Glu His Arg Gln Ser Lys Leu Ser Glu
                485                 490                 495

<210> SEQ ID NO 7
<211> LENGTH: 1578
<212> TYPE: DNA
<213> ORGANISM: Physcomitrella patens
<220> FEATURE:
<221> NAME/KEY: CDS
<222> LOCATION: (1)..(1578)

<400> SEQUENCE: 7 atg gta ttc gcg ggc ggt gga ctt cag cag ggc tct ctc gaa gaa aac    48
Met Val Phe Ala Gly Gly Gly Leu Gln Gln Gly Ser Leu Glu Glu Asn
 1               5                  10                  15 atc gac gtc gag cac att gcc agt atg tct ctc ttc agc gac ttc ttc    96
Ile Asp Val Glu His Ile Ala Ser Met Ser Leu Phe Ser Asp Phe Phe
             20                  25                  30 agt tat gtg tct tca act gtt ggt tcg tgg agc gta cac agt ata caa   144
Ser Tyr Val Ser Ser Thr Val Gly Ser Trp Ser Val His Ser Ile Gln
         35                  40                  45 cct ttg aag cgc ctg acg agt aag aag cgt gtt tcg gaa agc gct gcc   192
Pro Leu Lys Arg Leu Thr Ser Lys Lys Arg Val Ser Glu Ser Ala Ala
     50                  55                  60 gtg caa tgt ata tca gct gaa gtt cag aga aat tcg agt acc cag gga   240
Val Gln Cys Ile Ser Ala Glu Val Gln Arg Asn Ser Ser Thr Gln Gly
 65                  70                  75                  80 act gcg gag gca ctc gca gaa tca gtc gtg aag ccc acg aga cga agg   288
Thr Ala Glu Ala Leu Ala Glu Ser Val Val Lys Pro Thr Arg Arg Arg
                 85                  90                  95 tca tct cag tgg aag aag tcg aca cac ccc cta tca gaa gta gca gta   336
Ser Ser Gln Trp Lys Lys Ser Thr His Pro Leu Ser Glu Val Ala Val
```

-continued

```
            100                 105                 110
cac aac aag cca agc gat tgc tgg att gtt gta aaa aac aag gtg tat        384
His Asn Lys Pro Ser Asp Cys Trp Ile Val Val Lys Asn Lys Val Tyr
        115                 120                 125 gat gtt tcc aat ttt gcg gac gag cat ccc gga gga tca gtt att agt        432
Asp Val Ser Asn Phe Ala Asp Glu His Pro Gly Gly Ser Val Ile Ser
130                 135                 140 act tat ttt gga cga gac ggc aca gat gtt ttc tct agt ttt cat gca        480
Thr Tyr Phe Gly Arg Asp Gly Thr Asp Val Phe Ser Ser Phe His Ala
145                 150                 155                 160 gct tct aca tgg aaa att ctt caa gac ttt tac att ggt gac gtg gag        528
Ala Ser Thr Trp Lys Ile Leu Gln Asp Phe Tyr Ile Gly Asp Val Glu
        165                 170                 175 agg gtg gag ccg act cca gag ctg ctg aaa gat ttc cga gaa atg aga        576
Arg Val Glu Pro Thr Pro Glu Leu Leu Lys Asp Phe Arg Glu Met Arg
        180                 185                 190 gct ctt ttc ctg agg gag caa ctt ttc aaa agt tcg aaa ttg tac tat        624
Ala Leu Phe Leu Arg Glu Gln Leu Phe Lys Ser Ser Lys Leu Tyr Tyr
        195                 200                 205 gtt atg aag ctg ctc acg aat gtt gct att ttt gct gcg agc att gca        672
Val Met Lys Leu Leu Thr Asn Val Ala Ile Phe Ala Ala Ser Ile Ala
210                 215                 220 ata ata tgt tgg agc aag act att tca gcg gtt ttg gct tca gct tgt        720
Ile Ile Cys Trp Ser Lys Thr Ile Ser Ala Val Leu Ala Ser Ala Cys
225                 230                 235                 240 atg atg gct ctg tgt ttc caa cag tgc gga tgg cta tcc cat gat ttt        768
Met Met Ala Leu Cys Phe Gln Gln Cys Gly Trp Leu Ser His Asp Phe
        245                 250                 255 ctc cac aat cag gtg ttt gag aca cgc tgg ctt aat gaa gtt gtc ggg        816
Leu His Asn Gln Val Phe Glu Thr Arg Trp Leu Asn Glu Val Val Gly
        260                 265                 270 tat gtg atc ggc aac gcc gtt ctg ggg ttt agt aca ggg tgg tgg aag        864
Tyr Val Ile Gly Asn Ala Val Leu Gly Phe Ser Thr Gly Trp Trp Lys
        275                 280                 285 gag aag cat aac ctt cat cat gct gct cca aat gaa tgc gat cag act        912
Glu Lys His Asn Leu His His Ala Ala Pro Asn Glu Cys Asp Gln Thr
290                 295                 300 tac caa cca att gat gaa gat att gat act ctc ccc ctc att gcc tgg        960
Tyr Gln Pro Ile Asp Glu Asp Ile Asp Thr Leu Pro Leu Ile Ala Trp
305                 310                 315                 320 agc aag gac ata ctg gcc aca gtt gag aat aag aca ttc ttg cga atc       1008
Ser Lys Asp Ile Leu Ala Thr Val Glu Asn Lys Thr Phe Leu Arg Ile
        325                 330                 335 ctc caa tac cag cat ctg ttc ttc atg ggt ctg tta ttt ttc gcc cgt       1056
Leu Gln Tyr Gln His Leu Phe Phe Met Gly Leu Leu Phe Phe Ala Arg
        340                 345                 350 ggt agt tgg ctc ttt tgg agc tgg aga tat acc tct aca gca gtg ctc       1104
Gly Ser Trp Leu Phe Trp Ser Trp Arg Tyr Thr Ser Thr Ala Val Leu
        355                 360                 365 tca cct gtc gac agg ttg ttg gag aag gga act gtt ctg ttt cac tac       1152
Ser Pro Val Asp Arg Leu Leu Glu Lys Gly Thr Val Leu Phe His Tyr
370                 375                 380 ttt tgg ttc gtc ggg aca gcg tgc tat ctt ctc cct ggt tgg aag cca       1200
Phe Trp Phe Val Gly Thr Ala Cys Tyr Leu Leu Pro Gly Trp Lys Pro
385                 390                 395                 400 tta gta tgg atg gcg gtg act gag ctc atg tcc ggc atg ctg ctg ggc       1248
Leu Val Trp Met Ala Val Thr Glu Leu Met Ser Gly Met Leu Leu Gly
        405                 410                 415 ttt gta ttt gta ctt agc cac aat ggg atg gag gtt tat aat tcg tct       1296
Phe Val Phe Val Leu Ser His Asn Gly Met Glu Val Tyr Asn Ser Ser
```

-continued

```
                             420                         425                         430
aaa gaa ttc gtg agt gca cag atc gta tcc aca cgg gat atc aaa gga        1344
Lys Glu Phe Val Ser Ala Gln Ile Val Ser Thr Arg Asp Ile Lys Gly
        435                         440                         445 aac ata ttc aac gac tgg ttc act ggt ggc ctt aac agg caa ata gag        1392
Asn Ile Phe Asn Asp Trp Phe Thr Gly Gly Leu Asn Arg Gln Ile Glu
    450                         455                         460 cat cat ctt ttc cca aca atg ccc agg cat aat tta aac aaa ata gca        1440
His His Leu Phe Pro Thr Met Pro Arg His Asn Leu Asn Lys Ile Ala
465                         470                         475                         480 cct aga gtg gag gtg ttc tgt aag aaa cac ggt ctg gtg tac gaa gac        1488
Pro Arg Val Glu Val Phe Cys Lys Lys His Gly Leu Val Tyr Glu Asp
                485                         490                         495 gta tct att gct acc ggc act tgc aag gtt ttg aaa gca ttg aag gaa        1536
Val Ser Ile Ala Thr Gly Thr Cys Lys Val Leu Lys Ala Leu Lys Glu
            500                         505                         510 gtc gcg gag gct gcg gca gag cag cat gct acc acc agt taa                1578
Val Ala Glu Ala Ala Ala Glu Gln His Ala Thr Thr Ser
        515                         520                         525
```

<210> SEQ ID NO 8
<211> LENGTH: 525
<212> TYPE: PRT
<213> ORGANISM: Physcomitrella patens

<400> SEQUENCE: 8

```
Met Val Phe Ala Gly Gly Leu Gln Gln Gly Ser Leu Glu Glu Asn
  1               5                  10                  15

Ile Asp Val Glu His Ile Ala Ser Met Ser Leu Phe Ser Asp Phe Phe
                 20                  25                  30

Ser Tyr Val Ser Ser Thr Val Gly Ser Trp Ser Val His Ser Ile Gln
                 35                  40                  45

Pro Leu Lys Arg Leu Thr Ser Lys Lys Arg Val Ser Glu Ser Ala Ala
         50                  55                  60

Val Gln Cys Ile Ser Ala Glu Val Gln Arg Asn Ser Ser Thr Gln Gly
 65                  70                  75                  80

Thr Ala Glu Ala Leu Ala Glu Ser Val Val Lys Pro Thr Arg Arg Arg
                 85                  90                  95

Ser Ser Gln Trp Lys Lys Ser Thr His Pro Leu Ser Glu Val Ala Val
                100                 105                 110

His Asn Lys Pro Ser Asp Cys Trp Ile Val Lys Asn Lys Val Tyr
            115                 120                 125

Asp Val Ser Asn Phe Ala Asp Glu His Pro Gly Gly Ser Val Ile Ser
        130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
```

```
                        245                 250                 255
Leu His Asn Gln Val Phe Glu Thr Arg Trp Leu Asn Glu Val Val Gly
            260                 265                 270

Tyr Val Ile Gly Asn Ala Val Leu Gly Phe Ser Thr Gly Trp Trp Lys
        275                 280                 285

Glu Lys His Asn Leu His His Ala Ala Pro Asn Glu Cys Asp Gln Thr
    290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
            325                 330                 335

Leu Gln Tyr Gln His Leu Phe Phe Met Gly Leu Leu Phe Phe Ala Arg
        340                 345                 350

Gly Ser Trp Leu Phe Trp Ser Trp Arg Tyr Thr Ser Thr Ala Val Leu
    355                 360                 365

Ser Pro Val Asp Arg Leu Leu Glu Lys Gly Thr Val Leu Phe His Tyr
370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
            405                 410                 415

Phe Val Phe Val Leu Ser His Asn Gly Met Glu Val Tyr Asn Ser Ser
        420                 425                 430

Lys Glu Phe Val Ser Ala Gln Ile Val Ser Thr Arg Asp Ile Lys Gly
    435                 440                 445

Asn Ile Phe Asn Asp Trp Phe Thr Gly Gly Leu Asn Arg Gln Ile Glu
450                 455                 460

His His Leu Phe Pro Thr Met Pro Arg His Asn Leu Asn Lys Ile Ala
            470                 475                 480
465

Pro Arg Val Glu Val Phe Cys Lys Lys His Gly Leu Val Tyr Glu Asp
        485                 490                 495

Val Ser Ile Ala Thr Gly Thr Cys Lys Val Leu Lys Ala Leu Lys Glu
    500                 505                 510

Val Ala Glu Ala Ala Ala Glu Gln His Ala Thr Thr Ser
            515                 520                 525

<210> SEQ ID NO 9
<211> LENGTH: 873
<212> TYPE: DNA
<213> ORGANISM: Physcomitrella patens
<220> FEATURE:
<221> NAME/KEY: CDS
<222> LOCATION: (1)..(873)

<400> SEQUENCE: 9 atg gag gtc gtg gag aga ttc tac ggt gag ttg gat ggg aag gtc tcg      48
Met Glu Val Val Glu Arg Phe Tyr Gly Glu Leu Asp Gly Lys Val Ser
  1               5                  10                  15 cag ggc gtg aat gca ttg ctg ggt agt ttt ggg gtg gag ttg acg gat      96
Gln Gly Val Asn Ala Leu Leu Gly Ser Phe Gly Val Glu Leu Thr Asp
             20                  25                  30 acg ccc act acc aaa ggc ttg ccc ctc gtt gac agt ccc aca ccc atc     144
Thr Pro Thr Thr Lys Gly Leu Pro Leu Val Asp Ser Pro Thr Pro Ile
         35                  40                  45 gtc ctc ggt gtt tct gta tac ttg act att gtc att gga ggg ctt ttg     192
Val Leu Gly Val Ser Val Tyr Leu Thr Ile Val Ile Gly Gly Leu Leu
     50                  55                  60
```

```
tgg ata aag gcc agg gat ctg aaa ccg cgc gcc tcg gag cca ttt ttg      240
Trp Ile Lys Ala Arg Asp Leu Lys Pro Arg Ala Ser Glu Pro Phe Leu
 65                  70                  75                  80 ctc caa gct ttg gtg ctt gtg cac aac ctg ttc tgt ttt gcg ctc agt      288
Leu Gln Ala Leu Val Leu Val His Asn Leu Phe Cys Phe Ala Leu Ser
                 85                  90                  95 ctg tat atg tgc gtg ggc atc gct tat cag gct att acc tgg cgg tac      336
Leu Tyr Met Cys Val Gly Ile Ala Tyr Gln Ala Ile Thr Trp Arg Tyr
            100                 105                 110 tct ctc tgg ggc aat gca tac aat cct aaa cat aaa gag atg gcg att      384
Ser Leu Trp Gly Asn Ala Tyr Asn Pro Lys His Lys Glu Met Ala Ile
        115                 120                 125 ctg gta tac ttg ttc tac atg tct aag tac gtg gaa ttc atg gat acc      432
Leu Val Tyr Leu Phe Tyr Met Ser Lys Tyr Val Glu Phe Met Asp Thr
    130                 135                 140 gtt atc atg ata ctg aag cgc agc acc agg caa ata agc ttc ctc cac      480
Val Ile Met Ile Leu Lys Arg Ser Thr Arg Gln Ile Ser Phe Leu His
145                 150                 155                 160 gtt tat cat cat tct tca att tcc ctc att tgg tgg gct att gct cat      528
Val Tyr His His Ser Ser Ile Ser Leu Ile Trp Trp Ala Ile Ala His
                165                 170                 175 cac gct cct ggc ggt gaa gca tat tgg tct gcg gct ctg aac tca gga      576
His Ala Pro Gly Gly Glu Ala Tyr Trp Ser Ala Ala Leu Asn Ser Gly
            180                 185                 190 gtg cat gtt ctc atg tat gcg tat tac ttc ttg gct gcc tgc ctt cga      624
Val His Val Leu Met Tyr Ala Tyr Tyr Phe Leu Ala Ala Cys Leu Arg
        195                 200                 205 agt agc cca aag tta aaa aat aag tac ctt ttt tgg ggc agg tac ttg      672
Ser Ser Pro Lys Leu Lys Asn Lys Tyr Leu Phe Trp Gly Arg Tyr Leu
    210                 215                 220 aca caa ttc caa atg ttc cag ttt atg ctg aac tta gtg cag gct tac      720
Thr Gln Phe Gln Met Phe Gln Phe Met Leu Asn Leu Val Gln Ala Tyr
225                 230                 235                 240 tac gac atg aaa acg aat gcg cca tat cca caa tgg ctg atc aag att      768
Tyr Asp Met Lys Thr Asn Ala Pro Tyr Pro Gln Trp Leu Ile Lys Ile
                245                 250                 255 ttg ttc tac tac atg atc tcg ttg ctg ttt ctt ttc ggc aat ttt tac      816
Leu Phe Tyr Tyr Met Ile Ser Leu Leu Phe Leu Phe Gly Asn Phe Tyr
            260                 265                 270 gta caa aaa tac atc aaa ccc tct gac gga aag caa aag gga gct aaa      864
Val Gln Lys Tyr Ile Lys Pro Ser Asp Gly Lys Gln Lys Gly Ala Lys
        275                 280                 285 act gag tga                                                          873
Thr Glu
    290

<210> SEQ ID NO 10
<211> LENGTH: 290
<212> TYPE: PRT
<213> ORGANISM: Physcomitrella patens

<400> SEQUENCE: 10

Met Glu Val Val Glu Arg Phe Tyr Gly Glu Leu Asp Gly Lys Val Ser
  1               5                  10                  15

Gln Gly Val Asn Ala Leu Leu Gly Ser Phe Gly Val Glu Leu Thr Asp
                 20                  25                  30

Thr Pro Thr Thr Lys Gly Leu Pro Leu Val Asp Ser Pro Thr Pro Ile
             35                  40                  45

Val Leu Gly Val Ser Val Tyr Leu Thr Ile Val Ile Gly Gly Leu Leu
         50                  55                  60
```

```
Trp Ile Lys Ala Arg Asp Leu Lys Pro Arg Ala Ser Glu Pro Phe Leu
 65                  70                  75                  80

Leu Gln Ala Leu Val Leu Val His Asn Leu Phe Cys Phe Ala Leu Ser
                 85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 11
<211> LENGTH: 1526
<212> TYPE: DNA
<213> ORGANISM: Phaeodactylum tricornutum
<220> FEATURE:
<221> NAME/KEY: CDS
<222> LOCATION: (92)..(1402)

<400> SEQUENCE: 11
gcttccgtta gcgtcccata gtttgttaca cttggctgtg aaacgaatac gttcttggtc      60
tacttactac aacgaagcaa ccaccagcag c atg ggt aag gga ggt caa cga        112
                                  Met Gly Lys Gly Gly Gln Arg
                                    1               5 gct gta gct ccc aag agt gcc acc agc tct act ggc agt gct acc ctt       160
Ala Val Ala Pro Lys Ser Ala Thr Ser Ser Thr Gly Ser Ala Thr Leu
         10                  15                  20 agc caa agc aag gaa cag gta tgg act tcg tcg tac aac cct ctg gcg       208
Ser Gln Ser Lys Glu Gln Val Trp Thr Ser Ser Tyr Asn Pro Leu Ala
     25                  30                  35 aag gat tcc ccg gag ctg cca acc aaa ggc caa atc aag gcc gtc att       256
Lys Asp Ser Pro Glu Leu Pro Thr Lys Gly Gln Ile Lys Ala Val Ile
 40                  45                  50                  55 ccg aag gaa tgt ttc caa cgc tca gcc ttt tgg tct acc ttc tac ctg       304
Pro Lys Glu Cys Phe Gln Arg Ser Ala Phe Trp Ser Thr Phe Tyr Leu
                 60                  65                  70 atg cgc gat ctc gcc atg gct gcc gcc ttt tgc tac gga acc tca cag       352
Met Arg Asp Leu Ala Met Ala Ala Ala Phe Cys Tyr Gly Thr Ser Gln
```

```
                    75                  80                  85
gtc ctc tcc acc gac ctt ccc caa gac gcc acg ctc att ctg ccc tgg       400
Val Leu Ser Thr Asp Leu Pro Gln Asp Ala Thr Leu Ile Leu Pro Trp
             90                  95                 100 gct ctc ggc tgg ggc gtc tac gcc ttt tgg atg gga acc att ctc acc       448
Ala Leu Gly Trp Gly Val Tyr Ala Phe Trp Met Gly Thr Ile Leu Thr
    105                 110                 115 ggg cct tgg gta gtt gcg cac gaa tgt gga cac ggc gct tac tcc gac       496
Gly Pro Trp Val Val Ala His Glu Cys Gly His Gly Ala Tyr Ser Asp
120                 125                 130                 135 tcc cag acg ttc aat gac gtg gtc ggc ttt atc gtc cac caa gct ttg       544
Ser Gln Thr Phe Asn Asp Val Val Gly Phe Ile Val His Gln Ala Leu
            140                 145                 150 ctc gtc ccc tac ttt gcc tgg cag tac acc cac gcg aaa cac cac cgt       592
Leu Val Pro Tyr Phe Ala Trp Gln Tyr Thr His Ala Lys His His Arg
        155                 160                 165 cga acc aac cat ctg gtg gac ggc gag tcc cac gtc cct tct acc gcc       640
Arg Thr Asn His Leu Val Asp Gly Glu Ser His Val Pro Ser Thr Ala
    170                 175                 180 aag gat aac ggc ctc ggg ccg cac aac gag cga aac tcc ttc tac gcc       688
Lys Asp Asn Gly Leu Gly Pro His Asn Glu Arg Asn Ser Phe Tyr Ala
185                 190                 195 gcg tgg cac gag gcc atg gga gac ggc gcc ttt gcc gtc ttt caa gtc       736
Ala Trp His Glu Ala Met Gly Asp Gly Ala Phe Ala Val Phe Gln Val
200                 205                 210                 215 tgg tcg cac ttg ttc gtc ggc tgg cct ctc tac ttg gcc ggt ctg gcc       784
Trp Ser His Leu Phe Val Gly Trp Pro Leu Tyr Leu Ala Gly Leu Ala
            220                 225                 230 agt acc gga aag ctt gcg cac gaa ggt tgg tgg ctg gaa gaa cgg aac       832
Ser Thr Gly Lys Leu Ala His Glu Gly Trp Trp Leu Glu Glu Arg Asn
        235                 240                 245 gcg att gcg gat cac ttt cga ccc agc tct ccc atg ttc ccc gcc aag       880
Ala Ile Ala Asp His Phe Arg Pro Ser Ser Pro Met Phe Pro Ala Lys
    250                 255                 260 atc cgt gcc aag att gcc ctt tcc agc gcg acg gaa ctc gcc gtg ctc       928
Ile Arg Ala Lys Ile Ala Leu Ser Ser Ala Thr Glu Leu Ala Val Leu
265                 270                 275 gct gga ctc ttg tat gtc ggt aca cag gtc gga cac ctt ccc gtc ctg       976
Ala Gly Leu Leu Tyr Val Gly Thr Gln Val Gly His Leu Pro Val Leu
280                 285                 290                 295 ctg tgg tac tgg gga ccg tac acc ttt gtc aac gct tgg ctt gta ctc      1024
Leu Trp Tyr Trp Gly Pro Tyr Thr Phe Val Asn Ala Trp Leu Val Leu
            300                 305                 310 tac acg tgg ctg cag cat acg gac ccg tcc atc ccg cac tac ggt gaa      1072
Tyr Thr Trp Leu Gln His Thr Asp Pro Ser Ile Pro His Tyr Gly Glu
        315                 320                 325 ggc gag tgg acc tgg gtc aag ggc gcg ctc tct acc att gat cga gac      1120
Gly Glu Trp Thr Trp Val Lys Gly Ala Leu Ser Thr Ile Asp Arg Asp
    330                 335                 340 tac ggc atc ttc gat ttc ttt cac cac acc atc ggt tcc acg cac gtg      1168
Tyr Gly Ile Phe Asp Phe Phe His His Thr Ile Gly Ser Thr His Val
345                 350                 355 gta cac cat ttg ttc cac gaa atg ccc tgg tac aat gcc ggc att gcc      1216
Val His His Leu Phe His Glu Met Pro Trp Tyr Asn Ala Gly Ile Ala
360                 365                 370                 375 acg caa aag gtc aag gaa ttt ttg gaa ccc cag ggc ttg tac aat tac      1264
Thr Gln Lys Val Lys Glu Phe Leu Glu Pro Gln Gly Leu Tyr Asn Tyr
            380                 385                 390 gat ccg acc ccc tgg tac aag gcc atg tgg cgc att gcc cgg acc tgt      1312
Asp Pro Thr Pro Trp Tyr Lys Ala Met Trp Arg Ile Ala Arg Thr Cys
```

```
                    395                 400                 405
cac tat gtg gag tca aac gag ggt gtg cag tat ttc aag agt atg gaa    1360
His Tyr Val Glu Ser Asn Glu Gly Val Gln Tyr Phe Lys Ser Met Glu
            410                 415                 420 aac gtg ccg ctg act aag gat gtg cga aac aaa gcc gca tga            1402
Asn Val Pro Leu Thr Lys Asp Val Arg Asn Lys Ala Ala
        425                 430                 435 gaaaaagtgc caccgacgca taattttaca atcctaccaa caagaccaac attatatggt  1462
tttcgcttaa aagatagttt tttctaccat ctgtgtagtc ggcacaaaaa aaaaaaaaaa  1522
aaaa                                                               1526

<210> SEQ ID NO 12
<211> LENGTH: 436
<212> TYPE: PRT
<213> ORGANISM: Phaeodactylum tricornutum

<400> SEQUENCE: 12

Met Gly Lys Gly Gly Gln Arg Ala Val Ala Pro Lys Ser Ala Thr Ser
 1               5                  10                  15

Ser Thr Gly Ser Ala Thr Leu Ser Gln Ser Lys Glu Gln Val Trp Thr
            20                  25                  30

Ser Ser Tyr Asn Pro Leu Ala Lys Asp Ser Pro Glu Leu Pro Thr Lys
        35                  40                  45

Gly Gln Ile Lys Ala Val Ile Pro Lys Glu Cys Phe Gln Arg Ser Ala
    50                  55                  60

Phe Trp Ser Thr Phe Tyr Leu Met Arg Asp Leu Ala Met Ala Ala Ala
65                  70                  75                  80

Phe Cys Tyr Gly Thr Ser Gln Val Leu Ser Thr Asp Leu Pro Gln Asp
                85                  90                  95

Ala Thr Leu Ile Leu Pro Trp Ala Leu Gly Trp Gly Val Tyr Ala Phe
            100                 105                 110

Trp Met Gly Thr Ile Leu Thr Gly Pro Trp Val Val Ala His Glu Cys
        115                 120                 125

Gly His Gly Ala Tyr Ser Asp Ser Gln Thr Phe Asn Asp Val Val Gly
    130                 135                 140

Phe Ile Val His Gln Ala Leu Leu Val Pro Tyr Phe Ala Trp Gln Tyr
145                 150                 155                 160

Thr His Ala Lys His Arg Arg Thr Asn His Leu Val Asp Gly Glu
                165                 170                 175

Ser His Val Pro Ser Thr Ala Lys Asp Asn Gly Leu Gly Pro His Asn
            180                 185                 190

Glu Arg Asn Ser Phe Tyr Ala Ala Trp His Glu Ala Met Gly Asp Gly
        195                 200                 205

Ala Phe Ala Val Phe Gln Val Trp Ser His Leu Phe Val Gly Trp Pro
    210                 215                 220

Leu Tyr Leu Ala Gly Leu Ala Ser Thr Gly Lys Leu Ala His Glu Gly
225                 230                 235                 240

Trp Trp Leu Glu Glu Arg Asn Ala Ile Ala Asp His Phe Arg Pro Ser
                245                 250                 255

Ser Pro Met Phe Pro Ala Lys Ile Arg Ala Lys Ile Ala Leu Ser Ser
            260                 265                 270

Ala Thr Glu Leu Ala Val Leu Ala Gly Leu Leu Tyr Val Gly Thr Gln
        275                 280                 285

Val Gly His Leu Pro Val Leu Leu Trp Tyr Trp Gly Pro Tyr Thr Phe
    290                 295                 300
```

| | | | | | | | | | | | | |
|---|---|---|---|---|---|---|---|---|---|---|---|---|
|Val|Asn|Ala|Trp|Leu|Val|Leu|Tyr|Thr|Trp|Leu|Gln|His|Thr|Asp|Pro|
|305| | | |310| | | |315| | | |320|

Ser Ile Pro His Tyr Gly Glu Gly Glu Trp Thr Trp Val Lys Gly Ala
              325                 330                 335

Leu Ser Thr Ile Asp Arg Asp Tyr Gly Ile Phe Asp Phe Phe His His
              340                 345                 350

Thr Ile Gly Ser Thr His Val Val His His Leu Phe His Glu Met Pro
              355                 360                 365

Trp Tyr Asn Ala Gly Ile Ala Thr Gln Lys Val Lys Glu Phe Leu Glu
              370                 375                 380

Pro Gln Gly Leu Tyr Asn Tyr Asp Pro Thr Pro Trp Tyr Lys Ala Met
385                 390                 395                 400

Trp Arg Ile Ala Arg Thr Cys His Tyr Val Glu Ser Asn Glu Gly Val
              405                 410                 415

Gln Tyr Phe Lys Ser Met Glu Asn Val Pro Leu Thr Lys Asp Val Arg
              420                 425                 430

Asn Lys Ala Ala
        435

<210> SEQ ID NO 13
<211> LENGTH: 3598
<212> TYPE: DNA
<213> ORGANISM: Unknown
<220> FEATURE:
<223> OTHER INFORMATION: Sequence represents a plant
      promoter-terminator expression cassette
      in vector pUC19

<400> SEQUENCE: 13
tcgcgcgttt cggtgatgac ggtgaaaacc tctgacacat gcagctcccg gagacggtca      60
cagcttgtct gtaagcggat gccgggagca gacaagcccg tcaggcgcgc tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggcgcgccg agctcctcga     420
gcaaatttac acattgccac taaacgtcta aaccttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta     600
tttttgtctt ctaaatacat atactaatca actggaaatg taaatatttg ctaatatttc     660
tactatagga gaattaaagt gagtgaatat ggtaccacaa ggtttggaga tttaattgtt     720
gcaatgctgc atggatggca tatacaccaa acattcaata attcttgagg ataataatgg     780
taccacacaa gatttgaggt gcatgaacgt cacgtggaca aaaggtttag taattttca     840 agacaacaat gttaccacac acaagttttg aggtgcatgc atggatgccc tgtggaaagt     900
ttaaaaatat tttggaaatg atttgcatgg aagccatgtg taaaaccatg acatccactt     960
ggaggatgca ataatgaaga aaactacaaa tttacatgca actagttatg catgtagtct    1020
atataatgag gattttgcaa tactttcatt catacacact cactaagttt tacacgatta    1080
taatttcttc atagccagcc caccgcggtg ggcggccgcc tgcagtctag aaggcctcct    1140
gctttaatga gatatgcgag acgcctatga tcgcatgata tttgctttca attctgttgt    1200

```
gcacgttgta aaaaacctga gcatgtgtag ctcagatcct taccgccggt ttcggttcat    1260
tctaatgaat atatcacccg ttactatcgt attttatga ataatattct ccgttcaatt     1320
tactgattgt ccgtcgacga attcgagctc ggcgcgccaa gcttggcgta atcatggtca    1380
tagctgtttc ctgtgtgaaa ttgttatccg ctcacaattc cacacaacat acgagccgga    1440
agcataaagt gtaaagcctg gggtgcctaa tgagtgagct aactcacatt aattgcgttg    1500
cgctcactgc ccgcttttcc agtcgggaaac ctgtcgtgcc agctgcatta atgaatcggc    1560
caacgcgcgg ggagaggcgg tttgcgtatt gggcgctctt ccgcttcctc gctcactgac    1620
tcgctgcgct cggtcgttcg gctgcggcga gcggtatcag ctcactcaaa ggcggtaata    1680
cggttatcca cagaatcagg ggataacgca ggaaagaaca tgtgagcaaa aggccagcaa    1740
aaggccagga accgtaaaaa ggccgcgttg ctggcgtttt tccataggct ccgcccccct    1800
gacgagcatc acaaaaatcg acgctcaagt cagaggtggc gaaacccgac aggactataa    1860
agataccagg cgtttccccc tggaagctcc ctcgtgcgct ctcctgttcc gaccctgccg    1920
cttaccggat acctgtccgc ctttctccct tcgggaagcg tggcgctttc tcatagctca    1980
cgctgtaggt atctcagttc ggtgtaggtc gttcgctcca agctgggctg tgtgcacgaa    2040
ccccccgttc agcccgaccg ctgcgcctta tccggtaact atcgtcttga gtccaacccg    2100
gtaagacacg acttatcgcc actggcagca gccactggta acaggattag cagagcgagg    2160
tatgtaggcg gtgctacaga gttcttgaag tggtggccta actacggcta cactagaagg    2220
acagtatttg gtatctgcgc tctgctgaag ccagttacct tcggaaaaag agttggtagc    2280
tcttgatccg gcaaacaaac caccgctggt agcggtggtt tttttgtttg caagcagcag    2340
attacgcgca gaaaaaaagg atctcaagaa gatcctttga tcttttctac ggggtctgac    2400
gctcagtgga acgaaaactc acgttaaggg attttggtca tgagattatc aaaaaggatc    2460
ttcacctaga tccttttaaa ttaaaaatga agttttaaat caatctaaag tatatatgag    2520
taaacttggt ctgacagtta ccaatgctta atcagtgagg cacctatctc agcgatctgt    2580
ctatttcgtt catccatagt tgcctgactc ccgtcgtgt agataactac gatacgggag    2640
ggcttaccat ctggccccag tgctgcaatg ataccgcgag acccacgctc accggctcca    2700
gatttatcag caataaacca gccagccgga agggccgagc gcagaagtgg tcctgcaact    2760
ttatccgcct ccatccagtc tattaattgt tgccgggaag ctagagtaag tagttcgcca    2820
gttaatagtt tgcgcaacgt tgttgccatt gctacaggca tcgtggtgtc acgctcgtcg    2880
tttggtatgg cttcattcag ctccggttcc caacgatcaa ggcgagttac atgatccccc    2940
atgttgtgca aaaaagcggt tagctccttc ggtcctccga tcgttgtcag aagtaagttg    3000
gccgcagtgt tatcactcat ggttatggca gcactgcata attctcttac tgtcatgcca    3060
tccgtaagat gcttttctgt gactggtgag tactcaacca agtcattctg agaatagtgt    3120
atgcggcgac cgagttgctc ttgcccggcg tcaatacggg ataataccgc gccacatagc    3180
agaactttaa aagtgctcat cattggaaaa cgttcttcgg ggcgaaaact ctcaaggatc    3240
ttaccgctgt tgagatccag ttcgatgtaa cccactcgtg cacccaactg atcttcagca    3300
tcttttactt tcaccagcgt ttctgggtga gcaaaaacag gaaggcaaaa tgccgcaaaa    3360
aagggaataa gggcgacacg gaaatgttga atactcatac tcttcctttt tcaatattat    3420
tgaagcattt atcagggtta ttgtctcatg agcggataca tatttgaatg tatttagaaa    3480
aataaacaaa taggggttcc gcgcacattt ccccgaaaag tgccacctga cgtctaagaa    3540
accattatta tcatgacatt aacctataaa aataggcgta tcacgaggcc ctttcgtc    3598
```

<210> SEQ ID NO 14
<211> LENGTH: 3590
<212> TYPE: DNA
<213> ORGANISM: Unknown
<220> FEATURE:
<223> OTHER INFORMATION: Sequence represents a plant
      promoter-terminator expression cassette
      in vector pUC19

<400> SEQUENCE: 14

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggcgcgccg agctcctcga     420
gcaaatttac acattgccac taaacgtcta aaccttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta    600
tttttgtctt ctaaatacat atactaatca actggaaatg taaatatttg ctaatatttc    660
tactatagga gaattaaagt gagtgaatat ggtaccacaa ggtttggaga tttaattgtt    720
gcaatgctgc atggatggca tatacaccaa acattcaata attcttgagg ataataatgg    780
taccacacaa gatttgaggt gcatgaacgt cacgtggaca aaaggtttag taatttttca    840
agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct   1020
atataatgag gattttgcaa tactttcatt catacacact cactaagttt tacacgatta   1080
taatttcttc atagccagcg gatccgatat cgggcccgct agcgttaacc ctgctttaat   1140
gagatatgcg agacgcctat gatcgcatga tatttgcttt caattctgtt gtgcacgttg   1200
taaaaaaccct gagcatgtgt agctcagatc cttaccgccg gtttcggttc attctaatga   1260
atatatcacc cgttactatc gtatttttat gaataatatt ctccgttcaa tttactgatt   1320
gtccgtcgac gaattcgagc tcggcgcgcc aagcttggcg taatcatggt catagctgtt   1380
tcctgtgtga aattgttatc cgctcacaat tccacacaac atacgagccg gaagcataaa   1440
gtgtaaagcc tggggtgcct aatgagtgag ctaactcaca ttaattgcgt tgcgctcact   1500
gcccgctttc cagtcgggaa acctgtcgtg ccagctgcat taatgaatcg gccaacgcgc   1560
ggggagaggc ggtttgcgta ttgggcgctc ttccgcttcc tcgctcactg actcgctgcg   1620
ctcggtcgtt cggctgcggc gagcggtatc agctcactca aaggcggtaa tacggttatc   1680
cacagaatca gggaataacg caggaaagaa catgtgagca aaaggccagc aaaaggccag   1740
gaaccgtaaa aaggccgcgt tgctggcgtt tttccatagg ctccgccccc ctgacgagca   1800
tcacaaaaat cgacgctcaa gtcagaggtg gcgaaacccg acaggactat aaagatacca   1860
ggcgtttccc cctggaagct ccctcgtgcg ctctcctgtt ccgaccctgc cgcttaccgg   1920
atacctgtcc gcctttctcc cttcgggaag cgtggcgctt tctcatagct cacgctgtag   1980
gtatctcagt tcggtgtagg tcgttcgctc caagctgggc tgtgtgcacg aaccccccgt   2040
```

```
tcagcccgac cgctgcgcct tatccggtaa ctatcgtctt gagtccaacc cggtaagaca    2100
cgacttatcg ccactggcag cagccactgg taacaggatt agcagagcga ggtatgtagg    2160
cggtgctaca gagttcttga agtggtggcc taactacggc tacactagaa ggacagtatt    2220
tggtatctgc gctctgctga agccagttac cttcggaaaa agagttggta gctcttgatc    2280
cggcaaacaa accaccgctg gtagcggtgg ttttttttgtt tgcaagcagc agattacgcg    2340
cagaaaaaaa ggatctcaag aagatccttt gatcttttct acggggtctg acgctcagtg    2400
gaacgaaaac tcacgttaag ggattttggt catgagatta tcaaaaagga tcttcaccta    2460
gatcctttta aattaaaaat gaagttttaa atcaatctaa agtatatatg agtaaacttg    2520
gtctgacagt taccaatgct taatcagtga ggcacctatc tcagcgatct gtctatttcg    2580
ttcatccata gttgcctgac tccccgtcgt gtagataact acgatacggg agggcttacc    2640
atctggcccc agtgctgcaa tgataccgcg agacccacgc tcaccggctc cagatttatc    2700
agcaataaac cagccagccg gaagggccga gcgcagaagt ggtcctgcaa ctttatccgc    2760
ctccatccag tctattaatt gttgccggga agctagagta agtagttcgc cagttaatag    2820
tttgcgcaac gttgttgcca ttgctacagg catcgtggtg tcacgctcgt cgtttggtat    2880
ggcttcattc agctccggtt cccaacgatc aaggcgagtt acatgatccc ccatgttgtg    2940
caaaaaagcg gttagctcct tcggtcctcc gatcgttgtc agaagtaagt tggccgcagt    3000
gttatcactc atggttatgg cagcactgca taattctctt actgtcatgc catccgtaag    3060
atgcttttct gtgactggtg agtactcaac caagtcattc tgagaatagt gtatgcggcg    3120
accgagttgc tcttgcccgg cgtcaatacg ggataatacc gcgccacata gcagaacttt    3180
aaaagtgctc atcattggaa aacgttcttc ggggcgaaaa ctctcaagga tcttaccgct    3240
gttgagatcc agttcgatgt aacccactcg tgcacccaac tgatcttcag catcttttac    3300
tttcaccagc gtttctgggt gagcaaaaac aggaaggcaa aatgccgcaa aaaagggaat    3360
aagggcgaca cggaaatgtt gaatactcat actcttcctt tttcaatatt attgaagcat    3420
ttatcagggt tattgtctca tgagcggata catatttgaa tgtatttaga aaaataaaca    3480
aataggggtt ccgcgcacat ttccccgaaa agtgccacct gacgtctaag aaaccattat    3540
tatcatgaca ttaacctata aaaataggcg tatcacgagg ccctttcgtc                3590

<210> SEQ ID NO 15
<211> LENGTH: 3584
<212> TYPE: DNA
<213> ORGANISM: Unknown
<220> FEATURE:
<223> OTHER INFORMATION: Sequence represents a plant
      promoter-terminator expression cassette
      in vector pUC19

<400> SEQUENCE: 15
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cggcgcgccg agctcctcga     420
gcaaatttac acattgccac taaacgtcta aacccttgta atttgttttt gttttactat     480
```

```
gtgtgttatg tatttgattt gcgataaatt tttatatttg gtactaaatt tataacacct    540
tttatgctaa cgtttgccaa cacttagcaa tttgcaagtt gattaattga ttctaaatta    600
tttttgtctt ctaaatacat atactaatca actggaaatg taaatatttg ctaatatttc    660
tactatagga gaattaaagt gagtgaatat ggtaccacaa ggtttggaga tttaattgtt    720
gcaatgctgc atggatggca tatacaccaa acattcaata attcttgagg ataataatgg    780
taccacacaa gatttgaggt gcatgaacgt cacgtggaca aaaggtttag taattttca    840 agacaacaat gttaccacac acaagttttg aggtgcatgc atggatgccc tgtggaaagt    900
ttaaaaatat tttggaaatg atttgcatgg aagccatgtg taaaaccatg acatccactt    960
ggaggatgca ataatgaaga aaactacaaa tttacatgca actagttatg catgtagtct   1020
atataatgag gattttgcaa tactttcatt catacacact cactaagttt tacacgatta   1080
taatttcttc atagccagca gatctgccgg catcgatccc gggccatggc ctgctttaat   1140
gagatatgcg agacgcctat gatcgcatga tatttgcttt caattctgtt gtgcacgttg   1200
taaaaaacct gagcatgtgt agctcagatc cttaccgccg gtttcggttc attctaatga   1260
atatatcacc cgttactatc gtatttttat gaataatatt ctccgttcaa tttactgatt   1320
gtccgtcgac gagctcggcg cgccaagctt ggcgtaatca tggtcatagc tgtttcctgt   1380
gtgaaattgt tatccgctca caattccaca acatacga gccggaagca taagtgtaa    1440 agcctggggt gcctaatgag tgagctaact cacattaatt gcgttgcgct cactgcccgc   1500
tttccagtcg gaaacctgt cgtgccagct gcattaatga atcggccaac gcgcggggag    1560
aggcggtttg cgtattgggc gctcttccgc ttcctcgctc actgactcgc tgcgctcggt   1620
cgttcggctg cggcgagcgg tatcagctca ctcaaaggcg gtaatacggt tatccacaga   1680
atcaggggat aacgcaggaa agaacatgtg agcaaaaggc cagcaaaagg ccaggaaccg   1740
taaaaaggcc gcgttgctgg cgttttccca taggctccgc cccctgacg agcatcacaa    1800 aaatcgacgc tcaagtcaga ggtggcgaaa cccgacagga ctataaagat accaggcgtt   1860
tccccctgga agctccctcg tgcgctctcc tgttccgacc ctgccgctta ccggatacct   1920
gtccgccttt ctcccttcgg gaagcgtggc gctttctcat agctcacgct gtaggtatct   1980
cagttcggtg taggtcgttc gctccaagct gggctgtgtg cacgaacccc ccgttcagcc   2040
cgaccgctgc gccttatccg gtaactatcg tcttgagtcc aacccggtaa gacacgactt   2100
atcgccactg gcagcagcca ctggtaacag gattagcaga gcgaggtatg taggcggtgc   2160
tacagagttc ttgaagtggt ggcctaacta cggctacact agaaggacag tatttggtat   2220
ctgcgctctg ctgaagccag ttaccttcgg aaaaagagtt ggtagctctt gatccggcaa   2280
acaaaccacc gctggtagcg gtggttttt tgtttgcaag cagcagatta cgcgcagaaa   2340
aaaaggatct caagaagatc ctttgatctt ttctacgggg tctgacgctc agtggaacga   2400
aaactcacgt taagggattt tggtcatgag attatcaaaa aggatcttca cctagatcct   2460
tttaaattaa aaatgaagtt ttaaatcaat ctaaagtata tatgagtaaa cttggtctga   2520
cagttaccaa tgcttaatca gtgaggcacc tatctcagcg atctgtctat ttcgttcatc   2580
catagttgcc tgactccccg tcgtgtagat aactacgata cgggagggct taccatctgg   2640
ccccagtgct gcaatgatac gcgagaccc acgctcaccg ctccagatt tatcagcaat   2700 aaaccagcca gccggaaggg ccgagcgcag aagtggtcct gcaactttat ccgcctccat   2760
ccagtctatt aattgttgcc gggaagctag agtaagtagt tcgccagtta atagtttgcg   2820
caacgttgtt gccattgcta caggcatcgt ggtgtcacgc tcgtcgtttg gtatggcttc   2880
```

| | |
|---|---|
| attcagctcc ggttcccaac gatcaaggcg agttacatga tcccccatgt tgtgcaaaaa | 2940 |
| agcggttagc tccttcggtc ctccgatcgt tgtcagaagt aagttggccg cagtgttatc | 3000 |
| actcatggtt atggcagcac tgcataattc tcttactgtc atgccatccg taagatgctt | 3060 |
| ttctgtgact ggtgagtact caaccaagtc attctgagaa tagtgtatgc ggcgaccgag | 3120 |
| ttgctcttgc ccggcgtcaa tacgggataa taccgcgcca catagcagaa ctttaaaagt | 3180 |
| gctcatcatt ggaaaacgtt cttcggggcg aaaactctca aggatcttac cgctgttgag | 3240 |
| atccagttcg atgtaaccca ctcgtgcacc caactgatct tcagcatctt ttactttcac | 3300 |
| cagcgtttct gggtgagcaa aaacaggaag gcaaaatgcc gcaaaaaagg gaataagggc | 3360 |
| gacacggaaa tgttgaatac tcatactctt ccttttcaa tattattgaa gcatttatca | 3420 |
| gggttattgt ctcatgagcg gatacatatt tgaatgtatt tagaaaaata aacaaatagg | 3480 |
| ggttccgcgc acatttcccc gaaaagtgcc acctgacgtc taagaaacca ttattatcat | 3540 |
| gacattaacc tataaaaata ggcgtatcac gaggcccttt cgtc | 3584 |

<210> SEQ ID NO 16
<211> LENGTH: 4507
<212> TYPE: DNA
<213> ORGANISM: Unknown
<220> FEATURE:
<223> OTHER INFORMATION: Sequence represents a plant
      promoter-terminator expression cassette
      in vector pUC19

<400> SEQUENCE: 16

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cggcgcgccg agctcctcga | 420 |
| gcaaatttac acattgccac taaacgtcta aacccttgta atttgttttt gtttactat | 480 |
| gtgtgttatg tatttgattt gcgataaatt tttatatttg gtactaaatt tataacacct | 540 |
| tttatgctaa cgtttgccaa cacttagcaa tttgcaagtt gattaattga ttctaaatta | 600 |
| ttttttgtctt ctaaatacat atactaatca actggaaatg taaatatttg ctaatatttc | 660 |
| tactatagga gaattaaagt gagtgaatat ggtaccacaa ggtttggaga tttaattgtt | 720 |
| gcaatgctgc atggatggca tatacaccaa acattcaata attcttgagg ataataatgg | 780 |
| taccacacaa gatttgaggt gcatgaacgt cacgtggaca aaaggtttag taattttttca | 840 |
| agacaacaat gttaccacac acaagttttg aggtgcatgc atggatgccc tgtggaaagt | 900 |
| ttaaaaatat tttggaaatg atttgcatgg aagccatgtg taaaaccatg acatccactt | 960 |
| ggaggatgca ataatgaaga aaactacaaa tttacatgca actagttatg catgtagtct | 1020 |
| atataatgag gattttgcaa tactttcatt catacacact cactaagttt tacacgatta | 1080 |
| taatttcttc atagccagcc caccgcggtg gcggccgcc tgcagtctag aaggcctcct | 1140 |
| gctttaatga gatatgcgag acgcctatga tcgcatgata tttgctttca attctgttgt | 1200 |
| gcacgttgta aaaaacctga gcatgtgtag ctcagatcct taccgccggt ttcggttcat | 1260 |
| tctaatgaat atatcacccg ttactatcgt attttttatga ataatattct ccgttcaatt | 1320 |

```
tactgattgt ccgtcgagca aatttacaca ttgccactaa acgtctaaac ccttgtaatt    1380
tgtttttgtt ttactatgtg tgttatgtat ttgatttgcg ataaattttt atatttggta    1440
ctaaatttat aacacctttt atgctaacgt ttgccaacac ttagcaattt gcaagttgat    1500
taattgattc taaattattt ttgtcttcta aatacatata ctaatcaact ggaaatgtaa    1560
atatttgcta atatttctac tataggagaa ttaaagtgag tgaatatggt accacaaggt    1620
ttggagattt aattgttgca atgctgcatg gatggcatat acaccaaaca ttcaataatt    1680
cttgaggata ataatggtac cacacaagat ttgaggtgca tgaacgtcac gtggacaaaa    1740
ggtttagtaa tttttcaaga caacaatgtt accacacaca agttttgagg tgcatgcatg    1800
gatgccctgt ggaaagttta aaaatatttt ggaaatgatt tgcatggaag ccatgtgtaa    1860
aaccatgaca tccacttgga ggatgcaata atgaagaaaa ctacaaattt acatgcaact    1920
agttatgcat gtagtctata taatgaggat tttgcaatac tttcattcat acacactcac    1980
taagttttac acgattataa tttcttcata gccagcggat ccgatatcgg gcccgctagc    2040
gttaaccctg ctttaatgag atatgcgaga cgcctatgat cgcatgatat ttgctttcaa    2100
ttctgttgtg cacgttgtaa aaaacctgag catgtgtagc tcagatcctt accgccggtt    2160
tcggttcatt ctaatgaata tatcacccgt tactatcgta tttttatgaa taatattctc    2220
cgttcaattt actgattgtc cgtcgacgaa ttcgagctcg gcgcgccaag cttggcgtaa    2280
tcatggtcat agctgtttcc tgtgtgaaat tgttatccgc tcacaattcc acacaacata    2340
cgagccggaa gcataaagtg taaagcctgg ggtgcctaat gagtgagcta actcacatta    2400
attgcgttgc gctcactgcc cgcttttcag tcgggaaacc tgtcgtgcca gctgcattaa    2460
tgaatcggcc aacgcgcggg gagaggcggt ttgcgtattg ggcgctcttc cgcttcctcg    2520
ctcactgact cgctgcgctc ggtcgttcgg ctgcggcgag cggtatcagc tcactcaaag    2580
gcggtaatac ggttatccac agaatcaggg gataacgcag gaaagaacat gtgagcaaaa    2640
ggccagcaaa aggccaggaa ccgtaaaaag gccgcgttgc tggcgttttt ccataggctc    2700
cgcccccctg acgagcatca caaaaatcga cgctcaagtc agaggtggcg aaacccgaca    2760
ggactataaa gataccaggc gtttccccct ggaagctccc tcgtgcgctc tcctgttccg    2820
accctgccgc ttaccggata cctgtccgcc tttctccctt cgggaagcgt ggcgctttct    2880
catagctcac gctgtaggta tctcagttcg gtgtaggtcg ttcgctccaa gctgggctgt    2940
gtgcacgaac cccccgttca gcccgaccgc tgcgccttat ccggtaacta tcgtcttgag    3000
tccaacccgg taagacacga cttatcgcca ctggcagcag ccactggtaa caggattagc    3060
agagcgaggt atgtaggcgg tgctacagag ttcttgaagt ggtggcctaa ctacggctac    3120
actagaagga cagtatttgg tatctgcgct ctgctgaagc cagttacctt cggaaaaaga    3180
gttggtagct cttgatccgg caaacaaacc accgctggta gcggtggttt ttttgtttgc    3240
aagcagcaga ttacgcgcag aaaaaaagga tctcaagaag atcctttgat cttttctacg    3300
gggtctgacg ctcagtggaa cgaaaactca cgttaaggga ttttggtcat gagattatca    3360
aaaaggatct tcacctagat ccttttaaat taaaaatgaa gttttaaatc aatctaaagt    3420
atatatgagt aaacttggtc tgacagttac caatgcttaa tcagtgaggc acctatctca    3480
gcgatctgtc tatttcgttc atccatagtt gcctgactcc ccgtcgtgta gataactacg    3540
atacgggagg gcttaccatc tggccccagt gctgcaatga taccgcgaga cccacgctca    3600
ccggctccag atttatcagc aataaaccag ccagccggaa gggccgagcg cagaagtggt    3660
cctgcaactt tatccgcctc catccagtct attaattgtt gccgggaagc tagagtaagt    3720
```

-continued

```
agttcgccag ttaatagttt gcgcaacgtt gttgccattg ctacaggcat cgtggtgtca    3780
cgctcgtcgt ttggtatggc ttcattcagc tccggttccc aacgatcaag gcgagttaca    3840
tgatccccca tgttgtgcaa aaaagcggtt agctccttcg gtcctccgat cgttgtcaga    3900
agtaagttgg ccgcagtgtt atcactcatg gttatggcag cactgcataa ttctcttact    3960
gtcatgccat ccgtaagatg cttttctgtg actggtgagt actcaaccaa gtcattctga    4020
gaatagtgta tgcggcgacc gagttgctct tgcccggcgt caatacggga taataccgcg    4080
ccacatagca gaactttaaa agtgctcatc attggaaaac gttcttcggg gcgaaaactc    4140
tcaaggatct taccgctgtt gagatccagt tcgatgtaac ccactcgtgc acccaactga    4200
tcttcagcat cttttacttt caccagcgtt tctgggtgag caaaaacagg aaggcaaaat    4260
gccgcaaaaa agggaataag ggcgacacgg aaatgttgaa tactcatact cttcctttt    4320 caatattatt gaagcattta tcagggttat tgtctcatga gcggatacat atttgaatgt    4380
atttagaaaa ataaacaaat aggggttccg cgcacatttc cccgaaaagt gccacctgac    4440
gtctaagaaa ccattattat catgacatta acctataaaa ataggcgtat cacgaggccc    4500
tttcgtc                                                              4507
```

<210> SEQ ID NO 17
<211> LENGTH: 5410
<212> TYPE: DNA
<213> ORGANISM: Unknown
<220> FEATURE:
<223> OTHER INFORMATION: Sequence represents a plant
      promoter-terminator expression cassette
      in vector pUC19

<400> SEQUENCE: 17

```
ttttggaaat gatttgcatg gaagccatgt gtaaaaccat gacatccact tggaggatgc      60
aataatgaag aaaactacaa atttacatgc aactagttat gcatgtagtc tatataatga     120
ggattttgca atactttcat tcatacacac tcactaagtt ttacacgatt ataatttctt     180
catagccagc ggatccgata tcgggcccgc tagcgttaac cctgctttaa tgagatatgc     240
gagacgccta tgatcgcatg atatttgctt tcaattctgt tgtgcacgtt gtaaaaaacc     300
tgagcatgtg tagctcagat ccttaccgcc ggtttcggtt cattctaatg aatatatcac     360
ccgttactat cgtatttta tgaataatat tctccgttca atttactgat tgtccgtcga     420
gcaaatttac acattgccac taaacgtcta aacccttgta atttgttttt gttttactat     480
gtgtgttatg tatttgattt gcgataaatt tttatatttg gtactaaatt tataacacct     540
tttatgctaa cgtttgccaa cacttagcaa tttgcaagtt gattaattga ttctaaatta     600
tttttgtctt ctaaatacat atactaatca actggaaatg taaatatttg ctaatatttc     660
tactatagga gaattaaagt gagtgaatat ggtaccacaa ggtttggaga tttaattgtt     720
gcaatgctgc atggatggca tatacaccaa acattcaata attcttgagg ataataatgg     780
taccacacaa gatttgaggt gcatgaacgt cacgtggaca aaaggtttag taattttca     840 agacaacaat gttaccacac acaagttttg aggtgcatgc atggatgccc tgtgaaagt     900 ttaaaaatat tttggaaatg atttgcatgg aagccatgtg taaaaccatg acatccactt     960
ggaggatgca ataatgaaga aaactacaaa tttacatgca actagttatg catgtagtct    1020
atataatgag gattttgcaa tactttcatt catacacact cactaagttt tacacgatta    1080
taatttcttc atagccagca gatctgccgg catcgatccc gggccatggc ctgctttaat    1140
gagatatgcg agacgcctat gatcgcatga tatttgcttt caattctgtt gtgcacgttg    1200
```

```
taaaaaacct gagcatgtgt agctcagatc cttaccgccg gtttcggttc attctaatga   1260
atatatcacc cgttactatc gtatttttat gaataatatt ctccgttcaa tttactgatt   1320
gtccgtcgac gagctcggcg cgccaagctt ggcgtaatca tggtcatagc tgtttcctgt   1380
gtgaaattgt tatccgctca caattccaca acatacga gccggaagca taaagtgtaa    1440
agcctggggt gcctaatgag tgagctaact cacattaatt gcgttgcgct cactgcccgc   1500
tttccagtcg ggaaacctgt cgtgccagct gcattaatga atcggccaac gcgcggggag   1560
aggcggtttg cgtattgggc gctcttccgc ttcctcgctc actgactcgc tgcgctcggt   1620
cgttcggctg cggcgagcgg tatcagctca ctcaaaggcg gtaatacggt tatccacaga   1680
atcaggggat aacgcaggaa agaacatgtg agcaaaaggc cagcaaaagg ccaggaaccg   1740
taaaaaggcc gcgttgctgg cgttttttcca taggctccgc cccctgacg agcatcacaa    1800
aaatcgacgc tcaagtcaga ggtggcgaaa cccgacagga ctataaagat accaggcgtt   1860
tccccctgga agctccctcg tgcgctctcc tgttccgacc ctgccgctta ccggatacct    1920
gtccgccttt ctcccttcgg gaagcgtggc gctttctcat agctcacgct gtaggtatct   1980
cagttcggtg taggtcgttc gctccaagct gggctgtgtg cacgaacccc ccgttcagcc   2040
cgaccgctgc gccttatccg gtaactatcg tcttgagtcc aacccggtaa gacacgactt   2100
atcgccactg gcagcagcca ctggtaacag gattagcaga gcgaggtatg taggcggtgc   2160
tacagagttc ttgaagtggt ggcctaacta cggctacact agaaggacag tatttggtat   2220
ctgcgctctg ctgaagccag ttaccttcgg aaaaagagtt ggtagctctt gatccggcaa   2280
acaaaccacc gctggtagcg gtggttttt tgtttgcaag cagcagatta cgcgcagaaa    2340
aaaaggatct caagaagatc ctttgatctt ttctacgggg tctgacgctc agtggaacga   2400
aaactcacgt taagggattt tggtcatgag attatcaaaa aggatcttca cctagatcct   2460
tttaaattaa aaatgaagtt ttaaatcaat ctaaagtata tatgagtaaa cttggtctga   2520
cagttaccaa tgcttaatca gtgaggcacc tatctcagcg atctgtctat ttcgttcatc   2580
catagttgcc tgactccccg tcgtgtagat aactacgata cgggagggct taccatctgg   2640
ccccagtgct gcaatgatac cgcgagaccc acgctcaccg gctccagatt tatcagcaat   2700
aaaccagcca gccggaaggg ccgagcgcag aagtggtcct gcaactttat ccgcctccat   2760
ccagtctatt aattgttgcc gggaagctag agtaagtagt tcgccagtta atagtttgcg   2820
caacgttgtt gccattgcta caggcatcgt ggtgtcacgc tcgtcgtttg gtatggcttc   2880
attcagctcc ggttcccaac gatcaaggcg agttacatga tccccatgt tgtgcaaaaa    2940
agcggttagc tccttcggtc ctccgatcgt tgtcagaagt aagttggccg cagtgttatc   3000
actcatggtt atggcagcac tgcataattc tcttactgtc atgccatccg taagatgctt   3060
ttctgtgact ggtgagtact caaccaagtc attctgagaa tagtgtatgc ggcgaccgag   3120
ttgctcttgc ccggcgtcaa tacgggataa taccgcgcca catagcagaa ctttaaaagt   3180
gctcatcatt ggaaaacgtt cttcggggcg aaaactctca aggatcttac cgctgttgag   3240
atccagttcg atgtaaccca ctcgtgcacc caactgatct tcagcatctt ttactttcac   3300
cagcgtttct gggtgagcaa aaacaggaag gcaaaatgcc gcaaaaaagg gaataagggc   3360
gacacggaaa tgttgaatac tcatactctt cctttttcaa tattattgaa gcatttatca   3420
gggttattgt ctcatgagcg gatacatatt tgaatgtatt tagaaaaata aacaaatagg   3480
ggttccgcgc acatttcccc gaaaagtgcc acctgacgtc taagaaacca ttattatcat   3540
gacattaacc tataaaaata ggcgtatcac gaggcccttt cgtctcgcgc gtttcggtga   3600
```

| | |
|---|---|
| tgacggtgaa aacctctgac acatgcagct cccggagacg gtcacagctt gtctgtaagc | 3660 |
| ggatgccggg agcagacaag cccgtcaggg cgcgtcagcg ggtgttggcg ggtgtcgggg | 3720 |
| ctggcttaac tatgcggcat cagagcagat tgtactgaga gtgcaccata tgcggtgtga | 3780 |
| aataccgcac agatgcgtaa ggagaaaata ccgcatcagg cgccattcgc cattcaggct | 3840 |
| gcgcaactgt tgggaagggc gatcggtgcg ggcctcttcg ctattacgcc agctggcgaa | 3900 |
| aggggggatgt gctgcaaggc gattaagttg ggtaacgcca gggttttccc agtcacgacg | 3960 |
| ttgtaaaacg acggccagtg aattcggcgc gccgagctcc tcgagcaaat ttacacattg | 4020 |
| ccactaaacg tctaaaccct tgtaatttgt ttttgtttta ctatgtgtgt tatgtatttg | 4080 |
| atttgcgata aattttata tttggtacta aatttataac acctttatg ctaacgtttg | 4140 |
| ccaacactta gcaatttgca agttgattaa ttgattctaa attattttg tcttctaaat | 4200 |
| acatatacta atcaactgga aatgtaaata tttgctaata tttctactat aggagaatta | 4260 |
| aagtgagtga atatggtacc acaaggtttg gagatttaat tgttgcaatg ctgcatggat | 4320 |
| ggcatataca ccaaacattc aataattctt gaggataata atggtaccac acaagatttg | 4380 |
| aggtgcatga acgtcacgtg gacaaaaggt ttagtaattt ttcaagacaa caatgttacc | 4440 |
| acacacaagt tttgaggtgc atgcatggat gccctgtgga agtttaaaa atattttgga | 4500 |
| aatgatttgc atggaagcca tgtgtaaaac catgacatcc acttggagga tgcaataatg | 4560 |
| aagaaaacta caaatttaca tgcaactagt tatgcatgta gtctatataa tgaggatttt | 4620 |
| gcaatacttt cattcataca cactcactaa gttttacacg attataattt cttcatagcc | 4680 |
| agcccaccgc ggtgggcggc cgcctgcagt ctagaaggcc tcctgcttta atgagatatg | 4740 |
| cgagacgcct atgatcgcat gatatttgct ttcaattctg ttgtgcacgt tgtaaaaaac | 4800 |
| ctgagcatgt gtagctcaga tccttaccgc cggtttcggt tcattctaat gaatatatca | 4860 |
| cccgttacta tcgtattttt atgaataata ttctccgttc aatttactga ttgtccgtcg | 4920 |
| agcaaattta cacattgcca ctaaacgtct aaacccttgt aatttgtttt tgttttacta | 4980 |
| tgtgtgttat gtatttgatt tgcgataaat ttttatattt ggtactaaat ttataacacc | 5040 |
| ttttatgcta acgtttgcca acacttagca atttgcaagt tgattaattg attctaaatt | 5100 |
| attttgtct tctaaataca tatactaatc aactggaaat gtaaatattt gctaatattt | 5160 |
| ctactatagg agaattaaag tgagtgaata tggtaccaca aggtttggag atttaattgt | 5220 |
| tgcaatgctg catggatggc atatacacca acattcaat aattcttgag gataataatg | 5280 |
| gtaccacaca agatttgagg tgcatgaacg tcacgtggac aaaaggttta gtaattttc | 5340 |
| aagacaacaa tgttaccaca cacaagttt gaggtgcatg catggatgcc ctgtggaaag | 5400 |
| tttaaaaata | 5410 |

<210> SEQ ID NO 18
<211> LENGTH: 648
<212> TYPE: DNA
<213> ORGANISM: Phaeodactylum tricornutum
<220> FEATURE:
<221> NAME/KEY: CDS
<222> LOCATION: (1)..(648)
<220> FEATURE:
<223> OTHER INFORMATION: .

<400> SEQUENCE: 18

| tgg tgg aaa aac aag cac aac gga cac cac gcc gtc ccc aac ctc cac | 48 |
|---|---|
| Trp Trp Lys Asn Lys His Asn Gly His His Ala Val Pro Asn Leu His | |
| 1               5                   10                  15 | |

| tgc tcc tcc gca gtc gcg caa gat ggg gac ccg gac atc gat acc atg | 96 |
|---|---|

```
                Cys Ser Ser Ala Val Ala Gln Asp Gly Asp Pro Asp Ile Asp Thr Met
                                20                  25                  30 ccc ctt ctc gcc tgg tcc gtc cag caa gcc cag tct tac cgg gaa ctc          144
Pro Leu Leu Ala Trp Ser Val Gln Gln Ala Gln Ser Tyr Arg Glu Leu
             35                  40                  45 caa gcc gac gga aag gat tcg ggt ttg gtc aag ttc atg atc cgt aac          192
Gln Ala Asp Gly Lys Asp Ser Gly Leu Val Lys Phe Met Ile Arg Asn
 50                  55                  60 caa tcc tac ttt tac ttt ccc atc ttg ttg ctc gcc cgc ctg tcg tgg          240
Gln Ser Tyr Phe Tyr Phe Pro Ile Leu Leu Leu Ala Arg Leu Ser Trp
 65                  70                  75                  80 ttg aac gag tcc ttc aag tgc gcc ttt ggg ctt gga gct gcg tcg gag          288
Leu Asn Glu Ser Phe Lys Cys Ala Phe Gly Leu Gly Ala Ala Ser Glu
                 85                  90                  95 aac gct gct ctc gaa ctc aag gcc aag ggt ctt cag tac ccc ctt ttg          336
Asn Ala Ala Leu Glu Leu Lys Ala Lys Gly Leu Gln Tyr Pro Leu Leu
            100                 105                 110 gaa aag gct gga atc ctg ctg cac tac gct tgg atg ctt aca gtt tcg          384
Glu Lys Ala Gly Ile Leu Leu His Tyr Ala Trp Met Leu Thr Val Ser
        115                 120                 125 tcc ggc ttt gga cgc ttc tcg ttc gcg tac acc gca ttt tac ttt cta          432
Ser Gly Phe Gly Arg Phe Ser Phe Ala Tyr Thr Ala Phe Tyr Phe Leu
    130                 135                 140 acc gcg acc gcg tcc tgt gga ttc ttg ctc gcc att gtc ttt ggc ctc          480
Thr Ala Thr Ala Ser Cys Gly Phe Leu Leu Ala Ile Val Phe Gly Leu
145                 150                 155                 160 ggc cac aac ggc atg gcc acc tac aat gcc gac gcc cgt ccg gac ttc          528
Gly His Asn Gly Met Ala Thr Tyr Asn Ala Asp Ala Arg Pro Asp Phe
                165                 170                 175 tgg aag ctc caa gtc acc acg act cgc aac gtc acg ggc gga cac ggt          576
Trp Lys Leu Gln Val Thr Thr Thr Arg Asn Val Thr Gly Gly His Gly
            180                 185                 190 ttc ccc caa gcc ttt gtc gac tgg ttc tgt ggt ggc ctc cag tac caa          624
Phe Pro Gln Ala Phe Val Asp Trp Phe Cys Gly Gly Leu Gln Tyr Gln
        195                 200                 205 gtc gac cac cac tta ttc ccc agc                                          648
Val Asp His His Leu Phe Pro Ser
    210                 215

<210> SEQ ID NO 19
<211> LENGTH: 216
<212> TYPE: PRT
<213> ORGANISM: Phaeodactylum tricornutum

<400> SEQUENCE: 19

Trp Trp Lys Asn Lys His Asn Gly His His Ala Val Pro Asn Leu His
 1               5                  10                  15

Cys Ser Ser Ala Val Ala Gln Asp Gly Asp Pro Asp Ile Asp Thr Met
                20                  25                  30

Pro Leu Leu Ala Trp Ser Val Gln Gln Ala Gln Ser Tyr Arg Glu Leu
             35                  40                  45

Gln Ala Asp Gly Lys Asp Ser Gly Leu Val Lys Phe Met Ile Arg Asn
 50                  55                  60

Gln Ser Tyr Phe Tyr Phe Pro Ile Leu Leu Leu Ala Arg Leu Ser Trp
 65                  70                  75                  80

Leu Asn Glu Ser Phe Lys Cys Ala Phe Gly Leu Gly Ala Ala Ser Glu
                 85                  90                  95

Asn Ala Ala Leu Glu Leu Lys Ala Lys Gly Leu Gln Tyr Pro Leu Leu
            100                 105                 110
```

```
Glu Lys Ala Gly Ile Leu Leu His Tyr Ala Trp Met Leu Thr Val Ser
        115                 120                 125
Ser Gly Phe Gly Arg Phe Ser Phe Ala Tyr Thr Ala Phe Tyr Phe Leu
    130                 135                 140
Thr Ala Thr Ala Ser Cys Gly Phe Leu Leu Ala Ile Val Phe Gly Leu
145                 150                 155                 160
Gly His Asn Gly Met Ala Thr Tyr Asn Ala Asp Ala Arg Pro Asp Phe
                165                 170                 175
Trp Lys Leu Gln Val Thr Thr Thr Arg Asn Val Thr Gly Gly His Gly
                180                 185                 190
Phe Pro Gln Ala Phe Val Asp Trp Phe Cys Gly Gly Leu Gln Tyr Gln
            195                 200                 205
Val Asp His His Leu Phe Pro Ser
    210                 215

<210> SEQ ID NO 20
<211> LENGTH: 12093
<212> TYPE: DNA
<213> ORGANISM: Unknown
<220> FEATURE:
<223> OTHER INFORMATION: Plant expression vector with a promoter-
      terminator expression cassette

<400> SEQUENCE: 20
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt gggggttcag cagccggcgc     480
tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg cgatggcgcg cgcatccatg     660
ccggcacgcg accgggcgca ccgcagatgg aaacggccga cgcgcagctt cgcttcctct     720
gcgaggcggg ttttcggcc ggggacgccg tcaatgcgct gatgacaatc agctacttca     780
ctgttggggc cgtgcttgag gagcaggccg cgacagcga tgccggcgag cgcggcggca     840
ccgttgaaca ggctccgctc tcgccgctgt tgcgggccgc gatagacgcc ttcgacgaag     900
ccggtccgga cgcagcgttc gagcagggac tcgcggtgat tgtcgatgga ttggcgaaaa     960
ggaggctcgt tgtcaggaac gttgaaggac cgagaaaggg tgacgattga tcaggaccgc    1020
tgccggagcg caacccactc actacagcag agccatgtag acaacatccc ctcccccttt    1080
ccaccgcgtc agacgcccgt agcagcccgc tacgggcttt ttcatgccct gccctagcgt    1140
ccaagcctca cggccgcgct cggcctctct ggcggccttc tggcgctctt ccgcttcctc    1200
gctcactgac tcgctgcgct cggtcgttcg gctgcggcga cggtatcag ctcactcaaa     1260 ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
```

| | |
|---|---|
| aggactataa agataccagg cgtttccccc tggaagctcc ctcgtgcgct ctcctgttcc | 1500 |
| gaccctgccg cttaccggat acctgtccgc ctttctccct tcgggaagcg tggcgctttt | 1560 |
| ccgctgcata accctgcttc ggggtcatta tagcgatttt ttcggtatat ccatccttt | 1620 |
| tcgcacgata tacaggattt tgccaaaggg ttcgtgtaga ctttccttgg tgtatccaac | 1680 |
| ggcgtcagcc gggcaggata ggtgaagtag gcccacccgc gagcgggtgt tccttcttca | 1740 |
| ctgtccctta ttcgcacctg gcggtgctca acgggaatcc tgctctgcga ggctggccgg | 1800 |
| ctaccgccgg cgtaacagat gagggcaagc ggatggctga tgaaaccaag ccaaccagga | 1860 |
| agggcagccc acctatcaag gtgtactgcc ttccagacga acgaagagcg attgaggaaa | 1920 |
| aggcggcggc ggccggcatg agcctgtcgg cctacctgct ggccgtcggc cagggctaca | 1980 |
| aaatcacggg cgtcgtggac tatgagcacg tccgcgagct ggcccgcatc aatggcgacc | 2040 |
| tgggccgcct gggcggcctg ctgaaactct ggctcaccga cgacccgcgc acggcgcggt | 2100 |
| tcggtgatgc cacgatcctc gccctgctgg cgaagatcga agagaagcag gacgagcttg | 2160 |
| gcaaggtcat gatgggcgtg gtccgcccga gggcagagcc atgactttt tagccgctaa | 2220 |
| aacggccggg gggtgcgcgt gattgccaag cacgtcccca tgcgctccat caagaagagc | 2280 |
| gacttcgcgg agctggtgaa gtacatcacc gacgagcaag gcaagaccga gcgcctttgc | 2340 |
| gacgctcacc gggctggttg ccctcgccgc tgggctggcg gccgtctatg gcctgcaaa | 2400 |
| cgcgccagaa acgccgtcga agccgtgtgc gagacaccgc ggccgccggc gttgtggata | 2460 |
| cctcgcggaa aacttggccc tcactgacag atgaggggcg gacgttgaca cttgaggggc | 2520 |
| cgactcaccc ggcgcggcgt tgacagatga ggggcaggct cgatttcggc cggcgacgtg | 2580 |
| gagctggcca gcctcgcaaa tcggcgaaaa cgcctgattt tacgcgagtt tcccacagat | 2640 |
| gatgtggaca agcctgggga taagtgccct gcggtattga cacttgaggg gcgcgactac | 2700 |
| tgacagatga ggggcgcgat ccttgacact tgaggggcag agtgctgaca gatgaggggc | 2760 |
| gcacctattg acatttgagg ggctgtccac aggcagaaaa tccagcattt gcaagggttt | 2820 |
| ccgcccgttt ttcggccacc gctaacctgt ctttttaacct gcttttaaac caatatttat | 2880 |
| aaaccttgtt tttaaccagg gctgcgccct gtgcgcgtga ccgcgcacgc cgaagggggg | 2940 |
| tgccccccct tctcgaaccc tcccggcccg ctaacgcggg cctcccatcc ccccaggggc | 3000 |
| tgcgcccctc ggccgcgaac ggcctcaccc caaaaatggc agcgctggca gtccttgcca | 3060 |
| ttgccgggat cggggcagta acgggatggg cgatcagccc gagcgcgacg cccggaagca | 3120 |
| ttgacgtgcc gcaggtgctg gcatcgacat tcagcgacca ggtgccgggc agtgagggcg | 3180 |
| gcggcctggg tggcggcctg cccttcactt cggccgtcgg ggcattcacg gacttcatgg | 3240 |
| cggggccggc aattttttacc ttgggcattc ttggcatagt ggtcgcgggt gccgtgctcg | 3300 |
| tgttcgggg tgcgataaac ccagcgaacc atttgaggtg ataggtaaga ttataccgag | 3360 |
| gtatgaaaac gagaattgga cctttacaga attactctat gaagcgccat atttaaaaag | 3420 |
| ctaccaagac gaagaggatg aagaggatga ggaggcagat tgccttgaat atattgacaa | 3480 |
| tactgataag ataatatatc ttttatatag aagatatcgc cgtatgtaag gatttcaggg | 3540 |
| ggcaaggcat aggcagcgcg cttatcaata tatctataga atgggcaaag cataaaaact | 3600 |
| tgcatggact aatgcttgaa acccaggaca ataaccttat agcttgtaaa ttctatcata | 3660 |
| attgggtaat gactccaact tattgatagt gttttatgtt cagataatgc ccgatgactt | 3720 |
| tgtcatgcag ctccaccgat tttgagaacg acagcgactt ccgtcccagc cgtgccaggt | 3780 |
| gctgcctcag attcaggtta tgccgctcaa ttcgctgcgt atatcgcttg ctgattacgt | 3840 |

```
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga     4500 aaaagctgtt ttctggtatt taaggtttta gaatgcaagg aacagtgaat tggagttcgt    4560
cttgttataa ttagcttctt ggggtatctt taaatactgt agaaagagg aaggaaataa     4620 taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtgaacgg     4800 gaaaaggaca tgatgctatg gctggaagga agctgcctg ttccaaaggt cctgcacttt      4860
gaacggcatg atggctggag caatctgctc atgagtgagg ccgatggcgt cctttgctcg    4920
gaagagtatg aagatgaaca aagccctgaa agattatcg agctgtatgc ggagtgcatc      4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt ttcccacggc gacctggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat gccgataag gtggattatc tggacaccaa      5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgcggcgag gacctggcaa acaggtcag     6060 cgaggccaag caggccgcgt tgctgaaaca cacgaagcag cagatcaagg aaatgcagct    6120
ttccttgttc gatattgcgc cgtggccgga cacgatgcga gcgatgccaa cgacacggc     6180 ccgctctgcc ctgttcacca cgcgcaacaa gaaaatcccg cgcgaggcgc tgcaaaacaa    6240
```

-continued

```
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg     6360
cgagccgatc accttcacgt tctacgagct tgccaggac ctgggctggt cgatcaatgg     6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccgcgtg aagaagtggc gcgagcaggt     6780
cggcgaagcc tgcgaagagt tgcgaggcag cggcctggtg aacacgcct gggtcaatga     6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggct atttgcggaa ctgcgggcgt ggcgctgttg     7620
gtgttgacac caaacgcagc gctagatcct gtcggcgtcg cagcgggcct ggcgggggcg    7680
gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg cttttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520
gacgttttta atgtactggg gtggttttc ttttcaccag tgagacgggc aacagctgat     8580
tgcccttcac cgcctggccc tgagagagtt gcagcaagcg gtccacgctg gtttgcccca    8640
```

| | |
|---|---|
| gcaggcgaaa atcctgtttg atggtggttc cgaaatcggc aaaatcccctt ataaatcaaa | 8700 |
| agaatagccc gagatagggt tgagtgttgt tccagtttgg aacaagagtc cactattaaa | 8760 |
| gaacgtggac tccaacgtca aagggcgaaa aaccgtctat cagggcgatg gcccactacg | 8820 |
| tgaaccatca cccaaatcaa gttttttggg gtcgaggtgc cgtaaagcac taaatcggaa | 8880 |
| ccctaaaggg agcccccgat ttagagcttg acggggaaag ccggcgaacg tggcgagaaa | 8940 |
| ggaagggaag aaagcgaaag gagcgggcgc cattcaggct gcgcaactgt tgggaagggc | 9000 |
| gatcggtgcg ggcctcttcg ctattacgcc agctggcgaa aggggatgt gctgcaaggc | 9060 |
| gattaagttg ggtaacgcca gggttttccc agtcacgacg ttgtaaaacg acggccagtg | 9120 |
| aattaattcc catcttgaaa gaaatatagt ttaaatattt attgataaaa taacaagtca | 9180 |
| ggtattatag tccaagcaaa aacataaatt tattgatgca agtttaaatt cagaaatatt | 9240 |
| tcaataactg attatatcag ctggtacatt gccgtagatg aaagactgag tgcgatatta | 9300 |
| tgtgtaaatac ataaattgat gatatagcta gcttagctca tcgggggatc cgtcgaagct | 9360 |
| agcttgggtc ccgctcagaa gaactcgtca agaaggcgat agaaggcgat gcgctgcgaa | 9420 |
| tcgggagcgg cgataccgta aagcacgagg aagcggtcag cccattcgcc gccaagctct | 9480 |
| tcagcaatat cacgggtagc caacgctatg tcctgatagc ggtccgccac acccagccgg | 9540 |
| ccacagtcga tgaatccaga aaagcggcca ttttccacca tgatattcgg caagcaggca | 9600 |
| tcgccatggg tcacgacgag atcctcgccg tcggcatgc gcgccttgag cctggcgaac | 9660 |
| agttcggctg cgcgagccc ctgatgctct tcgtccagat catcctgatc gacaagaccg | 9720 |
| gcttccatcc gagtacgtgc tcgctcgatg cgatgtttcg cttggtggtc gaatgggcag | 9780 |
| gtagccggat caagcgtatg cagccgccgc attgcatcag ccatgatgga tactttctcg | 9840 |
| gcaggagcaa ggtgagatga caggagatcc tgccccggca cttcgcccaa tagcagccag | 9900 |
| tcccttcccg cttcagtgac aacgtcgagc acagctgcgc aaggaacgcc cgtcgtggcc | 9960 |
| agccacgata gccgcgctgc ctcgtcctgc agttcattca gggcaccgga caggtcggtc | 10020 |
| ttgacaaaaa gaaccgggcg cccctgcgct gacagccgga acacggcggc atcagagcag | 10080 |
| ccgattgtct gttgtgccca gtcatagccg aatagcctct ccacccaagc ggccggagaa | 10140 |
| cctgcgtgca atccatcttg ttcaatccaa gctcccatgg gccctcgact agagtcgaga | 10200 |
| tctgattga gagtgaatat gagactctaa ttggataccg aggggaattt atggaacgtc | 10260 |
| agtggagcat ttttgacaag aaatatttgc tagctgatag tgaccttagg cgacttttga | 10320 |
| acgcgcaata atgtttctg acgtatgtgc ttagctcatt aaactccaga aacccgcggc | 10380 |
| tgagtggctc cttcaacgtt gcggttctgt cagttccaaa cgtaaaacgg cttgtcccgc | 10440 |
| gtcatcggcg ggggtcataa cgtgactccc ttaattctcc gctcatgatc ttgatcccct | 10500 |
| gcgccatcag atccttggcg gcaagaaagc catccagttt actttgcagg gcttcccaac | 10560 |
| cttaccagag ggcgcccag ctggcaattc cggttcgctt gctgtccata aaaccgccca | 10620 |
| gtctagctat cgccatgtaa gcccactgca agctacctgc tttctctttg cgcttgcgtt | 10680 |
| ttcccttgtc cagatagccc agtagctgac attcatccgg ggtcagcacc gtttctgcgg | 10740 |
| actggctttc tacgtgttcc gcttccttta gcagcccttg cgccctgagt gcttgcggca | 10800 |
| gcgtgaagct tgcatgcctg caggtcgacg gcgcgccgag ctcctcgagc aaatttacac | 10860 |
| attgccacta aacgtctaaa cccttgtaat ttgttttttgt tttactatgt gtgttatgta | 10920 |
| tttgatttgc gataaatttt tatatttggt actaaattta taacacccttt tatgctaacg | 10980 |
| tttgccaaca cttagcaatt tgcaagttga ttaattgatt ctaaattatt tttgtcttct | 11040 |

| | |
|---|---|
| aaatacatat actaatcaac tggaaatgta aatatttgct aatatttcta ctataggaga | 11100 |
| attaaagtga gtgaatatgg taccacaagg tttggagatt taattgttgc aatgctgcat | 11160 |
| ggatggcata taccaaac attcaataat tcttgaggat aataatggta ccacacaaga | 11220 |
| tttgaggtgc atgaacgtca cgtggacaaa aggtttagta atttttcaag acaacaatgt | 11280 |
| taccacacac aagttttgag gtgcatgcat ggatgccctg tggaaagttt aaaaatattt | 11340 |
| tggaaatgat ttgcatggaa gccatgtgta aaaccatgac atccacttgg aggatgcaat | 11400 |
| aatgaagaaa actacaaatt tacatgcaac tagttatgca tgtagtctat ataatgagga | 11460 |
| ttttgcaata ctttcattca tacacactca ctaagttta cacgattata atttcttcat | 11520 |
| agccagccca ccgcggtggg cggccgcctg cagtctagaa ggcctcctgc tttaatgaga | 11580 |
| tatgcgagac gcctatgatc gcatgatatt tgctttcaat tctgttgtgc acgttgtaaa | 11640 |
| aaacctgagc atgtgtagct cagatcctta ccgccggttt cggttcattc taatgaatat | 11700 |
| atcacccgtt actatcgtat ttttatgaat aatattctcc gttcaattta ctgattgtcc | 11760 |
| gtcgacgaat tcgagctcgg cgcgcctcta gaggatcgat gaattcagat cggctgagtg | 11820 |
| gctccttcaa cgttgcggtt ctgtcagttc caaacgtaaa acggcttgtc ccgcgtcatc | 11880 |
| ggcggggggtc ataacgtgac tcccttaatt ctccgctcat gatcagattg tcgtttcccg | 11940 |
| ccttcagttt aaactatcag tgtttgacag gatatattgg cgggtaaacc taagagaaaa | 12000 |
| gagcgtttat tagaataatc ggatatttaa aagggcgtga aaaggtttat ccttcgtcca | 12060 |
| tttgtatgtg catgccaacc acagggttcc cca | 12093 |

<210> SEQ ID NO 21
<211> LENGTH: 12085
<212> TYPE: DNA
<213> ORGANISM: Unknown
<220> FEATURE:
<223> OTHER INFORMATION: Plant expression vector with a promoter-
      terminator expression cassette

<400> SEQUENCE: 21

| | |
|---|---|
| gatctggcgc cggccagcga gacgagcaag attggccgcc gcccgaaacg atccgacagc | 60 |
| gcgcccagca caggtgcgca ggcaaattgc accaacgcat acagcgccag cagaatgcca | 120 |
| tagtgggcgg tgacgtcgtt cgagtgaacc agatcgcgca ggaggcccgg cagcaccggc | 180 |
| ataatcaggc cgatgccgac agcgtcgagc gcgacagtgc tcagaattac gatcaggggt | 240 |
| atgttgggtt tcacgtctgg cctccggacc agcctccgct ggtccgattg aacgcgcgga | 300 |
| ttctttatca ctgataagtt ggtggacata ttatgtttat cagtgataaa gtgtcaagca | 360 |
| tgacaaagtt gcagccgaat acagtgatcc gtgccgccct ggacctgttg aacgaggtcg | 420 |
| gcgtagacgg tctgacgaca cgcaaactgg cggaacggtt gggggttcag cagccggcgc | 480 |
| tttactggca cttcaggaac aagcgggcgc tgctcgacgc actggccgaa gccatgctgg | 540 |
| cggagaatca tacgcattcg gtgccgagag ccgacgacga ctggcgctca tttctgatcg | 600 |
| ggaatgcccg cagcttcagg caggcgctgc tcgcctaccg cgatggcgcg cgcatccatg | 660 |
| ccggcacgcg accgggcgca ccgcagatgg aaacggccga cgcgcagctt cgcttcctct | 720 |
| gcgaggcggg ttttcggcc ggggacgccg tcaatgcgct gatgacaatc agctacttca | 780 |
| ctgttgggc cgtgcttgag gagcaggccg gcgacagcga tgccgcgag gcggcggca | 840 |
| ccgttgaaca ggctccgctc tcgccgctgt tgcgggccgc gatagacgcc ttcgacgaag | 900 |
| ccggtccgga cgcagcgttc gagcaggac tcgcggtgat tgtcgatgga ttggcgaaaa | 960 |
| ggaggctcgt tgtcaggaac gttgaaggac cgagaaaggg tgacgattga tcaggaccgc | 1020 |

```
tgccggagcg caacccactc actacagcag agccatgtag acaacatccc ctccccgttt    1080
ccaccgcgtc agacgcccgt agcagcccgc tacgggcttt ttcatgccct gccctagcgt    1140
ccaagcctca cggccgcgct cggcctctct ggcggccttc tggcgctctt ccgcttcctc    1200
gctcactgac tcgctgcgct cggtcgttcg gctgcggcga gcggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttt    1560
ccgctgcata accctgcttc ggggtcatta tagcgatttt ttcggtatat ccatcctttt    1620
tcgcacgata tacaggattt tgccaaaggg ttcgtgtaga cttccttgg tgtatccaac    1680
ggcgtcagcc gggcaggata ggtgaagtag gcccacccgc gagcgggtgt tccttcttca    1740
ctgtccctta ttcgcacctg gcggtgctca acgggaatcc tgctctgcga ggctggccgg    1800
ctaccgccgg cgtaacagat gagggcaagc ggatggctga tgaaaccaag ccaaccagga    1860
agggcagccc acctatcaag gtgtactgcc ttccagacga acgaagagcg attgaggaaa    1920
aggcggcggc ggccggcatg agcctgtcgg cctacctgct ggccgtcggc cagggctaca    1980
aaatcacggg cgtcgtggac tatgagcacg tccgcgagct ggcccgcatc aatggcgacc    2040
tgggccgcct gggcggcctg ctgaaactct ggctcaccga cgacccgcgc acggcgcggt    2100
tcggtgatgc cacgatcctc gccctgctgg cgaagatcga agagaagcag gacgagcttg    2160
gcaaggtcat gatgggcgtg gtccgcccga gggcagagcc atgactttt tagccgctaa    2220
aacggccggg gggtgcgcgt gattgccaag cacgtcccca tgcgctccat caagaagagc    2280
gacttcgcgg agctggtgaa gtacatcacc gacgagcaag gcaagaccga gcgccttttgc    2340
gacgctcacc gggctggttg ccctcgccgc tgggctggcg ccgtctatg gccctgcaaa    2400
cgcgccagaa acgccgtcga agccgtgtgc gagacaccgc ggccgccggc gttgtggata    2460
cctcgcggaa aacttggccc tcactgacag atgaggggcg gacgttgaca cttgagggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaaggggg    2940
tgcccccct tctcgaaccc tcccggcccg ctaacgcggg cctcccatcc cccaggggc    3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
```

```
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgg gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggtttta gaatgcaagg aacagtgaat tggagttcgt    4560
cttgttataa ttagcttctt ggggtatctt taaatactgt agaaaagagg aaggaaataa    4620
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataaaggga ccacctatga tgtggaacgg    4800
gaaaaggaca tgatgctatg gctggaagga agctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttaaa gacggaaaag    5160 cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340 ctatttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgaaggga    5580 cggccagacg gtctacggga ccgacttcat gccgataag gtggattatc tggacaccaa    5640
ggcaccaggc gggtcaaatc aggaataagg gcacattgcc ccggcgtgag tcgggcaat    5700 cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
```

```
gccccgcgaa accttccagt ccgtcggctc gatggtccag caagctacgg ccaagatcga    5880
gcgcgacagc gtgcaactgg ctcccctgc cctgcccgcg ccatcggccg ccgtggagcg     5940
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg     6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccgcgtg aagaagtggc gcgagcaggt    6780
cggcgaagcc tgcgaagagt tgcgaggcag cggcctggtg aacacgcct gggtcaatga    6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatgtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcgcgtcg cagcgggcct ggcggggcg     7680
gtttccatgg cgttcggaac cgtgctgacc cgcaagtggc aacctcccgt gcctctgctc    7740
accttaccg cctggcaact ggcggccgga ggacttctgc tcgttccagt agctttagtg     7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg ggtcgatca gccggggatg     7980
catcaggcca cagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
```

```
tttgatcaca ggcagcaacg ctctgtcatc gttacaatca acatgctacc ctccgcgaga   8280
tcatccgtgt ttcaaacccg gcagcttagt tgccgttctt ccgaatagca tcggtaacat   8340
gagcaaagtc tgccgcctta caacggctct cccgctgacg ccgtcccgga ctgatgggct   8400
gcctgtatcg agtggtgatt tgtgccgag ctgccggtcg gggagctgtt ggctggctgg    8460
tggcaggata tattgtggtg taaacaaatt gacgcttaga caacttaata acacattgcg   8520
gacgttttta atgtactggg gtggttttc ttttcaccag tgagacgggc aacagctgat    8580
tgcccttcac cgcctggccc tgagagagtt gcagcaagcg gtccacgctg gtttgcccca   8640
gcaggcgaaa atcctgtttg atggtggttc cgaaatcggc aaaatccctt ataaatcaaa   8700
agaatagccc gagatagggt tgagtgttgt tccagtttgg aacaagagtc cactattaaa   8760
gaacgtggac tccaacgtca aagggcgaaa aaccgtctat cagggcgatg gcccactacg   8820
tgaaccatca cccaaatcaa gttttttggg gtcgaggtgc cgtaaagcac taaatcggaa   8880
ccctaaaggg agcccccgat ttagagcttg acggggaaag ccggcgaacg tggcgagaaa   8940
ggaagggaag aaagcgaaag gagcgggcgc cattcaggct gcgcaactgt tgggaagggc   9000
gatcggtgcg ggcctcttcg ctattacgcc agctggcgaa aggggggatgt gctgcaaggc   9060
gattaagttg ggtaacgcca gggttttccc agtcacgacg ttgtaaaacg acggccagtg   9120
aattaattcc catcttgaaa gaaatatagt ttaaatattt attgataaaa taacaagtca   9180
ggtattatag tccaagcaaa acataaaatt tattgatgca agtttaaatt cagaaatatt   9240
tcaataactg attatatcag ctggtacatt gccgtgatg aaagactgag tgcgatatta    9300
tgtgtaatac ataaattgat gatatagcta gcttagctca tcgggggatc cgtcgaagct   9360
agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga ctttctcg    9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg cccctgcgct gacagccgga acacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg aggggaattt atggaacgtc  10260
agtggagcat ttttgacaag aaatatttgc tagctgatag tgaccttagg cgactttga   10320
acgcgcaata atggtttctg acgtatgtgc ttagctcatt aaactccaga aaccgcggc   10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgccccag ctggcaattc cggttcgctt gctgtccata aaaccgccca  10620
```

```
gtctagctat cgccatgtaa gcccactgca agctacctgc tttctctttg cgcttgcgtt    10680
ttcccttgtc cagatagccc agtagctgac attcatccgg ggtcagcacc gtttctgcgg    10740
actggctttc tacgtgttcc gcttcccttta gcagcccttg cgccctgagt gcttgcggca    10800
gcgtgaagct tgcatgcctg caggtcgacg gcgcgccgag ctcctcgagc aaatttacac    10860
attgccacta aacgtctaaa cccttgtaat ttgttttttgt tttactatgt gtgttatgta    10920
tttgatttgc gataaatttt tatatttggt actaaattta taacacccttt tatgctaacg    10980 tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta attttttcaag acaacaatgt    11280 taccacacac aagtttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagcgga tccgatatcg ggcccgctag cgttaacccct gctttaatga gatatgcgag    11580
acgcctatga tcgcatgata tttgctttca attctgttgt gcacgttgta aaaacctga    11640 gcatgtgtag ctcagatcct taccgccggt ttcggttcat tctaatgaat atatcacccg    11700
ttactatcgt atttttatga ataatattct ccgttcaatt tactgattgt ccgtcgacga    11760
attcgagctc ggcgcgcctc tagaggatcg atgaattcag atcggctgag tggctccttc    11820
aacgttgcgg ttctgtcagt tccaaacgta aaacggcttg tcccgcgtca tcggcggggg    11880
tcataacgtg actcccttaa ttctccgctc atgatcagat tgtcgtttcc cgccttcagt    11940
ttaaactatc agtgtttgac aggatatatt ggcgggtaaa cctaagagaa aagagcgttt    12000
attagaataa tcggatattt aaaagggcgt gaaaaggttt atccttcgtc catttgtatg    12060
tgcatgccaa ccacagggtt cccca                                         12085

<210> SEQ ID NO 22
<211> LENGTH: 12079
<212> TYPE: DNA
<213> ORGANISM: Unknown
<220> FEATURE:
<223> OTHER INFORMATION: Plant expression vector with a promoter-
      terminator expression cassette

<400> SEQUENCE: 22
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt gggggttcag cagccggcgc     480
tttactggca cttcaggaac aagcgggcgc tgctcgacgc actggccgaa gccatgctgg     540
```

```
cggagaatca tacgcattcg gtgccgagag ccgacgacga ctggcgctca tttctgatcg    600
ggaatgcccg cagcttcagg caggcgctgc tcgcctaccg cgatggcgcg cgcatccatg    660
ccggcacgcg accgggcgca ccgcagatgg aaacggccga cgcgcagctt cgcttcctct    720
gcgaggcggg ttttcggcc ggggacgccg tcaatgcgct gatgacaatc agctacttca    780 ctgttgggc cgtgcttgag gagcaggccg cgacagcga tgccggcgag cgcggcggca     840
ccgttgaaca ggctccgctc tcgccgctgt tgcgggccgc gatagacgcc ttcgacgaag    900
ccggtccgga cgcagcgttc gagcagggac tcgcggtgat tgtcgatgga ttggcgaaaa    960
ggaggctcgt tgtcaggaac gttgaaggac cgagaaaggg tgacgattga tcaggaccgc   1020
tgccggagcg caacccactc actacagcag agccatgtag acaacatccc ctcccccttt   1080
ccaccgcgtc agacgcccgt agcagcccgc tacgggcttt ttcatgccct gcccctagcgt  1140 ccaagcctca cggccgcgct cggcctctct ggcggccttc tggcgctctt ccgcttcctc   1200
gctcactgac tcgctgcgct cggtcgttcg gctgcggcga gcggtatcag ctcactcaaa   1260
ggcggtaata cggttatcca cagaatcagg ggataacgca ggaaagaaca tgtgagcaaa   1320
aggccagcaa aaggccagga accgtaaaaa ggccgcgttg ctggcgtttt tccataggct   1380
ccgcccccct gacgagcatc acaaaaatcg acgctcaagt cagaggtggc gaaacccgac   1440
aggactataa agataccagg cgtttccccc tggaagctcc ctcgtgcgct ctcctgttcc   1500
gaccctgccg cttaccggat acctgtccgc ctttctccct tcgggaagcg tggcgctttt   1560
ccgctgcata cccctgcttc ggggtcatta tagcgatttt ttcggtatat ccatcctttt   1620
tcgcacgata tacaggattt tgccaaaggg ttcgtgtaga cttttcttgg tgtatccaac   1680
ggcgtcagcc gggcaggata ggtgaagtag gcccacccgc gagcgggtgt tccttcttca   1740
ctgtccctta ttcgcacctg gcggtgctca acgggaatcc tgctctgcga ggctggccgg   1800
ctaccgccgg cgtaacagat gagggcaagc ggatggctga tgaaaccaag ccaaccagga   1860
agggcagccc acctatcaag gtgtactgcc ttccagacga acgaagagcg attgaggaaa   1920
aggcggcggc ggccgcatg agcctgtcgg cctacctgct ggcgtcggc cagggctaca    1980 aaatcacggg cgtcgtggac tatgagcacg tccgcgagct ggcccgcatc aatggcgacc   2040
tgggccgcct gggcggcctg ctgaaactct ggctcaccga cgacccgcgc acggcgcggt   2100
tcggtgatgc cacgatcctc gccctgctgg cgaagatcga agagaagcag gacgagcttg   2160
gcaaggtcat gatgggcgtg gtccgcccga gggcagagcc atgactttt tagccgctaa    2220 aacggccggg gggtgcgcgt gattgccaag cacgtcccca tgcgctccat caagaagagc   2280
gacttcgcgg agctggtgaa gtacatcacc gacgagcaag gcaagaccga gcgcctttgc   2340
gacgctcacc gggctggttg ccctcgccgc tgggctggcg gccgtctatg gcctgcaaa    2400 cgcgccagaa acgccgtcga agccgtgtgc gagacaccgc ggccgccggc gttgtggata   2460
cctcgcggaa aacttggccc tcactgacag atgaggggcg gacgttgaca cttgaggggc   2520
cgactcaccc ggcgcggcgt tgacagatga ggggcaggct cgatttcggc cggcgacgtg   2580
gagctggcca gcctcgcaaa tcggcgaaaa cgcctgattt tacgcgagtt tcccacagat   2640
gatgtggaca agcctgggga taagtgccct gcggtattga cacttgaggg gcgcgactac   2700
tgacagatga ggggcgcgat ccttgacact tgaggggcag agtgctgaca gatgaggggc   2760
gcacctattg acatttgagg ggctgtccac aggcagaaaa tccagcattt gcaagggttt   2820
ccgcccgttt ttcggccacc gctaacctgt cttttaacct gcttttaaac caatattttt   2880
aaaccttgtt tttaaccagg gctgcgccct gtgcgcgtga ccgcgcacgc cgaaggggg    2940
```

```
tgcccccccct tctcgaaccc tcccggcccg ctaacgcggg cctcccatcc ccccagggc     3000 tgcgcccctc ggccgcgaac ggcctcaccc caaaaatggc agcgctggca gtccttgcca     3060
ttgccgggat cggggcagta acgggatggg cgatcagccc gagcgcgacg cccggaagca     3120
ttgacgtgcc gcaggtgctg gcatcgacat tcagcgacca ggtgccgggc agtgagggcg     3180
gcggcctggg tggcggcctg cccttcactt cggccgtcgg ggcattcacg gacttcatgg     3240
cggggccggc aattttttacc ttgggcattc ttggcatagt ggtcgcgggt gccgtgctcg     3300
tgttcggggg tgcgataaac ccagcgaacc atttgaggtg ataggtaaga ttataccgag     3360
gtatgaaaac gagaattgga cctttacaga attactctat gaagcgccat atttaaaaag     3420
ctaccaagac gaagaggatg aagaggatga ggaggcagat tgccttgaat atattgacaa     3480
tactgataag ataatatatc ttttatatag aagatatcgc cgtatgtaag gatttcaggg     3540
ggcaaggcat aggcagcgcg cttatcaata tatctataga atgggcaaag cataaaaact     3600
tgcatggact aatgcttgaa acccaggaca ataaccttat agcttgtaaa ttctatcata     3660
attgggtaat gactccaact tattgatagt gttttatgtt cagataatgc ccgatgactt     3720
tgtcatgcag ctccaccgat tttgagaacg acagcgactt ccgtcccagc cgtgccaggt     3780
gctgcctcag attcaggtta tgccgctcaa ttcgctgcgt atatcgcttg ctgattacgt     3840 gcagcttttcc cttcaggcgg gattcataca gcggccagcc atccgtcatc catatccacca    3900 cgtcaaaggg tgacagcagg ctcataagac gccccagcgt cgccatagtg cgttcaccga     3960
atacgtgcgc aacaaccgtc ttccggagac tgtcatacgc gtaaaacagc cagcgctggc     4020
gcgatttagc cccgacatag ccccactgtt cgtccatttc cgcgcagacg atgacgtcac     4080
tgcccggctg tatgcgcgag gttaccgact gcggcctgag ttttttaagt gacgtaaaat     4140
cgtgttgagg ccaacgccca taatgcgggc tgttgcccgg catccaacgc cattcatggc     4200
catatcaatg attttctggt gcgtaccggg ttgagaagcg gtgtaagtga actgcagttg     4260
ccatgtttta cggcagtgag agcagagata gcgctgatgt ccggcggtgc ttttgccgtt     4320
acgcaccacc ccgtcagtag ctgaacagga gggacagctg atagacacag aagccactgg     4380
agcacctcaa aaacaccatc atacactaaa tcagtaagtt ggcagcatca cccataattg     4440
tggtttcaaa atcggctccg tcgatactat gttatacgcc aactttgaaa acaactttga     4500
aaaagctgtt ttctggtatt taaggtttta gaatgcaagg aacagtgaat tggagttcgt     4560
cttgttataa ttagcttctt ggggtatctt taaatactgt agaaagagg aaggaaataa      4620 taaatggcta aaatgagaat atcaccggaa ttgaaaaaac tgatcgaaaa ataccgctgc     4680
gtaaaagata cggaaggaat gtctcctgct aaggtatata agctggtggg agaaaatgaa     4740
aacctatatt taaaaatgac ggacagccgg tataaaggga ccacctatga tgtggaacgg     4800
gaaaaggaca tgatgctatg gctggaagga agctgcctg ttccaaaggt cctgcacttt      4860
gaacggcatg atgctggag caatctgctc atgagtgagg ccgatggcgt cctttgctcg     4920
gaagagtatg aagatgaaca aagccctgaa aagattatcg agctgtatgc ggagtgcatc     4980
aggctctttc actccatcga catatcggat tgtccctata cgaatagctt agacagccgc     5040
ttagccgaat tggattactt actgaataac gatctggccg atgtggattg cgaaaactgg     5100
gaagaagaca ctccatttaa agatccgcgc gagctgtatg attttttaaa gacgaaaag      5160 cccgaagagg aacttgtctt tcccacggc gacctgggag acagcaacat ctttgtgaaa      5220
gatggcaaag taagtggctt tattgatctt gggagaagcg gcagggcgga caagtggtat     5280
gacattgcct tctgcgtccg gtcgatcagg gaggatatcg gggaagaaca gtatgtcgag     5340
```

```
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccgcgtg aagaagtggc gcgagcaggt    6780
cggcgaagcc tgcgaagagt tgcgaggcag cggcctggtg gaacacgcct gggtcaatga    6840
tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcggcgtcg cagcgggcct ggcggggggcg    7680
gtttccatgg cgttcggaac cgtgctgacc cgcaagtggc aacctcccgt gcctctgctc    7740
```

```
accctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt tgtgccgag ctgccggtcg gggagctgtt ggctggctgg     8460
tggcaggata tattgtggtg taaacaaatt gacgcttaga caacttaata acacattgcg    8520
gacgttttta atgtactggg gtggttttc ttttcaccag tgagacgggc aacagctgat     8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagatagggt tgagtgttgt tccagtttgg aacaagagtc cactattaaa    8760
gaacgtggac tccaacgtca aagggcgaaa aaccgtctat cagggcgatg cccactacg     8820
tgaaccatca cccaaatcaa gttttttggg gtcgaggtgc cgtaaagcac taaatcggaa    8880
ccctaaaggg agcccccgat ttagagcttg acggggaaag ccggcgaacg tggcgagaaa    8940
ggaagggaag aaagcgaaag gagcgggcgc cattcaggct gcgcaactgt tgggaagggc    9000
gatcggtgcg ggcctcttcg ctattacgcc agctggcgaa aggggggatgt gctgcaaggc   9060
gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcgggggatc cgtcgaagct    9360
agcttgggtc ccgctcagaa gaactcgtca agaaggcgat agaaggcgat gcgctgcgaa    9420
tcgggagcgc cgataccgta aagcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
agttcggctg cgcgagccc ctgatgctct tcgtccagat catcctgatc gacaagaccg     9720
gcttccatcc gagtacgtgc tcgctcgatg cgatgtttcg cttggtggtc gaatgggcag    9780
gtagccggat caagcgtatg cagccgccgc attgcatcag ccatgatgga tactttctcg    9840
gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata gccgcgctgc ctcgtcctgc agttcattca gggcaccgga caggtcggtc   10020
ttgacaaaaa gaaccgggcg cccctgcgct gacagccgga acacggcggc atcagagcag   10080
ccgattgtct gttgtgccca gtcatagccg aatagcctct ccacccaagc ggccggagaa   10140
```

```
cctgcgtgca atccatcttg ttcaatccaa gctcccatgg gccctcgact agagtcgaga    10200
tctggattga gagtgaatat gagactctaa ttggataccg aggggaattt atggaacgtc    10260
agtggagcat ttttgacaag aaatatttgc tagctgatag tgaccttagg cgactttga    10320 acgcgcaata atggtttctg acgtatgtgc ttagctcatt aaactccaga aacccgcggc    10380
tgagtggctc cttcaacgtt gcggttctgt cagttccaaa cgtaaaacgg cttgtcccgc    10440
gtcatcggcg ggggtcataa cgtgactccc ttaattctcc gctcatgatc ttgatcccct    10500
gcgccatcag atccttggcg gcaagaaagc catccagttt actttgcagg gcttcccaac    10560
cttaccagag ggcgccccag ctggcaattc cggttcgctt gctgtccata aaaccgccca    10620
gtctagctat cgccatgtaa gcccactgca agctacctgc tttctctttg cgcttgcgtt    10680
ttcccttgtc cagatagccc agtagctgac attcatccgg ggtcagcacc gtttctgcgg    10740
actggctttc tacgtgttcc gcttccttta gcagcccttg cgccctgagt gcttgcggca    10800
gcgtgaagct tgcatgcctg caggtcgacg gcgcgccgag ctcctcgagc aaatttacac    10860
attgccacta aacgtctaaa cccttgtaat tgttttttgt tttactatgt gtgttatgta    10920
tttgatttgc gataaatttt tatatttggt actaaattta taacaccttt tatgctaacg    10980
tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta attttttcaag acaacaatgt    11280 taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagcaga tctgccggca tcgatcccgg gccatggcct gctttaatga gatatgcgag    11580
acgcctatga tcgcatgata tttgctttca attctgttgt gcacgttgta aaaacctga    11640 gcatgtgtag ctcagatcct taccgccggt ttcggttcat tctaatgaat atatcacccg    11700
ttactatcgt atttttatga ataatattct ccgttcaatt tactgattgt ccgtcgacga    11760
gctcggcgcg cctctagagg atcgatgaat tcagatcggc tgagtggctc cttcaacgtt    11820
gcggttctgt cagttccaaa cgtaaaacgg cttgtcccgc gtcatcggcg ggggtcataa    11880
cgtgactccc ttaattctcc gctcatgatc agattgtcgt ttcccgcctt cagtttaaac    11940
tatcagtgtt tgacaggata tattggcggg taaacctaag agaaaagagc gtttattaga    12000
ataatcggat atttaaaagg gcgtgaaaag gtttatcctt cgtccatttg tatgtgcatg    12060
ccaaccacag ggttcccca                                                 12079
```

<210> SEQ ID NO 23
<211> LENGTH: 13002
<212> TYPE: DNA
<213> ORGANISM: Unknown
<220> FEATURE:
<223> OTHER INFORMATION: Plant expression vector with two promoter-
      terminator expression cassettes

<400> SEQUENCE: 23

```
gatctggcgc cggccagcga gacgagcaag attggccgcc gccgaaacg atccgacagc     60 gcgcccagca caggtgcgca ggcaaattgc accaacgcat acagcgccag cagaatgcca    120
```

```
tagtgggcgg tgacgtcgtt cgagtgaacc agatcgcgca ggaggccggg cagcaccggc      180
ataatcaggc cgatgccgac agcgtcgagc gcgacagtgc tcagaattac gatcaggggt      240
atgttgggtt tcacgtctgg cctccggacc agcctccgct ggtccgattg aacgcgcgga      300
ttctttatca ctgataagtt ggtggacata ttatgtttat cagtgataaa gtgtcaagca      360
tgacaaagtt gcagccgaat acagtgatcc gtgccgccct ggacctgttg aacgaggtcg      420
gcgtagacgg tctgacgaca cgcaaactgg cggaacggtt gggggttcag cagccggcgc      480
tttactggca cttcaggaac aagcgggcgc tgctcgacgc actggccgaa gccatgctgg      540
cggagaatca tacgcattcg gtgccgagag ccgacgacga ctggcgctca tttctgatcg      600
ggaatgcccg cagcttcagg caggcgctgc tcgcctaccg cgatggcgcg cgcatccatg      660
ccggcacgcg accgggcgca ccgcagatgg aaacggccga cgcgcagctt cgcttcctct      720
gcgaggcggg ttttcggcc ggggacgccg tcaatgcgct gatgacaatc agctacttca      780
ctgttggggc cgtgcttgag gagcaggccg gcgacagcga tgccggcgag cgcggcggca      840
ccgttgaaca ggctccgctc tcgccgctgt tgcgggccgc gatagacgcc ttcgacgaag      900
ccggtccgga cgcagcgttc gagcagggac tcgcggtgat tgtcgatgga ttggcgaaaa      960
ggaggctcgt tgtcaggaac gttgaaggac cgagaaaggg tgacgattga tcaggaccgc     1020
tgccggagcg caacccactc actacagcag agccatgtag acaacatccc ctccccttt     1080 ccaccgcgtc agacgcccgt agcagcccgc tacgggcttt ttcatgccct gccctagcgt     1140
ccaagcctca cggccgcgct cggcctctct ggcggccttc tggcgctctt ccgcttcctc     1200
gctcactgac tcgctgcgct cggtcgttcg gctgcggcga gcggtatcag ctcactcaaa     1260
ggcggtaata cggttatcca cagaatcagg ggataacgca ggaaagaaca tgtgagcaaa     1320
aggccagcaa aaggccagga accgtaaaaa ggccgcgttg ctggcgtttt tccataggct     1380
ccgcccccct gacgagcatc acaaaaatcg acgctcaagt cagaggtggc gaaacccgac     1440
aggactataa agataccagg cgtttccccc tggaagctcc ctcgtgcgct ctcctgttcc     1500
gaccctgccg cttaccggat acctgtccgc ctttctccct tcgggaagcg tggcgctttt     1560
ccgctgcata accctgcttc ggggtcatta tagcgatttt ttcggtatat ccatcctttt     1620
tcgcacgata tacaggattt tgccaaaggg ttcgtgtaga cttccttgg tgtatccaac     1680 ggcgtcagcc gggcaggata ggtgaagtag cccaccccgc gagcgggtgt tccttcttca     1740
ctgtccctta ttcgcacctg gcggtgctca acgggaatcc tgctctgcga ggctggccgg     1800
ctaccgccgg cgtaacagat gagggcaagc ggatggctga tgaaaccaag ccaaccagga     1860
agggcagccc acctatcaag gtgtactgcc ttccagacga acgaagagcg attgaggaaa     1920
aggcggcggc ggccggcatg agcctgtcgg cctacctgct ggccgtcggc cagggctaca     1980
aaatcacggg cgtcgtggac tatgagcacg tccgcgagct ggcccgcatc aatggcgacc     2040
tgggccgcct gggcggcctg ctgaaaactct ggctcaccga cgacccgcgc acggcgcggt     2100
tcggtgatgc cacgatcctc gccctgctgg cgaagatcga agagaagcag gacgagcttg     2160
gcaaggtcat gatgggcgtg gtccgcccga gggcagagcc atgactttt tagccgctaa     2220 aacggccggg gggtgcgcgt gattgccaag cacgtcccca tgcgctccat caagaagagc     2280
gacttcgcgc agctggtgaa gtacatcacc gacgagcaag gcaagaccga gcgcctttgc     2340
gacgctcacc gggctggttg ccctcgccgc tgggctggcg ccgtctatg gccctgcaaa     2400 cgcgccagaa acgccgtcga agccgtgtgc gagacaccgc ggccgccggc gttgtggata     2460
cctcgcggaa aacttggccc tcactgacag atgaggggcg gacgttgaca cttgagggc     2520
```

```
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaaggggg    2940 tgccccccct tctcgaaccc tcccggcccg ctaacgcggg cctcccatcc ccccaggggc    3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa acaactttga    4500
aaaagctgtt ttctggtatt taaggtttta gaatgcaagg aacagtgaat tggagttcgt    4560
cttgttataa ttagcttctt ggggtatctt taaatactgt agaaagagg aaggaaataa    4620 taaatggcta aaatgagaat atcaccggaa ttgaaaaaac tgatcgaaaa ataccgctgc    4680 gtaaagata cggaaggaat gtctcctgct aaggtatata agctggtggg agaaaatgaa    4740
aacctatatt taaaaatgac ggacagccgg tataagggga ccacctatga tgtggaacgg    4800
gaaaaggaca tgatgctatg gctggaagga agctgcctg ttccaaaggt cctgcacttt    4860
gaacggcatg atggctggag caatctgctc atgagtgagg ccgatggcgt cctttgctcg    4920
```

```
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacggaaaag    5160
cccgaagagg aacttgtctt tcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcgggcaat    5700 cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccccgcgtg aagaagtggc gcgagcaggt    6780
cggcgaagcc tgcgaagagt tgcgaggcag cggcctggtg aacacgcct gggtcaatga    6840 tgacctggtg cattgcaaac gctagggcct tgtgggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
```

```
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctgggggct atttgcggaa ctgcgggcgt ggcgctgttg    7620
gtgttgacac caaacgcagc gctagatcct gtcggcgtcg cagcgggcct ggcggggggcg   7680
gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct   7920
acagttgttt ccttactggg ctttctcagc cccagatctg gggtcgatca gccggggatg    7980
catcaggcca cagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt tgtgccgag ctgccggtcg gggagctgtt ggctggctgg    8460
tggcaggata tattgtggtg taaacaaatt gacgcttaga caacttaata acacattgcg    8520
gacgtttta atgtactggg gtggttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatcccctt ataaatcaaa   8700
agaatagccc gagatagggt tgagtgttgt tccagtttgg aacaagagtc cactattaaa    8760
gaacgtggac tccaacgtca aagggcgaaa accgtctat cagggcgatg gcccactacg     8820
tgaaccatca cccaaatcaa gttttttggg gtcgaggtgc cgtaaagcac taaatcggaa    8880
ccctaaaggg agcccccgat ttagagcttg acggggaaag ccggcgaacg tggcgagaaa    8940
ggaagggaag aaagcgaaag gagcgggcgc cattcaggct gcgcaactgt tgggaagggc    9000
gatcggtgcg ggcctcttcg ctattacgcc agctggcgaa aggggggatgt gctgcaaggc    9060
gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa acataaatt tattgatgca agtttaaatt cagaaatatt     9240
tcaataactg attatatcag ctggtacatt gccgtagatg aaagactgag tgcgatatta    9300
tgtgtaatac ataaattgat gatatagcta gcttagctca tcggggatc cgtcgaagct     9360
agcttgggtc ccgctcagaa gaactcgtca agaaggcgat agaaggcgat gcgctgcgaa    9420
tcggagcgg cgataccgta aagcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
agttcggctg gcgcgagccc ctgatgctct tcgtccagat catcctgatc gacaagaccg    9720
```

```
gcttccatcc gagtacgtgc tcgctcgatg cgatgtttcg cttggtggtc aatgggcag    9780 gtagccggat caagcgtatg cagccgccgc attgcatcag ccatgatgga tactttctcg    9840
gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata gccgcgctgc ctcgtcctgc agttcattca gggcaccgga caggtcggtc   10020
ttgacaaaaa gaaccgggcg cccctgcgct gacagccgga cacggcggc atcagagcag    10080 ccgattgtct gttgtgccca gtcatagccg aatagcctct ccacccaagc ggccggagaa   10140
cctgcgtgca atccatcttg ttcaatccaa gctcccatgg gccctcgact agagtcgaga   10200
tctggattga gagtgaatat gagactctaa ttggataccg aggggaattt atggaacgtc    10260
agtggagcat ttttgacaag aaatatttgc tagctgatag tgaccttagg cgacttttga   10320
acgcgcaata atggtttctg acgtatgtgc ttagctcatt aaactccaga aacccgcggc    10380
tgagtggctc cttcaacgtt gcggttctgt cagttccaaa cgtaaaacgg cttgtcccgc    10440
gtcatcggcg ggggtcataa cgtgactccc ttaattctcc gctcatgatc ttgatcccct    10500
gcgccatcag atccttggcg gcaagaaagc catccagttt actttgcagg cttcccaac    10560 cttaccagag ggcgccccag ctggcaattc cggttcgctt gctgtccata aaaccgccca    10620
gtctagctat cgccatgtaa gcccactgca agctacctgc tttctctttg cgcttgcgtt    10680
ttcccttgtc cagatagccc agtagctgac attcatccgg ggtcagcacc gtttctgcgg    10740
actggctttc tacgtgttcc gcttccttta gcagcccttg cgcctgagt gcttgcggca    10800 gcgtgaagct tgcatgcctg caggtcgacg gcgcgccgag ctcctcgagc aaatttacac    10860
attgccacta aacgtctaaa cccttgtaat ttgttttgt tttactatgt gtgttatgta    10920
tttgatttgc gataaatttt tatatttggt actaaattta taacaccttt tatgctaacg    10980
tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta attttttcaag acaacaatgt   11280 taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagccca ccgcggtggg cggccgcctg cagtctagaa ggcctcctgc tttaatgaga    11580
tatgcgagac gcctatgatc gcatgatatt tgctttcaat tctgttgtgc acgttgtaaa    11640
aaacctgagc atgtgtagct cagatcctta ccgccggttt cggttcattc taatgaatat    11700
atcacccgtt actatcgtat ttttatgaat aatattctcc gttcaattta ctgattgtcc    11760
gtcgagcaaa tttacacatt gccactaaac gtctaaaccc ttgtaatttg ttttgttttt    11820
actatgtgtg ttatgtattt gatttgcgat aaattttat atttggtact aaatttataa    11880
caccttttat gctaacgttt gccaacactt agcaatttgc aagttgatta attgattcta    11940
aattattttt gtcttctaaa tacatatact aatcaactgg aaatgtaaat atttgctaat    12000
atttctacta taggagaatt aaagtgagtg aatatggtac cacaaggttt ggagatttaa    12060
ttgttgcaat gctgcatgga tggcatatac accaaacatt caataattct tgaggataat    12120
```

```
aatggtacca cacaagattt gaggtgcatg aacgtcacgt ggacaaaagg tttagtaatt    12180
tttcaagaca acaatgttac cacacacaag ttttgaggtg catgcatgga tgccctgtgg    12240
aaagtttaaa aatattttgg aaatgatttg catggaagcc atgtgtaaaa ccatgacatc    12300
cacttggagg atgcaataat gaagaaaact acaaatttac atgcaactag ttatgcatgt    12360
agtctatata atgaggattt tgcaatactt tcattcatac acactcacta agttttacac    12420
gattataatt tcttcatagc cagcggatcc gatatcgggc ccgctagcgt taaccctgct    12480
ttaatgagat atgcgagacg cctatgatcg catgatattt gctttcaatt ctgttgtgca    12540
cgttgtaaaa aacctgagca tgtgtagctc agatccttac cgccggtttc ggttcattct    12600
aatgaatata tcacccgtta ctatcgtatt tttatgaata atattctccg ttcaatttac    12660
tgattgtccg tcgacgaatt cgagctcggc gcgcctctag aggatcgatg aattcagatc    12720
ggctgagtgg ctccttcaac gttgcggttc tgtcagttcc aaacgtaaaa cggcttgtcc    12780
cgcgtcatcg gcggggtca taacgtgact cccttaattc tccgctcatg atcagattgt    12840
cgtttcccgc cttcagttta aactatcagt gtttgacagg atatattggc gggtaaacct    12900
aagagaaaag agcgttatt agaataatcg gatatttaaa agggcgtgaa aaggtttatc    12960
cttcgtccat ttgtatgtgc atgccaacca cagggttccc ca                      13002
```

<210> SEQ ID NO 24
<211> LENGTH: 13905
<212> TYPE: DNA
<213> ORGANISM: Unknown
<220> FEATURE:
<223> OTHER INFORMATION: Plant expression vector with three promoter-
      terminator expression cassettes

<400> SEQUENCE: 24

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgt tctgacgaca cgcaaactgg cggaacggtt gggggttcag cagccggcgc     480
tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg cgatggcgcg cgcatccatg     660
ccggcacgcg accggcgca ccgcagatgg aaacggccga cgcgcagctt cgcttcctct     720
gcgaggcggg tttttcggcc ggggacgccg tcaatgcgct gatgacaatc agctacttca     780
ctgttggggc cgtgcttgag gagcaggccg gcgacagcga tgccggcgag gcggcggca     840 ccgttgaaca ggctccgctc tcgccgctgt tgcgggccgc gatagacgcc ttcgacgaag     900
ccggtccgga cgcagcgttc gagcaggac tcgcggtgat tgtcgatgga ttggcgaaaa     960
ggaggctcgt tgtcaggaac gttgaaggac cgagaaaggg tgacgattga tcaggaccgc    1020
tgccggagcg caaccactc actacagcag agcatgtag acaacatccc ctcccccttt    1080
ccaccgcgtc agacgcccgt agcagcccgc tacgggcttt ttcatgccct gccctagcgt    1140
```

```
ccaagcctca cggccgcgct cggcctctct ggcggccttc tggcgctctt ccgcttcctc      1200
gctcactgac tcgctgcgct cggtcgttcg gctgcggcga gcggtatcag ctcactcaaa      1260
ggcggtaata cggttatcca cagaatcagg ggataacgca ggaaagaaca tgtgagcaaa      1320
aggccagcaa aaggccagga accgtaaaaa ggccgcgttg ctggcgtttt tccataggct      1380
ccgcccccct gacgagcatc acaaaaatcg acgctcaagt cagaggtggc gaaacccgac      1440
aggactataa agataccagg cgtttccccc tggaagctcc ctcgtgcgct ctcctgttcc      1500
gaccctgccg cttaccggat acctgtccgc ctttctccct tcgggaagcg tggcgctttt      1560
ccgctgcata accctgcttc ggggtcatta tagcgatttt ttcggtatat ccatcctttt      1620
tcgcacgata tacaggattt tgccaaaggg ttcgtgtaga cttccttgg tgtatccaac      1680 ggcgtcagcc gggcaggata ggtgaagtag gcccacccgc gagcgggtgt tccttcttca      1740
ctgtccctta ttcgcacctg gcggtgctca acgggaatcc tgctctgcga ggctggccgg      1800
ctaccgccgg cgtaacagat gagggcaagc ggatggctga tgaaaccaag ccaaccagga      1860
agggcagccc acctatcaag gtgtactgcc ttccagacga acgaagagcg attgaggaaa      1920
aggcggcggc ggccggcatg agcctgtcgg cctacctgct ggccgtcggc cagggctaca      1980
aaatcacggg cgtcgtggac tatgagcacg tccgcgagct ggcccgcatc aatggcgacc      2040
tgggccgcct gggcggcctg ctgaaactct ggctcaccga cgaccgcgc acggcgcggt      2100 tcggtgatgc cacgatcctc gccctgctgg cgaagatcga agagaagcag gacgagcttg      2160
gcaaggtcat gatgggcgtg gtccgcccga gggcagagcc atgactttt tagccgctaa      2220 aacggccggg gggtgcgcgt gattgccaag cacgtcccca tgcgctccat caagaagagc      2280
gacttcgcgg agctggtgaa gtacatcacc gacgagcaag gcaagaccga gcgcctttgc      2340
gacgctcacc gggctggttg ccctcgccgc tgggctggcg gccgtctatg gcctgcaaa      2400 cgcgccagaa acgccgtcga agccgtgtgc gagacaccgc ggccgccggc gttgtggata      2460
cctcgcggaa aacttggccc tcactgacag atgaggggcg gacgttgaca cttgaggggc      2520
cgactcaccc ggcgcggcgt tgacagatga ggggcaggct cgatttcggc cggcgacgtg      2580
gagctggcca gcctcgcaaa tcggcgaaaa cgcctgattt tacgcgagtt tcccacagat      2640
gatgtggaca gcctggggga taagtgccct gcggtattga cacttgaggg gcgcgactac      2700
tgacagatga ggggcgcgat ccttgacact tgaggggcag agtgctgaca gatgaggggc      2760
gcacctattg acatttgagg ggctgtccac aggcagaaaa tccagcattt gcaagggttt      2820
ccgcccgttt tcggccacc gctaacctgt cttttaacct gcttttaaac caatatttat      2880
aaaccttgtt tttaaccagg ctgcgccct gtgcgcgtga ccgcgcacgc cgaaggggg      2940 tgccccccct tctcgaaccc tcccggcccg ctaacgcggg cctcccatcc ccccagggc      3000 tgcgcccctc ggccgcgaac ggcctcaccc caaaaatggc agcgctggca gtccttgcca      3060
ttgccgggat cggggcagta acgggatggg cgatcagccc gagcgcgacg cccggaagca      3120
ttgacgtgcc gcaggtgctg gcatcgacat tcagcgacca ggtgccgggc agtgagggcg      3180
gcggcctggg tggcggcctg cccttcactt cggccgtcgg ggcattcacg gacttcatgg      3240
cggggccggc aattttttacc ttgggcattc ttggcatagt ggtcgcgggt gccgtgctcg      3300
tgttcggggg tgcgataaac ccagcgaacc atttgaggtg ataggtaaga ttataccgag      3360
gtatgaaaac gagaattgga cctttacaga attactctat gaagcgccat atttaaaaag      3420
ctaccaagac gaagaggatg aagaggatga ggaggcagat tgccttgaat atattgacaa      3480
tactgataag ataatatatc ttttatatag aagatatcgc cgtatgtaag gatttcaggg      3540
```

```
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagcttttc cttcaggcgg gattcataca gcggccagcc atccgtcatc catatcacca    3900
cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080 tgcccgctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500 aaaagctgtt ttctggtatt taaggtttta gaatgcaagg aacagtgaat tggagttcgt    4560
cttgttataa ttagcttctt ggggtatctt taaatactgt agaaaagagg aaggaaataa    4620
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataagggga ccacctatga tgtggaacgg    4800
gaaaaggaca tgatgctatg gctgaaggaa agctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttttaaa gacgaaaag    5160 cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580 cggcagacg gtctacggga ccgacttcat tgccgataag gtggattatc tggacaccaa    5640
ggcaccaggc gggtcaaatc aggaataagg gcacattgcc ccggcgtgag tcgggcaat    5700 cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctccccctgc cctgcccgcg ccatcggccg ccgtggagcg    5940
```

```
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca cccctatcgg    6360
cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc cacccgcgtg aagaagtggc gcgagcaggt    6780
cggcgaagcc tgcgaagagt tgcgaggcag cggcctggtg gaacacgcct gggtcaatga    6840
tgacctggtg cattgcaaac gctagggcct tgtgggggtca gttccggctg ggggttcagc    6900
agccagcgct ttactggcat tcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatggcggt cctggggggct atttgcggaa ctgcgggcgt ggcgctgttg    7620
gtgttgacac caaacgcagc gctagatcct gtcggcgtcg cagcgggcct ggcggggggcg    7680 gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg cttttctcagc cccagatctg gggtcgatca gccggggatg    7980
catcaggccg acagtcggaa cttcgggtcc ccgacctgta ccattcggtg agcaatggat    8040
aggggagttg atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
tcatccgtgt ttcaaacccg gcagcttagt tgccgttctt ccgaatagca tcggtaacat    8340
```

```
gagcaaagtc tgccgcctta caacggctct cccgctgacg ccgtcccgga ctgatgggct   8400
gcctgtatcg agtggtgatt ttgtgccgag ctgccggtcg gggagctgtt ggctggctgg   8460
tggcaggata tattgtggtg taaacaaatt gacgcttaga caacttaata acacattgcg   8520
gacgttttta atgtactggg gtggtttttc ttttcaccag tgagacgggc aacagctgat   8580
tgcccttcac cgcctggccc tgagagagtt gcagcaagcg gtccacgctg gtttgcccca   8640
gcaggcgaaa atcctgtttg atggtggttc cgaaatcggc aaaatccctt ataaatcaaa   8700
agaatagccc gagatagggt tgagtgttgt tccagtttgg aacaagagtc cactattaaa   8760
gaacgtggac tccaacgtca aagggcgaaa aaccgtctat cagggcgatg gcccactacg   8820
tgaaccatca cccaaatcaa gttttttggg gtcgaggtgc cgtaaagcac taaatcggaa   8880
ccctaaaggg agcccccgat ttagagcttg acggggaaag ccggcgaacg tggcgagaaa   8940
ggaagggaag aaagcgaaag gagcgggcgc cattcaggct gcgcaactgt gggaagggc   9000 gatcggtgcg ggcctcttcg ctattacgcc agctggcgaa aggggatgt gctgcaaggc   9060 gattaagttg ggtaacgcca gggttttccc agtcacgacg ttgtaaaacg acggccagtg   9120
aattaattcc catcttgaaa gaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300
tgtgtaatac ataaattgat gatatagcta gcttagctca tcggggatc cgtcgaagct   9360 agcttgggtc ccgctcagaa gaactcgtca agaaggcgat agaaggcgat gcgctgcgaa   9420
tcgggagcgg cgataccgta aagcacgagg aagcggtcag cccattcgcc gccaagctct   9480
tcagcaatat cacgggtagc caacgctatg tcctgatagc ggtccgccac acccagccgg   9540
ccacagtcga tgaatccaga aaagcggcca ttttccacca tgatattcgg caagcaggca   9600
tcgccatggg tcacgacgag atcctcgccg tcgggcatgc gcgccttgag cctggcgaac   9660
agttcggctg gcgcgagccc ctgatgctct tcgtccagat catcctgatc gacaagaccg   9720
gcttccatcc gagtacgtgc tcgctcgatg cgatgtttcg cttggtggtc gaatgggcag   9780
gtagccggat caagcgtatg cagccgccgc attgcatcag ccatgatgga tactttctcg   9840
gcaggagcaa ggtgagatga caggagatcc tgccccggca cttcgcccaa tagcagccag   9900
tcccttcccg cttcagtgac aacgtcgagc acagctgcgc aaggaacgcc cgtcgtggcc   9960
agccacgata gccgcgctgc ctcgtcctgc agttcattca gggcaccgga caggtcggtc  10020
ttgacaaaaa gaaccgggcg cccctgcgct gacagccgga acacggcggc atcagagcag  10080
ccgattgtct gttgtgccca gtcatagccg aatagcctct ccacccaagc ggccggagaa  10140
cctgcgtgca atccatcttg ttcaatccaa gctcccatgg gccctcgact agagtcgaga  10200
tctggattga gagtgaatat gagactctaa ttggataccg aggggaattt atggaacgtc  10260
agtggagcat ttttgacaag aaatatttgc tagctgatag tgaccttagg cgactttga   10320 acgcgcaata atggtttctg acgtatgtgc ttagctcatt aaactccaga aacccgcggc  10380
tgagtggctc cttcaacgtt gcggttctgt cagttccaaa cgtaaaacgg cttgtcccgc  10440
gtcatcggcg ggggtcataa cgtgactccc ttaattctcc gctcatgatc ttgatcccct  10500
gcgccatcag atccttggcg gcaagaaagc catccagttt actttgcagg gcttcccaac  10560
cttaccagag ggcgccccag ctggcaattc cggttcgctt gctgtccata aaaccgccca  10620
gtctagctat cgccatgtaa gcccactgca agctacctgc tttctctttg cgcttgcgtt  10680
ttcccttgtc cagatagccc agtagctgac attcatccgg ggtcagcacc gtttctgcgg  10740
```

```
actggctttc tacgtgttcc gcttccttta gcagcccttg cgccctgagt gcttgcggca    10800
gcgtgaagct tgcatgcctg caggtcgacg gcgcgccgag ctcctcgagc aaatttacac    10860
attgccacta aacgtctaaa cccttgtaat ttgtttttgt tttactatgt gtgttatgta    10920
tttgatttgc gataaatttt tatatttggt actaaattta taacaccttt tatgctaacg    10980
tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta atttttcaag acaacaatgt    11280
taccacacac aagttttgag gtgcatgcat ggatgccctg tggaaagttt aaaaatattt    11340
tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagtttta cacgattata atttcttcat    11520
agccagccca ccgcggtggg cggccgcctg cagtctagaa ggcctcctgc tttaatgaga    11580
tatgcgagac gcctatgatc gcatgatatt tgctttcaat tctgttgtgc acgttgtaaa    11640
aaacctgagc atgtgtagct cagatcctta ccgccggttt cggttcattc taatgaatat    11700
atcacccgtt actatcgtat ttttatgaat aatattctcc gttcaattta ctgattgtcc    11760
gtcgagcaaa tttacacatt gccactaaac gtctaaaccc ttgtaatttg tttttgtttt    11820
actatgtgtg ttatgtattt gatttgcgat aaatttttat atttggtact aaatttataa    11880
cacctttat gctaacgttt gccaacactt agcaatttgc aagttgatta attgattcta    11940
aattattttt gtcttctaaa tacatatact aatcaactgg aaatgtaaat atttgctaat    12000
atttctacta taggagaatt aaagtgagtg aatatggtac acaaggtttg gagatttaa    12060
ttgttgcaat gctgcatgga tggcatatac accaaacatt caataattct tgaggataat    12120
aatggtacca cacaagattt gaggtgcatg aacgtcacgt ggacaaaagg tttagtaatt    12180
tttcaagaca acaatgttac cacacacaag ttttgaggtg catgcatgga tgccctgtgg    12240
aaagtttaaa atatttggg aaatgatttg catggaagcc atgtgtaaaa ccatgacatc    12300
cacttggagg atgcaataat gaagaaaact acaaatttac atgcaactag ttatgcatgt    12360
agtctatata tgaggattt tgcaatactt tcattcatac acactcacta gttttacac    12420
gattataatt tcttcatagc cagcggatcc gatatcgggc cgctagcgt taaccctgct    12480
ttaatgagat atgcgagacg cctatgatcg catgatattt gctttcaatt ctgttgtgca    12540
cgttgtaaaa aacctgagca tgtgtagctc agatccttac cgccggtttc ggttcattct    12600
aatgaatata tcacccgtta ctatcgtatt tttatgaata atattctccg ttcaattttac    12660
tgattgtccg tcgagcaaat ttacacattg ccactaaacg tctaaaccct tgtaatttgt    12720
ttttgtttta ctatgtgtgt tatgtatttg atttgcgata aatttttata tttggtacta    12780
aatttataac accttttatg ctaacgtttg ccaacactta gcaatttgca agttgattaa    12840
ttgattctaa attattttg tcttctaaat acatatacta atcaactgga aatgtaaata    12900
tttgctaata tttctactat aggagaatta aagtgagtga atatggtacc acaaggtttg    12960
gagatttaat tgttgcaatg ctgcatggat ggcatataca ccaaacattc aataattctt    13020
gaggataata atggtaccac acaagatttg aggtgcatga acgtcacgtg gacaaaaggt    13080
ttagtaattt ttcaagacaa caatgttacc acacacaagt tttgaggtgc atgcatggat    13140
```

```
gccctgtgga aagtttaaaa atatttggga aatgatttgc atggaagcca tgtgtaaaac    13200
catgacatcc acttggagga tgcaataatg aagaaaacta caaatttaca tgcaactagt    13260
tatgcatgta gtctatataa tgaggatttt gcaatacttt cattcataca cactcactaa    13320
gttttacacg attataattt cttcatagcc agcagatctg ccggcatcga tcccgggcca    13380
tggcctgctt taatgagata tgcgagacgc ctatgatcgc atgatatttg ctttcaattc    13440
tgttgtgcac gttgtaaaaa acctgagcat gtgtagctca gatccttacc gccggtttcg    13500
gttcattcta atgaatatat cacccgttac tatcgtattt ttatgaataa tattctccgt    13560
tcaatttact gattgtccgt cgacgagctc ggcgcgcctc tagaggatcg atgaattcag    13620
atcggctgag tggctccttc aacgttgcgg ttctgtcagt tccaaacgta aaacggcttg    13680
tcccgcgtca tcggcgggggg tcataacgtg actcccttaa ttctccgctc atgatcagat    13740 tgtcgttttcc cgccttcagt ttaaactatc agtgtttgac aggatatatt ggcgggtaaa    13800
cctaagagaa aagagcgttt attagaataa tcggatattt aaaagggcgt gaaaaggttt    13860
atccttcgtc catttgtatg tgcatgccaa ccacagggtt cccca                    13905
```

<210> SEQ ID NO 25
<211> LENGTH: 15430
<212> TYPE: DNA
<213> ORGANISM: Unknown
<220> FEATURE:
<223> OTHER INFORMATION: Plant expression vector with two promoter-terminator expression cassettes; Physcomitrella patens elongase and desaturase are inserted
<220> FEATURE:
<221> NAME/KEY: CDS
<222> LOCATION: (11543)..(12415)
<220> FEATURE:
<221> NAME/KEY: CDS
<222> LOCATION: (13313)..(14890)

<400> SEQUENCE: 25

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt gggggttcag cagccggcgc     480
tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg cgatggcgcg cgcatccatg     660
ccggcacgcg accgggcgca ccgcagatgg aaacggccga cgcgcagctt cgcttcctct     720
gcgaggcggt ttttcggcc ggggacgccg tcaatgcgct gatgacaatc agctacttca     780 ctgttgggc cgtgcttgag gagcaggccg gcgacagcga tgccggcgag gcggcggca      840 ccgttgaaca ggctccgctc tcgccgctgt gcgggccgc gatagacgcc ttcgacgaag     900
ccggtccgga cgcagcgttc gagcagggac tcgcggtgat tgtcgatgga ttggcgaaaa     960
ggaggctcgt tgtcaggaac gttgaaggac cgagaagggg tgacgattga tcaggaccgc    1020
tgccggagcg caacccactc actacagcag agccatgtag acaacatccc ctccccctttt    1080
```

```
ccaccgcgtc agacgcccgt agcagcccgc tacgggcttt tcatgccct gccctagcgt    1140
ccaagcctca cggccgcgct cggcctctct ggcggccttc tggcgctctt ccgcttcctc    1200
gctcactgac tcgctgcgct cggtcgttcg gctgcggcga gcggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttt    1560
ccgctgcata accctgcttc ggggtcatta tagcgatttt ttcggtatat ccatcctttt    1620
tcgcacgata tacaggattt tgccaaaggg ttcgtgtaga cttccttgg tgtatccaac     1680
ggcgtcagcc gggcaggata ggtgaagtag gcccacccgc gagcgggtgt tccttcttca    1740
ctgtccctta ttcgcacctg cggtgctca acgggaatcc tgtctgcga ggctggccgg      1800
ctaccgccgg cgtaacagat gagggcaagc ggatggctga tgaaaccaag ccaaccagga    1860
agggcagccc acctatcaag gtgtactgcc ttccagacga acgaagagcg attgaggaaa    1920
aggcggcggc ggccggcatg agcctgtcgg cctacctgct ggccgtcggc cagggctaca    1980
aaatcacggg cgtcgtggac tatgagcacg tccgcgagct ggcccgcatc aatgcgacc     2040
tgggccgcct gggcggcctg ctgaaactct ggctcaccga cgacccgcgc acggcgcggt    2100
tcggtgatgc cacgatcctc gccctgctgg cgaagatcga agagaagcag gacgagcttg    2160
gcaaggtcat gatgggcgtg gtccgcccga gggcagagcc atgactttt tagccgctaa     2220
aacggccggg gggtgcgcgt gattgccaag cacgtcccca tgcgctccat caagaagagc    2280
gacttcgcgg agctggtgaa gtacatcacc gacgagcaag gcaagaccga gcgcctttgc    2340
gacgctcacc gggctggttg ccctcgccgc tgggctggcg gccgtctatg gcctgcaaa     2400
cgcgccagaa acgccgtcga agccgtgtgc gagacaccgc ggccgccggc gttgtggata    2460
cctcgcggaa aacttggccc tcactgacag atgagggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt cccacagat     2640
gatgtgtgaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg ctgcgccct gtgcgcgtga ccgcgcacgc cgaaggggg      2940
tgcccccct tctcgaaccc tcccggcccg ctaacgcggg cctcccatcc ccccaggggc     3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aatttttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
```

```
tactgataag ataatatatc ttttatatag aagatatcgc cgtatgtaag gatttcaggg   3540
ggcaaggcat aggcagcgcg cttatcaata tatctataga atgggcaaag cataaaaact   3600
tgcatggact aatgcttgaa acccaggaca ataaccttat agcttgtaaa ttctatcata   3660
attgggtaat gactccaact tattgatagt gttttatgtt cagataatgc ccgatgactt   3720
tgtcatgcag ctccaccgat tttgagaacg acagcgactt ccgtcccagc cgtgccaggt   3780
gctgcctcag attcaggtta tgccgctcaa ttcgctgcgt atatcgcttg ctgattacgt   3840
gcagctttcc cttcaggcgg gattcataca gcggccagcc atccgtcatc catatcacca   3900
cgtcaaaggg tgacagcagg ctcataagac gccccagcgt cgccatagtg cgttcaccga   3960
atacgtgcgc aacaaccgtc ttccggagac tgtcatacgc gtaaaacagc cagcgctggc   4020
gcgatttagc cccgacatag ccccactgtt cgtccatttc cgcgcagacg atgacgtcac   4080
tgcccggctg tatgcgcgag gttaccgact gcggcctgag ttttttaagt gacgtaaaat   4140
cgtgttgagg ccaacgccca taatgcgggc tgttgcccgg catccaacgc cattcatggc   4200
catatcaatg attttctggt gcgtaccggg ttgagaagcg gtgtaagtga actgcagttg   4260
ccatgtttta cggcagtgag agcagagata gcgctgatgt ccggcggtgc ttttgccgtt   4320
acgcaccacc ccgtcagtag ctgaacagga gggacagctg atagacacag aagccactgg   4380
agcacctcaa aaaccatcc atacactaaa tcagtaagtt ggcagcatca cccataattg   4440
tggtttcaaa atcggctccg tcgatactat gttatacgcc aactttgaaa caactttga   4500
aaaagctgtt ttctggtatt taaggtttta gaatgcaagg aacagtgaat tggagttcgt   4560
cttgttataa ttagcttctt ggggtatctt taaatactgt agaaagagg aaggaaataa   4620
taaatggcta aaatgagaat atcaccggaa ttgaaaaaac tgatcgaaaa ataccgctgc   4680
gtaaaagata cggaaggaat gtctcctgct aaggtatata agctggtggg agaaaatgaa   4740
aacctatatt taaaaatgac ggacagccgg tataaaggga ccacctatga tgtggaacgg   4800
gaaaaggaca tgatgctatg gctggaagga agctgcctg ttccaaaggt cctgcacttt   4860
gaacggcatg atggctggag caatctgctc atgagtgagg ccgatggcgt cctttgctcg   4920
gaagagtatg aagatgaaca aagccctgaa aagattatcg agctgtatgc ggagtgcatc   4980
aggctctttc actccatcga catatcggat tgtccctata cgaatagctt agacagccgc   5040
ttagccgaat tggattactt actgaataac gatctggccg atgtggattg cgaaaactgg   5100
gaagaagaca ctccatttaa agatccgcgc gagctgtatg atttttaaa gacggaaaag   5160
cccgaagagg aacttgtctt ttcccacggc gacctgggag acagcaacat ctttgtgaaa   5220
gatggcaaag taagtggctt tattgatctt gggagaagcg gcagggcgga caagtggtat   5280
gacattgcct tctgcgtccg gtcgatcagg gaggatatcg gggaagaaca gtatgtcgag   5340
ctattttttg acttactggg gatcaagcct gattgggaga aaataaaata ttatatttta   5400
ctggatgaat gtttttagta cctagatgtg gcgcaacgat gccggcgaca agcaggagcg   5460
caccgacttc ttccgcatca agtgttttgg ctctcaggcc gaggcccacg gcaagtattt   5520
gggcaagggg tcgctggtat tcgtgcaggg caagattcgg aataccaagt acgagaagga   5580
cggccagacg gtctacggga ccgacttcat tgccgataag gtggattatc tggacaccaa   5640
ggcaccaggc gggtcaaatc aggaataagg gcacattgcc ccggcgtgag tcggggcaat   5700
cccgcaagga gggtgaatga atcggacgtt tgaccggaag gcatacaggc aagaactgat   5760
cgacgcgggg ttttccgccg aggatgccga accatcgca agccgcaccg tcatgcgtgc   5820
gccccgcgaa accttccagt ccgtcggctc gatggtccag caagctacgg ccaagatcga   5880
```

```
gcgcgacagc gtgcaactgg ctcccctgc cctgcccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa aacaggtcag    6060
cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg     6360 cgagccgatc accttcacgt tctacgagct tgccaggac ctgggctggt cgatcaatgg     6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc cacccgcgtg aagaagtggc gcgagcaggt    6780
cggcgaagcc tgcgaagagt tgcgaggcag cggcctggtg gaaacgcgcct gggtcaatga    6840 tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
cacgaggaga aaaagcccat ggaggcgttc gctgaacggt tgcgagatgc cgtggcattc    7200
ggcgcctaca tcgacggcga gatcattggg ctgtcggtct tcaaacagga ggacggcccc    7260
aaggacgctc acaaggcgca tctgtccggc gttttcgtgg agcccgaaca gcgaggccga    7320
ggggtcgccg gtatgctgct gcgggcgttg ccggcgggtt tattgctcgt gatgatcgtc    7380
cgacagattc caacgggaat ctggtggatg cgcatcttca tcctcggcgc acttaatatt    7440
tcgctattct ggagcttgtt gtttatttcg gtctaccgcc tgccgggcgg ggtcgcggcg    7500
acggtaggcg ctgtgcagcc gctgatggtc gtgttcatct ctgccgctct gctaggtagc    7560
ccgatacgat tgatgcgcgt cctggggggct atttgcggaa ctgcgggcgt ggcgctgttg    7620
gtgttgacac caaacgcagc gctagatcct gtcggcgtcg cagcgggcct ggcggggggcg    7680 gtttccatgg cgttcggaac cgtgctgacc cgcaagtggc aacctcccgt gcctctgctc    7740
acctttaccg cctggcaact ggcggccgga ggacttctgc tcgttccagt agctttagtg    7800
tttgatccgc caatcccgat gcctacagga accaatgttc tcggcctggc gtggctcggc    7860
ctgatcggag cgggtttaac ctacttcctt tggttccggg ggatctcgcg actcgaacct    7920
acagttgttt ccttactggg ctttctcagc cccagatctg gggtcgatca gccggggatg    7980
catcaggccg acagtcggaa cttcgggtcc ccgacctgta ccattcggtg agcaatggat    8040
aggggagtta atatcgtcaa cgttcacttc taaagaaata gcgccactca gcttcctcag    8100
cggctttatc cagcgatttc ctattatgtc ggcatagttc tcaagatcga cagcctgtca    8160
cggttaagcg agaaatgaat aagaaggctg ataattcgga tctctgcgag ggagatgata    8220
tttgatcaca ggcagcaacg ctctgtcatc gttacaatca acatgctacc ctccgcgaga    8280
```

```
tcatccgtgt tcaaacccg gcagcttagt tgccgttctt ccgaatagca tcggtaacat    8340
gagcaaagtc tgccgccta caacggctct cccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520
gacgttttta atgtactggg gtggtttttc ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatcccctt ataaatcaaa    8700 agaatagccc gagatagggt tgagtgttgt tccagtttgg aacaagagtc cactattaaa    8760
gaacgtggac tccaacgtca aagggcgaaa aaccgtctat cagggcgatg cccactacg    8820 tgaaccatca cccaaatcaa gttttttggg gtcgaggtgc cgtaaagcac taaatcggaa    8880
ccctaaaggg agccccgat ttagagcttg acggggaaag ccggcgaacg tggcgagaaa    8940
ggaagggaag aaagcgaaag gagcgggcgc cattcaggct gcgcaactgt tgggaagggc    9000
gatcggtgcg ggcctcttcg ctattacgcc agctggcgaa aggggatgt gctgcaaggc    9060 gattaagttg ggtaacgcca gggttttccc agtcacgacg ttgtaaaacg acggccagtg    9120
aattaattcc catcttgaaa gaaatatagt ttaaatattt attgataaaa taacaagtca    9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataattgat gatatagcta gcttagctca tcggggatc cgtcgaagct    9360 agcttgggtc ccgctcagaa gaactcgtca agaaggcgat agaaggcgat gcgctgcgaa    9420
tcgggagcgg cgataccgta aagcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
agttcggctg cgcgagccc ctgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga ctttctcg    9840 gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata gccgcgctgc ctcgtcctgc agttcattca gggcaccgga caggtcggtc    10020
ttgacaaaaa gaaccgggcg cccctgcgct gacagccgga acacggcggc atcagagcag    10080
ccgattgtct gttgtgccca gtcatagccg aatagcctct ccacccaagc ggccggagaa    10140
cctgcgtgca atccatcttg ttcaatccaa gctcccatgg gccctcgact agagtcgaga    10200 tctgattga gagtgaatat gagactctaa ttggataccg aggggaattt atggaacgtc    10260
agtggagcat ttttgacaag aaatatttgc tagctgatag tgaccttagg cgacttttga    10320
acgcgcaata atggtttctg acgtatgtgc ttagctcatt aaactccaga aaccccgcggc    10380 tgagtggctc cttcaacgtt gcggttctgt cagttccaaa cgtaaaacgg cttgtcccgc    10440
gtcatcggcg ggggtcataa cgtgactccc ttaattctcc gctcatgatc ttgatcccct    10500
gcgccatcag atccttggcg gcaagaaagc catccagttt actttgcagg gcttcccaac    10560
cttaccagag ggcgccccag ctggcaattc cggttcgctt gctgtccata aaaccgccca    10620
gtctagctat cgccatgtaa gcccactgca agctacctgc tttctctttg cgcttgcgtt    10680
```

```
                                          -continued ttcccttgtc cagatagccc agtagctgac attcatccgg ggtcagcacc gtttctgcgg    10740
actggctttc tacgtgttcc gcttcctttta gcagcccttg cgccctgagt gcttgcggca    10800
gcgtgaagct tgcatgcctg caggtcgacg gcgcgccgag ctcctcgagc aaatttacac    10860
attgccacta aacgtctaaa cccttgtaat ttgttttttgt tttactatgt gtgttatgta    10920
tttgatttgc gataaatttt tatatttggt actaaattta taacacccttt tatgctaacg    10980 tttgccaaca cttagcaatt tgcaagttga ttaattgatt ctaaattatt tttgtcttct    11040
aaatacatat actaatcaac tggaaatgta aatatttgct aatatttcta ctataggaga    11100
attaaagtga gtgaatatgg taccacaagg tttggagatt taattgttgc aatgctgcat    11160
ggatggcata tacaccaaac attcaataat tcttgaggat aataatggta ccacacaaga    11220
tttgaggtgc atgaacgtca cgtggacaaa aggtttagta attttttcaag acaacaatgt    11280 taccacacac aagttttgag gtgcatgcat ggatgccctg tggaaagttt aaaaatatttt    11340 tggaaatgat ttgcatggaa gccatgtgta aaaccatgac atccacttgg aggatgcaat    11400
aatgaagaaa actacaaatt tacatgcaac tagttatgca tgtagtctat ataatgagga    11460
ttttgcaata ctttcattca tacacactca ctaagttttta cacgattata atttcttcat    11520
agccagccca ccgcggtgga aa atg gag gtc gtg gag aga ttc tac ggt gag    11572
                       Met Glu Val Val Glu Arg Phe Tyr Gly Glu
                        1               5                   10 ttg gat ggg aag gtc tcg cag ggc gtg aat gca ttg ctg ggt agt ttt       11620
Leu Asp Gly Lys Val Ser Gln Gly Val Asn Ala Leu Leu Gly Ser Phe
                15                  20                  25 ggg gtg gag ttg acg gat acg ccc act acc aaa ggc ttg ccc ctc gtt       11668
Gly Val Glu Leu Thr Asp Thr Pro Thr Thr Lys Gly Leu Pro Leu Val
            30                  35                  40 gac agt ccc aca ccc atc gtc ctc ggt gtt tct gta tac ttg act att       11716
Asp Ser Pro Thr Pro Ile Val Leu Gly Val Ser Val Tyr Leu Thr Ile
        45                  50                  55 gtc att gga ggg ctt ttg tgg ata aag gcc agg gat ctg aaa ccg cgc       11764
Val Ile Gly Gly Leu Leu Trp Ile Lys Ala Arg Asp Leu Lys Pro Arg
    60                  65                  70 gcc tcg gag cca ttt ttg ctc caa gct ttg gtg ctt gtg cac aac ctg       11812
Ala Ser Glu Pro Phe Leu Leu Gln Ala Leu Val Leu Val His Asn Leu
75                  80                  85                  90 ttc tgt ttt gcg ctc agt ctg tat atg tgc gtg ggc atc gct tat cag       11860
Phe Cys Phe Ala Leu Ser Leu Tyr Met Cys Val Gly Ile Ala Tyr Gln
                95                  100                 105 gct att acc tgg cgg tac tct ctc tgg ggc aat gca tac aat cct aaa       11908
Ala Ile Thr Trp Arg Tyr Ser Leu Trp Gly Asn Ala Tyr Asn Pro Lys
            110                 115                 120 cat aaa gag atg gcg att ctg gta tac ttg ttc tac atg tct aag tac       11956
His Lys Glu Met Ala Ile Leu Val Tyr Leu Phe Tyr Met Ser Lys Tyr
        125                 130                 135 gtg gaa ttc atg gat acc gtt atc atg ata ctg aag cgc agc acc agg       12004
Val Glu Phe Met Asp Thr Val Ile Met Ile Leu Lys Arg Ser Thr Arg
    140                 145                 150 caa ata agc ttc ctc cac gtt tat cat cat tct tca att tcc ctc att       12052
Gln Ile Ser Phe Leu His Val Tyr His His Ser Ser Ile Ser Leu Ile
155                 160                 165                 170 tgg tgg gct att gct cat cac gct cct ggc ggt gaa gca tat tgg tct       12100
Trp Trp Ala Ile Ala His His Ala Pro Gly Gly Glu Ala Tyr Trp Ser
                175                 180                 185 gcg gct ctg aac tca gga gtg cat gtt ctc atg tat gcg tat tac ttc       12148
Ala Ala Leu Asn Ser Gly Val His Val Leu Met Tyr Ala Tyr Tyr Phe
            190                 195                 200
```

```
ttg gct gcc tgc ctt cga agt agc cca aag tta aaa aat aag tac ctt    12196
Leu Ala Ala Cys Leu Arg Ser Ser Pro Lys Leu Lys Asn Lys Tyr Leu
        205                 210                 215 ttt tgg ggc agg tac ttg aca caa ttc caa atg ttc cag ttt atg ctg    12244
Phe Trp Gly Arg Tyr Leu Thr Gln Phe Gln Met Phe Gln Phe Met Leu
220                 225                 230 aac tta gtg cag gct tac tac gac atg aaa acg aat gcg cca tat cca    12292
Asn Leu Val Gln Ala Tyr Tyr Asp Met Lys Thr Asn Ala Pro Tyr Pro
235                 240                 245                 250 caa tgg ctg atc aag att ttg ttc tac tac atg atc tcg ttg ctg ttt    12340
Gln Trp Leu Ile Lys Ile Leu Phe Tyr Tyr Met Ile Ser Leu Leu Phe
            255                 260                 265 ctt ttc ggc aat ttt tac gta caa aaa tac atc aaa ccc tct gac gga    12388
Leu Phe Gly Asn Phe Tyr Val Gln Lys Tyr Ile Lys Pro Ser Asp Gly
            270                 275                 280 aag caa aag gga gct aaa act gag tga tctagaaggc ctcctgcttt          12435
Lys Gln Lys Gly Ala Lys Thr Glu
            285                 290 aatgagatat gcgagacgcc tatgatcgca tgatatttgc tttcaattct gttgtgcacg  12495
ttgtaaaaaa cctgagcatg tgtagctcag atccttaccg ccggtttcgg ttcattctaa  12555
tgaatatatc acccgttact atcgtatttt tatgaataat attctccgtt caatttactg  12615
attgtccgtc gagcaaattt acacattgcc actaaacgtc taaacccttg taatttgttt  12675 ttgtttttact atgtgtgtta tgtatttgat ttgcgataaa ttttatatt tggtactaaa  12735 tttataacac cttttatgct aacgtttgcc aacacttagc aatttgcaag ttgattaatt  12795
gattctaaat tattttgtc ttctaaatac atatactaat caactggaaa tgtaaatatt   12855
tgctaatatt tctactatag gagaattaaa gtgagtgaat atggtaccac aaggtttgga  12915
gatttaattg ttgcaatgct gcatggatgg catatacacc aaacattcaa taattcttga  12975
ggataataat ggtaccacac aagatttgag gtgcatgaac gtcacgtgga caaaaggttt  13035
agtaattttt caagacaaca atgttaccac acacaagttt tgaggtgcat gcatggatgc  13095
cctgtggaaa gtttaaaaat attttggaaa tgatttgcat ggaagccatg tgtaaaacca  13155
tgacatccac ttggaggatg caataatgaa gaaaactaca aatttacatg caactagtta  13215
tgcatgtagt ctatataatg aggattttgc aatactttca ttcatacaca ctcactaagt  13275
tttacacgat tataatttct tcatagccag cggatcc atg gta ttc gcg ggc ggt   13330
                                       Met Val Phe Ala Gly Gly
                                                       295 gga ctt cag cag ggc tct ctc gaa gaa aac atc gac gtc gag cac att    13378
Gly Leu Gln Gln Gly Ser Leu Glu Glu Asn Ile Asp Val Glu His Ile
            300                 305                 310 gcc agt atg tct ctc ttc agc gac ttc ttc agt tat gtg tct tca act    13426
Ala Ser Met Ser Leu Phe Ser Asp Phe Phe Ser Tyr Val Ser Ser Thr
            315                 320                 325 gtt ggt tcg tgg agc gta cac agt ata caa cct ttg aag cgc ctg acg    13474
Val Gly Ser Trp Ser Val His Ser Ile Gln Pro Leu Lys Arg Leu Thr
            330                 335                 340 agt aag aag cgt gtt tcg gaa agc gct gcc gtg caa tgt ata tca gct    13522
Ser Lys Lys Arg Val Ser Glu Ser Ala Ala Val Gln Cys Ile Ser Ala
345                 350                 355                 360 gaa gtt cag aga aat tcg agt acc cag gga act gcg gag gca ctc gca    13570
Glu Val Gln Arg Asn Ser Ser Thr Gln Gly Thr Ala Glu Ala Leu Ala
                365                 370                 375 gaa tca gtc gtg aag ccc acg aga cga agg tca tct cag tgg aag aag    13618
Glu Ser Val Val Lys Pro Thr Arg Arg Arg Ser Ser Gln Trp Lys Lys
            380                 385                 390
```

```
tcg aca cac ccc cta tca gaa gta gca gta cac aac aag cca agc gat    13666
Ser Thr His Pro Leu Ser Glu Val Ala Val His Asn Lys Pro Ser Asp
        395                 400                 405 tgc tgg att gtt gta aaa aac aag gtg tat gat gtt tcc aat ttt gcg    13714
Cys Trp Ile Val Val Lys Asn Lys Val Tyr Asp Val Ser Asn Phe Ala
    410                 415                 420 gac gag cat ccc gga gga tca gtt att agt act tat ttt gga cga gac    13762
Asp Glu His Pro Gly Gly Ser Val Ile Ser Thr Tyr Phe Gly Arg Asp
425                 430                 435                 440 ggc aca gat gtt ttc tct agt ttt cat gca gct tct aca tgg aaa att    13810
Gly Thr Asp Val Phe Ser Ser Phe His Ala Ala Ser Thr Trp Lys Ile
                445                 450                 455 ctt caa gac ttt tac att ggt gac gtg gag agg gtg gag ccg act cca    13858
Leu Gln Asp Phe Tyr Ile Gly Asp Val Glu Arg Val Glu Pro Thr Pro
            460                 465                 470 gag ctg ctg aaa gat ttc cga gaa atg aga gct ctt ttc ctg agg gag    13906
Glu Leu Leu Lys Asp Phe Arg Glu Met Arg Ala Leu Phe Leu Arg Glu
        475                 480                 485 caa ctt ttc aaa agt tcg aaa ttg tac tat gtt atg aag ctg ctc acg    13954
Gln Leu Phe Lys Ser Ser Lys Leu Tyr Tyr Val Met Lys Leu Leu Thr
    490                 495                 500 aat gtt gct att ttt gct gcg agc att gca ata ata tgt tgg agc aag    14002
Asn Val Ala Ile Phe Ala Ala Ser Ile Ala Ile Ile Cys Trp Ser Lys
505                 510                 515                 520 act att tca gcg gtt ttg gct tca gct tgt atg atg gct ctg tgt ttc    14050
Thr Ile Ser Ala Val Leu Ala Ser Ala Cys Met Met Ala Leu Cys Phe
                525                 530                 535 caa cag tgc gga tgg cta tcc cat gat ttt ctc cac aat cag gtg ttt    14098
Gln Gln Cys Gly Trp Leu Ser His Asp Phe Leu His Asn Gln Val Phe
            540                 545                 550 gag aca cgc tgg ctt aat gaa gtt gtc ggg tat gtg atc ggc aac gcc    14146
Glu Thr Arg Trp Leu Asn Glu Val Val Gly Tyr Val Ile Gly Asn Ala
        555                 560                 565 gtt ctg ggg ttt agt aca ggg tgg tgg aag gag aag cat aac ctt cat    14194
Val Leu Gly Phe Ser Thr Gly Trp Trp Lys Glu Lys His Asn Leu His
    570                 575                 580 cat gct gct cca aat gaa tgc gat cag act tac caa cca att gat gaa    14242
His Ala Ala Pro Asn Glu Cys Asp Gln Thr Tyr Gln Pro Ile Asp Glu
585                 590                 595                 600 gat att gat act ctc ccc ctc att gcc tgg agc aag gac ata ctg gcc    14290
Asp Ile Asp Thr Leu Pro Leu Ile Ala Trp Ser Lys Asp Ile Leu Ala
                605                 610                 615 aca gtt gag aat aag aca ttc ttg cga atc ctc caa tac cag cat ctg    14338
Thr Val Glu Asn Lys Thr Phe Leu Arg Ile Leu Gln Tyr Gln His Leu
            620                 625                 630 ttc ttc atg ggt ctg tta ttt ttc gcc cgt ggt agt tgg ctc ttt tgg    14386
Phe Phe Met Gly Leu Leu Phe Phe Ala Arg Gly Ser Trp Leu Phe Trp
        635                 640                 645 agc tgg aga tat acc tct aca gca gtg ctc tca cct gtc gac agg ttg    14434
Ser Trp Arg Tyr Thr Ser Thr Ala Val Leu Ser Pro Val Asp Arg Leu
    650                 655                 660 ttg gag aag gga act gtt ctg ttt cac tac ttt tgg ttc gtc ggg aca    14482
Leu Glu Lys Gly Thr Val Leu Phe His Tyr Phe Trp Phe Val Gly Thr
665                 670                 675                 680 gcg tgc tat ctt ctc cct ggt tgg aag cca tta gta tgg atg gcg gtg    14530
Ala Cys Tyr Leu Leu Pro Gly Trp Lys Pro Leu Val Trp Met Ala Val
                685                 690                 695 act gag ctc atg tcc ggc atg ctg ctg ggc ttt gta ttt gta ctt agc    14578
Thr Glu Leu Met Ser Gly Met Leu Leu Gly Phe Val Phe Val Leu Ser
            700                 705                 710
```

| | | | | | | | | | | | | | | | | |
|---|---|---|---|---|---|---|---|---|---|---|---|---|---|---|---|---|
| cac | aat | ggg | atg | gag | gtt | tat | aat | tcg | tct | aaa | gaa | ttc | gtg | agt | gca | 14626 |
| His | Asn | Gly | Met | Glu | Val | Tyr | Asn | Ser | Ser | Lys | Glu | Phe | Val | Ser | Ala | |
| | | | 715 | | | | 720 | | | | | 725 | | | | |
| cag | atc | gta | tcc | aca | cgg | gat | atc | aaa | gga | aac | ata | ttc | aac | gac | tgg | 14674 |
| Gln | Ile | Val | Ser | Thr | Arg | Asp | Ile | Lys | Gly | Asn | Ile | Phe | Asn | Asp | Trp | |
| | 730 | | | | | 735 | | | | | 740 | | | | | |
| ttc | act | ggt | ggc | ctt | aac | agg | caa | ata | gag | cat | cat | ctt | ttc | cca | aca | 14722 |
| Phe | Thr | Gly | Gly | Leu | Asn | Arg | Gln | Ile | Glu | His | His | Leu | Phe | Pro | Thr | |
| 745 | | | | | 750 | | | | | 755 | | | | | 760 | |
| atg | ccc | agg | cat | aat | tta | aac | aaa | ata | gca | cct | aga | gtg | gag | gtg | ttc | 14770 |
| Met | Pro | Arg | His | Asn | Leu | Asn | Lys | Ile | Ala | Pro | Arg | Val | Glu | Val | Phe | |
| | | | 765 | | | | | 770 | | | | | 775 | | | |
| tgt | aag | aaa | cac | ggt | ctg | gtg | tac | gaa | gac | gta | tct | att | gct | acc | ggc | 14818 |
| Cys | Lys | Lys | His | Gly | Leu | Val | Tyr | Glu | Asp | Val | Ser | Ile | Ala | Thr | Gly | |
| | | 780 | | | | | 785 | | | | | 790 | | | | |
| act | tgc | aag | gtt | ttg | aaa | gca | ttg | aag | gaa | gtc | gcg | gag | gct | gcg | gca | 14866 |
| Thr | Cys | Lys | Val | Leu | Lys | Ala | Leu | Lys | Glu | Val | Ala | Glu | Ala | Ala | Ala | |
| | 795 | | | | | 800 | | | | | 805 | | | | | |
| gag | cag | cat | gct | acc | acc | agt | taa | gctagcgtta | acctgctttt | aatgagatat | | | | | | 14920 |
| Glu | Gln | His | Ala | Thr | Thr | Ser | | | | | | | | | | |
| 810 | | | | | 815 | | | | | | | | | | | |

```
gcgagacgcc tatgatcgca tgatatttgc tttcaattct gttgtgcacg ttgtaaaaaa      14980
cctgagcatg tgtagctcag atccttaccg ccggtttcgg ttcattctaa tgaatatatc      15040
acccgttact atcgtatttt tatgaataat attctccgtt caatttactg attgtccgtc      15100
gacgaattcg agctcggcgc gcctctagag gatcgatgaa ttcagatcgg ctgagtggct      15160
ccttcaacgt tgcggttctg tcagttccaa acgtaaaacg gcttgtcccg cgtcatcggc      15220
gggggtcata acgtgactcc cttaattctc cgctcatgat cagattgtcg tttcccgcct      15280
tcagtttaaa ctatcagtgt ttgacaggat atattggcgg gtaaacctaa agaaaaagag      15340
cgtttattag aataatcgga tatttaaaag ggcgtgaaaa ggtttatcct tcgtccattt      15400
gtatgtgcat gccaaccaca gggttcccca                                        15430
```

```
<210> SEQ ID NO 26
<211> LENGTH: 290
<212> TYPE: PRT
<213> ORGANISM: Unknown
<220> FEATURE:
<223> OTHER INFORMATION: Physcomitrella patens elongase

<400> SEQUENCE: 26
```

| | | | | | | | | | | | | | | |
|---|---|---|---|---|---|---|---|---|---|---|---|---|---|---|
| Met | Glu | Val | Val | Glu | Arg | Phe | Tyr | Gly | Glu | Leu | Asp | Gly | Lys | Val | Ser |
| 1 | | | | 5 | | | | | 10 | | | | | 15 | |
| Gln | Gly | Val | Asn | Ala | Leu | Leu | Gly | Ser | Phe | Gly | Val | Glu | Leu | Thr | Asp |
| | | | 20 | | | | | 25 | | | | | 30 | | |
| Thr | Pro | Thr | Thr | Lys | Gly | Leu | Pro | Leu | Val | Asp | Ser | Pro | Thr | Pro | Ile |
| | | 35 | | | | | 40 | | | | | 45 | | | |
| Val | Leu | Gly | Val | Ser | Val | Tyr | Leu | Thr | Ile | Val | Ile | Gly | Gly | Leu | Leu |
| | 50 | | | | | 55 | | | | | 60 | | | | |
| Trp | Ile | Lys | Ala | Arg | Asp | Leu | Lys | Pro | Arg | Ala | Ser | Glu | Pro | Phe | Leu |
| 65 | | | | | 70 | | | | | 75 | | | | | 80 |
| Leu | Gln | Ala | Leu | Val | Leu | Val | His | Asn | Leu | Phe | Cys | Phe | Ala | Leu | Ser |
| | | | | 85 | | | | | 90 | | | | | 95 | |
| Leu | Tyr | Met | Cys | Val | Gly | Ile | Ala | Tyr | Gln | Ala | Ile | Thr | Trp | Arg | Tyr |
| | | | 100 | | | | | 105 | | | | | 110 | | |
| Ser | Leu | Trp | Gly | Asn | Ala | Tyr | Asn | Pro | Lys | His | Lys | Glu | Met | Ala | Ile |
| | | 115 | | | | | 120 | | | | | 125 | | | |

```
Leu Val Tyr Leu Phe Tyr Met Ser Lys Tyr Val Glu Phe Met Asp Thr
            130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 27
<211> LENGTH: 525
<212> TYPE: PRT
<213> ORGANISM: Unknown
<220> FEATURE:
<223> OTHER INFORMATION: Physcomitrella patens desaturases

<400> SEQUENCE: 27

Met Val Phe Ala Gly Gly Leu Gln Gln Gly Ser Leu Glu Glu Asn
1               5                   10                  15

Ile Asp Val Glu His Ile Ala Ser Met Ser Leu Phe Ser Asp Phe Phe
                20                  25                  30

Ser Tyr Val Ser Ser Thr Val Gly Ser Trp Ser Val His Ser Ile Gln
            35                  40                  45

Pro Leu Lys Arg Leu Thr Ser Lys Lys Arg Val Ser Glu Ser Ala Ala
    50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
            100                 105                 110

His Asn Lys Pro Ser Asp Cys Trp Ile Val Lys Asn Lys Val Tyr
    115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
```

```
                195                 200                 205
Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
                260                 265                 270

Tyr Val Ile Gly Asn Ala Val Leu Gly Phe Ser Thr Gly Trp Trp Lys
            275                 280                 285

Glu Lys His Asn Leu His His Ala Ala Pro Asn Glu Cys Asp Gln Thr
    290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
                340                 345                 350

Gly Ser Trp Leu Phe Trp Ser Trp Arg Tyr Thr Ser Thr Ala Val Leu
            355                 360                 365

Ser Pro Val Asp Arg Leu Leu Glu Lys Gly Thr Val Leu Phe His Tyr
    370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
                420                 425                 430

Lys Glu Phe Val Ser Ala Gln Ile Val Ser Thr Arg Asp Ile Lys Gly
            435                 440                 445

Asn Ile Phe Asn Asp Trp Phe Thr Gly Gly Leu Asn Arg Gln Ile Glu
    450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
                500                 505                 510

Val Ala Glu Ala Ala Ala Glu Gln His Ala Thr Thr Ser
            515                 520                 525

<210> SEQ ID NO 28
<211> LENGTH: 17752
<212> TYPE: DNA
<213> ORGANISM: Unknown
<220> FEATURE:
<223> OTHER INFORMATION: Plant expression vector with 3 promoter-
      terminator expression cassettes with Physcomitrella elongase +
      desaturase + Phaeodactylum desaturase inserted
<220> FEATURE:
<221> NAME/KEY: CDS
<222> LOCATION: (11543)..(12415)
<220> FEATURE:
<221> NAME/KEY: CDS
<222> LOCATION: (13313)..(14890)
<220> FEATURE:
<221> NAME/KEY: CDS
<222> LOCATION: (15791)..(17200)
```

<400> SEQUENCE: 28

```
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240
atgttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt gggggttcag cagccggcgc     480
tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg cgatggcgcg cgcatccatg     660
ccggcacgcg accgggcgca ccgcagatgg aaacggccga cgcgcagctt cgcttcctct     720
gcgaggcggg ttttcggcc ggggacgccg tcaatgcgct gatgacaatc agctacttca     780
ctgttggggc cgtgcttgag gagcaggccg gcgacagcga tgccggcgag gcgggcggca     840
ccgttgaaca ggctccgctc tcgccgctgt tgcgggccgc gatagacgcc ttcgacgaag     900
ccggtccgga cgcagcgttc gagcagggac tcgcggtgat tgtcgatgga ttggcgaaaa     960
ggaggctcgt tgtcaggaac gttgaaggac cgagaaaggg tgacgattga tcaggaccgc    1020
tgccggagcg caacccactc actacagcag agccatgtag acaacatccc ctcccccttt    1080
ccaccgcgtc agacgcccgt agcagcccgc tacgggcttt tcatgcccct gcctagcgt     1140
ccaagcctca cggccgcgct cggcctctct ggcggccttc tggcgctctt ccgcttcctc    1200
gctcactgac tcgctgcgct cggtcgttcg gctgcggcga gcggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttt    1560
ccgctgcata accctgcttc gggtcatta tagcgatttt ttcggtatat ccatcctttt    1620
tcgcacgata tacaggattt tgccaaaggg ttcgtgtaga cttccttgg tgtatccaac    1680
ggcgtcagcc gggcaggata ggtgaagtag gcccacccgc gagcgggtgt tccttcttca    1740
ctgtcccta ttcgcacctg gcggtgctca acgggaatcc tgctctgcga ggctggccgg    1800
ctaccgccgg cgtaacagat gagggcaagc ggatggctga tgaaaccaag ccaaccagga    1860
agggcagccc acctatcaag gtgtactgcc ttccagacga acgaagagcg attgaggaaa    1920
aggcggcggc ggccggcatg agcctgtcgg cctacctgct ggcgtcggc cagggctaca    1980
aaatcacggg cgtcgtggac tatgagcacg tccgcgagct ggcccgcatc aatgcgacc    2040
tgggccgcct gggcggcctg ctgaaactct ggctcaccga cgaccgcgc acggcgcggt    2100
tcggtgatgc cacgatcctc gccctgctgg cgaagatcga agagaagcag gacgagcttg    2160
gcaaggtcat gatgggcgtg gtccgcccga gggcagagcc atgactttt tagccgctaa    2220
aacgccgggg ggtgcgcgt gattgccaag cacgtcccca tgcgctccat caagaagagc    2280
gacttcgcgg agctggtgaa gtacatcacc gacgagcaag gcaagaccga gcgcctttgc    2340
```

```
gacgctcacc gggctggttg ccctcgccgc tgggctggcg gccgtctatg gccctgcaaa    2400
cgcgccagaa acgccgtcga agccgtgtgc gagacaccgc ggccgccggc gttgtggata    2460
cctcgcggaa aacttggccc tcactgacag atgaggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca agcctgggga taagtgccct gcggtattga cacttgaggg gcgcgactac    2700
tgacagatga ggggcgcgat ccttgacact tgaggggcag agtgctgaca gatgaggggc    2760
gcacctattg acatttgagg ggctgtccac aggcagaaaa tccagcattt gcaagggttt    2820
ccgcccgttt ttcggccacc gctaacctgt cttttaacct gcttttaaac caatatttat    2880
aaaccttgtt tttaaccagg gctgcgccct gtgcgcgtga ccgcgcacgc cgaagggggg    2940
tgccccccct tctcgaaccc tcccggcccg ctaacgcggg cctccatcc ccccagggc    3000 tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttttacc ttgggcattc ttggcatagt ggtcgcgggt gccgtgctcg    3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggaggcagat tgccttgaat atattgacaa    3480
tactgataag ataatatatc ttttatatag aagatatcgc cgtatgtaag gatttcaggg    3540
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatccacca   3900 cgtcaaaggg tgacagcagg ctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag ttttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260 ccatgttttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa acaactttga    4500
aaaagctgtt ttctggtatt taaggtttta gaatgcaagg aacagtgaat tggagttcgt    4560
cttgttataa ttagcttctt ggggtatctt taaatactgt agaaaagagg aaggaaataa    4620 taaatgcta aaatgagaat atcaccggaa ttgaaaaaac tgatcgaaaa ataccgctgc     4680
gtaaaagata cggaaggaat gtctcctgct aaggtatata agctggtggg agaaaatgaa    4740
```

```
aacctatatt taaaaatgac ggacagccgg tataaaggga ccaccatgca tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg attttttaaa gacgaaaaag    5160
cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctattttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca agtgttttgg ctctcaggcc gaggcccacg gcaagtattt    5520
gggcaagggg tcgctggtat tcgtgcaggg caagattcgg aataccaagt acgagaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
gcgcgacagc gtgcaactgg ctcccccctgc cctgccgcg ccatcggccg ccgtggagcg    5940
ttcgcgtcgt ctcgaacagg aggcggcagg tttggcgaag tcgatgacca tcgacacgcg    6000
aggaactatg acgaccaaga agcgaaaaac cgccggcgag gacctggcaa acaggtcag    6060 cgaggccaag caggccgcgt tgctgaaaca cacgaagcag cagatcaagg aaatgcagct    6120
ttccttgttc gatattgcgc cgtggccgga cacgatgcga gcgatgccaa acgacacggc    6180
ccgctctgcc ctgttcacca cgcgcaacaa gaaaatcccg cgcgaggcgc tgcaaaacaa    6240
ggtcattttc cacgtcaaca aggacgtgaa gatcacctac accggcgtcg agctgcgggc    6300
cgacgatgac gaactggtgt ggcagcaggt gttggagtac gcgaagcgca ccctatcgg    6360 cgagccgatc accttcacgt tctacgagct ttgccaggac ctgggctggt cgatcaatgg    6420
ccggtattac acgaaggccg aggaatgcct gtcgcgccta caggcgacgg cgatgggctt    6480
cacgtccgac cgcgttgggc acctggaatc ggtgtcgctg ctgcaccgct tccgcgtcct    6540
ggaccgtggc aagaaaacgt cccgttgcca ggtcctgatc gacgaggaaa tcgtcgtgct    6600
gtttgctggc gaccactaca cgaaattcat atgggagaag taccgcaagc tgtcgccgac    6660
ggcccgacgg atgttcgact atttcagctc gcaccgggag ccgtacccgc tcaagctgga    6720
aaccttccgc ctcatgtgcg gatcggattc caccgcgtg aagaagtggc gcgagcaggt    6780
cggcgaagcc tgcgaagagt tgcgaggcag cggcctggtg aacacgcct gggtcaatga    6840 tgacctggtg cattgcaaac gctagggcct tgtggggtca gttccggctg ggggttcagc    6900
agccagcgct ttactggcat ttcaggaaca agcgggcact gctcgacgca cttgcttcgc    6960
tcagtatcgc tcgggacgca cggcgcgctc tacgaactgc cgataaacag aggattaaaa    7020
ttgacaattg tgattaaggc tcagattcga cggcttggag cggccgacgt gcaggatttc    7080
cgcgagatcc gattgtcggc cctgaagaaa gctccagaga tgttcgggtc cgtttacgag    7140
```

```
cacgaggaga aaaagcccat ggaggcgttc gctgaacggt tgcgagatgc cgtggcattc   7200
ggcgcctaca tcgacggcga gatcattggg ctgtcggtct tcaaacagga ggacggcccc   7260
aaggacgctc acaaggcgca tctgtccggc gttttcgtgg agcccgaaca gcgaggccga   7320
ggggtcgccg gtatgctgct gcgggcgttg ccggcgggtt tattgctcgt gatgatcgtc   7380
cgacagattc caacgggaat ctggtggatg cgcatcttca tcctcggcgc acttaatatt   7440
tcgctattct ggagcttgtt gtttatttcg gtctaccgcc tgccgggcgg ggtcgcggcg   7500
acggtaggcg ctgtgcagcc gctgatggtc gtgttcatct ctgccgctct gctaggtagc   7560
ccgatacgat tgatggcggt cctgggggct atttgcggaa ctgcgggcgt ggcgctgttg   7620
gtgttgacac caaacgcagc gctagatcct gtcggcgtcg cagcgggcct ggcggggggcg   7680 gtttccatgg cgttcggaac cgtgctgacc cgcaagtggc aacctcccgt gcctctgctc   7740
acctttaccg cctggcaact ggcggccgga ggacttctgc tcgttccagt agctttagtg   7800
tttgatccgc caatcccgat gcctacagga accaatgttc tcggcctggc gtggctcggc   7860
ctgatcggag cgggtttaac ctacttcctt tggttccggg ggatctcgcg actcgaacct   7920
acagttgttt ccttactggg cttttctcagc cccagatctg gggtcgatca gccggggatg   7980
catcaggccg acagtcggaa cttcgggtcc ccgacctgta ccattcggtg agcaatggat   8040
aggggagttg atatcgtcaa cgttcacttc taaagaaata gcgccactca gcttcctcag   8100
cggctttatc cagcgatttc ctattatgtc ggcatagttc tcaagatcga cagcctgtca   8160
cggttaagcg agaaatgaat aagaaggctg ataattcgga tctctgcgag ggagatgata   8220
tttgatcaca ggcagcaacg ctctgtcatc gttacaatca acatgctacc ctccgcgaga   8280
tcatccgtgt ttcaaacccg gcagcttagt tgccgttctt ccgaatagca tcggtaacat   8340
gagcaaagtc tgccgcctta caacggctct cccgctgacg ccgtcccgga ctgatgggct   8400
gcctgtatcg agtggtgatt tgtgccgag ctgccggtcg gggagctgtt ggctggctgg   8460
tggcaggata tattgtggtg taaacaaatt gacgcttaga caacttaata acacattgcg   8520
gacgttttta atgtactggg gtggttttttc ttttcaccag tgagacgggc aacagctgat   8580
tgcccttcac cgcctggccc tgagagagtt gcagcaagcg gtccacgctg gtttgcccca   8640
gcaggcgaaa atcctgtttg atggtggttc cgaaatcggc aaaatcccctt ataaatcaaa   8700 agaatagccc gagataggggt tgagtgttgt tccagtttgg aacaagagtc cactattaaa   8760
gaacgtggac tccaacgtca aagggcgaaa aacgtctat cagggcgatg cccactacg   8820 tgaaccatca cccaaatcaa gttttttggg gtcgaggtgc cgtaaagcac taaatcggaa   8880
ccctaaaggg agccccccgat ttagagcttg acggggaaag ccggcgaacg tggcgagaaa   8940
ggaagggaag aaagcgaaag gagcgggcgc cattcaggct gcgcaactgt tgggaagggc   9000
gatcggtgcg ggcctcttcg ctattacgcc agctggcgaa aggggggatgt gctgcaaggc   9060 gattaagttg ggtaacgcca gggttttccc agtcacgacg ttgtaaaacg acggccagtg   9120
aattaattcc catcttgaaa gaaatatagt ttaaatattt attgataaaa taacaagtca   9180
ggtattatag tccaagcaaa aacataaatt tattgatgca agtttaaatt cagaaatatt   9240
tcaataactg attatatcag ctggtacatt gccgtagatg aaagactgag tgcgatatta   9300
tgtgtaatac ataaattgat gatatagcta gcttagctca tcgggggatc cgtcgaagct   9360
agcttgggtc ccgctcagaa gaactcgtca agaaggcgat agaaggcgat gcgctgcgaa   9420
tcgggagcgc cgataccgta aagcacgagg aagcggtcag cccattcgcc gccaagctct   9480
tcagcaatat cacgggtagc caacgctatg tcctgatagc ggtccgccac acccagccgg   9540
```

```
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
agttcggctg gcgcgagccc ctgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga tactttctcg    9840
gcaggagcaa ggtgagatga caggagatcc tgccccggca cttcgcccaa tagcagccag    9900
tcccttcccg cttcagtgac aacgtcgagc acagctgcgc aaggaacgcc cgtcgtggcc    9960
agccacgata gccgcgctgc ctcgtcctgc agttcattca gggcaccgga caggtcggtc   10020
ttgacaaaaa gaaccgggcg cccctgcgct gacagccgga acacggcggc atcagagcag   10080
ccgattgtct gttgtgccca gtcatagccg aatagcctct ccacccaagc ggccggagaa   10140
cctgcgtgca atccatcttg ttcaatccaa gctcccatgg gccctcgact agagtcgaga   10200
tctggattga gagtgaatat gagactctaa ttggataccg aggggaattt atggaacgtc   10260
agtggagcat ttttgacaag aaatatttgc tagctgatag tgaccttagg cgacttttga   10320
acgcgcaata atggtttctg acgtatgtgc ttagctcatt aaactccaga aacccgcggc   10380
tgagtggctc cttcaacgtt gcggttctgt cagttccaaa cgtaaaacgg cttgtcccgc   10440
gtcatcggcg ggggtcataa cgtgactccc ttaattctcc gctcatgatc ttgatcccct   10500
gcgccatcag atccttggcg gcaagaaagc catccagttt actttgcagg gcttcccaac   10560
cttaccagag ggcgcccag ctggcaattc cggttcgctt gctgtccata aaccgccca   10620
gtctagctat cgccatgtaa gcccactgca agctacctgc tttctctttg cgcttgcgtt   10680
ttcccttgtc cagatagccc agtagctgac attcatccgg ggtcagcacc gtttctgcgg   10740
actggctttc tacgtgttcc gcttccttta gcagcccttg cgccctgagt gcttgcggca   10800
gcgtgaagct tgcatgcctg caggtcgacg gcgcgccgag ctcctcgagc aaatttacac   10860
attgccacta aacgtctaaa cccttgtaat ttgttttttgt tttactatgt gtgttatgta   10920
tttgatttgc gataaatttt tatatttggt actaaattta taacacccttt tatgctaacg   10980
tttgccaaca cttagcaatt tgcaagttga ttaattgatt ctaaattatt tttgtcttct   11040
aaatacatat actaatcaac tggaaatgta aatatttgct aatatttcta ctataggaga   11100
attaaagtga gtgaatatgg taccacaagg tttggagatt taattgttgc aatgctgcat   11160
ggatggcata taccaaaac attcaataat tcttgaggat aataatggta ccacacaaga   11220
tttgaggtgc atgaacgtca cgtggacaaa aggtttagta attttttcaag acaacaatgt   11280
taccacacac aagttttgag gtgcatgcat ggatgccctg tggaaagttt aaaaatattt   11340
tggaaatgat ttgcatggaa gccatgtgta aaaccatgac atccacttgg aggatgcaat   11400
aatgaagaaa actacaaatt tacatgcaac tagttatgca tgtagtctat ataatgagga   11460
ttttgcaata ctttcattca tacacactca ctaagttta cacgattata atttcttcat   11520
agccagccca ccgcggtgga aa atg gag gtc gtg gag aga ttc tac ggt gag   11572
                        Met Glu Val Val Glu Arg Phe Tyr Gly Glu
                         1               5                  10
ttg gat ggg aag gtc tcg cag ggc gtg aat gca ttg ctg ggt agt ttt   11620
Leu Asp Gly Lys Val Ser Gln Gly Val Asn Ala Leu Leu Gly Ser Phe
             15                  20                  25
ggg gtg gag ttg acg gat acg ccc act acc aaa ggc ttg ccc ctc gtt   11668
Gly Val Glu Leu Thr Asp Thr Pro Thr Thr Lys Gly Leu Pro Leu Val
         30                  35                  40
gac agt ccc aca ccc atc gtc ctc ggt gtt tct gta tac ttg act att   11716
```

```
Asp Ser Pro Thr Pro Ile Val Leu Gly Val Ser Val Tyr Leu Thr Ile
         45                  50                  55 gtc att gga ggg ctt ttg tgg ata aag gcc agg gat ctg aaa ccg cgc    11764
Val Ile Gly Gly Leu Leu Trp Ile Lys Ala Arg Asp Leu Lys Pro Arg
 60                  65                  70 gcc tcg gag cca ttt ttg ctc caa gct ttg gtg ctt gtg cac aac ctg    11812
Ala Ser Glu Pro Phe Leu Leu Gln Ala Leu Val Leu Val His Asn Leu
 75                  80                  85                  90 ttc tgt ttt gcg ctc agt ctg tat atg tgc gtg ggc atc gct tat cag    11860
Phe Cys Phe Ala Leu Ser Leu Tyr Met Cys Val Gly Ile Ala Tyr Gln
                 95                 100                 105 gct att acc tgg cgg tac tct ctc tgg ggc aat gca tac aat cct aaa    11908
Ala Ile Thr Trp Arg Tyr Ser Leu Trp Gly Asn Ala Tyr Asn Pro Lys
        110                 115                 120 cat aaa gag atg gcg att ctg gta tac ttg ttc tac atg tct aag tac    11956
His Lys Glu Met Ala Ile Leu Val Tyr Leu Phe Tyr Met Ser Lys Tyr
        125                 130                 135 gtg gaa ttc atg gat acc gtt atc atg ata ctg aag cgc agc acc agg    12004
Val Glu Phe Met Asp Thr Val Ile Met Ile Leu Lys Arg Ser Thr Arg
140                 145                 150 caa ata agc ttc ctc cac gtt tat cat cat tct tca att tcc ctc att    12052
Gln Ile Ser Phe Leu His Val Tyr His His Ser Ser Ile Ser Leu Ile
155                 160                 165                 170 tgg tgg gct att gct cat cac gct cct ggc ggt gaa gca tat tgg tct    12100
Trp Trp Ala Ile Ala His His Ala Pro Gly Gly Glu Ala Tyr Trp Ser
                175                 180                 185 gcg gct ctg aac tca gga gtg cat gtt ctc atg tat gcg tat tac ttc    12148
Ala Ala Leu Asn Ser Gly Val His Val Leu Met Tyr Ala Tyr Tyr Phe
                190                 195                 200 ttg gct gcc tgc ctt cga agt agc cca aag tta aaa aat aag tac ctt    12196
Leu Ala Ala Cys Leu Arg Ser Ser Pro Lys Leu Lys Asn Lys Tyr Leu
        205                 210                 215 ttt tgg ggc agg tac ttg aca caa ttc caa atg ttc cag ttt atg ctg    12244
Phe Trp Gly Arg Tyr Leu Thr Gln Phe Gln Met Phe Gln Phe Met Leu
        220                 225                 230 aac tta gtg cag gct tac tac gac atg aaa acg aat gcg cca tat cca    12292
Asn Leu Val Gln Ala Tyr Tyr Asp Met Lys Thr Asn Ala Pro Tyr Pro
235                 240                 245                 250 caa tgg ctg atc aag att ttg ttc tac tac atg atc tcg ttg ctg ttt    12340
Gln Trp Leu Ile Lys Ile Leu Phe Tyr Tyr Met Ile Ser Leu Leu Phe
                255                 260                 265 ctt ttc ggc aat ttt tac gta caa aaa tac atc aaa ccc tct gac gga    12388
Leu Phe Gly Asn Phe Tyr Val Gln Lys Tyr Ile Lys Pro Ser Asp Gly
                270                 275                 280 aag caa aag gga gct aaa act gag tga tctagaaggc ctcctgcttt          12435
Lys Gln Lys Gly Ala Lys Thr Glu
        285                 290 aatgagatat gcgagacgcc tatgatcgca tgatatttgc tttcaattct gttgtgcacg  12495
ttgtaaaaaa cctgagcatg tgtagctcag atccttaccg ccggtttcgg ttcattctaa  12555
tgaatatatc acccgttact atcgtatttt tatgaataat attctccgtt caatttactg  12615
attgtccgtc gagcaaattt acacattgcc actaaacgtc taaaccctg taatttgttt   12675 ttgttttact atgtgtgtta tgtatttgat ttgcgataaa ttttatatt tggtactaaa   12735 tttataacac cttttatgct aacgtttgcc aacacttagc aatttgcaag ttgattaatt  12795
gattctaaat tattttttgtc ttctaaatac atatactaat caactggaaa tgtaaatatt 12855 tgctaatatt tctactatag gagaattaaa gtgagtgaat atggtaccac aaggtttgga  12915
gatttaattg ttgcaatgct gcatggatgg catatacacc aaacattcaa taattcttga  12975
```

```
                                                       -continued ggataataat ggtaccacac aagatttgag gtgcatgaac gtcacgtgga caaaaggttt   13035
agtaattttt caagacaaca atgttaccac acacaagttt tgaggtgcat gcatggatgc   13095
cctgtggaaa gtttaaaaat attttggaaa tgatttgcat ggaagccatg tgtaaaacca   13155
tgacatccac ttggaggatg caataatgaa gaaaactaca aatttacatg caactagtta   13215
tgcatgtagt ctatataatg aggattttgc aatactttca ttcatacaca ctcactaagt   13275
tttacacgat tataatttct tcatagccag cggatcc atg gta ttc gcg ggc ggt   13330
                                          Met Val Phe Ala Gly Gly
                                                          295 gga ctt cag cag ggc tct ctc gaa gaa aac atc gac gtc gag cac att   13378
Gly Leu Gln Gln Gly Ser Leu Glu Glu Asn Ile Asp Val Glu His Ile
        300                 305                 310 gcc agt atg tct ctc ttc agc gac ttc ttc agt tat gtg tct tca act   13426
Ala Ser Met Ser Leu Phe Ser Asp Phe Phe Ser Tyr Val Ser Ser Thr
            315                 320                 325 gtt ggt tcg tgg agc gta cac agt ata caa cct ttg aag cgc ctg acg   13474
Val Gly Ser Trp Ser Val His Ser Ile Gln Pro Leu Lys Arg Leu Thr
        330                 335                 340 agt aag aag cgt gtt tcg gaa agc gct gcc gtg caa tgt ata tca gct   13522
Ser Lys Lys Arg Val Ser Glu Ser Ala Ala Val Gln Cys Ile Ser Ala
345                 350                 355                 360 gaa gtt cag aga aat tcg agt acc cag gga act gcg gag gca ctc gca   13570
Glu Val Gln Arg Asn Ser Ser Thr Gln Gly Thr Ala Glu Ala Leu Ala
                365                 370                 375 gaa tca gtc gtg aag ccc acg aga cga agg tca tct cag tgg aag aag   13618
Glu Ser Val Val Lys Pro Thr Arg Arg Arg Ser Ser Gln Trp Lys Lys
            380                 385                 390 tcg aca cac ccc cta tca gaa gta gca gta cac aac aag cca agc gat   13666
Ser Thr His Pro Leu Ser Glu Val Ala Val His Asn Lys Pro Ser Asp
        395                 400                 405 tgc tgg att gtt gta aaa aac aag gtg tat gat gtt tcc aat ttt gcg   13714
Cys Trp Ile Val Val Lys Asn Lys Val Tyr Asp Val Ser Asn Phe Ala
    410                 415                 420 gac gag cat ccc gga gga tca gtt att agt act tat ttt gga cga gac   13762
Asp Glu His Pro Gly Gly Ser Val Ile Ser Thr Tyr Phe Gly Arg Asp
425                 430                 435                 440 ggc aca gat gtt ttc tct agt ttt cat gca gct tct aca tgg aaa att   13810
Gly Thr Asp Val Phe Ser Ser Phe His Ala Ala Ser Thr Trp Lys Ile
                445                 450                 455 ctt caa gac ttt tac att ggt gac gtg gag agg gtg gag ccg act cca   13858
Leu Gln Asp Phe Tyr Ile Gly Asp Val Glu Arg Val Glu Pro Thr Pro
            460                 465                 470 gag ctg ctg aaa gat ttc cga gaa atg aga gct ctt ttc ctg agg gag   13906
Glu Leu Leu Lys Asp Phe Arg Glu Met Arg Ala Leu Phe Leu Arg Glu
        475                 480                 485 caa ctt ttc aaa agt tcg aaa ttg tac tat gtt atg aag ctc ctc acg   13954
Gln Leu Phe Lys Ser Ser Lys Leu Tyr Tyr Val Met Lys Leu Leu Thr
    490                 495                 500 aat gtt gct att ttt gct gcg agc att gca ata ata tgt tgg agc aag   14002
Asn Val Ala Ile Phe Ala Ala Ser Ile Ala Ile Ile Cys Trp Ser Lys
505                 510                 515                 520 act att tca gcg gtt ttg gct tca gct tgt atg atg gct ctg tgt ttc   14050
Thr Ile Ser Ala Val Leu Ala Ser Ala Cys Met Met Ala Leu Cys Phe
                525                 530                 535 caa cag tgc gga tgg cta tcc cat gat ttt ctc cac aat cag gtg ttt   14098
Gln Gln Cys Gly Trp Leu Ser His Asp Phe Leu His Asn Gln Val Phe
            540                 545                 550 gag aca cgc tgg ctt aat gaa gtt gtc ggg tat gtg atc ggc aac gcc   14146
```

```
                                                          -continued

Glu Thr Arg Trp Leu Asn Glu Val Val Gly Tyr Val Ile Gly Asn Ala
            555                 560                 565 gtt ctg ggg ttt agt aca ggg tgg tgg aag gag aag cat aac ctt cat        14194
Val Leu Gly Phe Ser Thr Gly Trp Trp Lys Glu Lys His Asn Leu His
570                 575                 580 cat gct gct cca aat gaa tgc gat cag act tac caa cca att gat gaa        14242
His Ala Ala Pro Asn Glu Cys Asp Gln Thr Tyr Gln Pro Ile Asp Glu
585                 590                 595                 600 gat att gat act ctc ccc ctc att gcc tgg agc aag gac ata ctg gcc        14290
Asp Ile Asp Thr Leu Pro Leu Ile Ala Trp Ser Lys Asp Ile Leu Ala
                605                 610                 615 aca gtt gag aat aag aca ttc ttg cga atc ctc caa tac cag cat ctg        14338
Thr Val Glu Asn Lys Thr Phe Leu Arg Ile Leu Gln Tyr Gln His Leu
            620                 625                 630 ttc ttc atg ggt ctg tta ttt ttc gcc cgt ggt agt tgg ctc ttt tgg        14386
Phe Phe Met Gly Leu Leu Phe Phe Ala Arg Gly Ser Trp Leu Phe Trp
        635                 640                 645 agc tgg aga tat acc tct aca gca gtg ctc tca cct gtc gac agg ttg        14434
Ser Trp Arg Tyr Thr Ser Thr Ala Val Leu Ser Pro Val Asp Arg Leu
    650                 655                 660 ttg gag aag gga act gtt ctg ttt cac tac ttt tgg ttc gtc ggg aca        14482
Leu Glu Lys Gly Thr Val Leu Phe His Tyr Phe Trp Phe Val Gly Thr
665                 670                 675                 680 gcg tgc tat ctt ctc cct ggt tgg aag cca tta gta tgg atg gcg gtg        14530
Ala Cys Tyr Leu Leu Pro Gly Trp Lys Pro Leu Val Trp Met Ala Val
                685                 690                 695 act gag ctc atg tcc ggc atg ctg ctg ggc ttt gta ttt gta ctt agc        14578
Thr Glu Leu Met Ser Gly Met Leu Leu Gly Phe Val Phe Val Leu Ser
            700                 705                 710 cac aat ggg atg gag gtt tat aat tcg tct aaa gaa ttc gtg agt gca        14626
His Asn Gly Met Glu Val Tyr Asn Ser Ser Lys Glu Phe Val Ser Ala
        715                 720                 725 cag atc gta tcc aca cgg gat atc aaa gga aac ata ttc aac gac tgg        14674
Gln Ile Val Ser Thr Arg Asp Ile Lys Gly Asn Ile Phe Asn Asp Trp
    730                 735                 740 ttc act ggt ggc ctt aac agg caa ata gag cat cat ctt ttc cca aca        14722
Phe Thr Gly Gly Leu Asn Arg Gln Ile Glu His His Leu Phe Pro Thr
745                 750                 755                 760 atg ccc agg cat aat tta aac aaa ata gca cct aga gtg gag gtg ttc        14770
Met Pro Arg His Asn Leu Asn Lys Ile Ala Pro Arg Val Glu Val Phe
                765                 770                 775 tgt aag aaa cac ggt ctg gtg tac gaa gac gta tct att gct acc ggc        14818
Cys Lys Lys His Gly Leu Val Tyr Glu Asp Val Ser Ile Ala Thr Gly
            780                 785                 790 act tgc aag gtt ttg aaa gca ttg aag gaa gtc gcg gag gct gcg gca        14866
Thr Cys Lys Val Leu Lys Ala Leu Lys Glu Val Ala Glu Ala Ala Ala
        795                 800                 805 gag cag cat gct acc acc agt taa gctagcgtta accctgcttt aatgagatat       14920
Glu Gln His Ala Thr Thr Ser
    810                 815 gcgagacgcc tatgatcgca tgatatttgc tttcaattct gttgtgcacg ttgtaaaaaa      14980
cctgagcatg tgtagctcag atccttaccg ccggtttcgg ttcattctaa tgaatatatc      15040
acccgttact atcgtatttt tatgaataat attctccgtt caatttactg attgtccgtc      15100
gagcaaattt acacattgcc actaaacgtc taaacccttg taatttgttt ttgttttact      15160
atgtgtgtta tgtatttgat ttgcgataaa ttttatatt tggtactaaa tttataacac       15220
cttttatgct aacgtttgcc aacacttagc aatttgcaag ttgattaatt gattctaaat      15280 tattttttgtc ttctaaatac atatactaat caactggaaa tgtaaatatt tgctaatatt    15340
```

```
tctactatag gagaattaaa gtgagtgaat atggtaccac aaggtttgga gatttaattg     15400
ttgcaatgct gcatggatgg catatacacc aaacattcaa taattcttga ggataataat     15460
ggtaccacac aagatttgag gtgcatgaac gtcacgtgga caaaaggttt agtaattttt     15520
caagacaaca atgttaccac acacaagttt tgaggtgcat gcatggatgc cctgtggaaa     15580
gtttaaaaat atttttggaaa tgatttgcat ggaagccatg tgtaaaacca tgacatccac     15640
ttggaggatg caataatgaa gaaaactaca aatttacatg caactagtta tgcatgtagt     15700
ctatataatg aggattttgc aatactttca ttcatacaca ctcactaagt tttacacgat     15760
tataatttct tcatagccag cagatctaaa atg gct ccg gat gcg gat aag ctt     15814
                                 Met Ala Pro Asp Ala Asp Lys Leu
                                                820
```

```
cga caa cgc cag acg act gcg gta gcg aag cac aat gct gct acc ata     15862
Arg Gln Arg Gln Thr Thr Ala Val Ala Lys His Asn Ala Ala Thr Ile
    825             830             835 tcg acg cag gaa cgc ctt tgc agt ctg tct tcg ctc aaa ggc gaa gaa     15910
Ser Thr Gln Glu Arg Leu Cys Ser Leu Ser Ser Leu Lys Gly Glu Glu
840             845             850             855 gtc tgc atc gac gga atc atc tat gac ctc caa tca ttc gat cat ccc     15958
Val Cys Ile Asp Gly Ile Ile Tyr Asp Leu Gln Ser Phe Asp His Pro
                860             865             870 ggg ggt gaa acg atc aaa atg ttt ggt ggc aac gat gtc act gta cag     16006
Gly Gly Glu Thr Ile Lys Met Phe Gly Gly Asn Asp Val Thr Val Gln
    875             880             885 tac aag atg att cac ccg tac cat acc gag aag cat ttg gaa aag atg     16054
Tyr Lys Met Ile His Pro Tyr His Thr Glu Lys His Leu Glu Lys Met
        890             895             900 aag cgt gtc ggc aag gtg acg gat ttc gtc tgc gag tac aag ttc gat     16102
Lys Arg Val Gly Lys Val Thr Asp Phe Val Cys Glu Tyr Lys Phe Asp
905             910             915 acc gaa ttt gaa cgc gaa atc aaa cga gaa gtc ttc aag att gtg cga     16150
Thr Glu Phe Glu Arg Glu Ile Lys Arg Glu Val Phe Lys Ile Val Arg
920             925             930             935 cga ggc aag gat ttc ggt act ttg gga tgg ttc ttc cgt gcg ttt tgc     16198
Arg Gly Lys Asp Phe Gly Thr Leu Gly Trp Phe Phe Arg Ala Phe Cys
                940             945             950 tac att gcc att ttc ttc tac ctg cag tac cat tgg gtc acc acg gga     16246
Tyr Ile Ala Ile Phe Phe Tyr Leu Gln Tyr His Trp Val Thr Thr Gly
    955             960             965 acc tct tgg ctg ctg gcc gtg gcc tac gga atc tcc caa gcg atg att     16294
Thr Ser Trp Leu Leu Ala Val Ala Tyr Gly Ile Ser Gln Ala Met Ile
        970             975             980 ggc atg aat gtc cag cac gat gcc aac cac ggg gcc acc tcc aag cgt     16342
Gly Met Asn Val Gln His Asp Ala Asn His Gly Ala Thr Ser Lys Arg
985             990             995 ccc tgg gtc aac gac atg cta ggc ctc ggt gcg gat ttt att ggt     16387
Pro Trp Val Asn Asp Met Leu Gly Leu Gly Ala Asp Phe Ile Gly
1000             1005             1010 ggt tcc aag tgg ctc tgg cag gaa caa cac tgg acc cac cac gct     16432
Gly Ser Lys Trp Leu Trp Gln Glu Gln His Trp Thr His His Ala
1015             1020             1025 tac acc aat cac gcc gag atg gat ccc gat agc ttt ggt gcc gaa     16477
Tyr Thr Asn His Ala Glu Met Asp Pro Asp Ser Phe Gly Ala Glu
1030             1035             1040 cca atg ctc cta ttc aac gac tat ccc ttg gat cat ccc gct cgt     16522
Pro Met Leu Leu Phe Asn Asp Tyr Pro Leu Asp His Pro Ala Arg
1045             1050             1055 acc tgg cta cat cgc ttt caa gca ttc ttt tac atg ccc gtc ttg     16567
```

|     |     |     |     |     |     |     |     |     |     |     |     |       |
|-----|-----|-----|-----|-----|-----|-----|-----|-----|-----|-----|-----|-------|
| Thr | Trp | Leu | His | Arg | Phe | Gln | Ala | Phe | Phe | Tyr | Met | Pro Val Leu |
| 1060 |    |     |     |     | 1065 |    |     |     | 1070 |    |     |       |

| gct | gga | tac | tgg | ttg | tcc | gct | gtc | ttc | aat | cca | caa | att ctt gac | 16612 |
|-----|-----|-----|-----|-----|-----|-----|-----|-----|-----|-----|-----|-------------|-------|
| Ala | Gly | Tyr | Trp | Leu | Ser | Ala | Val | Phe | Asn | Pro | Gln | Ile Leu Asp |       |
| 1075 |    |     |     |     | 1080 |    |     |     | 1085 |    |     |             |       |

| ctc | cag | caa | cgc | ggc | gca | ctt | tcc | gtc | ggt | atc | cgt | ctc gac aac | 16657 |
|-----|-----|-----|-----|-----|-----|-----|-----|-----|-----|-----|-----|-------------|-------|
| Leu | Gln | Gln | Arg | Gly | Ala | Leu | Ser | Val | Gly | Ile | Arg | Leu Asp Asn |       |
| 1090 |    |     |     |     | 1095 |    |     |     | 1100 |    |     |             |       |

| gct | ttc | att | cac | tcg | cga | cgc | aag | tat | gcg | gtt | ttc | tgg cgg gct | 16702 |
|-----|-----|-----|-----|-----|-----|-----|-----|-----|-----|-----|-----|-------------|-------|
| Ala | Phe | Ile | His | Ser | Arg | Arg | Lys | Tyr | Ala | Val | Phe | Trp Arg Ala |       |
| 1105 |    |     |     |     | 1110 |    |     |     | 1115 |    |     |             |       |

| gtg | tac | att | gcg | gtg | aac | gtg | att | gct | ccg | ttt | tac | aca aac tcc | 16747 |
|-----|-----|-----|-----|-----|-----|-----|-----|-----|-----|-----|-----|-------------|-------|
| Val | Tyr | Ile | Ala | Val | Asn | Val | Ile | Ala | Pro | Phe | Tyr | Thr Asn Ser |       |
| 1120 |    |     |     |     | 1125 |    |     |     | 1130 |    |     |             |       |

| ggc | ctc | gaa | tgg | tcc | tgg | cgt | gtc | ttt | gga | aac | atc | atg ctc atg | 16792 |
|-----|-----|-----|-----|-----|-----|-----|-----|-----|-----|-----|-----|-------------|-------|
| Gly | Leu | Glu | Trp | Ser | Trp | Arg | Val | Phe | Gly | Asn | Ile | Met Leu Met |       |
| 1135 |    |     |     |     | 1140 |    |     |     | 1145 |    |     |             |       |

| ggt | gtg | gcg | gaa | tcg | ctc | gcg | ctg | gcg | gtc | ctg | ttt | tcg ttg tcg | 16837 |
|-----|-----|-----|-----|-----|-----|-----|-----|-----|-----|-----|-----|-------------|-------|
| Gly | Val | Ala | Glu | Ser | Leu | Ala | Leu | Ala | Val | Leu | Phe | Ser Leu Ser |       |
| 1150 |    |     |     |     | 1155 |    |     |     | 1160 |    |     |             |       |

| cac | aat | ttc | gaa | tcc | gcg | gat | cgc | gat | ccg | acc | gcc | cca ctg aaa | 16882 |
|-----|-----|-----|-----|-----|-----|-----|-----|-----|-----|-----|-----|-------------|-------|
| His | Asn | Phe | Glu | Ser | Ala | Asp | Arg | Asp | Pro | Thr | Ala | Pro Leu Lys |       |
| 1165 |    |     |     |     | 1170 |    |     |     | 1175 |    |     |             |       |

| aag | acg | gga | gaa | cca | gtc | gac | tgg | ttc | aag | aca | cag | gtc gaa act | 16927 |
|-----|-----|-----|-----|-----|-----|-----|-----|-----|-----|-----|-----|-------------|-------|
| Lys | Thr | Gly | Glu | Pro | Val | Asp | Trp | Phe | Lys | Thr | Gln | Val Glu Thr |       |
| 1180 |    |     |     |     | 1185 |    |     |     | 1190 |    |     |             |       |

| tcc | tgc | act | tac | ggt | gga | ttc | ctt | tcc | ggt | tgc | ttc | acg gga ggt | 16972 |
|-----|-----|-----|-----|-----|-----|-----|-----|-----|-----|-----|-----|-------------|-------|
| Ser | Cys | Thr | Tyr | Gly | Gly | Phe | Leu | Ser | Gly | Cys | Phe | Thr Gly Gly |       |
| 1195 |    |     |     |     | 1200 |    |     |     | 1205 |    |     |             |       |

| ctc | aac | ttt | cag | gtt | gaa | cac | cac | ttg | ttc | cca | cgc | atg agc agc | 17017 |
|-----|-----|-----|-----|-----|-----|-----|-----|-----|-----|-----|-----|-------------|-------|
| Leu | Asn | Phe | Gln | Val | Glu | His | His | Leu | Phe | Pro | Arg | Met Ser Ser |       |
| 1210 |    |     |     |     | 1215 |    |     |     | 1220 |    |     |             |       |

| gct | tgg | tat | ccc | tac | att | gcc | ccc | aag | gtc | cgc | gaa | att tgc gcc | 17062 |
|-----|-----|-----|-----|-----|-----|-----|-----|-----|-----|-----|-----|-------------|-------|
| Ala | Trp | Tyr | Pro | Tyr | Ile | Ala | Pro | Lys | Val | Arg | Glu | Ile Cys Ala |       |
| 1225 |    |     |     |     | 1230 |    |     |     | 1235 |    |     |             |       |

| aaa | cac | ggc | gtc | cac | tac | gcc | tac | tac | ccg | tgg | atc | cac caa aac | 17107 |
|-----|-----|-----|-----|-----|-----|-----|-----|-----|-----|-----|-----|-------------|-------|
| Lys | His | Gly | Val | His | Tyr | Ala | Tyr | Tyr | Pro | Trp | Ile | His Gln Asn |       |
| 1240 |    |     |     |     | 1245 |    |     |     | 1250 |    |     |             |       |

| ttt | ctc | tcc | acc | gtc | cgc | tac | atg | cac | gcg | gcc | ggg | acc ggt gcc | 17152 |
|-----|-----|-----|-----|-----|-----|-----|-----|-----|-----|-----|-----|-------------|-------|
| Phe | Leu | Ser | Thr | Val | Arg | Tyr | Met | His | Ala | Ala | Gly | Thr Gly Ala |       |
| 1255 |    |     |     |     | 1260 |    |     |     | 1265 |    |     |             |       |

| aac | tgg | cgc | cag | atg | gcc | aga | gaa | aat | ccc | ttg | acc | gga cgg gcg | 17197 |
|-----|-----|-----|-----|-----|-----|-----|-----|-----|-----|-----|-----|-------------|-------|
| Asn | Trp | Arg | Gln | Met | Ala | Arg | Glu | Asn | Pro | Leu | Thr | Gly Arg Ala |       |
| 1270 |    |     |     |     | 1275 |    |     |     | 1280 |    |     |             |       |

| taa agatctgccg gcatcgatcc cgggccatgg cctgctttaa tgagatatgc | 17250 |
|-----------------------------------------------------------|-------|
| gagacgccta tgatcgcatg atatttgctt tcaattctgt tgtgcacgtt gtaaaaaacc | 17310 |
| tgagcatgtg tagctcagat ccttaccgcc ggtttcggtt cattctaatg aatatatcac | 17370 |
| ccgttactat cgtattttta tgaataatat tctccgttca atttactgat tgtccgtcga | 17430 |
| cgagctcggc gcgcctctag aggatcgatg aattcagatc ggctgagtgg ctccttcaac | 17490 |
| gttgcggttc tgtcagttcc aaacgtaaaa cggcttgtcc cgcgtcatcg gcggggtca | 17550 |
| taacgtgact cccttaattc tccgctcatg atcagattgt cgtttccgc cttcagttta | 17610 |
| aactatcagt gtttgacagg atatattggc gggtaaacct aagagaaaag agcgtttatt | 17670 |
| agaataatcg atatttaaa agggcgtgaa aaggtttatc cttcgtccat tgtatgtgc | 17730 |
| atgccaacca cagggttccc ca | 17752 |

<210> SEQ ID NO 29
<211> LENGTH: 290
<212> TYPE: PRT
<213> ORGANISM: Unknown
<220> FEATURE:
<223> OTHER INFORMATION: Physcomitrella elongase

<400> SEQUENCE: 29

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 30
<211> LENGTH: 525
<212> TYPE: PRT
<213> ORGANISM: Unknown
<220> FEATURE:
<223> OTHER INFORMATION: Physcomitrella desaturase

<400> SEQUENCE: 30

Met Val Phe Ala Gly Gly Gly Leu Gln Gln Gly Ser Leu Glu Glu Asn
1               5                   10                  15

Ile Asp Val Glu His Ile Ala Ser Met Ser Leu Phe Ser Asp Phe Phe

```
                20                  25                  30
Ser Tyr Val Ser Ser Thr Val Gly Ser Trp Ser Val His Ser Ile Gln
                35                  40                  45
Pro Leu Lys Arg Leu Thr Ser Lys Lys Arg Val Ser Glu Ser Ala Ala
                50                  55                  60
Val Gln Cys Ile Ser Ala Glu Val Gln Arg Asn Ser Ser Thr Gln Gly
                65                  70                  75                  80
Thr Ala Glu Ala Leu Ala Glu Ser Val Val Lys Pro Thr Arg Arg Arg
                                85                  90                  95
Ser Ser Gln Trp Lys Lys Ser Thr His Pro Leu Ser Glu Val Ala Val
                    100                 105                 110
His Asn Lys Pro Ser Asp Cys Trp Ile Val Lys Asn Lys Val Tyr
                    115                 120                 125
Asp Val Ser Asn Phe Ala Asp Glu His Pro Gly Gly Ser Val Ile Ser
                    130                 135                 140
Thr Tyr Phe Gly Arg Asp Gly Thr Asp Val Phe Ser Ser Phe His Ala
    145                 150                 155                 160
Ala Ser Thr Trp Lys Ile Leu Gln Asp Phe Tyr Ile Gly Asp Val Glu
                    165                 170                 175
Arg Val Glu Pro Thr Pro Glu Leu Leu Lys Asp Phe Arg Glu Met Arg
                    180                 185                 190
Ala Leu Phe Leu Arg Glu Gln Leu Phe Lys Ser Lys Leu Tyr Tyr
                    195                 200                 205
Val Met Lys Leu Leu Thr Asn Val Ala Ile Phe Ala Ala Ser Ile Ala
                    210                 215                 220
Ile Ile Cys Trp Ser Lys Thr Ile Ser Ala Val Leu Ala Ser Ala Cys
    225                 230                 235                 240
Met Met Ala Leu Cys Phe Gln Cys Gly Trp Leu Ser His Asp Phe
                    245                 250                 255
Leu His Asn Gln Val Phe Glu Thr Arg Trp Leu Asn Glu Val Val Gly
                    260                 265                 270
Tyr Val Ile Gly Asn Ala Val Leu Gly Phe Ser Thr Gly Trp Trp Lys
                    275                 280                 285
Glu Lys His Asn Leu His His Ala Ala Pro Asn Glu Cys Asp Gln Thr
                    290                 295                 300
Tyr Gln Pro Ile Asp Glu Asp Ile Asp Thr Leu Pro Leu Ile Ala Trp
    305                 310                 315                 320
Ser Lys Asp Ile Leu Ala Thr Val Glu Asn Lys Thr Phe Leu Arg Ile
                    325                 330                 335
Leu Gln Tyr Gln His Leu Phe Phe Met Gly Leu Leu Phe Phe Ala Arg
                    340                 345                 350
Gly Ser Trp Leu Phe Trp Ser Trp Arg Tyr Thr Ser Thr Ala Val Leu
                    355                 360                 365
Ser Pro Val Asp Arg Leu Leu Glu Lys Gly Thr Val Leu Phe His Tyr
                    370                 375                 380
Phe Trp Phe Val Gly Thr Ala Cys Tyr Leu Leu Pro Gly Trp Lys Pro
    385                 390                 395                 400
Leu Val Trp Met Ala Val Thr Glu Leu Met Ser Gly Met Leu Leu Gly
                    405                 410                 415
Phe Val Phe Val Leu Ser His Asn Gly Met Glu Val Tyr Asn Ser Ser
                    420                 425                 430
Lys Glu Phe Val Ser Ala Gln Ile Val Ser Thr Arg Asp Ile Lys Gly
                    435                 440                 445
```

```
Asn Ile Phe Asn Asp Trp Phe Thr Gly Gly Leu Asn Arg Gln Ile Glu
            450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Ala Glu Gln His Ala Thr Thr Ser
            515                 520                 525

<210> SEQ ID NO 31
<211> LENGTH: 469
<212> TYPE: PRT
<213> ORGANISM: Unknown
<220> FEATURE:
<223> OTHER INFORMATION: Phaeodactylum desaturase

<400> SEQUENCE: 31

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65              70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145             150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225             230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
```

```
                    290                 295                 300
Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
                340                 345                 350

Glu Ser Ala Asp Arg Asp Pro Thr Ala Pro Leu Lys Lys Thr Gly Glu
                355                 360                 365

Pro Val Asp Trp Phe Lys Thr Gln Val Glu Thr Ser Cys Thr Tyr Gly
370                 375                 380

Gly Phe Leu Ser Gly Cys Phe Thr Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
                420                 425                 430

Tyr Pro Trp Ile His Gln Asn Phe Leu Ser Thr Val Arg Tyr Met His
                435                 440                 445

Ala Ala Gly Thr Gly Ala Asn Trp Arg Gln Met Ala Arg Glu Asn Pro
                450                 455                 460

Leu Thr Gly Arg Ala
465

<210> SEQ ID NO 32
<211> LENGTH: 18
<212> TYPE: DNA
<213> ORGANISM: Artificial sequence
<220> FEATURE:
<223> OTHER INFORMATION: Sequencing primer

<400> SEQUENCE: 32
caggaaacag ctatgacc                                                 18

<210> SEQ ID NO 33
<211> LENGTH: 19
<212> TYPE: DNA
<213> ORGANISM: Artificial sequence
<220> FEATURE:
<223> OTHER INFORMATION: Sequencing primer

<400> SEQUENCE: 33
ctaaagggaa caaaagctg                                                19

<210> SEQ ID NO 34
<211> LENGTH: 18
<212> TYPE: DNA
<213> ORGANISM: Artificial sequence
<220> FEATURE:
<223> OTHER INFORMATION: Sequencing primer

<400> SEQUENCE: 34
tgtaaaacga cggccagt                                                 18

<210> SEQ ID NO 35
<211> LENGTH: 20
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
```

```
<222> LOCATION: (15)..(15)
<223> OTHER INFORMATION: n is inosine

<400> SEQUENCE: 35
tggtggaart ggaancayaa                                            20

<210> SEQ ID NO 36
<211> LENGTH: 20
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (15)..(15)
<223> OTHER INFORMATION: n is inosine

<400> SEQUENCE: 36
tggtggaart ggacncayaa                                            20

<210> SEQ ID NO 37
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (5)..(5)
<223> OTHER INFORMATION: Xaa is Asn or Thr
<220> FEATURE:
<221> NAME/KEY: MISC_FEATURE
<222> LOCATION: (7)..(7)
<223> OTHER INFORMATION: Xaa is Lys or Asn

<400> SEQUENCE: 37

Trp Trp Lys Trp Xaa His Xaa
1               5

<210> SEQ ID NO 38
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (7)..(7)
<223> OTHER INFORMATION: Xaa is Lys or Asn

<400> SEQUENCE: 38

Trp Trp Lys Trp Lys His Xaa
1               5

<210> SEQ ID NO 39
<211> LENGTH: 19
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (2)..(14)
<223> OTHER INFORMATION: n located at position 2, 11 and 14; each n is
      inosine

<400> SEQUENCE: 39
gntggaarga nmancayaa                                             19
```

```
<210> SEQ ID NO 40
<211> LENGTH: 19
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (2)..(14)
<223> OTHER INFORMATION: n located at position 2 and 14; each n is
      inosine

<400> SEQUENCE: 40
gntggaartt gmancayaa                                              19

<210> SEQ ID NO 41
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (1)..(1)
<223> OTHER INFORMATION: Xaa is Gly or Trp
<220> FEATURE:
<221> NAME/KEY: MISC_FEATURE
<222> LOCATION: (4)..(4)
<223> OTHER INFORMATION: Xaa is Glu or Asp
<220> FEATURE:
<221> NAME/KEY: MISC_FEATURE
<222> LOCATION: (5)..(5)
<223> OTHER INFORMATION: Xaa is Lys, Gln or Asn
<220> FEATURE:
<221> NAME/KEY: MISC_FEATURE
<222> LOCATION: (7)..(7)
<223> OTHER INFORMATION: Xaa is Lys or Asn

<400> SEQUENCE: 41

Xaa Trp Lys Xaa Xaa His Xaa
 1               5

<210> SEQ ID NO 42
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (1)..(1)
<223> OTHER INFORMATION: Xaa is Gly or Trp
<220> FEATURE:
<221> NAME/KEY: MISC_FEATURE
<222> LOCATION: (5)..(5)
<223> OTHER INFORMATION: Xaa is Lys, Gln or Asn
<220> FEATURE:
<221> NAME/KEY: MISC_FEATURE
<222> LOCATION: (7)..(7)
<223> OTHER INFORMATION: Xaa is Lys or Asn

<400> SEQUENCE: 42

Xaa Trp Lys Trp Xaa His Xaa
 1               5

<210> SEQ ID NO 43
<211> LENGTH: 17
<212> TYPE: DNA
<213> ORGANISM: Artificial sequence
<220> FEATURE:
<223> OTHER INFORMATION: Oligonucleotide sequence
```

```
<220> FEATURE:
<221> NAME/KEY: misc_feature
<222> LOCATION: (3)..(15)
<223> OTHER INFORMATION: n located at position 3, 9 and 15; each n is
      inosine

<400> SEQUENCE: 43
twnttgaanm armrnca                                                        17

<210> SEQ ID NO 44
<211> LENGTH: 17
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(15)
<223> OTHER INFORMATION: n located at position 3, 9 and 15; each n is
      inosine

<400> SEQUENCE: 44
twnttgaanm arcanca                                                        17

<210> SEQ ID NO 45
<211> LENGTH: 6
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (3)..(3)
<223> OTHER INFORMATION: Xaa is Lys or Asn
<220> FEATURE:
<221> NAME/KEY: MISC_FEATURE
<222> LOCATION: (4)..(4)
<223> OTHER INFORMATION: Xaa is His or Asn
<220> FEATURE:
<221> NAME/KEY: MISC_FEATURE
<222> LOCATION: (5)..(5)
<223> OTHER INFORMATION: Xaa is Arg or Gln

<400> SEQUENCE: 45

Trp Trp Xaa Xaa Xaa His
 1               5

<210> SEQ ID NO 46
<211> LENGTH: 6
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (3)..(3)
<223> OTHER INFORMATION: Xaa is Lys or Asn
<220> FEATURE:
<221> NAME/KEY: MISC_FEATURE
<222> LOCATION: (4)..(4)
<223> OTHER INFORMATION: Xaa is His or Asn
<220> FEATURE:
<221> NAME/KEY: MISC_FEATURE
<222> LOCATION: (5)..(5)
<223> OTHER INFORMATION: Xaa is Arg or Gln

<400> SEQUENCE: 46

Tyr Trp Xaa Xaa Xaa His
 1               5
```

```
<210> SEQ ID NO 47
<211> LENGTH: 17
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(3)
<223> OTHER INFORMATION: n is inosine

<400> SEQUENCE: 47
gtntggawrg arcarca                                                    17

<210> SEQ ID NO 48
<211> LENGTH: 17
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(3)
<223> OTHER INFORMATION: n is inosine

<400> SEQUENCE: 48
gtntggawrw aycarca                                                    17

<210> SEQ ID NO 49
<211> LENGTH: 6
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (3)..(3)
<223> OTHER INFORMATION: Xaa is Lys or Met

<400> SEQUENCE: 49

Val Trp Xaa Glu Gln His
 1               5

<210> SEQ ID NO 50
<211> LENGTH: 6
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (3)..(3)
<223> OTHER INFORMATION: Xaa is Lys or Met
<220> FEATURE:
<221> NAME/KEY: MISC_FEATURE
<222> LOCATION: (4)..(4)
<223> OTHER INFORMATION: Xaa is Asn or Tyr

<400> SEQUENCE: 50

Val Trp Xaa Xaa Gln His
 1               5

<210> SEQ ID NO 51
<211> LENGTH: 19
<212> TYPE: DNA
<213> ORGANISM: Artificial sequence
<220> FEATURE:
<223> OTHER INFORMATION: Oligonucleotide sequence

<400> SEQUENCE: 51
```

```
caytaytgga araaycagc                                                19
```

<210> SEQ ID NO 52
<211> LENGTH: 19
<212> TYPE: DNA
<213> ORGANISM: Artificial sequence
<220> FEATURE:
<223> OTHER INFORMATION: Oligonucleotide sequence

<400> SEQUENCE: 52

```
caytaytgga araaycaac                                                19
```

<210> SEQ ID NO 53
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (7)..(7)
<223> OTHER INFORMATION: Xaa is His or Gln

<400> SEQUENCE: 53

```
His Tyr Trp Lys Asn Gln Xaa
 1               5
```

<210> SEQ ID NO 54
<211> LENGTH: 20
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (9)..(15)
<223> OTHER INFORMATION: n located at position 9 and 15; each n is
      inosine

<400> SEQUENCE: 54

```
ttgttgaanm araancayaa                                               20
```

<210> SEQ ID NO 55
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (3)..(3)
<223> OTHER INFORMATION: Xaa is Lys or Asn
<220> FEATURE:
<221> NAME/KEY: MISC_FEATURE
<222> LOCATION: (4)..(4)
<223> OTHER INFORMATION: Xaa is His or Asn
<220> FEATURE:
<221> NAME/KEY: MISC_FEATURE
<222> LOCATION: (5)..(5)
<223> OTHER INFORMATION: Xaa is Lys or Asn
<220> FEATURE:
<221> NAME/KEY: MISC_FEATURE
<222> LOCATION: (7)..(7)
<223> OTHER INFORMATION: Xaa is Lys or Asn

<400> SEQUENCE: 55

```
Trp Trp Xaa Xaa Xaa His Xaa
 1               5
```

```
<210> SEQ ID NO 56
<211> LENGTH: 17
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (6)..(6)
<223> OTHER INFORMATION: n is inosine

<400> SEQUENCE: 56
ggraanagrt grtgytc                                                    17

<210> SEQ ID NO 57
<211> LENGTH: 17
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (6)..(6)
<223> OTHER INFORMATION: n is inosine

<400> SEQUENCE: 57
ggraanaart grtgytc                                                    17

<210> SEQ ID NO 58
<211> LENGTH: 6
<212> TYPE: PRT
<213> ORGANISM: Artificial sequence
<220> FEATURE:
<223> OTHER INFORMATION: Amino acids derived from oligonucleotide
      sequence

<400> SEQUENCE: 58

Pro Phe Leu His His Glu
 1               5

<210> SEQ ID NO 59
<211> LENGTH: 6
<212> TYPE: PRT
<213> ORGANISM: Artificial sequence
<220> FEATURE:
<223> OTHER INFORMATION: Amino acids derived from oligonucleotide
      sequence

<400> SEQUENCE: 59

Pro Phe Phe His His Glu
 1               5

<210> SEQ ID NO 60
<211> LENGTH: 19
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(15)
<223> OTHER INFORMATION: n located at position 3, 12 and 15; each n is
      inosine

<400> SEQUENCE: 60
aanagrtgrt gnaynrytg                                                  19

<210> SEQ ID NO 61
<211> LENGTH: 19
```

```
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (12)..(15)
<223> OTHER INFORMATION: n located at position 12 and 15; each n is
      inosine

<400> SEQUENCE: 61
aayaartgrt gnaynrytg                                                  19

<210> SEQ ID NO 62
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (5)..(5)
<223> OTHER INFORMATION: Xaa is Val or Ile
<220> FEATURE:
<221> NAME/KEY: MISC_FEATURE
<222> LOCATION: (6)..(6)
<223> OTHER INFORMATION: Xaa is Val or Ala

<400> SEQUENCE: 62

Phe Leu His His Xaa Xaa Gln
 1               5

<210> SEQ ID NO 63
<211> LENGTH: 20
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(12)
<223> OTHER INFORMATION: n located at position 3, 6 and 12; each n is
      inosine

<400> SEQUENCE: 63
atntgnggra anaartgrtg                                                 20

<210> SEQ ID NO 64
<211> LENGTH: 20
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (6)..(12)
<223> OTHER INFORMATION: n located at position 6 and 12; each n is
      inosine

<400> SEQUENCE: 64
atrttnggra anaartgrtg                                                 20

<210> SEQ ID NO 65
<211> LENGTH: 20
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(12)
```

<223> OTHER INFORMATION: n located at position 3, 6 and 12; each n is
      inosine

<400> SEQUENCE: 65
atntgnggra anagrtgrtg                                                    20

<210> SEQ ID NO 66
<211> LENGTH: 20
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (6)..(12)
<223> OTHER INFORMATION: n located at position 6 and 12; each n is
      inosine

<400> SEQUENCE: 66
atrttnggra anagrtgrtg                                                    20

<210> SEQ ID NO 67
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (1)..(1)
<223> OTHER INFORMATION: Xaa is Ile or Met
<220> FEATURE:
<221> NAME/KEY: MISC_FEATURE
<222> LOCATION: (2)..(2)
<223> OTHER INFORMATION: Xaa is His or Gln

<400> SEQUENCE: 67

Xaa Xaa Pro Phe Phe His His
 1               5

<210> SEQ ID NO 68
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (1)..(1)
<223> OTHER INFORMATION: Xaa is Ile or Met

<400> SEQUENCE: 68

Xaa Asn Pro Phe Leu His His
 1               5

<210> SEQ ID NO 69
<211> LENGTH: 17
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(9)
<223> OTHER INFORMATION: n located at position 3 and 9; each n is
      inosine

<400> SEQUENCE: 69
ctnggraana rrtgrtg                                                       17

```
<210> SEQ ID NO 70
<211> LENGTH: 17
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(9)
<223> OTHER INFORMATION: n located at position 3 and 9; each n is
      inosine

<400> SEQUENCE: 70
ganggraana rrtgrtg                                                      17

<210> SEQ ID NO 71
<211> LENGTH: 17
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(9)
<223> OTHER INFORMATION: n located at position 3 and 9; each n is
      inosine

<400> SEQUENCE: 71
gtnggraana rrtgrtg                                                      17

<210> SEQ ID NO 72
<211> LENGTH: 6
<212> TYPE: PRT
<213> ORGANISM: Artificial sequence
<220> FEATURE:
<223> OTHER INFORMATION: Amino acids derived from oligonucleotide
      sequence
<220> FEATURE:
<221> NAME/KEY: MISC_FEATURE
<222> LOCATION: (1)..(1)
<223> OTHER INFORMATION: Xaa is Thr, Arg or Ser
<220> FEATURE:
<221> NAME/KEY: MISC_FEATURE
<222> LOCATION: (4)..(4)
<223> OTHER INFORMATION: Xaa is Phe or Leu

<400> SEQUENCE: 72

Xaa Pro Phe Xaa His His
  1               5

<210> SEQ ID NO 73
<211> LENGTH: 20
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (3)..(3)
<223> OTHER INFORMATION: n is inosine

<400> SEQUENCE: 73
aanaartgrt gytcdatytg                                                   20

<210> SEQ ID NO 74
<211> LENGTH: 20
<212> TYPE: DNA
<213> ORGANISM: Artificial sequence
<220> FEATURE:
<223> OTHER INFORMATION: Oligonucleotide sequence
```

```
<220> FEATURE:
<221> NAME/KEY: misc_feature
<222> LOCATION: (3)..(3)
<223> OTHER INFORMATION: n is inosine

<400> SEQUENCE: 74
aanagrtgrt gytcdatytg                                              20

<210> SEQ ID NO 75
<211> LENGTH: 7
<212> TYPE: PRT
<213> ORGANISM: Artificial sequence
<220> FEATURE:
<223> OTHER INFORMATION: Amino acids derived from oligonucleotide
      sequence

<400> SEQUENCE: 75

Phe Phe His His Glu Ile Gln
 1               5

<210> SEQ ID NO 76
<211> LENGTH: 7
<212> TYPE: PRT
<213> ORGANISM: Artificial sequence
<220> FEATURE:
<223> OTHER INFORMATION: Amino acids derived from oligonucleotide
      sequence

<400> SEQUENCE: 76

Phe Leu His His Glu Ile Gln
 1               5

<210> SEQ ID NO 77
<211> LENGTH: 19
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (2)..(17)
<223> OTHER INFORMATION: n located at position 2, 5, 8 and 17; each n
      is inosine

<400> SEQUENCE: 77
tnggnarnaa rtgrtgnac                                               19

<210> SEQ ID NO 78
<211> LENGTH: 19
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (2)..(17)
<223> OTHER INFORMATION: n located at position 2, 5, 8 and 17; each n
      is inosine

<400> SEQUENCE: 78
tnggnarnag rtgrtgnac                                               19

<210> SEQ ID NO 79
<211> LENGTH: 7
<212> TYPE: PRT
<213> ORGANISM: Artificial sequence
<220> FEATURE:
<223> OTHER INFORMATION: Amino acids derived from oligonucleotide
      sequence
<220> FEATURE:
```

```
<221> NAME/KEY: MISC_FEATURE
<222> LOCATION: (1)..(1)
<223> OTHER INFORMATION: Xaa is Thr or Asn
<220> FEATURE:
<221> NAME/KEY: MISC_FEATURE
<222> LOCATION: (4)..(4)
<223> OTHER INFORMATION: Xaa is Phe or Leu

<400> SEQUENCE: 79

Xaa Pro Leu Xaa His His Val
 1               5

<210> SEQ ID NO 80
<211> LENGTH: 47
<212> TYPE: DNA
<213> ORGANISM: Artificial sequence
<220> FEATURE:
<223> OTHER INFORMATION: Oligonucleotide sequence

<400> SEQUENCE: 80
ccggaattcg gcgcgccgag ctcctcgagc aaatttacac attgcca                47

<210> SEQ ID NO 81
<211> LENGTH: 48
<212> TYPE: DNA
<213> ORGANISM: Artificial sequence
<220> FEATURE:
<223> OTHER INFORMATION: Oligonucleotide sequence

<400> SEQUENCE: 81
aaaactgcag gcggccgccc accgcggtgg gctggctatg aagaaatt               48

<210> SEQ ID NO 82
<211> LENGTH: 27
<212> TYPE: DNA
<213> ORGANISM: Artificial sequence
<220> FEATURE:
<223> OTHER INFORMATION: Oligonucleotide sequence

<400> SEQUENCE: 82
cgcggatccg ctggctatga agaaatt                                      27

<210> SEQ ID NO 83
<211> LENGTH: 45
<212> TYPE: DNA
<213> ORGANISM: Artificial sequence
<220> FEATURE:
<223> OTHER INFORMATION: Oligonucleotide sequence

<400> SEQUENCE: 83
tcccccggga tcgatgccgg cagatctgct ggctatgaag aaatt                  45

<210> SEQ ID NO 84
<211> LENGTH: 40
<212> TYPE: DNA
<213> ORGANISM: Artificial sequence
<220> FEATURE:
<223> OTHER INFORMATION: Oligonucleotide sequence

<400> SEQUENCE: 84
aaaactgcag tctagaaggc ctcctgcttt aatgagatat                        40

<210> SEQ ID NO 85
<211> LENGTH: 51
<212> TYPE: DNA
<213> ORGANISM: Artificial sequence
<220> FEATURE:
<223> OTHER INFORMATION: Oligonucleotide sequence
```

<400> SEQUENCE: 85
cgcggatccg atatcgggcc cgctagcgtt aaccctgctt taatgagata t    51

<210> SEQ ID NO 86
<211> LENGTH: 33
<212> TYPE: DNA
<213> ORGANISM: Artificial sequence
<220> FEATURE:
<223> OTHER INFORMATION: Oligonucleotide sequence

<400> SEQUENCE: 86
tcccccgggc catggcctgc tttaatgaga tat    33

<210> SEQ ID NO 87
<211> LENGTH: 53
<212> TYPE: DNA
<213> ORGANISM: Artificial sequence
<220> FEATURE:
<223> OTHER INFORMATION: Oligonucleotide sequence

<400> SEQUENCE: 87
cccaagcttg gcgcgccgag ctcgaattcg tcgacggaca atcagtaaat tga    53

<210> SEQ ID NO 88
<211> LENGTH: 47
<212> TYPE: DNA
<213> ORGANISM: Artificial sequence
<220> FEATURE:
<223> OTHER INFORMATION: Oligonucleotide sequence

<400> SEQUENCE: 88
cccaagcttg gcgcgccgag ctcgtcgacg gacaatcagt aaattga    47

<210> SEQ ID NO 89
<211> LENGTH: 33
<212> TYPE: DNA
<213> ORGANISM: Artificial sequence
<220> FEATURE:
<223> OTHER INFORMATION: Primer

<400> SEQUENCE: 89
gagctcacat aatggctccg gatgcggata agc    33

<210> SEQ ID NO 90
<211> LENGTH: 27
<212> TYPE: DNA
<213> ORGANISM: Artificial sequence
<220> FEATURE:
<223> OTHER INFORMATION: Primer

<400> SEQUENCE: 90
ctcgagttac gcccgtccgg tcaaggg    27

<210> SEQ ID NO 91
<211> LENGTH: 36
<212> TYPE: DNA
<213> ORGANISM: Artificial sequence
<220> FEATURE:
<223> OTHER INFORMATION: Primer

<400> SEQUENCE: 91
ggatccacat aatgggcaaa ggaggggacg ctcggg    36

<210> SEQ ID NO 92
<211> LENGTH: 27

-continued

```
<212> TYPE: DNA
<213> ORGANISM: Artificial sequence
<220> FEATURE:
<223> OTHER INFORMATION: Primer

<400> SEQUENCE: 92
ctcgagttac atggcgggtc catcggg                                        27

<210> SEQ ID NO 93
<211> LENGTH: 32
<212> TYPE: DNA
<213> ORGANISM: Artificial sequence
<220> FEATURE:
<223> OTHER INFORMATION: Primer

<400> SEQUENCE: 93
ggatccacat aatggttcgc ttttcaacag cc                                  32

<210> SEQ ID NO 94
<211> LENGTH: 26
<212> TYPE: DNA
<213> ORGANISM: Artificial sequence
<220> FEATURE:
<223> OTHER INFORMATION: Primer

<400> SEQUENCE: 94
ctcgagttat tcgctcgata atttgc                                         26

<210> SEQ ID NO 95
<211> LENGTH: 31
<212> TYPE: DNA
<213> ORGANISM: Artificial sequence
<220> FEATURE:
<223> OTHER INFORMATION: Primer

<400> SEQUENCE: 95
ggatccacat aatgggtaag ggaggtcaac g                                   31

<210> SEQ ID NO 96
<211> LENGTH: 25
<212> TYPE: DNA
<213> ORGANISM: Artificial sequence
<220> FEATURE:
<223> OTHER INFORMATION: Primer

<400> SEQUENCE: 96
ctcgagtcat gcggctttgt ttcgc                                          25
```